US008663639B2

(12) United States Patent
Dor et al.

(10) Patent No.: US 8,663,639 B2
(45) Date of Patent: Mar. 4, 2014

(54) FORMULATIONS FOR TREATING OCULAR DISEASES AND CONDITIONS

(75) Inventors: Philippe J. M. Dor, Cupertino, CA (US); Sreenivasu Mudumba, Union City, CA (US); Thierry Nivaggioli, Atherton, CA (US); David A. Weber, Danville, CA (US); Sidiq Farooq, Newark, CA (US); Sudeep Takhar, Fremont, CA (US)

(73) Assignee: Santen Pharmaceutical Co., Ltd., Osaka (JP)

( * ) Notice: Subject to any disclaimer, the term of this patent is extended or adjusted under 35 U.S.C. 154(b) by 885 days.

(21) Appl. No.: 12/193,686

(22) Filed: Aug. 18, 2008

(65) Prior Publication Data

US 2009/0074786 A1 Mar. 19, 2009

Related U.S. Application Data

(63) Continuation-in-part of application No. 11/386,290, filed on Mar. 21, 2006, now abandoned, and a continuation-in-part of application No. 11/351,761, filed on Feb. 9, 2006, now abandoned, and a continuation-in-part of application No. 11/352,092, filed on Feb. 9, 2006.

(60) Provisional application No. 60/651,790, filed on Feb. 9, 2005, provisional application No. 60/664,040, filed on Mar. 21, 2005, provisional application No. 60/664,306, filed on Mar. 21, 2005, provisional application No. 60/664,119, filed on Mar. 21, 2005, provisional application No. 60/666,872, filed on Mar. 30, 2005, provisional application No. 60/965,282, filed on Aug. 16, 2007, provisional application No. 60/965,258, filed on Aug. 16, 2007.

(51) Int. Cl.
*A61K 39/395* (2006.01)
*A61K 31/44* (2006.01)
*A01N 43/42* (2006.01)

(52) U.S. Cl.
USPC ........................................ 424/141.1; 514/291

(58) Field of Classification Search
USPC ........................................ 424/141.1; 514/291
See application file for complete search history.

(56) References Cited

U.S. PATENT DOCUMENTS

| | | |
|---|---|---|
| 3,416,530 A | 12/1968 | Ness |
| 3,630,200 A | 12/1971 | Higuchi |
| 3,828,777 A | 8/1974 | Ness |
| 3,914,402 A | 10/1975 | Shell |
| 3,926,188 A | 12/1975 | Baker et al. |
| 4,014,335 A | 3/1977 | Arnold |
| 4,093,709 A | 6/1978 | Choi et al. |
| 4,300,557 A | 11/1981 | Refojo et al. |
| 4,316,885 A | 2/1982 | Rakhit |
| 4,650,803 A | 3/1987 | Stella et al. |
| 4,853,224 A | 8/1989 | Wong |
| 4,946,450 A | 8/1990 | Erwin |
| 4,997,652 A | 3/1991 | Wong |
| 5,011,844 A | 4/1991 | Fehr |
| 5,023,262 A | 6/1991 | Caufield et al. |
| 5,078,999 A | 1/1992 | Warner et al. |
| 5,100,899 A | 3/1992 | Calne |
| 5,120,725 A | 6/1992 | Kao et al. |
| 5,120,727 A | 6/1992 | Kao et al. |
| 5,120,842 A | 6/1992 | Failli et al. |
| 5,147,647 A | 9/1992 | Darougar |
| 5,164,188 A | 11/1992 | Wong |
| 5,177,203 A | 1/1993 | Failli et al. |
| 5,178,635 A | 1/1993 | Gwon et al. |
| 5,189,042 A | 2/1993 | Goulet et al. |
| 5,192,773 A | 3/1993 | Armistead et al. |

(Continued)

FOREIGN PATENT DOCUMENTS

| | | |
|---|---|---|
| CA | 2498191 A1 | 4/2004 |
| CN | 1333018 A | 1/2002 |

(Continued)

OTHER PUBLICATIONS

Amol Kulkarni & Baruch Kuppermann, Wet Age-Related Macular Degeneration, 57 Adv. Drug Del. Rev. 1994, 2004 (2005).*
Thomas Ciulla, et al, Changing Therapeutic Paradigms for Exudative Age-Related Macular Degeneration: Antiangiogenic Agents and Photodynamic Therapy, 8 Exp. Opin. Invest. Drugs 2173 (1999).*
United States Office Action mailed Feb. 7, 2008, for U.S. Appl. No. 10/945,682, filed Sep. 20, 2004, 8 pages.
United States Office Action mailed Jun. 11, 2009, for U.S. Appl. No. 11/726,813, filed Mar. 23, 2007, 17 pages.
United States Office Action mailed Mar. 12, 2009, for U.S. Appl. No. 11/351,844, filed Feb. 6, 22 pages.
United States Office Action mailed Nov. 12, 2009, for U.S. Appl. No. 11/351,761, filed Feb. 9, 2006, 10 pages.

(Continued)

*Primary Examiner* — Sean Basquill
(74) *Attorney, Agent, or Firm* — Morrison & Foerster LLP

(57) ABSTRACT

Diseases and conditions associated with tissues of the body, including but not limited to tissues in the eye, can be effectively treated, prevented, inhibited, onset delayed, or regression caused by administering therapeutic agents to those tissues. Described herein are liquid formulations which deliver a variety of therapeutic agents, including but not limited to rapamycin, to a subject for an extended period of time; liquid formulations which form a non-dispersed mass when placed in an aqueous medium of a subject; non-dispersed mass-forming liquid formulations which form a gel or gel-like substance in an aqueous medium; liquid formulations, comprising a therapeutic agent and a plurality of polymers; and methods for delivering therapeutic agents to a subject for an extended period of time using the liquid formulations. The liquid formulation may be placed in an aqueous medium of a subject, including but not limited to via intraocular or periocular administration, or placement proximate to a site of a disease or condition to be treated in a subject. A method may be used to administer rapamycin to treat or prevent angiogenesis, choroidal neovascularization, or age-related macular degeneration, or wet age-related macular degeneration in a subject. The liquid formulations may comprise rapamycin or other therapeutic agents.

11 Claims, 12 Drawing Sheets

(56) References Cited

U.S. PATENT DOCUMENTS

| | | | |
|---|---|---|---|
| 5,192,802 A | 3/1993 | Rencher |
| 5,258,389 A | 11/1993 | Goulet et al. |
| 5,300,114 A | 4/1994 | Gwon et al. |
| 5,322,691 A | 6/1994 | Darougar et al. |
| 5,368,865 A | 11/1994 | Asakura et al. |
| 5,378,475 A | 1/1995 | Smith et al. |
| 5,387,589 A | 2/1995 | Kulkarni |
| 5,395,618 A | 3/1995 | Darougar et al. |
| 5,403,901 A | 4/1995 | Namdaran et al. |
| 5,443,505 A | 8/1995 | Wong et al. |
| 5,457,111 A | 10/1995 | Luly et al. |
| 5,466,233 A | 11/1995 | Weiner et al. |
| 5,514,686 A | 5/1996 | Mochizuki et al. |
| 5,516,522 A | 5/1996 | Peyman et al. |
| 5,516,770 A | 5/1996 | Waranis et al. |
| 5,516,781 A | 5/1996 | Morris et al. |
| 5,527,907 A | 6/1996 | Or et al. |
| 5,530,006 A | 6/1996 | Waranis et al. |
| 5,532,248 A | 7/1996 | Goulet et al. |
| 5,536,729 A | 7/1996 | Waranis et al. |
| 5,559,121 A | 9/1996 | Harrison et al. |
| 5,583,139 A | 12/1996 | Or et al. |
| 5,601,844 A | 2/1997 | Kagayama et al. |
| 5,614,547 A | 3/1997 | Hamilton et al. |
| 5,616,588 A | 4/1997 | Waranis et al. |
| 5,621,108 A | 4/1997 | Smith, III et al. |
| 5,632,984 A | 5/1997 | Wong et al. |
| 5,672,605 A | 9/1997 | Or et al. |
| 5,679,666 A | 10/1997 | Clark |
| 5,696,135 A | 12/1997 | Steiner et al. |
| 5,725,493 A | 3/1998 | Avery et al. |
| 5,743,274 A | 4/1998 | Peyman |
| 5,766,242 A | 6/1998 | Wong et al. |
| 5,766,619 A | 6/1998 | Aiache et al. |
| 5,770,592 A | 6/1998 | Clark |
| 5,773,019 A | 6/1998 | Ashton et al. |
| 5,773,021 A | 6/1998 | Gurtler et al. |
| 5,798,355 A | 8/1998 | Steiner et al. |
| 5,800,807 A | 9/1998 | Hu et al. |
| 5,824,072 A | 10/1998 | Wong |
| 5,830,173 A | 11/1998 | Avery et al. |
| 5,883,082 A | 3/1999 | Bennett et al. |
| 5,902,598 A | 5/1999 | Chen et al. |
| 5,904,144 A | 5/1999 | Hammang et al. |
| 5,912,253 A | 6/1999 | Cottens et al. |
| 6,004,973 A | 12/1999 | Guitard et al. |
| 6,007,510 A | 12/1999 | Nigam |
| 6,015,815 A | 1/2000 | Mollison |
| 6,034,239 A | 3/2000 | Ohkawa et al. |
| 6,074,661 A | 6/2000 | Olejnik et al. |
| 6,110,485 A | 8/2000 | Olejnik et al. |
| 6,126,687 A | 10/2000 | Peyman |
| 6,142,969 A | 11/2000 | Nigam |
| 6,217,895 B1 | 4/2001 | Guo et al. |
| 6,239,102 B1 | 5/2001 | Tiemessen |
| 6,239,113 B1 | 5/2001 | Dawson et al. |
| 6,254,860 B1 | 7/2001 | Garst |
| 6,258,856 B1 | 7/2001 | Chamberlain et al. |
| 6,267,985 B1 | 7/2001 | Chen et al. |
| 6,306,422 B1 | 10/2001 | Batich et al. |
| 6,326,387 B1 | 12/2001 | Armistead |
| 6,329,386 B1 | 12/2001 | Mollison |
| 6,331,313 B1 | 12/2001 | Wong et al. |
| 6,350,442 B2 | 2/2002 | Garst |
| 6,361,760 B1 | 3/2002 | Murata et al. |
| 6,375,972 B1 | 4/2002 | Guo et al. |
| 6,376,517 B1 | 4/2002 | Ross et al. |
| 6,378,526 B1 | 4/2002 | Bowman et al. |
| 6,387,918 B1 | 5/2002 | Yamanaka et al. |
| 6,397,849 B1 | 6/2002 | Bowman et al. |
| 6,399,629 B1 | 6/2002 | Chamberland et al. |
| 6,413,245 B1 | 7/2002 | Yaacobi et al. |
| 6,413,540 B1 | 7/2002 | Yaacobi |
| 6,416,777 B1 | 7/2002 | Yaacobi |
| 6,440,990 B1 | 8/2002 | Cottens et al. |
| 6,455,518 B2 | 9/2002 | Zenke et al. |
| 6,482,802 B1 | 11/2002 | Hu et al. |
| 6,489,335 B2 | 12/2002 | Peyman |
| 6,534,693 B2 | 3/2003 | Fischell et al. |
| 6,569,443 B1 | 5/2003 | Dawson et al. |
| 6,576,224 B1 | 6/2003 | Osbakken et al. |
| 6,617,345 B1 | 9/2003 | Gregory et al. |
| 6,632,836 B1 | 10/2003 | Baker et al. |
| 6,656,460 B2 | 12/2003 | Benita et al. |
| 6,699,493 B2 | 3/2004 | Wong |
| 6,713,081 B2 | 3/2004 | Robinson et al. |
| 6,719,750 B2 | 4/2004 | Varner et al. |
| 6,777,000 B2 | 8/2004 | Ni et al. |
| 6,787,179 B2 | 9/2004 | Timm et al. |
| 6,812,220 B2 | 11/2004 | Jackson et al. |
| 6,864,232 B1 | 3/2005 | Ueno |
| 6,872,383 B2 | 3/2005 | Ueno |
| 6,890,546 B2 | 5/2005 | Mollison et al. |
| 6,939,878 B2 | 9/2005 | Naicker et al. |
| 6,956,043 B2 | 10/2005 | Guitard et al. |
| 7,014,861 B2 | 3/2006 | Roorda et al. |
| 7,018,808 B2 | 3/2006 | Leadlay et al. |
| 7,026,374 B2 | 4/2006 | Nathan et al. |
| 7,033,604 B2 | 4/2006 | Ueno |
| 7,033,605 B2 | 4/2006 | Wong |
| 7,034,037 B2 | 4/2006 | Arnold et al. |
| 7,063,857 B1 | 6/2006 | Ueno |
| 7,083,802 B2 * | 8/2006 | Peyman ............... 424/422 |
| 7,083,803 B2 | 8/2006 | Peyman |
| 7,087,237 B2 | 8/2006 | Peyman |
| 7,128,897 B2 | 10/2006 | Osbakken et al. |
| 7,160,867 B2 | 1/2007 | Abel et al. |
| 7,181,287 B2 | 2/2007 | Greenberg |
| 7,183,289 B2 | 2/2007 | Zhang et al. |
| 7,186,518 B2 | 3/2007 | Wang et al. |
| 7,223,286 B2 | 5/2007 | Wright et al. |
| 7,354,574 B2 | 4/2008 | Peyman |
| 7,402,399 B2 | 7/2008 | Mukherjeei et al. |
| 7,534,448 B2 | 5/2009 | Saltzman et al. |
| 7,550,158 B2 | 6/2009 | Appel et al. |
| 8,367,097 B2 | 2/2013 | Mudumba et al. |
| 2002/0123505 A1 | 9/2002 | Mollison et al. |
| 2002/0187998 A1 | 12/2002 | Ueno |
| 2003/0018044 A1 | 1/2003 | Peyman |
| 2003/0027744 A1 | 2/2003 | Dana et al. |
| 2003/0069232 A1 | 4/2003 | Chiou |
| 2003/0069560 A1 | 4/2003 | Adamis et al. |
| 2003/0077297 A1 | 4/2003 | Chen et al. |
| 2003/0171320 A1 | 9/2003 | Guyer |
| 2003/0190286 A1 | 10/2003 | Dugger, III |
| 2003/0203892 A1 * | 10/2003 | Keller et al. ............ 514/211.09 |
| 2004/0018228 A1 | 1/2004 | Fischell et al. |
| 2004/0022755 A1 | 2/2004 | Kamath |
| 2004/0057958 A1 | 3/2004 | Waggoner, Jr. et al. |
| 2004/0091455 A1 | 5/2004 | Zeldis |
| 2004/0167152 A1 | 8/2004 | Rubino et al. |
| 2004/0180075 A1 | 9/2004 | Robinson et al. |
| 2004/0198763 A1 | 10/2004 | Ueno |
| 2004/0219181 A1 | 11/2004 | Viscasillas |
| 2004/0224394 A1 | 11/2004 | Katz et al. |
| 2004/0234611 A1 | 11/2004 | Ahlheim et al. |
| 2005/0025810 A1 | 2/2005 | Peyman |
| 2005/0031650 A1 | 2/2005 | Leroux et al. |
| 2005/0032826 A1 | 2/2005 | Mollison et al. |
| 2005/0042215 A1 | 2/2005 | Owen et al. |
| 2005/0048123 A1 | 3/2005 | Su et al. |
| 2005/0064010 A1 | 3/2005 | Cooper et al. |
| 2005/0074497 A1 | 4/2005 | Schultz |
| 2005/0084514 A1 | 4/2005 | Shebuski et al. |
| 2005/0123605 A1 | 6/2005 | Hunter et al. |
| 2005/0142162 A1 | 6/2005 | Hunter et al. |
| 2005/0143363 A1 | 6/2005 | De Juan et al. |
| 2005/0187241 A1 * | 8/2005 | Wen et al. ............... 514/291 |
| 2005/0196440 A1 | 9/2005 | Masters et al. |
| 2005/0222191 A1 | 10/2005 | Falotico et al. |
| 2005/0232952 A1 | 10/2005 | Lambert et al. |
| 2005/0232965 A1 | 10/2005 | Falotico |
| 2005/0249710 A1 | 11/2005 | Wong |
| 2005/0250804 A1 | 11/2005 | Kannan et al. |

(56) References Cited

U.S. PATENT DOCUMENTS

| | | |
|---|---|---|
| 2005/0255144 A1 | 11/2005 | Schultz |
| 2006/0024350 A1 | 2/2006 | Varner et al. |
| 2006/0034891 A1 | 2/2006 | Lawin et al. |
| 2006/0073182 A1 | 4/2006 | Wong et al. |
| 2006/0121115 A1 | 6/2006 | Leroux et al. |
| 2006/0141049 A1 | 6/2006 | Lyons et al. |
| 2006/0182771 A1 | 8/2006 | Dor et al. |
| 2006/0182783 A1 | 8/2006 | Hughes et al. |
| 2006/0198867 A1 | 9/2006 | Toner et al. |
| 2006/0216288 A1 | 9/2006 | Chang |
| 2006/0228393 A1 | 10/2006 | Peyman |
| 2006/0228394 A1 | 10/2006 | Peyman |
| 2006/0247265 A1 | 11/2006 | Clackson et al. |
| 2006/0257450 A1 | 11/2006 | Mudumba et al. |
| 2006/0258698 A1* | 11/2006 | Mudumba et al. ............ 514/291 |
| 2006/0263409 A1 | 11/2006 | Peyman |
| 2006/0264453 A1 | 11/2006 | Mudumba et al. |
| 2006/0275218 A1 | 12/2006 | Tamarkin et al. |
| 2007/0014760 A1 | 1/2007 | Peyman |
| 2007/0015697 A1 | 1/2007 | Peyman |
| 2007/0134244 A1 | 6/2007 | Slakter et al. |
| 2007/0173538 A1* | 7/2007 | Han et al. ............... 514/406 |
| 2007/0197567 A1 | 8/2007 | Sherris |
| 2007/0203173 A1 | 8/2007 | Mudumba et al. |
| 2007/0265294 A1 | 11/2007 | Kleinman et al. |
| 2009/0036479 A1 | 2/2009 | Wen et al. |
| 2009/0324686 A1 | 12/2009 | Cooper et al. |
| 2009/0324687 A1 | 12/2009 | Cooper et al. |
| 2009/0324688 A1 | 12/2009 | Cooper et al. |
| 2009/0324689 A1 | 12/2009 | Cooper et al. |
| 2009/0324690 A1 | 12/2009 | Cooper et al. |
| 2010/0227879 A1 | 9/2010 | Mudumba et al. |
| 2012/0034279 A1 | 2/2012 | Cooper et al. |

FOREIGN PATENT DOCUMENTS

| | | |
|---|---|---|
| CN | 1340358 A | 3/2002 |
| CN | 1456350 A | 11/2003 |
| DE | 40225553 A1 | 1/1992 |
| DE | 19810655 A1 | 9/1999 |
| EP | 0041745 A1 | 12/1981 |
| EP | 0041795 A2 | 12/1981 |
| EP | 0467606 A1 | 1/1992 |
| EP | 0650730 A1 | 5/1995 |
| EP | 0904787 A1 | 3/1999 |
| EP | 1142566 A1 | 10/2001 |
| EP | 1126849 B1 | 3/2005 |
| FR | 2382240 | 9/1978 |
| GB | 2278780 A | 12/1994 |
| JP | 09-030966 A | 2/1997 |
| JP | 09-315954 A | 12/1997 |
| JP | 10-218787 A | 8/1998 |
| JP | 2001-064198 A | 3/2001 |
| JP | 2002-522485 A | 7/2002 |
| JP | 2002-534139 A | 10/2002 |
| JP | 2002-332225 A | 11/2002 |
| JP | 2006-511475 A | 4/2006 |
| JP | 2007-509931 A | 4/2007 |
| RU | 2123314 C1 | 12/1998 |
| RU | 2149615 C1 | 5/2000 |
| WO | WO-89/01772 A1 | 3/1989 |
| WO | WO-92/05179 A1 | 4/1992 |
| WO | WO-93/19763 A1 | 10/1993 |
| WO | WO-94/05257 A1 | 3/1994 |
| WO | WO-94/21642 A1 | 9/1994 |
| WO | WO-95/14023 A1 | 5/1995 |
| WO | WO-95/26734 A1 | 10/1995 |
| WO | WO-95/28984 A1 | 11/1995 |
| WO | WO-96/36377 A1 | 11/1996 |
| WO | WO-96/40140 A1 | 12/1996 |
| WO | WO-96/41865 A1 | 12/1996 |
| WO | WO-97/10806 A1 | 3/1997 |
| WO | WO-97/16068 A1 | 5/1997 |
| WO | WO-99/07418 A2 | 2/1999 |
| WO | WO-99/11244 A1 | 3/1999 |
| WO | WO-99/20261 A2 | 4/1999 |
| WO | WO-99/22722 A2 | 5/1999 |
| WO | WO-99/34830 A1 | 7/1999 |
| WO | WO-99/37667 A1 | 7/1999 |
| WO | WO-99/45920 A2 | 9/1999 |
| WO | WO-99/58126 A1 | 11/1999 |
| WO | WO-00/06121 A1 | 2/2000 |
| WO | WO-00/09109 A2 | 2/2000 |
| WO | WO-00/09112 A2 | 2/2000 |
| WO | WO-00/09479 A2 | 2/2000 |
| WO | WO-00/28945 A2 | 5/2000 |
| WO | WO-00/33878 A2 | 6/2000 |
| WO | WO-00/37066 A2 | 6/2000 |
| WO | 00/40089 A1 | 7/2000 |
| WO | WO-00/38703 A1 | 7/2000 |
| WO | WO-00/40089 A1 | 7/2000 |
| WO | WO-00/56340 A1 | 9/2000 |
| WO | WO-00/66122 A1 | 11/2000 |
| WO | WO-01/28522 A2 | 4/2001 |
| WO | WO-01/30386 A1 | 5/2001 |
| WO | WO-01/42219 A2 | 6/2001 |
| WO | WO-01/47495 A1 | 7/2001 |
| WO | 01/60345 A2 | 8/2001 |
| WO | WO-01/93830 A1 | 12/2001 |
| WO | WO-02/28387 A1 | 4/2002 |
| WO | WO-02/062335 A2 | 8/2002 |
| WO | WO-02/066019 A2 | 8/2002 |
| WO | WO-02/074196 A1 | 9/2002 |
| WO | WO-02/100318 A2 | 12/2002 |
| WO | 03/007944 A1 | 1/2003 |
| WO | WO-03/017990 A2 | 3/2003 |
| WO | WO-03/051385 A1 | 6/2003 |
| WO | WO-03/068186 A1 | 8/2003 |
| WO | 03/075885 A1 | 9/2003 |
| WO | WO-03/074027 A2 | 9/2003 |
| WO | WO-03/074029 A1 | 9/2003 |
| WO | 03/092671 A1 | 11/2003 |
| WO | 03/097009 A1 | 11/2003 |
| WO | WO-03/090684 A2 | 11/2003 |
| WO | WO-2004/007709 A2 | 1/2004 |
| WO | WO-2004/011000 A1 | 2/2004 |
| WO | WO-2004/014373 A1 | 2/2004 |
| WO | WO-2004/019904 A1 | 3/2004 |
| WO | WO-2004/027027 A2 | 4/2004 |
| WO | WO-2004/028477 A2 | 4/2004 |
| WO | WO-2004/043480 A2 | 5/2004 |
| WO | 2004/050060 A | 6/2004 |
| WO | WO-2004/060283 A2 | 7/2004 |
| WO | WO-2004/074445 A2 | 9/2004 |
| WO | WO-2004/096261 A1 | 11/2004 |
| WO | WO-2005/002625 A2 | 1/2005 |
| WO | WO-2005/011813 A2 | 2/2005 |
| WO | WO-2005/020962 A1 | 3/2005 |
| WO | WO-2005/027906 A1 | 3/2005 |
| WO | WO-2005/030205 A1 | 4/2005 |
| WO | 2005/044259 A1 | 5/2005 |
| WO | WO-2005/051452 A2 | 6/2005 |
| WO | WO-2005/055945 A2 | 6/2005 |
| WO | WO-2005/082376 A1 | 9/2005 |
| WO | WO-2005/094279 A2 | 10/2005 |
| WO | WO-2005/099715 A2 | 10/2005 |
| WO | WO-2005/110436 A2 | 11/2005 |
| WO | WO-2005/110473 A2 | 11/2005 |
| WO | WO-2006/002365 A2 | 1/2006 |
| WO | WO-2006/002366 A2 | 1/2006 |
| WO | WO-2006/002399 A2 | 1/2006 |
| WO | WO-2006/014484 A2 | 2/2006 |
| WO | WO-2006/020755 A2 | 2/2006 |
| WO | WO-2006/023627 A1 | 3/2006 |
| WO | WO-2006/026531 A1 | 3/2006 |
| WO | WO-2006/039336 A2 | 4/2006 |
| WO | WO-2006/041942 A2 | 4/2006 |
| WO | WO-2006/053007 A2 | 5/2006 |
| WO | WO-2006/086744 A1 | 8/2006 |
| WO | WO-2006/086750 A1 | 8/2006 |
| WO | WO-2006/102378 A1 | 9/2006 |
| WO | WO-2006/108239 A1 | 10/2006 |
| WO | WO-2006/110487 A1 | 10/2006 |

(56) References Cited

FOREIGN PATENT DOCUMENTS

| WO | WO-2006/116716 A2 | 11/2006 |
| WO | WO-2006/133052 A2 | 12/2006 |
| WO | WO-2007/011880 A2 | 1/2007 |
| WO | WO-2007/065588 A1 | 6/2007 |
| WO | WO-2007/083316 A2 | 7/2007 |
| WO | WO-2007/092620 A2 | 8/2007 |
| WO | WO-2007/112052 A2 | 10/2007 |

OTHER PUBLICATIONS

United States Office Action mailed Apr. 22, 2009, for U.S. Appl. No. 11/386,290, filed Mar. 21, 2006, 13 pages.

United States Office Action mailed Apr. 3, 2008, for U.S. Appl. No. 10/665,203, filed Sep. 18, 2003, 6 pages.

United States Office Action mailed Aug. 6, 2008, for U.S. Appl. No. 11/386,290, filed Mar. 21, 2006, 8 pages.

United States Office Action mailed Feb. 11, 2009, for U.S. Appl. No. 11/352,092, filed Feb. 9, 2006, 13 pages.

United States Office Action mailed Feb. 2, 2009, for U.S. Appl. No. 11/351,761, filed Feb. 9, 2006, 14 pages.

United States Office Action mailed Jan. 12, 2009, for U.S. Appl. No. 10/665,203, filed Sep. 18, 2003, 6 pages.

United States Office Action mailed Jan. 29, 2009, for U.S. Appl. No. 10/945,682, filed Sep. 20, 2004, 8 pages.

United States Office Action mailed Jan. 5, 2010, for U.S. Appl. No. 11/351,844, filed Feb. 8, 2006, 11 pages.

United States Office Action mailed Jul. 6, 2007, for U.S. Appl. No. 10/665,203, filed Sep. 18, 2003, 4 pages.

United States Office Action mailed Mar. 16, 2010, for U.S. Appl. No. 11/726,813, filed Mar. 23, 2007, 12 pages.

United States Office Action mailed Nov. 25, 2009, for U.S. Appl. No. 11/352,092, filed Feb. 9, 2006, 7 pages.

Xue et al. (Nov. 15, 2008). "Palomid 529, a novel small-molecule drug, is a TORC1/TORC2 inhibitor that reduces tumor growth, tumor angiogenesis, and vascular permeability," *Cancer Res.* 68(22):9551-9557.

Phung, T. L. et al. (Aug. 2006). "Pathological Angiogenesis is Induced by Sustained Akt Signaling and Inhibited by Rapamycin," *Cancer Cell* 10:159-170.

Raghava, S. et al. (Nov. 2004). "Periocular Routes for Retinal Drug Delivery," *Expert Opinion on Drug Delivery* 1(1):99-114.

Renau, T. E. et al. (2003). "Conformationally-Restricted Analogues of Efflux Pump Inhibitors that Potentiate the Activity of Levofloxaxin in *Pseudomonas aeruginosa*," *Bioorganic & Medicinal Chemistry Letters* 13:2755-2758.

Renau, T. E. et al., (2001). "Addressing the Stability of C-Capped Dipeptide Efflux Pump Inhibitors that Potentiate the Activity of Levofloxacin in *Pseudomonas aeruginosa*," *Bioorganic & Medicinal Chemistry Letters* 11:663-667.

Rivera, V. M. et al. (Jul. 1999). "Long-Term Regulated Expression of Growth Hormone in Mice after Intramuscular Gene Transfer," *Proceedings of the National Academy of Sciences of the United States of America* 96:8657-8662.

Robinson, J. R. et al. (1995). "Bioadhesive and Phase-Change Polymers for Ocular Drug Delivery," *Advanced Drug Delivery Reviews* 16:45-50.

Romo, D. et al. (1993). "Total Synthesis of (-)-Rapamycin Using an Evans-Tishchenko Fragment Coupling," *Journal of the American Chemical Society* 115(17):7906-7907.

Schlingemann, R. O. et al. (Jun. 1997). "Role of Vascular Permeability Factor/Vascular Endothelial Growth Factor in Eye Disease," *British Journal of Ophthalmology* 81(6):501-512.

Sehgal, S. N. et al. (Apr. 1983). "Demethoxyrapamycin (AY-24,668), A New Antifungal Antibiotic," *The Journal of Antibiotics* 36(4):351-354.

Sehgal, S. N. et al. (Oct. 1975). "Rapamycin (AY-22,989), A New Antifungal Antibiotic, II. Fermentation, Isolation and Characterization," *The Journal of Antibiotics* 28(10):727-732.

Shen, W.-Y. et al. (Jul. 2001). "Combined Effect of Cyclosporine and Sirolimus on Improving the Longevity of Recombinant Adenovirus-Mediated Transgene Expression in the Retina," *Archives of Ophthalmology* 119:1033-1043.

Simamora, P. et al. (Feb. 1, 2001). "Solubilization of Rapamycin," *International Journal of Pharmaceutics* 213(1-2):25-29.

Spaide, R. F. et al. (Aug. 2003). "Combined Photodynamic Therapy With Verteporfin and Intravitreal Triamcinolone Acetonide for Choroidal Neovascularization," *Ophthalmology* 110(8):1517-1525.

Stepkowski, S. M. et al. (Jan. 1991). "Rapamycin, a Potent Immunosuppressive Drug for Vascularized Heart, Kidney, and Small Bowel Transplantation in the Rat," *Transplantation* 51(1):22-26.

Treatment of Age-Related Macular Degeneration with Photodynamic Therapy (TAP) Study Group. (Apr. 2000). Correction for "Photodynamic Therapy of Subfoveal Choroidal Neovascularization in Age-Related Macular Degeneration with Verteporfin, One-Year Results of 2 Randomized Clinical Trials-TAP Report 1," *Archives of Ophthalmology* 118:488.

Treatment of Age-Related Macular Degeneration with Photodynamic Therapy (TAP) Study Group. (Oct. 1999). "Photodynamic Therapy of Subfoveal Choroidal Neovascularization in Age-Related Macular Degeneration With Verteporfin, One-Year Results of 2 Randomized Clinical Trials-TAP Report 1," *Archives of Ophthalmology* 117:1329-1345.

Treins, C. et al. (Aug. 2, 2002). "Insulin Stimulates Hypoxia-Inducible Factor 1 Through a Phosphatidylinositol 3-kinase/Target of Rapamycin-Dependent Signaling Pathway," *The Journal of Biological Chemistry* 277(31):27975-27981.

Vézina, C. et al. (Oct. 1975). "Rapamycin (AY-22,989), A New Antifungal Antibiotic, I. Taxonomy of the Producing Streptomycete and Isolation of the Active Principle," *The Journal of Antibiotics* 28(10):721-726.

Wen, R. et al. (2003). "Rapamycin Inhibits Choroidal Neovascularization," *Investigative Ophthalmology & Visual Science* 44:E-Abstract 3928, 2 pages.

Extended European Search Report received for EP Patent Application No. 08827362.8, mailed on Sep. 23, 2010, 8 pages.

Non Final Office Action received for U.S. Appl. No. 11/386,290, mailed on Sep. 27, 2010, 13 pages.

Non Final Office Action received for U.S. Appl. No. 11/726,813, mailed on Oct. 4, 2010, 16 pages.

Bradley et al., "Combination therapy for the treatment of ocular neovascularization", Angiogenesis, vol. 10, No. 2, Jan. 2007, pp. 141-148.

Chun et al., "A pilot study of multiple intravitreal injections of ranibizumab in patients with center-involving clinically significant diabetic macular edema", Ophthalmology. vol. 113, No. 10, Oct. 2006, pp. 1706-1712.

El-Harazi et al., "Control of intra-ocular inflammation associated with cataract surgery", Current Opinion in Ophthalmology, vol. 12, 2001, pp. 4-8.

Eng et al., "Ranibizumab in neovascular age-related macular degeneration", Clinical Interventions in Aging, vol. 1, No. 4, 2006, pp. 451-466.

Hikita, "Immunosuppressive effect of topical FK506 on penetrating keratoplasty in rats", Journal of the Kurume Medical Association, vol. 57, No. 1, Japan, Jan. 1994, pp. 176-189 (Article in Japanese, English Abstract at p. 189).

Jaissle et al., "Bevacizumab for treatment of macular edema secondary to retinal vein occlusion", Ophthalmologe, vol. 103, No. 6, 2006, pp. 471-475 (Article in German, English Abstract on the First page).

Kimura, Angiogenesis Inhibitors, Atarashii Ganka (New Ophthalmology), vol. 18, No. 7, Japan, Jul. 30, 2001, pp. 867-870 (Article in Japanese).

Kleinman et al., "Sirolimus Inhibits VEGF-Induced Microvascular Hyperpermeability", Investigative Ophthalmology & Visual Science, vol. 48, 2007, E-Abstract 1422, 2 pages.

Sloper et al., "Tacrolimus (FK506) in the treatment of posterior uveitis refractory to cyclosporine", Ophthalmology, vol. 106, No. 4, Apr. 1999, pp. 723-728.

(56) References Cited

OTHER PUBLICATIONS

Zubilewicz et al., "Two distinct signalling pathways are involved in FGF2-stimulated proliferation of choriocapillary endothelial cells: A comparative study with VEGF", Oncogene, vol. 20, No. 12, Mar. 22, 2001, pp. 1403-1413.

Akselband, Y. et al. (Dec. 1991). "Rapamycin Inhibits Spontaneous and Fibroblast Growth Factor Beta-Stimulated Proliferation of Endothelial Cells and Fibroblasts," *Transplantation Proceedings* 23(6):2833-2836.

Alteheld, A. et al. (2005). "Biodegradable Amorphous Copolyester-Urethane Networks Having Shape-Memory Properties," *Angewandte Chemie International Edition* 44:1188-1192.

Apel, A. et al. (Aug. 1995). "A Subconjuctival Degradable Implant for Cyclosporine Delivery in Corneal Transplant Therapy," *Current Eye Research* 14(8):659-667.

Aramoto, H. et al. (Oct. 2004). "Vascular Endothelial Growth Factor Stimulates Differential Signaling Pathways in in Vivo Microcirculation," *American Journal of Physiology—Heart and Circulatory Physiology* 287:H1590-H1598.

Arias, L. (2007). "Management of Diabetic Macular Edema with Antiangiogenic Therapy," *Expert Review of Ophthalmology* 2(1):23-26.

Auricchio, A. et al. (Aug. 2002). "Pharmacological Regulation of Protein Expression from Adeno-Associated Viral Vectors in the Eye," *Molecular Therapy* 6(2):238-242.

Averbukh, E. et al. (Feb. 2006). "Diabetic Macular Edema: Towards Therapy Aimed at the Underlying Pathogenic Mechanisms," *The Israel Medical Association Journal* 8:127-128.

Bainbridge, J. W. B. et al. (2003). "Hypoxia-Regulated Transgene Expression in Experimental Retinal Choroidal Neovascularization," *Gene Therapy* 10:1049-1054.

Beeley, N. R. F. et al. (Mar. 15, 2006). "Development, Implantation, In Vivo Elution, and Retrieval of a Biocompatible, Sustained Release Subretinal Drug Delivery System," *Journal of Biomedical Materials Research Part A* 76A:690-698.

Behl, C. (Dec. 1997). "Amyloid Beta-Protein Toxicity and Oxidative Stress in Alzheimer's Disease," *Cell & Tissue Research* 290(3):471-480.

Bergers, G. et al. (Jun. 2003). "Tumorigenesis and the Angiogenic Switch," *Nature Reviews-Cancer* 3(6):401-410.

Bertelmann, E. et al. (2004). "Immunomodulatory Therapy in Ophthalmology—Is There a Place for Topical Application?," *Ophthalmologica* 218:359-367.

Bourne, R. R. et al., (1998). "Epidemic Optic Neuropathy in Primary School Children in Dar es Salaam, Tanzania," *British Journal of Ophthalmology* 82:232-234.

Bucci, M. et al. (Dec. 2000). "In Vivo Delivery of the Caveolin-1 Scaffolding Domain Inhibits Nitric Oxide Synthesis and Reduces Inflammation," *Nature Medicine* 6(12):1362-1367.

Cancer Weekly Editors. (Jan. 14, 2003). "Cancer Therapy: Study of Possible Anticancer Drug Reveals New Mechanism of Gene Regulation," *Cancer Weekly via NewsRx.com and NewsRx.net*, 2 pages.

Chusid, M. J. et al. (Oct. 1986). "The Role of the Polymorphonuclear Leukocyte in the Induction of Corneal Edema," *Investigative Ophthalmology & Visual Science* 27(10):1466-1469.

Cicciarelli, N. et al. (Mar. 15, 2001). "Pharmacokinetics of Subconjunctivally Administered Cyclosporine A: Local Delivery Prior to Chemotherapy for Retinoblastoma," IOVS, Apr. 29-May 4, 2001, Fort Lauderdale, Florida, 42(4):S332, Abstract 1792-B42.

Ciulla, T. A. et al. (Sep. 2003). "Diabetic Retinopathy and Diabetic Macular Edema: Pathophysiology, Screening, and Novel Therapies," *Diabetes Care* 26(9):2653-2664.

Ciulla. T. A. et al. (Sep.-Oct. 1998). "Age-Related Macular Degeneration: A Review of Experimental Treatments," *Survey of Ophthalmology* 43(2):134-146.

Edinger, A. L. et al. (Dec. 1, 2003). "Differential Effects of Rapamycin on Mammalian Target of Rapamycin Signaling Functions in Mammalian Cells," *Cancer Research* 63:8451-8460.

Gardner, T. W. et al. (2008). "Novel Potential Mechanisms for Diabetic Macular Edema: Leveraging New Investigational Approaches," *Current Diabetes Reports* 8:263-269.

Geroski, D. H. et al. (2001). "Transscleral Drug Delivery for Posterior Segment Disease," *Advanced Drug Delivery Reviews* 52:37-48.

Gilbard, J. P. (Feb. 1999). "EW Interview: Electrolyte Balance is Key to Dry-eye Product's Success," *EyeWorld*, pp. 20-21.

Guba, M. et al. (2001). "Rapamycin Inhibits Tumor Growth and Metastasis by Antiangiogenesis," *Chirurgisches Forum 2001*, pp. 37-39. (English Abstract attached).

Guba, M. et al. (Feb. 2002). "Rapamycin Inhibits Primary and Metastatic Tumor Growth By Antiangiogenesis: Involvement of Vascular Endothelial Growth Factor," *Nature Medicine* 8(2):128-135.

Hackstein, H. et al. (Aug. 1, 2002). "Rapamycin Inhibits Macropinocytosis and Mannose Receptor-Mediated Endocytosis by Bone Marrow-Derived Dendritic Cells," *Blood* 100(3):1084-1087.

Hafizi, S. et al. (2005). "Differential Effects of Rapamycin, Cyclosporine A, and FK506 on Human Coronary Artery Smooth Muscle Cell Proliferation and Signaling," *Vascular Pharmacology* 41:167-176.

Harris, A. et al. (2001). "Implantation of a Sustained-Release Ganciclovir Implant," Chapter 45 in *Vitreoretinal Surgical Techniques*, pp. 521-531.

Hayward, C. M. et al. (Sep. 22, 1993). "Total Synthesis of Rapamycin via a Novel Titanium-Mediated Aldol Macrocyclization Reaction," *Journal of the American Chemical Society* 115(20):9345-9346.

Humar, R. et al. (2002). "Hypoxia Enhances Vascular Cell Proliferation and Angiogenesis in Vitro Via Rapamycin (mTOR)-Dependent Signaling," *The FASEB Journal* 16:771-780.

International Search Report mailed Feb. 23, 2009, for PCT Application No. PCT/US08/73520 filed Aug. 18, 2008, 3 pages.

Kulkarni, P. S. (1994). "Steroidal and Nonsteroidal Drugs in Endotoxin-Induced Uveitis," *Journal of Ocular Pharmacology* 10(1):329-334.

Kuroki, A. et al. (2003). "Rapamycin Inhibits Retinal and Choroidal Neovascularization in Mice," *Investigative Ophthalmology & Visual Science* 44:E-Abstract 573, 2 pages.

Lal, A. (1993). "Drop Volume of Commercial Anti-Glaucoma Eye Drops," *Indian Journal of Pharmacology* 25:163-164.

Lallemand, F. et al. (2003). "Cyclosporine a Delivery to the Eye: A Pharmaceutical Challenge," *European Journal of Pharmaceutics and Biopharmaceutics* 56:307-318.

Lipner, M. (Feb. 1999). "Dry Eye 101: Developing Etiologies and Treatments for the Widespread Syndrome," *Eye World*, pp. 19, 21.

Macular Photocoagulation Study Group. (May 1986). "Argon Laser Photocoagulation for Neovascular Maculopathy, Three-Year Results from Randomized Clinical Trials," *Archives of Ophthalmology* 104:694-701.

Macular Photocoagulation Study Group. (Sep. 1991). "Laser Photocoagulation of Subfoveal Neovascular Lesions in Age-Related Macular Degeneration, Results of a Randomized Clinical Trial," *Archives of Ophthalmology* 109:1220-1231.

Macular Photocoagulation Study Group. (Sep. 1991). "Laser Photocoagulation of Subfoveal Recurrent Neovascular Lesions in Age-Related Macular Degeneration, Results of a Randomized Clinical Trial," *Archives of Ophthalmology* 109:1232-1241.

Macular Photocoagulation Study Group. (Sep. 1991). "Subfoveal Neovascular Lesions in Age-Related Macular Degeneration, Guidelines for Evaluation and Treatment in the Macular Photocoagulation Study," *Archives of Ophthalmology* 109:1242-1257.

MacuSight, Inc. "Safety and Tolerability of MS-R001 in Patients with Diabetic Macular Edema Secondary to Diabetic Retinopathy," located at <http://clinicaltrials.gov/ct2/show/NCT00401115?term=macular+edema+and+rapamycin&rank=3> visited on Jan. 26, 2009. (3 pages).

Marsland, A. M. et al. (Nov.-Dec. 2002). "The Macrolide Immunosuppressants in Dermatology: Mechanisms of Action," *European Journal of Dermatology* 12:618-621.

Martin, D. F. et al. (Jan. 15, 1995). "Synergistic Effect of Rapamycin and Cyclosporin A in the Treatment of Experimental Autoimmune Uveoretinitis," *The Journal of Immunology* 154(2):922-927.

Mayhan, W. G. et al. (Sep. 1984). "The Effect of Altering the External Calcium Concentration and a Calcium Channel Blocker, Verapamil,

(56) References Cited

OTHER PUBLICATIONS on Microvascular Leaky Sites and Dextran Clearance in the Hamster Cheek Pouch," *Microvascular Research* 28(2):159-179.

MediVas. (2007). "MediVas Announces Signing of Collaboration Agreement with Pfizer," located at <www.medivas.com/News/news_MediVas_Announces_Signing_of_Collaboration_Agreement_with_Pfizer.html> visited on Jul. 28, 2008. (1 page).

Murphy, R. P. (Mar. 1995). "Management of Diabetic Retinopathy," *American Family Physician* 51(4):785-796.

Napoli, K. L. et al. (2001). "From Beach to Bedside: History of the Development of Sirolimus," *Therapeutic Drug Monitoring* 23(5):559-586.

National Eye Institute (NEI). "Sirolimus to Treat Diabetic Macular Edema," located at <http://clinicaltrials.gov/ct2/show/NCT00711490?term=macular+edema+and+rapamycin&rank=1> visited on Jan. 26, 2009. (6 pages).

Nicolaou, K. C. et al. (1993). "Total Synthesis of Rapamycin," *Journal of the American Chemical Society* 115(10):4419-4420.

Ohia, E. O. et al. (1992). "Effects of Steroids and Immunosuppressive Drugs on Endotoxin-Uveitis in Rabbits," *Journal of Ocular Pharmacology* 8(4):295-307.

Olsen, T. W. et al. (Nov. 1994). "Rapamycin Inhibits Corneal Allograft Rejection and Neovascularization," Archives of Ophthalmology 112:1471-1475.

Paiva, N. L. et al. (Jan.-Feb. 1991). "Incorporation of Acetate, Propionate, and Methionine Into Rapamycin by *Streptomyces hygroscopicus*," *Journal of Natural Products* 54(1):167-177.

Passos, E. et al. (Mar./Apr. 2002). "Ocular Toxcity of Intravitreal Tacrolimus," *Ophthalmic Surgery and Lasers* 33(2):140-144.

Pavan-Langston, D. (1996). *Manual of Ocular Diagnosis and Therapy*. Fourth Edition, Little, Brown and Company: New York, pp. 162-165.

Extended European Search Report received for European Patent Application No. 12004712.1, mailed on Oct. 25, 2012, 13 pages.

Extended European Search Report (includes Supplementary European Search Report and Search Opinion) received for European Patent Application No. 06734887.0, mailed on Nov. 26, 2012, 6 pages.

Anonymous, "Dry AMD", AMD.org, Macular degeneration partnership, available online at <http://www.amd.org/what-is-amd/dry-amd.html?tmpl=component&print=1&page=>, Retrieved on Jul. 10, 2013, 1 page.

Bainbridge et al., "Gene Therapy Progress and Prospects: The Eye", Gene Therapy, vol. 13, 2006, pp. 1191-1197.

Hatefi et al., "Biodegradable Injectable in Situ Forming Drug Delivery Systems", Journal of Controlled Release, vol. 80, 2002, pp. 9-28.

Kok et al., "Developments in the Treatment of Uveitis", Expert Opinion on Investigational Drugs, vol. 11, No. 1, 2002, pp. 59-67.

News Release, "Study of Possible Anticancer Drug Reveals New Mechanism of Gene Regulation", available at: http://www.siteman.wustl.edu/ContentPage.aspx?id=560, retrieved on Oct. 31, 2013, 2 pages.

Serajuddin et al., "Water Migration from Soft Gelatin Capsule Shell to Fill Material and Its Effect on Drug Solubility", Journal of Pharmaceutical Sciences, vol. 75, No. 1, Jan. 1986, pp. 62-64.

Whiting et al., "The Effect of Rapamycin on Renal Function in the Rat: A Comparative Study with Cyclosporine", Toxicology Letters, vol. 58, 1991, pp. 169-179.

\* cited by examiner

FORMULATIONS FOR TREATING OCULAR DISEASES AND CONDITIONS

This application is a Continuation-In-Part of U.S. application Ser. No. 11/351,761, filed Feb. 9, 2006, which claims benefit of Provisional Application No. 60/651,790, filed Feb. 9, 2005, Provisional Application No. 60/664,040, filed Mar. 21, 2005, and Provisional Application No. 60/664,306, filed Mar. 21, 2005. This application is also a Continuation-In-Part of U.S. application Ser. No. 11/352,092, filed Feb. 9, 2006, which claims benefit of Provisional Application No. 60/651,790, filed Feb. 9, 2005, Provisional Application No. 60/664,040, filed Mar. 21, 2005, and Provisional Application No. 60/664,306, filed Mar. 21, 2005. In addition this application is a Continuation-In-Part of U.S. application Ser. No. 11/386,290, filed Mar. 21, 2006, which claims benefit of Provisional Application No. 60/664,119, filed Mar. 21, 2005, and Provisional Application No. 60/666,872, filed Mar. 30, 2005. This Application claims benefit of Provisional Application No. 60/965,282, filed Aug. 16, 2007, and Provisional Application No. 60/965,258, filed Aug. 16, 2007.

FIELD

Described herein are liquid formulations for treatment, prevention, inhibition, delaying onset of, or causing regression of a disease or condition by delivery of therapeutic agents to a subject, including but not limited to a human subject, including but not limited to the treatment of age-related macular degeneration (AMD) and macular edema by delivery of a liquid formulation comprising a therapeutic agent, including but not limited to rapamycin (sirolimus), to the eye of a subject, including but not limited to a human subject. Nonlimiting examples of liquid formulations include solutions, suspensions, and in situ gelling formulations.

BACKGROUND

The retina of the eye contains the cones and rods that detect light. In the center of the retina is the macula lutea, which is about ⅓ to ½ cm in diameter. The macula provides detailed vision, particularly in the center (the fovea), because the cones are higher in density. Blood vessels, ganglion cells, inner nuclear layer and cells, and the plexiform layers are all displaced to one side (rather than resting above the cones), thereby allowing light a more direct path to the cones.

Under the retina are the choroid, comprising a collection of blood vessels embedded within a fibrous tissue, and the deeply pigmented epithelium, which overlays the choroid layer. The choroidal blood vessels provide nutrition to the retina (particularly its visual cells).

There are a variety of retinal disorders for which there is currently no treatment or for which the current treatment is not optimal. Retinal disorders such as uveitis (an inflammation of the uveal tract: iris, ciliary body, and choroid), central retinal vein occlusive diseases (CRVO), branch retinal venous occlusion (BRVO), macular degeneration, macular edema, proliferative diabetic retinopathy, and retinal detachment generally are all retinal disorders that are difficult to treat with conventional therapies.

Age-related macular degeneration (AMD) is the major cause of severe visual loss in the United States for individuals over the age of 60. AMD occurs in either an atrophic or less commonly an exudative form. The atrophic form of AMD is also called "dry AMD," and the exudative form of AMD is also called "wet AMD."

In exudative AMD, blood vessels grow from the choriocapillaris through defects in Bruch's membrane, and in some cases the underlying retinal pigment epithelium. Organization of serous or hemorrhagic exudates escaping from these vessels results in fibrovascular scarring of the macular region with attendant degeneration of the neuroretina, detachment and tears of the retinal pigment epithelium, vitreous hemorrhage and permanent loss of central vision. This process is responsible for more than 80% of cases of significant visual loss in subjects with AMD. Current or forthcoming treatments include laser photocoagulation, photodynamic therapy, treatment with VEGF antibody fragments, treatment with pegylated aptamers, and treatment with certain small molecule agents.

Several studies have recently described the use of laser photocoagulation in the treatment of initial or recurrent neovascular lesions associated with AMD (Macular Photocoagulation Study Groups (1991) in *Arch. Ophthal.* 109:1220; *Arch. Ophthal.* 109:1232; *Arch. Ophthal.* 109:1242). Unfortunately, AMD subjects with subfoveal lesions subjected to laser treatment experienced a rather precipitous reduction in visual acuity (mean 3 lines) at 3 months follow-up. Moreover, at two years post-treatment treated eyes had only marginally better visual acuity than their untreated counterparts (means of 20/320 and 20/400, respectively). Another drawback of the procedure is that vision after surgery is immediately worse.

Photodynamic therapy (PDT) is a form of phototherapy, a term encompassing all treatments that use light to produce a beneficial reaction in a subject. Optimally, PDT destroys unwanted tissue while sparing normal tissue. Typically, a compound called a photosensitizer is administered to the subject. Usually, the photosensitizer alone has little or no effect on the subject. When light, often from a laser, is directed onto a tissue containing the photosensitizer, the photosensitizer is activated and begins destroying targeted tissue. Because the light provided to the subject is confined to a particularly targeted area, PDT can be used to selectively target abnormal tissue, thus sparing surrounding healthy tissue. PDT is currently used to treat retinal diseases such as AMD. PDT is currently the mainstay of treatment for subfoveal choroidal neovascularization in subjects with AMD (Photodynamic Therapy for Subfoveal Choroidal Neovascularization in Age Related Macular Degeneration with Verteporfin (TAP Study Group) *Arch Opthalmol.* 1999 117:1329-1345.

Choroidal neovascularization (CNV) has proven to be recalcitrant to treatment in most cases. Conventional laser treatment can ablate CNV and help to preserve vision in selected cases not involving the center of the retina, but this is limited to only about 10% of the cases. Unfortunately, even with successful conventional laser photocoagulation, the neovascularization recurs in about 50-70% of eyes (50% over 3 years and >60% at 5 years). (Macular Photocoagulation Study Group, *Arch. Opthalmol.* 204:694-701 (1986)). In addition, many subjects who develop CNV are not good candidates for laser therapy because the CNV is too large for laser treatment, or the location cannot be determined so that the physician cannot accurately aim the laser. Photodynamic therapy, although utilized in up to 50% of new cases of subfoveal CNV has only marginal benefits over natural history, and generally delays progression of visual loss rather than improving vision which is already decreased secondary to the subfoveal lesion. PDT is neither preventive or definitive. Several PDT treatments are usually required per subject and additionally, certain subtypes of CNV fare less well than others.

Thus, there remains a long-felt need for methods, compositions, and formulations that may be used to optimally prevent or significantly inhibit choroidal neovascularization and to prevent and treat wet AMD.

In addition to AMD, choroidal neovascularization is associated with such retinal disorders as presumed ocular histoplasmosis syndrome, myopic degeneration, angioid streaks, idiopathic central serous chorioretinopathy, inflammatory conditions of the retina and or choroid, and ocular trauma. Angiogenic damage associated with neovascularization occurs in a wide range of disorders including diabetic retinopathy, venous occlusions, sickle cell retinopathy, retinopathy of prematurity, retinal detachment, ocular ischemia and trauma.

Uveitis is another retinal disorder that has proven difficult to treat using existing therapies. Uveitis is a general term that indicates an inflammation of any component of the uveal tract. The uveal tract of the eye consists of the iris, ciliary body, and choroid. Inflammation of the overlying retina, called retinitis, or of the optic nerve, called optic neuritis, may occur with or without accompanying uveitis.

Uveitis is most commonly classified anatomically as anterior, intermediate, posterior, or diffuse. Posterior uveitis signifies any of a number of forms of retinitis, choroiditis, or optic neuritis. Diffuse uveitis implies inflammation involving all parts of the eye, including anterior, intermediate, and posterior structures.

The symptoms and signs of uveitis may be subtle, and vary considerably depending on the site and severity of the inflammation. Regarding posterior uveitis, the most common symptoms include the presence of floaters and decreased vision. Cells in the vitreous humor, white or yellow-white lesions in the retina and/or underlying choroid, exudative retinal detachments, retinal vasculitis, and optic nerve edema may also be present in a subject suffering from posterior uveitis.

Ocular complications of uveitis may produce profound and irreversible loss of vision, especially when unrecognized or treated improperly. The most frequent complications of posterior uveitis include retinal detachment; neovascularization of the retina, optic nerve, or iris; and cystoid macular edema.

Macular edema (ME) can occur if the swelling, leaking, and hard exudates noted in background diabetic retinopathy (BDR) occur within the macula, the central 5% of the retina most critical to vision. Background diabetic retinopathy (BDR) typically consists of retinal microaneurisms that result from changes in the retinal microcirculation. These microaneurisms are usually the earliest visible change in retinopathy seen on exam with an opthalmoscope as scattered red spots in the retina where tiny, weakened blood vessels have ballooned out. The ocular findings in background diabetic retinopathy progress to cotton wool spots, intraretinal hemorrhages, leakage of fluid from the retinal capillaries, and retinal exudates. The increased vascular permeability is also related to elevated levels of local growth factors such as vascular endothelial growth factor. The macula is rich in cones, the nerve endings that detect color and upon which daytime vision depends. When increased retinal capillary permeability effects the macula, blurring occurs in the middle or just to the side of the central visual field, rather like looking through cellophane. Visual loss may progress over a period of months, and can be very annoying because of the inability to focus clearly. ME is a common cause of severe visual impairment.

There have been many attempts to treat CNV and its related diseases and conditions, as well as other conditions such as macular edema and chronic inflammation, with pharmaceuticals. For example, use of rapamycin to inhibit CNV and wet AMD has been described in U.S. application Ser. No. 10/665,203, which is incorporated herein by reference in its entirety. The use of rapamycin to treat inflammatory diseases of the eye has been described in U.S. Pat. No. 5,387,589, titled Method of Treating Ocular Inflammation, with inventor Prassad Kulkarni, assigned to University of Louisville Research Foundation, the contents of which is incorporated herein in its entirety.

Particularly for chronic diseases, including those described herein, there is a great need for long acting methods for delivering therapeutic agents to the eye, such as to the posterior segment to treat CNV in such diseases as AMD, macular edema, proliferative retinopathies, and chronic inflammation. Formulations with extended delivery of therapeutic agent are more comfortable and convenient for a subject, due to a diminished frequency of ocular injections of the therapeutic agent.

Direct delivery of therapeutic agents to the eye rather than systemic administration may be advantageous because the therapeutic agent concentration at the site of action is increased relative to the therapeutic agent concentration in a subject's circulatory system. Additionally, therapeutic agents may have undesirable side effects when delivered systemically to treat posterior segment disease. Thus, localized drug delivery may promote efficacy while decreasing side effects and systemic toxicity.

SUMMARY

The methods, compositions, and liquid formulations described herein allow delivery of a therapeutic agent to a subject, including but not limited to a human subject or to the eye(s) of a subject. Described herein are methods, compositions, and liquid formulations for delivering a variety of therapeutic agents for extended periods of time which can be used for the treatment, prevention, inhibition, delaying onset of, or causing regression of a number of conditions or diseases, including but not limited to diseases or conditions of the eye. The liquid formulations include, without limitation, solutions, suspensions, and in situ gelling formulations.

Described herein are methods, compositions and liquid formulations for administering to a human subject an amount of rapamycin effective to treat, prevent, inhibit, delay onset of, or cause regression of wet AMD, dry AMD, or macular edema (including, without limitation, diabetic macular edema).

As described in further detail in the Detailed Description section, the methods, compositions and liquid formulations may also be used for delivery to a subject, including but not limited to a human subject or to the eye(s) of a human subject of therapeutically effective amounts of rapamycin for the treatment, prevention, inhibition, delaying of the onset of, or causing the regression of wet AMD, dry AMD, or macular edema. In some variations, the methods, compositions, and liquid formulations are used to treat wet AMD. In some variations, the methods, compositions, and liquid formulations are used to prevent wet AMD. In some variations, the methods, compositions, and liquid formulations are used to treat dry AMD. In some variations, the methods, compositions, and liquid formulations are used to prevent dry AMD. In some variations, the methods and formulations described herein are used to prevent the transition from dry AMD to wet AMD. In some variations, the methods and formulations described herein are used to treat macular edema (including, without limitation, diabetic macular edema). In some variations, the methods and formulations described herein are used to prevent macular edema. The methods, compositions and liquid formulations may also be used for delivery to a subject, including but not limited to a human subject or to the eye of a subject of therapeutically effective amounts of rapamycin for the treatment, prevention, inhibition, delaying of the onset of, or causing the regression of CNV. In some variations, the methods, compositions and liquid formulations are used to treat CNV. The methods, compositions and liquid formulations may also be used for delivery to a subject, including but not limited to a human subject or to the eye of a subject of therapeutically effective amounts of rapamycin for the treatment, prevention, inhibition, delaying of the onset of, or causing the regression of angiogenesis in the eye. In some variations, the methods, compositions and liquid formulations are used to treat angiogenesis. Other diseases and conditions that may be treated, prevented, inhibited, have onset delayed, or caused to regress using rapamycin are described in the Diseases and Conditions section of the Detailed Description.

As described in further detail in the Detailed Description, the methods, compositions and liquid formulations may also be used for delivery to a subject, including but not limited to a human subject or to the eye of a subject of therapeutically effective amounts of therapeutic agents other than rapamycin for the treatment, prevention, inhibition, delaying of the onset of, or causing the regression of wet AMD or macular edema. In some variations, the methods, compositions and liquid formulations are used to treat wet AMD. In some variations, the methods, compositions and liquid formulations are used to treat macular edema. Therapeutic agents that may be used are described in detail in the Therapeutic Agents section. Such therapeutic agents include but are not limited to immunophilin binding compounds. Immunophilin binding compounds that may be used include but are not limited to the limus family of compounds described further in the Therapeutic Agents section herein, including rapamycin, SDZ-RAD, tacrolimus, everolimus, pimecrolimus, CCI-779, AP23841, ABT-578, derivatives, analogs, prodrugs, salts and esters thereof. In certain variations, the therapeutic agent is dasatinib, or a salt or ester thereof. The methods, compositions and liquid formulations may also be used for delivery to a subject, including but not limited to a human subject or to the eye of a subject of therapeutically effective amounts of therapeutic agents for the treatment, prevention, inhibition, delaying of the onset of, or causing the regression of CNV. In some variations, the methods, compositions and liquid formulations are used to treat CNV. The methods, compositions and liquid formulations may also be used for delivery to a subject, including but not limited to a human subject or to the eye of a subject of therapeutically effective amounts of therapeutic agents for the treatment, prevention, inhibition, delaying of the onset of, or causing the regression of angiogenesis in the eye. In some variations, the methods, compositions and liquid formulations are used to treat angiogenesis. Other diseases and conditions that may be treated, prevented, inhibited, have onset delayed, or caused to regress using therapeutic agents other than rapamycin are described in the Diseases and Conditions section of the Detailed Description.

One liquid formulation described herein comprises a solution that includes a therapeutic agent dissolved in a solvent. Generally, any solvent that has the desired effect may be used in which the therapeutic agent dissolves and which can be administered to a subject, including but not limited to a human subject or an eye of a subject. Generally, any concentration of therapeutic agent that has the desired effect can be used. The formulation in some variations is a solution which is unsaturated, a saturated or a supersaturated solution. The solvent may be a pure solvent or may be a mixture of liquid solvent components. In some variations the solution formed is an in situ gelling formulation. Solvents and types of solutions that may be used are well known to those versed in such drug delivery technologies.

The liquid formulations described herein may form a non-dispersed mass when placed into a rabbit eye, including but not limited to the vitreous of a rabbit eye. In some variations the non-dispersed mass comprises a gel. In some variations, the liquid formulation comprises a therapeutic agent and a plurality of polymers. In some variations one of the polymers is polyacrylate or polymethacrylate. In some variations one of the polymers is polyvinylpyrrolidone.

The liquid formulations described herein may form a non-dispersed mass when placed into a human eye, including, but not limited to, injected into the vitreous of a human eye or injected between the sclera and conjunctiva of a human eye.

In some variations, the non-dispersed mass comprises a depot. In some variations, the non-dispersed mass consists of a depot.

For liquid formulations which form a non-dispersed mass, the non-dispersed mass may generally be any geometry or shape. The non-dispersed mass-forming liquid formulations may, for instance, appear as a compact spherical mass when placed in the vitreous. In some variations the liquid formulations described herein form a milky or whitish colored semi-contiguous or semi-solid non-dispersed mass relative to the medium in which it is placed, when placed in the vitreous.

The liquid formulations may generally be administered in any volume that has the desired effect. In one method a volume of a liquid formulation is administered to the vitreous and the liquid formulation is less than one half the volume of the vitreous.

Routes of administration that may be used to administer a liquid formulation include but are not limited to (1) placement of the liquid formulation by placement, including by injection, into a medium, including but not limited to an aqueous medium in the body, including but not limited to intraocular or periocular injection; or (2) oral administration of the liquid formulation. The liquid formulation may be administered systemically, including but not limited to the following delivery routes: rectal, vaginal, infusion, intramuscular, intraperitoneal, intraarterial, intrathecal, intrabronchial, intracisternal, cutaneous, subcutaneous, intradermal, transdermal, intravenous, intracervical, intraabdominal, intracranial, intrapulmonary, intrathoracic, intratracheal, nasal, buccal, sublingual, oral, parenteral, or nebulised or aerosolized using aerosol propellants. In some variations, the liquid formulation is administered subconjunctivally. In some variations, the liquid formulation is administered intravitreally. In some alternative variations, the liquid formulation is administered by subtenon injection. In some variations, the liquid formulation is administered topically.

The liquid formulations described herein may be delivered to any medium of a subject, including but not limited to a human subject, including but not limited to an aqueous medium of a subject.

One liquid formulation described herein comprises a liquid formulation of rapamycin or other therapeutic agent. The liquid formulations may comprise a solution, suspension, an in situ gelling formulation, or an emulsion. The droplets in the emulsion may generally be of any size, including but not limited to up to about 5,000 nm.

In some formulations described herein, the liquid formulations may comprise a therapeutic agent including but not limited to rapamycin, and one or more solubilizing agents or solvents. In some variations, the solubilizing agent or solvent is glycerin, DMSO, DMA, N-methylpyrrolidone, ethanol, benzyl alcohol, isopropyl alcohol, polyethylene glycol of various molecular weights, including but not limited to PEG 300 and PEG 400, or propylene glycol or a mixture of one or more thereof.

In some formulations described herein, the liquid formulation includes hyaluronic acid.

The liquid formulations described herein may deliver a therapeutic agent or agents for an extended period of time. One nonlimiting example of such an extended release delivery system is a liquid formulation that delivers a therapeutic agent or agents to a subject, including but not limited to a human subject or to the eye of a subject in an amount sufficient to maintain an amount effective to treat, prevent, inhibit, delay onset of, or cause regression of a disease or condition in a subject for an extended period of time. In some variations, the liquid formulation is used to treat a disease or condition in a subject, including but not limited to a human subject. In some variations, the liquid formulation delivers the therapeutic agent for at least about one, about two, about three, about six, about nine, or about twelve months.

The liquid formulations described herein may deliver rapamycin or other therapeutic agents for an extended period of time. One nonlimiting example of such an extended release delivery system is a liquid formulation that delivers rapamycin to a subject, including but not limited to a human subject or to the eye of a subject in an amount sufficient to maintain an amount effective to treat, prevent, inhibit, delay onset of, or cause regression of wet age-related macular degeneration for an extended period of time. In some variations, the liquid formulation is used to treat wet age-related macular degeneration for an extended period of time. In some variations, the liquid formulation is used to prevent wet age-related macular degeneration for an extended period of time. In some variations, the liquid formulation is used to prevent transition of dry AMD to wet AMD for an extended period of time. In one nonlimiting example, the liquid formulation delivers the rapamycin to the vitreous, sclera, retina, choroid, macula, or other tissues of a subject, including but not limited to a human subject in an amount sufficient to treat, prevent, inhibit, delay onset of, or cause regression of wet age-related macular degeneration for at least about three, about six, about nine, or about twelve months. In some variations, the level of rapamycin is sufficient to treat AMD. In some variations, the level of rapamycin is sufficient to prevent onset of wet AMD.

Other extended periods of release are described in the Detailed Description.

Described herein is a liquid formulation comprising a therapeutic agent, wherein the liquid formulation contains less than about 90% (w/w) of any material having a hygroscopicity that is about equal to or greater than that of polyethylene glycol (PEG 400). In some variations, the liquid formulation contains less than about 80%, less than about 70%, less than about 60%, less than about 50%, or less than about 40% of the material having a hygroscopicity that is about equal to or greater than that of polyethylene glycol (PEG 400). In some variations, the material is a solvent. Methods are provided for treating an ocular disease in a human subject comprising administering to the subject by intraocular or periocular delivery a volume of the liquid formulation containing an amount of the therapeutic agent effective to treat an ocular disease in the subject. Methods for preventing an ocular disease in a human subject comprising administering to the subject by intraocular or periocular delivery a volume of the liquid formulation containing an effective amount of the therapeutic agent are also provided.

Also described herein is a method for treating an ocular disease in a human subject comprising administering to the human subject a volume of a liquid formulation by placement between the sclera and conjunctiva of the subject, wherein the liquid formulation comprises: (a) an effective amount of a therapeutic agent; and (b) a material selected from the group consisting of polyethylene glycol 400 (PEG 400), a material about as hygroscopic as PEG 400, or a material more hygroscopic than PEG 400. In certain variations, the liquid formulation comprises less than about 80 µl, less than about 60 µl, or less than about 40 µl of such a material. In some variations, the material is a solvent.

Also described herein is a method for preventing an ocular disease in a human subject comprising administering to the human subject a volume of a liquid formulation by placement between the sclera and conjunctiva of the subject, wherein the liquid formulation comprises: (a) an effective amount of a therapeutic agent; and (b) a material selected from the group consisting of polyethylene glycol 400 (PEG 400), a material about as hygroscopic as PEG 400, or a material more hygroscopic than PEG 400. In certain variations, the liquid formulation comprises less than about 80 µl, less than about 60 µl, or less than about 40 µl of such a material. In some variations, the material is a solvent.

Further described herein is a method for treating an ocular disease in a human subject, the method comprising administering periocularly to the subject a volume of formulation comprising an amount of therapeutic agent and a volume of an excipient, wherein the amount of therapeutic agent is sufficient to treat the ocular disease, and wherein the excipient is PEG 400 or a material having a hygroscopicity about equal to or less than PEG 400 and the volume of the excipient is less than or equal to about 100 µl. In some variations, the volume of the excipient is less than or equal to about 80 µl, less than or equal to about 60 µl, or less than or equal to about 40 µl. In some variations, the volume of formulation is administered between the sclera and conjunctiva of the subject. In some variations, the ocular disease is dry age-related macular degeneration, wet age-related macular degeneration or macular edema. In some variations, the excipient is a solvent. In some variations, the excipient is PEG 400.

Further described herein is a method for preventing an ocular disease in a human subject, the method comprising administering periocularly to the subject a volume of formulation comprising an amount of therapeutic agent and a volume of an excipient, P wherein the amount of therapeutic agent is sufficient to prevent the ocular disease, and wherein the excipient is PEG 400 or a material having a hygroscopicity about equal to or less than PEG 400 and the volume of the excipient is less than or equal to about 100 µl. In some variations, the volume of the excipient is less than or equal to about 80 µl, less than or equal to about 60 µl, or less than or equal to about 40 µl. In some variations, the volume of formulation is administered between the sclera and conjunctiva of the subject. In some variations, the ocular disease is dry age-related macular degeneration, wet age-related macular degeneration or macular edema. In some variations, the excipient is a solvent. In some variations, the excipient is PEG 400.

Described herein is also a liquid formulation comprising a therapeutic agent, water, and one or more excipients selected from the group consisting of N-methylpyrrolidone (NMP), dimethyl acetamine (DMA), dimethyl sulfoxide (DMSO), propylene glycol (PG), polyethylene glycol 600 (PEG 600), and polyethylene glycol 400. In some variations, the excipient is a solvent. In certain variations, the formulation comprises at least about five percent (w/w) of water. In some variations, in addition to the therapeutic agent and water, the formulation comprises both (i) an excipient selected from the group consisting of N-methyl pyrrolidone (NMP), dimethyl acetamine (DMA), and dimethyl sulfoxide (DMSO); and (ii)

an excipient selected from the group consisting of propylene glycol (PG), polyethylene glycol 600 (PEG 600), and polyethylene glycol 400. The formulation, may, in some variations, comprise up to about five percent (w/w) therapeutic agent. In some variations, the formulation further comprises ethanol. Methods are provided for treating an ocular disease in a human subject comprising administering to the subject by intraocular or periocular delivery a volume of the liquid formulation containing an amount of the therapeutic agent effective to treat the ocular disease in the subject. Methods for preventing an ocular disease in a human subject comprising administering to the subject by intraocular or periocular delivery a volume of the liquid formulation containing an effective amount of the therapeutic agent are also provided.

In some variations of each of the aforementioned methods and/or formulations, as well as other methods and/or formulations described herein, the liquid formulation, when injected between the sclera and conjunctiva of a rabbit eye delivers an amount of the therapeutic agent sufficient to achieve, for a period of time of at least 30 days following administration of the liquid formulation, one or both of the following: (a) an average concentration of therapeutic agent in the vitreous of the rabbit eye equivalent to a rapamycin concentration of at least 0.01 ng/ml; or (b) an average concentration of therapeutic agent in the retina choroid tissues of the rabbit eye equivalent to a rapamycin concentration of at least 0.001 ng/mg.

In some variations of each of the aforementioned methods and/or formulations, as well as other methods and/or formulations described herein, the liquid formulation, when injected into the vitreous of a rabbit eye delivers an amount of the therapeutic agent sufficient to achieve, for a period of time of at least 30 days following administration of the liquid formulation, one or both of the following: (a) an average concentration of therapeutic agent in the retina choroid tissues of the rabbit eye equivalent to a rapamycin concentration of at least 0.01 ng/mg; or (b) an average concentration of therapeutic agent in the vitreous of the rabbit eye equivalent to a rapamycin concentration of at least 1000 ng/ml.

Described herein is a liquid formulation comprising a therapeutic agent, wherein the liquid formulation when administered by subtenon injection to a rabbit eye delivers an amount of the therapeutic agent sufficient to achieve, for a period of time of at least 30 days following administration of the liquid formulation, one or both of the following: (a) an average concentration of therapeutic agent in the vitreous of the rabbit eye equivalent to a rapamycin concentration of at least 0.01 ng/ml; or (b) an average concentration of therapeutic agent in the retina choroid tissues of the rabbit eye equivalent to a rapamycin concentration of at least 0.001 ng/mg. Methods are provided for treating an ocular disease in a human subject comprising administering to the subject by intraocular or periocular delivery a volume of the liquid formulation containing an amount of the therapeutic agent effective to treat an ocular disease in the subject. Methods for preventing an ocular disease in a human subject comprising administering to the subject by intraocular or periocular delivery a volume of the liquid formulation containing an effective amount of the therapeutic agent are also provided.

In some variations of each of the aforementioned methods and/or formulations, as well as other methods and/or formulations described herein, the liquid formulation is administered by intravitreal, subconjunctival, topical, or subtenon administration.

Also described herein is a liquid formulation comprising: (a) a therapeutic agent; (b) a first component selected from the group consisting of ethoxlyated p-tert-octylphenol formaldehyde polymer, polyoxyl 35 castor oil, propylene glycol monolaurate, propylene glycol dicaprylate/dicaprate, and macrogol 15 hydroxystearate; and (c) a second component comprising monoglycerides and/or diglycerides of caprylate. In some variations, the formulation further comprises ethanol and/or water. Methods for treating an ocular disease in a human subject, comprising administering to the subject by topical delivery a volume of the liquid formulation containing an amount of the therapeutic agent effective to treat the ocular disease in the human subject are also provided. Methods for preventing an ocular disease in a human subject, comprising administering to the subject by topical delivery a volume of the liquid formulation containing an amount of the therapeutic agent effective to prevent the ocular disease in the human subject are also provided. In some variations, the liquid formulation is applied topically to an eye of the subject about once or less a day, about once or less every 5 days, or about once or less every 10 days. In some variations, the methods are methods of treatment. In some variations, the disease to be treated is a disease of the retina. In some variations, the disease is AMD or macular edema.

In addition, described herein is a method for treating an ocular disease in a human subject, the method comprising administering to the human subject by topical delivery a volume of a liquid formulation containing an amount of a therapeutic agent effective to treat the ocular disease in the human subject, wherein the liquid formulation when topically applied to a rabbit eye in a volume of 80 µl a day for six days delivers an amount of the therapeutic agent sufficient to achieve: (a) an average concentration of the therapeutic agent in the cornea of the rabbit eye at day 6 equivalent to a rapamycin concentration of at least 0.01 ng/mg; or (b) an average concentration of therapeutic agent in the retina choroid tissues of the rabbit eye at day 6 equivalent to a rapamycin concentration of at least 0.001 ng/mg. In some variations, the liquid formulation is applied topically to an eye of the subject about once or less a day, about once or less every 5 days, or about once or less every 10 days. In some variations, the method is a method of treatment. In some variations, the liquid formulation consists essentially of about 2% (w/w) rapamycin, about 4% (w/w) ethanol, and about 94% (w/w) PEG 400.

In addition, described herein is a method for preventing an ocular disease in a human subject, the method comprising administering to the human subject by topical delivery a volume of a liquid formulation containing an amount of a therapeutic agent effective to prevent the ocular disease in the human subject, wherein the liquid formulation when topically applied to a rabbit eye in a volume of 80 µl a day for six days delivers an amount of the therapeutic agent sufficient to achieve: (a) an average concentration of the therapeutic agent in the cornea of the rabbit eye at day 6 equivalent to a rapamycin concentration of at least 0.01 ng/mg; or (b) an average concentration of therapeutic agent in the retina choroid tissues of the rabbit eye at day 6 equivalent to a rapamycin concentration of at least 0.001 ng/mg. In some variations, the liquid formulation is applied topically to an eye of the subject about once or less a day, about once or less every 5 days, or about once or less every 10 days. In some variations, the method is a method of treatment. In some variations, the liquid formulation consists essentially of about 2% (w/w) rapamycin, about 4% (w/w) ethanol, and about 94% (w/w) PEG 400.

Further described herein is a liquid formulation comprising a therapeutic agent and water, wherein the liquid formulation when applied to a rabbit eye in a volume of 80 µl a day for six days delivers an amount of the therapeutic agent sufficient to achieve: (a) an average concentration of the therapeutic agent in the cornea of the rabbit eye at day 6 equivalent to a rapamycin concentration of at least 0.01 ng/mg; or (b) an average concentration of therapeutic agent in the retina choroid tissues of the rabbit eye at day 6 equivalent to a rapamycin concentration of at least 0.001 ng/mg. Methods for treating an ocular disease in a human subject, comprising administering to the subject by topical delivery a volume of the liquid formulation containing an amount of the therapeutic agent effective to treat the ocular disease in the human subject are also provided. Methods for preventing an ocular disease in a human subject, comprising administering to the subject by topical delivery a volume of the liquid formulation containing an amount of the therapeutic agent effective to prevent the ocular disease in the human subject are also provided. In some variations, the liquid formulation is applied topically to an eye of the subject about once or less a day, about once or less every 5 days, or about once or less every 10 days. In some variations, the methods are methods of treatment.

Also described herein is a method for treating an ocular disease in a human subject, the method comprising topically administering to the subject a liquid formulation comprising a therapeutic agent, wherein the liquid formulation, when a volume of about 40 µl is applied topically to a rabbit eye, delivers an amount of the therapeutic agent sufficient to achieve: (a) an average concentration of the therapeutic agent in the cornea of the rabbit eye equivalent to an average rapamycin concentration of at least 0.01 ng/mg for at least about ten days after administration of the liquid formulation; or (b) an average concentration of therapeutic agent in the retina choroid tissues of the rabbit eye equivalent to an average rapamycin concentration of at least 0.001 ng/mg for at least about ten days after administration of the liquid formulation. In some variations, the liquid formulation further comprises polyethylene glycol. In some variations, the liquid formulation is applied topically to an eye of the subject about once or less a day, about once or less every 5 days, or about once or less every 10 days. In some variations, the methods are methods of treatment. In some variations, the liquid formulation consists essentially of about 2% (w/w) rapamycin, about 4% (w/w) ethanol, and about 94% (w/w) PEG 400.

Also described herein is a method for preventing an ocular disease in a human subject, the method comprising topically administering to the subject a liquid formulation comprising a therapeutic agent, wherein the liquid formulation, when a volume of about 40 µl is applied topically to a rabbit eye, delivers an amount of the therapeutic agent sufficient to achieve: (a) an average concentration of the therapeutic agent in the cornea of the rabbit eye equivalent to an average rapamycin concentration of at least 0.01 ng/mg for at least about ten days after administration of the liquid formulation; or (b) an average concentration of therapeutic agent in the retina choroid tissues of the rabbit eye equivalent to an average rapamycin concentration of at least 0.001 ng/mg for at least about ten days after administration of the liquid formulation. In some variations, the liquid formulation further comprises polyethylene glycol. In some variations, the liquid formulation is applied topically to an eye of the subject about once or less a day, about once or less every 5 days, or about once or less every 10 days. In some variations, the methods are methods of treatment. In some variations, the liquid formulation consists essentially of about 2% (w/w) rapamycin, about 4% (w/w) ethanol, and about 94% (w/w) PEG 400.

In some variations of each of the aforementioned methods and/or formulations, as well as other methods and/or formulations described herein, the therapeutic agent is rapamycin, SDZ-RAD, tacrolimus, everolimus, pimecrolimus, CCI-779, AP23841, or ABT-578, or is a derivative, analog, prodrug, salt or ester of rapamycin, SDZ-RAD, tacrolimus, everolimus, pimecrolimus, CCI-779, AP23841, or ABT-578.

In some variations of each of the aforementioned methods and/or formulations, as well as other methods and/or formulations described herein, the therapeutic agent is rapamycin, or a pharmaceutically acceptable salt or ester thereof.

In some variations of each of the aforementioned methods and/or formulations, as well as other methods and/or formulations described herein, the therapeutic agent is dasatinib, or a pharmaceutically acceptable salt or ester thereof.

Further described herein is a liquid formulation consisting essentially of about 2% (w/w) rapamycin, about 4% (w/w) ethanol, and about 94% (w/w) PEG 400, as well as a liquid formulation consisting essentially of about 4% (w/w) rapamycin, about 4% (w/w) ethanol, and about 92% (w/w) PEG 400. A liquid formulation consisting essentially of about 1.47% (w/w) rapamycin, about 2.93% (w/w) ethanol, about 26.6% (w/w) normal saline, and about 69% (w/w) PEG 400 is also provided. Methods of using such formulations in the treatment of an ocular disease are also provided. Methods of using such formulations in the prevention of an ocular disease are also provided. In some variations, the methods comprise administering the liquid formulation by intravitreal, subconjunctival, topical, or subtenon administration.

A method for treating an ocular disease in a human subject, the method comprising administering to the human subject a volume of a liquid formulation by placement in the vitreous of the subject, wherein the volume of the liquid formulation comprises between about 20 µg and about 750 µg of rapamycin, or a pharmaceutically acceptable salt or ester thereof, is also provided herein. In some variations, the volume of the liquid formulation is about 30 µl or less, about 20 µl or less, or about 10 µl or less. In certain variations, the volume of the liquid formulation contains between about 30 µg and about 200 µg of rapamycin. The liquid formulation, in some variations, consists essentially of about 2% (w/w) rapamycin, about 4% (w/w) ethanol, and about 94% (w/w) PEG 400.

A method for preventing an ocular disease in a human subject, the method comprising administering to the human subject a volume of a liquid formulation by placement in the vitreous of the subject, wherein the volume of the liquid formulation comprises between about 20 µg and about 750 µg of rapamycin, or a pharmaceutically acceptable salt or ester thereof, is also provided herein. In some variations, the volume of the liquid formulation is about 30 µl or less, about 20 µl or less, or about 10 µl or less. In certain variations, the volume of the liquid formulation contains between about 30 µg and about 200 µg of rapamycin. The liquid formulation, in some variations, consists essentially of about 2% (w/w) rapamycin, about 4% (w/w) ethanol, and about 94% (w/w) PEG 400.

In addition, described herein is a method for treating an ocular disease in a human subject, the method comprising administering to the human subject a volume of a liquid formulation by placement between the sclera and conjunctiva of the subject, wherein the liquid formulation comprises between about 50 µg and about 3 mg of rapamycin, or a pharmaceutically acceptable salt or ester thereof. In some variations, the volume of the liquid formulation is about 150 µl or less, about 100 µl or less, or about 40 µl or less. In some variations, the volume of the liquid formulation comprises between about 300 µg and about 1000 µg of rapamycin. In some variations, the amount of rapamycin in the volume of the formulation that is administered is about 400 µg to about 900 µg, about 500 µg to about 800 µg, or about 600 µg to about 700 µg of rapamycin. In some embodiments, the volume of the formulation that is administered to the subject is about 10 µl to about 50 µl, about 15 µl to about 45 µl, about 20 µl to about 40 µl, or about 25 µl to about 35 µl. In some variations, the volume of the formulation that is administered comprises about 440 µg of rapamycin in about 20 µl. In some variations, the volume of the formulation that is administered comprises about 660 µg of rapamycin in about 30 µl. In some variations, the volume of the formulation that is administered comprises about 880 µg of rapamycin in about 40 µl. The liquid formulation, in some variations, consists essentially of about 2% (w/w) rapamycin, about 4% (w/w) ethanol, and about 94% (w/w) PEG 400. In some variations, the liquid formulation comprises less than about 40 µl of polyethylene glycol. In some alternative variations, the formulation comprises less than about 80 µl of polyethylene glycol (including, without limitation, PEG 400), less than about 60 µl of polyethylene glycol, or less than about 40 µl of polyethylene glycol. In some variations, the formulation comprises no polyethylene glycol.

In addition, described herein is a method for preventing an ocular disease in a human subject, the method comprising administering to the human subject a volume of a liquid formulation by placement between the sclera and conjunctiva of the subject, wherein the liquid formulation comprises between about 50 µg and about 3 mg of rapamycin, or a pharmaceutically acceptable salt or ester thereof. In some variations, the volume of the liquid formulation is about 150 µl or less, about 100 µl or less, or about 40 µl or less. In some variations, the volume of the liquid formulation comprises between about 300 µg and about 1000 µg of rapamycin. In some variations, the amount of rapamycin in the volume of the formulation that is administered is about 400 µg to about 900 µg, about 500 µg to about 800 µg, or about 600 µg to about 700 µg of rapamycin. In some embodiments, the volume of the formulation that is administered to the subject is about 10 µl to about 50 µl, about 15 µl to about 45 µl, about 20 µl to about 40 µl, or about 25 µl to about 35 µl. In some variations, the volume of the formulation that is administered comprises about 440 µg of rapamycin in about 20 µl. In some variations, the volume of the formulation that is administered comprises about 660 µg of rapamycin in about 30 µl. In some variations, the volume of the formulation that is administered comprises about 880 µg of rapamycin in about 40 µl. The liquid formulation, in some variations, consists essentially of about 2% (w/w) rapamycin, about 4% (w/w) ethanol, and about 94% (w/w) PEG 400. In some variations, the liquid formulation comprises less than about 40 µl of polyethylene glycol. In some alternative variations, the formulation comprises less than about 80 µl of polyethylene glycol (including, without limitation, PEG 400), less than about 60 µl of polyethylene glycol, or less than about 40 µl of polyethylene glycol. In some variations, the formulation comprises no polyethylene glycol.

Further described herein is a method for treating an ocular disease in a human subject, the method comprising administering by subtenon injection to the subject a volume of a liquid formulation comprising between about 50 µg and about 3 mg of a therapeutic agent. In some variations, the therapeutic agent is selected from the group consisting of rapamycin or dasatinib, or a pharmaceutically acceptable salt or ester of either agent. In some variations, the liquid formulation comprises greater than about 30 µl, greater than about 60 µl, or greater than about 80 µl of polyethylene glycol 400 (PEG 400), or a material having a hygroscopicity equal to or greater than PEG 400. In some variations, the material is a solvent. In some variations, the liquid formulation consists essentially of about 2% (w/w) rapamycin, about 4% (w/w) ethanol, and about 94% (w/w) PEG 400.

Further described herein is a method for preventing an ocular disease in a human subject, the method comprising administering by subtenon injection to the subject a volume of a liquid formulation comprising between about 50 µg and about 3 mg of a therapeutic agent. In some variations, the therapeutic agent is selected from the group consisting of rapamycin or dasatinib, or a pharmaceutically acceptable salt or ester of either agent. In some variations, the liquid formulation comprises greater than about 30 µl, greater than about 60 µl, or greater than about 80 µl of polyethylene glycol 400 (PEG 400), or a material having a hygroscopicity equal to or greater than PEG 400. In some variations, the material is a solvent. In some variations, the liquid formulation consists essentially of about 2% (w/w) rapamycin, about 4% (w/w) ethanol, and about 94% (w/w) PEG 400.

Also described herein is a method for treating an ocular disease in a human subject comprising: (a) administering to the human subject a volume of a first liquid formulation by placement in the vitreous of the subject, wherein the first liquid formulation comprises a first therapeutic agent; and (b) administering to the human subject a volume of a second liquid formulation by placement between the sclera and conjunctiva of the subject, wherein the second liquid formulation comprises rapamycin, or a pharmaceutically acceptable salt or ester thereof; wherein an amount of the first and second therapeutic agents effective to treat the ocular disease is administered to the subject. In some variations, step (b) is subsequent to step (a). In some variations, the first therapeutic agent is rapamycin, or a pharmaceutically acceptable salt or ester thereof. The first liquid formulation may be identical to the second liquid formulation or different from the second liquid formulation. In some variations, the first therapeutic agent is selected from the group consisting of ranibizumab and bevacizumab. In some variations, both step (a) and step (b) are performed during a single administration session (including, but not limited to, a single visit with a physician or other medical professional or other single session in which the administrations are performed by the subject, a physician, or other medical professional). In some variations, the first and/or second liquid formulation is a liquid formulation consisting essentially of about 2% (w/w) rapamycin, about 4% (w/w) ethanol, and about 94% (w/w) PEG 400.

Also described herein is a method for preventing an ocular disease in a human subject comprising: (a) administering to the human subject a volume of a first liquid formulation by placement in the vitreous of the subject, wherein the first liquid formulation comprises a first therapeutic agent; and (b) administering to the human subject a volume of a second liquid formulation by placement between the sclera and conjunctiva of the subject, wherein the second liquid formulation comprises rapamycin, or a pharmaceutically acceptable salt or ester thereof; wherein an amount of the first and second therapeutic agents effective to prevent the ocular disease is administered to the subject. In some variations, step (b) is subsequent to step (a). In some variations, the first therapeutic agent is rapamycin, or a pharmaceutically acceptable salt or ester thereof. The first liquid formulation may be identical to the second liquid formulation or different from the second liquid formulation. In some variations, the first therapeutic agent is selected from the group consisting of ranibizumab and bevacizumab. In some variations, both step (a) and step (b) are performed during a single administration session (including, but not limited to, a single visit with a physician or other medical professional or other single session in which the administrations are performed by the subject, a physician, or other medical professional). In some variations, the first and/or second liquid formulation is a liquid formulation consisting essentially of about 2% (w/w) rapamycin, about 4% (w/w) ethanol, and about 94% (w/w) PEG 400.

In some variations of each of the aforementioned methods and/or formulations, as well as other methods and/or formulations described herein, the liquid formulation comprises between about 0.001% (w/w) to about 10% (w/w) therapeutic agent. In some variations, the formulation comprises between about 0.001% (w/w) to about 1.0% (w/w) the therapeutic agent. In some variations, the formulation comprises between about 0.01% (w/w) to about 0.1% (w/w) therapeutic agent. In further variations, the formulation comprises between about 0.1% (w/w) to about 6% (w/w) therapeutic agent. In some variations, the formulation contains up to about 5% rapamycin.

Further described herein is a method for treating an ocular disease in a human subject, the method comprising: (a) administering to the human subject a volume of a first therapeutic agent; and (b) administering to the human subject by intraocular or periocular delivery a volume of a liquid formulation (including, without limitation, by intravitreal, subconjunctival, topical, or subtenon administration), wherein the liquid formulation consists essentially of about 2% (w/w) rapamycin, about 4% (w/w) ethanol, and about 94% (w/w) PEG 400, and wherein an amount of the first therapeutic agent and rapamycin effective to treat the ocular disease is administered to the subject. In some variations, the first therapeutic agent is selected from the group consisting of ranibizumab, bevacizumab, and verteporfin. The first therapeutic agent may, in some variations, be administered to the subject by intraocular delivery.

Further described herein is a method for preventing an ocular disease in a human subject, the method comprising: (a) administering to the human subject a volume of a first therapeutic agent; and (b) administering to the human subject by intraocular or periocular delivery a volume of a liquid formulation (including, without limitation, by intravitreal, subconjunctival, topical, or subtenon administration), wherein the liquid formulation consists essentially of about 2% (w/w) rapamycin, about 4% (w/w) ethanol, and about 94% (w/w) PEG 400, and wherein an amount of the first therapeutic agent and rapamycin effective to prevent the ocular disease is administered to the subject. In some variations, the first therapeutic agent is selected from the group consisting of ranibizumab, bevacizumab, and verteporfin. The first therapeutic agent may, in some variations, be administered to the subject by intraocular delivery.

Also described herein is a method for treating an ocular disease in a human subject, the method comprising: (a) diluting a liquid formulation consisting essentially of about 2% (w/w) rapamycin, about 4% (w/w) ethanol, and about 94% (w/w) PEG 400 with aqueous liquid to produce a diluted liquid formulation; and (b) administering to the human subject by intraocular or periocular delivery a volume of the diluted liquid formulation, wherein an amount of rapamycin effective to treat the ocular disease is administered to the subject. In some variations, the formulation is a clear solution. In some variations, the dilution is up to about a 1.4-fold dilution. In some variations, the liquid formulation is diluted up to about 1.2 fold. In some variations, the aqueous liquid is saline. In some variations, the diluted liquid formulation is administered by intravitreal, subconjunctival, topical, or subtenon administration.

Also described herein is a method for preventing an ocular disease in a human subject, the method comprising: (a) diluting a liquid formulation consisting essentially of about 2% (w/w) rapamycin, about 4% (w/w) ethanol, and about 94% (w/w) PEG 400 with aqueous liquid to produce a diluted liquid formulation; and (b) administering to the human subject by intraocular or periocular delivery a volume of the diluted liquid formulation, wherein an amount of rapamycin effective to prevent the ocular disease is administered to the subject. In some variations, the formulation is a clear solution. In some variations, the dilution is up to about a 1.4-fold dilution. In some variations, the liquid formulation is diluted up to about 1.2 fold. In some variations, the aqueous liquid is saline. In some variations, the diluted liquid formulation is administered by intravitreal, subconjunctival, topical, or subtenon administration.

In some variations of each of the aforementioned methods and/or formulations, as well as other methods and/or formulations described herein, the ocular disease is a disease of the retina. In some variations, the ocular disease is wet age-related macular degeneration. In some variations, the ocular disease is dry age-related macular degeneration. In some variations, the ocular disease is macular edema (including, without limitation, diabetic macular edema).

The present invention provides methods of treating macular edema in a human subject by repeated administration of rapamycin, the method comprising: administering two or more doses of a rapamycin formulation to an eye of the human subject, wherein the period between consecutive doses is at least 8 weeks, and the cumulative amount of rapamycin in the two or more doses is effective to treat macular edema in the human subject for an extended period of at least 16 weeks. In some embodiments, the period between consecutive doses is at least 12 weeks, and the cumulative amount of rapamycin in the two or more doses is effective to treat macular edema in the human subject for an extended period of at least 24 weeks. In some embodiments, the two or more doses of the rapamycin formulation are administered by subconjunctival placement. In some embodiments, the rapamycin formulation is a solution of rapamycin dissolved in a solvent system. In some embodiments, the solvent system comprises polyethylene glycol. In some embodiments, the solvent system further comprises ethanol. In some embodiments, the rapamycin formulation comprises a suspension of particles of rapamycin.

The present invention also provides methods of treating diabetic macular edema in a human subject by repeated administration of rapamycin, the method comprising: administering two or more doses of a rapamycin formulation to an eye of the human subject, wherein the rapamycin formulation is a solution comprising rapamycin and polyethylene glycol, the rapamycin formulation is administered by placement of each dose between a sclera and a conjunctiva of the eye of the subject, the period between consecutive doses is at least 8 weeks, and wherein the cumulative amount of rapamycin in the two or more doses is effective to treat diabetic macular edema in the human subject for an extended period of at least 16 weeks. In some embodiments, the period between consecutive doses is at least 12 weeks and the cumulative amount of rapamycin in the two or more doses is effective to treat diabetic macular edema in the human subject for an extended period of at least 24 weeks. In some embodiments, the rapamycin formulation further comprises ethanol. In a subset of these embodiments, each dose of the rapamycin formulation contains between about 200 µg and about 2,000 µg of rapamycin, while in some preferred embodiments, each dose of the rapamycin formulation contains about 220 µg, about 440 µg, about 880 µg, or about 1320 µg of rapamycin. In some preferred embodiments, the rapamycin formulation comprises: (a) about 2% (w/w) rapamycin, about 4% (w/w) ethanol, and about 94% (w/w) polyethylene glycol 400 (PEG 400); (b) about 4% (w/w) rapamycin, about 4% (w/w) ethanol, and about 92% (w/w) polyethylene glycol 400 (PEG 400); or (c) about 1% (w/w) rapamycin, about 4% (w/w) ethanol, and about 95% (w/w) polyethylene glycol 400 (PEG 400). In some embodiments, the rapamycin formulation consists essentially of: (a) about 2% (w/w) rapamycin, about 4% (w/w) ethanol, and about 94% (w/w) polyethylene glycol 400 (PEG 400); (b) about 4% (w/w) rapamycin, about 4% (w/w) ethanol, and about 92% (w/w) polyethylene glycol 400 (PEG 400); or (c) about 1% (w/w) rapamycin, about 4% (w/w) ethanol, and about 95% (w/w) polyethylene glycol 400 (PEG 400).

Moreover, the present invention provides liquid formulations comprising: (a) between about 0.001% (w/w) to about 1.0% (w/w) rapamycin; (b) a first component selected from the group consisting of ethoxlyated p-tert-octylphenol formaldehyde polymer, and polyoxyl 35 castor oil; and (c) a second component selected from the group consisting of glycerol caprylate, and glycerol caprate. In some embodiments, the liquid formulations further comprise (d) a third component selected from the group consisting of ethanol, phosphatidylcholine in propylene glycol/ethanol carrier, and propylene glycol monolaurate. In some embodiments, the liquid formulations further comprise water. In some preferred embodiments, the liquid formulations comprise between about 0.01% (w/w) to about 0.1% (w/w) rapamycin. In addition the present invention provides methods for treating an ocular disease in a human subject, the method comprising administering to the human subject by topical delivery to an eye a volume of the liquid formulation containing an amount of rapamycin effective to treat the ocular disease in the human subject. In some embodiments, the ocular disease is selected from the group consisting of age-related macular degeneration, macular edema, dry eye, allergic conjunctivitis, scleritis, uveitis, and corneal transplant. In a subset of these embodiments, the age-related macular degeneration is wet age-related macular degeneration. In some embodiments, the period of time between consecutive administrations of the liquid formulation is at least about 1 day, while in others the period of time between consecutive administrations of the liquid formulation is at least about 7 days or at least about 14 days.

In addition the present invention provides methods for treating an ocular disease in a human subject, the method comprising administering to the human subject by topical delivery a volume of a liquid formulation containing an amount of a therapeutic agent effective to prevent or treat the ocular disease in the human subject, wherein the liquid formulation when topically applied to a rabbit eye in a volume of at least about 40 µl a day for six days delivers an amount of the therapeutic agent sufficient to achieve one or more of: (a) an average concentration of the therapeutic agent in the cornea of the rabbit eye at day 8 equivalent to a rapamycin concentration of at least 0.01 ng/g; (b) an average concentration of the therapeutic agent in the retina choroid of the rabbit eye at day 8 equivalent to a rapamycin concentration of at least 0.01 ng/g; and (c) an average concentration of the therapeutic agent in the sclera of the rabbit eye at day 8 equivalent to a rapamycin concentration of at least 0.01 ng/g. In some embodiments, the liquid formulation when topically applied achieves one or more of (a), (b), and (c), and further achieves: (d) an average concentration of therapeutic agent in the blood of the rabbit at day 8 less than the average concentration of the therapeutic agent in one or more of the cornea, the retina choroid and the sclera. In some embodiments, the therapeutic agent is rapamycin, or a pharmaceutically acceptable salt or ester thereof, while in others the therapeutic agent is dasatinib, or a pharmaceutically acceptable salt or ester thereof. In some preferred embodiments, the ocular disease is selected from the group consisting of age-related macular degeneration, macular edema, dry eye, allergic conjunctivitis, scleritis, uveitis, and corneal transplant. In some preferred embodiments, the age-related macular degeneration is wet age-related macular degeneration. In some embodiments, the period of time between consecutive administrations of the liquid formulation is at least about 1 day, while in others the period of time between consecutive administrations of the liquid formulation is at least about 7 days, or at least about 14 days. In a subset of these embodiments, the liquid formulation consists essentially of (a) about 2% (w/w) rapamycin, about 4% (w/w) ethanol, and about 94% (w/w) PEG 400; (b) about 4% (w/w) rapamycin, about 4% (w/w) ethanol, and about 92% (w/w) PEG 400; or (c) about 1% (w/w) rapamycin, about 4% (w/w) ethanol, and about 95% (w/w) PEG 400.

The present invention also provides methods for treating an ocular disease in a human subject, the method comprising topically administering to the subject a liquid formulation comprising a therapeutic agent, wherein the liquid formulation, when a volume of at least about 40 µL is applied topically to a rabbit eye, delivers an amount of the therapeutic agent sufficient to achieve one or more of: (a) an average concentration of the therapeutic agent in the cornea of the rabbit eye equivalent to an average rapamycin concentration of at least 0.01 ng/g for at least about seven days after administration of the liquid formulation; (b) an average concentration of therapeutic agent in the retina choroid of the rabbit eye equivalent to an average rapamycin concentration of at least 0.01 ng/g for at least about seven days after administration of the liquid formulation; and (c) an average concentration of the therapeutic agent in the sclera of the rabbit eye equivalent to an average rapamycin concentration of at least 0.01 ng/g for at least about seven days after administration of the liquid formulation. In some embodiments, the liquid formulation when topically applied achieves one or more of (a), (b), and (c), and further achieves: (d) an average concentration of therapeutic agent in the blood of the rabbit at day seven less than the average concentration of the therapeutic agent in one or more of the cornea, the retina choroid and the sclera. In some embodiments, the therapeutic agent is rapamycin or a pharmaceutically acceptable salt or ester thereof. In some preferred embodiments, the ocular disease is selected from the group consisting of age-related macular degeneration, macular edema, dry eye, allergic conjunctivitis, scleritis, uveitis, and corneal transplant. In some particularly preferred embodiments, the age-related macular degeneration is wet age-related macular degeneration. In some embodiments, the liquid formulation comprises between about 0.001% (w/w) to about 10% (w/w) rapamycin. In a subset of these embodiments, the liquid formulation comprises between about 0.01% (w/w) to about 1.0% (w/w) rapamycin. In some embodiments, the liquid formulation further comprises polyethylene glycol. In some preferred embodiments, the period of time between consecutive administrations of the liquid formulation is at least about 1 day, while in others the period of time between consecutive administrations of the liquid formulation is at least about 7 days or at least about 14 days.

Moreover the present invention provides methods of administering by a periocular route a liquid formulation to an eye of a subject without causing chemosis of the eye, comprising: administering less than 40 µl of the liquid formulation between a sclera and a conjunctiva of the eye of the subject, wherein the liquid formulation comprises a therapeutic agent and a solvent, and wherein the liquid formulation has a hygroscopicity that is 80% or greater than the hygroscopicity of a liquid formulation consisting essentially of about 2% (w/w) rapamycin, about 4% (w/w) ethanol, and about 94% (w/w) polyethylene glycol 400 (PEG 400). As used herein, the term "chemosis" refers to edema of the conjunctiva of the eye, forming a swelling partly or fully around the iris of the eye. In some embodiments, the therapeutic agent is rapamycin. In some embodiments, the solvent comprises polyethylene glycol, while in a subset of these embodiments, the polyethylene glycol is polyethylene glycol 400 (PEG 400). In some embodiments, about 1 μg to about 5,000 μg rapamycin is administered to the subject. In a subset of these embodiments, about 220 μg, about 440 μg, about 880 μg, or about 1320 μg rapamycin is administered to the subject. Also provided are methods for treating an ocular disease in a human subject, wherein the ocular disease is selected from the group consisting of age-related macular degeneration, macular edema and dry eye, the method comprising administering to the subject, an amount of the therapeutic agent effective to treat the ocular disease in the human subject. In some embodiments, the ocular disease is age-related macular degeneration, which in preferred embodiments is wet age-related macular degeneration. In some embodiments, the ocular disease is macular edema, which in preferred embodiments is diabetic macular edema. In other preferred embodiments, the ocular disease is dry eye.

In addition, the present invention provides methods for treating an ocular disease in a human subject, the method comprising: (a) administering to the human subject a volume of a first formulation by intraocular or periocular delivery to the subject, wherein the volume of the first formulation comprises an amount of ranibizumab or bevacizumab; and (b) administering to the human subject a volume of a second formulation by periocular delivery to the subject, wherein the volume of the second formulation comprises an amount of rapamycin, or a pharmaceutically acceptable salt or ester thereof; wherein the amount of ranibizumab or bevacizumab and the amount of rapamycin or a pharmaceutically acceptable salt or ester thereof, together are effective to treat the ocular disease when administered to the human subject. In some embodiments, the first formulation is administered by intravitreal placement, and the second formulation is administered by subconjunctival placement. In some embodiments, step (a) is coincident with step (b) (same doctor visit or occurring on the same day). In other embodiments, step (b) is subsequent to step (a) (different doctor visits or occurring on different days). In some embodiments, the ocular disease is age-related macular degeneration, or macular edema. In some preferred embodiments, the age-related macular degeneration is wet age-related macular degeneration, or the macular edema is diabetic macular edema. In some embodiments, the volume of the first formulation contains between about 100 μg and about 500 μg of ranibizumab or bevacizumab. In some embodiments, the volume of the second formulation contains between about 200 μg and about 2000 μg of rapamycin.

The present invention also provides methods for treating an ocular disease in a human subject, the method comprising: (a) administering to the human subject by intraocular or periocular delivery a volume of a first formulation comprising an amount of a first therapeutic agent; and (b) administering to the human subject by periocular delivery a volume of a second formulation comprising an amount of rapamycin, wherein the second formulation consists essentially of rapamycin, ethanol, and polyethylene glycol 400 (PEG 400), and wherein the amount of the first therapeutic agent and the amount of rapamycin together are effective to treat the ocular disease when administered to the human subject. In some embodiments, wherein the first therapeutic agent is selected from the group consisting of ranibizumab, bevacizumab, and verteporfin. In some embodiments, the second formulation consists essentially of: (a) about 2% (w/w) rapamycin, about 4% (w/w) ethanol, and about 94% (w/w) PEG 400; (b) about 4% (w/w) rapamycin, about 4% (w/w) ethanol, and about 92% (w/w) PEG 400; or (c) about 1% (w/w) rapamycin, about 4% (w/w) ethanol, and about 95% (w/w) PEG 400. In some embodiments, the administration of the first formulation is by a route selected from the group consisting of intravitreal, subconjunctival, and subtenon placement, and the administration of the second formulation is by subconjunctival or subtenon placement. In some embodiments, step (a) is coincident with step (b) (same doctor visit or occurring on the same day). In other embodiments, step (b) is subsequent to step (a) (different doctor visits or occurring on different days). In some embodiments, the ocular disease is age-related macular degeneration or macular edema. In some preferred embodiments, the age-related macular degeneration is wet age-related macular degeneration. In some embodiments, the ocular disease is macular edema. In some preferred embodiments, the macular edema is diabetic macular edema.

Furthermore the present invention provides methods for treating wet age-related macular degeneration or diabetic macular edema in a human subject, the method comprising: (a) administering to the human subject a volume of a first formulation by intravitreal placement, wherein the volume of the first formulation comprises an amount of ranibizumab or bevacizumab; and (b) administering to the human subject a volume of a second formulation by subconjunctival placement, wherein the volume of the second formulation comprises an amount of rapamycin, or a pharmaceutically acceptable salt or ester thereof; wherein the amount of ranibizumab or bevacizumab and the amount of rapamycin or a pharmaceutically acceptable salt or ester thereof, together are effective to treat wet age-related macular degeneration or diabetic macular edema when administered to the human subject. In some embodiments, step (a) is coincident with step (b) (same doctor visit or occurring on the same day). In other embodiments, step (b) is subsequent to step (a) (different doctor visits or occurring on different days). In some embodiments, the volume of the first formulation contains between about 100 μg and about 500 μg of ranibizumab or bevacizumab. In some embodiments, the volume of the second formulation contains between about 200 μg and about 2000 μg of rapamycin. In some embodiments, the second formulation consists essentially of (a) about 2% (w/w) rapamycin, about 4% (w/w) ethanol, and about 94% (w/w) polyethylene glycol 400 (PEG 400); (b) about 4% (w/w) rapamycin, about 4% (w/w) ethanol, and about 92% (w/w) polyethylene glycol 400 (PEG 400); or (c) about 1% (w/w) rapamycin, about 4% (w/w) ethanol, and about 95% (w/w) polyethylene glycol 400 (PEG 400).

Moreover the present invention provides liquid formulations comprising (i) a solvent selected from the group consisting of N-methylpyrrolidone (NMP), dimethyl acetamine (DMA), and dimethyl sulfoxide (DMSO); (ii) poly(D,L-lactide-co-glycolide) (PLGA), or a solvent selected from the group consisting of propylene glycol (PG), polyethylene glycol 600 (PEG 600), polyethylene glycol 400 (PEG 400); and (iii) a therapeutic agent. In some embodiments, the liquid formulation when: (a) injected between the sclera and conjunctiva of a rabbit eye delivers an amount of the therapeutic agent sufficient to achieve, for a period of time of at least 30 days following administration of the liquid formulation, one or both of the following: (i) an average concentration of therapeutic agent in the vitreous of the rabbit eye equivalent to a rapamycin concentration of at least 0.01 ng/ml; or (ii) an average concentration of therapeutic agent in the retina choroid tissues of the rabbit eye equivalent to a rapamycin concentration of at least 0.01 ng/g; (b) administered by subtenon injection to a rabbit eye delivers an amount of the therapeutic agent sufficient to achieve, for a period of time of at least 30 days following administration of the liquid formulation, one or both of the following: (i) an average concentration of therapeutic agent in the vitreous of the rabbit eye equivalent to a rapamycin concentration of at least 0.01 ng/ml; or (ii) an average concentration of therapeutic agent in the retina choroid tissues of the rabbit eye equivalent to a rapamycin concentration of at least 0.01 ng/g; or (c) injected into the vitreous of a rabbit eye delivers an amount of the therapeutic agent sufficient to achieve, for a period of time of at least 30 days following administration of the liquid formulation, one or both of the following: (a) an average concentration of therapeutic agent in the vitreous of the rabbit eye equivalent to a rapamycin concentration of at least 100 ng/ml; or (b) an average concentration of therapeutic agent in the retina choroid tissues of the rabbit eye equivalent to a rapamycin concentration of at least 0.01 ng/g. In some embodiments, the liquid formulation comprises between about 0.001% (w/w) to about 10% (w/w) of the therapeutic agent. In some embodiments, the therapeutic agent is rapamycin, or a pharmaceutically acceptable salt or ester thereof. In other embodiments, the therapeutic agent is dasatinib, or a pharmaceutically acceptable salt or ester thereof. In some embodiments, the liquid formulation consists essentially of (a) about 4% (w/w) rapamycin, about 4% (w/w) ethanol, and about 92% (w/w) PEG 400; or (b) about 1.0-4.0% (w/w) rapamycin, about 2.0-4.0% (w/w) ethanol, about 20-30% (w/w) normal saline, and quantity of PEG 400 sufficient for the total formula weight percentage to equal 100%. The present invention further provides methods for treating an ocular disease in a human subject, the method comprising administering to the human subject by intraocular or periocular delivery a volume of the liquid formulation containing an amount of the therapeutic agent effective to treat the ocular disease in the human subject. In some embodiments, the ocular disease is age-related macular degeneration, macular edema, or dry eye. In some preferred embodiments, the age-related macular degeneration is wet age-related macular degeneration. In other preferred embodiments, the macular edema is diabetic macular edema. In still further preferred embodiments, the ocular disease is dry eye. In some particularly preferred embodiments, the administration of the liquid formulation is by intravitreal, subconjunctival, or subtenon administration.

Additionally, the present invention provides methods for treating an ocular disease in a human subject, the method comprising administering to the human subject a volume of a liquid formulation comprising between about 200 µg and about 5000 µg of rapamycin, or a pharmaceutically acceptable salt or ester thereof. In some embodiments, the volume of the liquid formulation contains between about 200 µg and about 1500 µg of rapamycin. In some embodiments, when administration is by placement of the liquid formulation in the vitreous of the subject, the volume of the liquid formulation is about 100 µl or less, preferably about 25 µl or less. In some embodiments, when administration is by placement of the liquid formulation between the sclera and conjunctiva of the subject, the volume of the liquid formulation is about 1,000 µl or less, preferably about 50 µl or less. In some embodiments, when administration is by placement of the liquid formulation in the subtenon space of the subject, the volume of the liquid formulation is about 5,000 µl or less, preferably about 100 µl or less. In some embodiments, the ocular disease is age-related macular degeneration, macular edema, or dry eye. In some preferred embodiments, the age-related macular degeneration is wet age-related macular degeneration. In some preferred embodiments, the macular edema is diabetic macular edema.

The present invention also provides a solid formulation comprising rapamycin, polyvinylpyrrolidone, a phospholipid solution, and polyethylene glycol. In some embodiments, the formulation further comprises one or both of gamma tocopherol and ascorbyl palmatate. In further embodiments, methods are provided for treating an ocular disease in a human subject, the method comprising administering to an eye of the human subject by topical or periocular delivery a volume of the solid formulation containing an amount of rapamycin effective to treat the ocular disease in the human subject. In some embodiments, the ocular disease is age-related macular degeneration, macular edema, or dry eye. In some embodiments, the amount of rapamycin in the solid formulation is effective to treat the ocular disease in the human subject for an extended period of at least two weeks, at least four weeks, at least six weeks or at least eight weeks.

DETAILED DESCRIPTION

Figure 1:
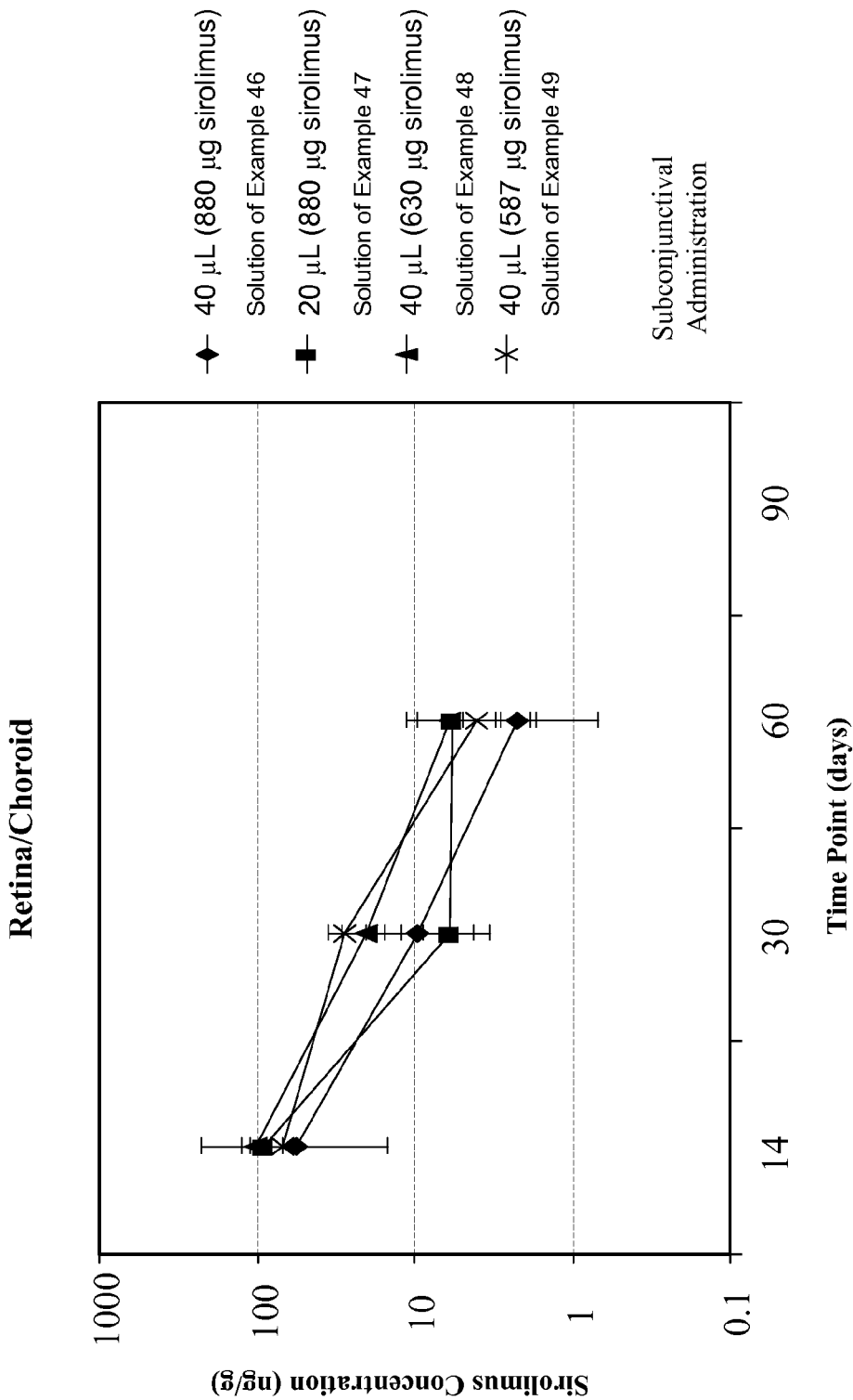
FIG. 1 depicts the average level of rapamycin in the retina choroid tissue (ng/g) of rabbit eyes at 14, 30, 60, and 90 days after subconjunctival injection of 40 µl of 2% solution of rapamycin in ethanol and PEG 400, 1.47% solution of rapamycin in ethanol and PEG 400, or 1.38% solution of rapamycin in ethanol and PEG 400 or 20 µl of a 4% solution of rapamycin in ethanol and PEG 400.

Described herein are compositions, liquid formulations and methods relating to delivery of therapeutic agents to a subject, including but not limited to a human subject or to the eye of a subject. These compositions, liquid formulations, and methods may be used for the treatment, prevention, inhibition, delaying onset of, or causing regression of diseases and conditions of the eye including but not limited to diseases or conditions of the posterior segment, including but not limited to choroidal neovascularization; macular degeneration; age-related macular degeneration, including wet AMD and dry AMD; retinal angiogenesis; chronic uveitis; and other retinoproliferative conditions. In some variations, the compositions, liquid formulations, and methods are used for the treatment of the aforementioned diseases or conditions of the eye.

Herein are described (1) the therapeutic agents that may be delivered to a subject, including but not limited to a human subject or an eye of a subject using the compositions, liquid formulations, and methods described herein, (2) the diseases and conditions that may be treated, prevented, inhibited, onset delayed, or regression caused by delivery of the therapeutic agents, (3) liquid formulations that may be used to deliver the therapeutic agents, (4) routes of administration for delivery of the liquid formulations, (5) extended delivery of therapeutic agents including but not limited to rapamycin, and (6) description of the treatment of CNV and wet AMD by delivery of rapamycin to a subject, including but not limited to a human subject or to the eye of a subject for an extended period of time using the described compositions and liquid formulations.

The term "about," as used herein, refers to the level of accuracy that is obtained when the methods described herein, such as the methods in the examples, are used. However, by "about" a certain amount of a component of a formulation is meant 90-110% of the amount stated.

Therapeutic Agents

Most generally, any compounds and compositions currently known or yet to be discovered that are useful in treating, preventing, inhibiting, delaying the onset of, or causing the regression of the diseases and conditions described herein may be therapeutic agents for use in the compositions, liquid formulations, and methods described herein.

Therapeutic agents that may be used include compounds that act by binding members of the immunophilin family of cellular proteins. Such compounds are known as "immunophilin binding compounds." Immunophilin binding compounds include but are not limited to the "limus" family of compounds. Examples of limus compounds that may be used include but are not limited to cyclophilins and FK506-binding proteins (FKBPs), including sirolimus (rapamycin) and its water soluble analog SDZ-RAD (Novartis), TAFA-93 (Isotechnika), tacrolimus, everolimus, RAD-001 (Novartis), pimecrolimus, temsirolimus, CCI-779 (Wyeth), AP23841 (Ariad), AP23573 (Ariad), and ABT-578 (Abbott Laboratories). Limus compound analogs and derivatives that may be used include but are not limited to the compounds described in U.S. Pat. Nos. 5,527,907; 6,376,517; and 6,329,386 and U.S. patent application Ser. No. 09/950,307, each of which is incorporated herein by reference in their entirety. Therapeutic agents also include analogs, prodrugs, salts and esters of limus compounds.

The terms rapamycin, rapa, and sirolimus are used interchangeably herein.

Other rapamycin derivatives that may be used include, without limitation, 7-epi-rapamycin, 7-thiomethyl-rapamycin, 7-epi-trimethoxyphenyl-rapamycin, 7-epi-thiomethyl-rapamycin, 7-demethoxy-rapamycin, 32-demethoxy-rapamycin, 2-desmethyl-rapamycin, mono- and di-ester derivatives of rapamycin, 27-oximes of rapamycin; 42-oxo analog of rapamycin; bicyclic rapamycins; rapamycin dimers; silyl ethers of rapamycin; rapamycin arylsulfonates and sulfamates, mono-esters and di-esters at positions 31 and 42, 30-demethoxy rapamycin, and other derivatives described in Vezina et al., "Rapamycin (AY-22,989), A New Antifungal Antibiotic. I. Taxonomy Of The Producing Streptomycete And Isolation Of The Active Principle" J. Antibiot. (Tokyo) 28:721-726 (1975); Sehgal et al., "Rapamycin (AY-22,989), A New Antifungal Antibiotic. II. Fermentation, Isolation And Characterization" J. Antibiot. (Tokyo) 28:727-732 (1975); Sehgal et al., "Demethoxyrapamycin (AY-24,668), A New Antifungal Antibiotic" J. Antibiot. (Tokyo) 36:351-354 (1983); and Paiva et al., "Incorporation Of Acetate, Propionate, And Methionine Into Rapamycin By *Streptomycetes hygroscopicus*" J Nat Prod 54:167-177 (1991), WO 92/05179, EP 467606, Caufield et al., "Hydrogenated Rapamycin Derivatives" U.S. Pat. No. 5,023,262; Kao et al., "Bicyclic Rapamycins" U.S. Pat. No. 5,120,725; Kao et al., "Rapamycin Dimers" U.S. Pat. No. 5,120,727; Failli et al., "Silyl Ethers Of Rapamycin" U.S. Pat. No. 5,120,842; Failli et al., "Rapamycin 42-Sulfonates And 42-(N-carboalkoxy) Sulfamates Useful As Immunosuppressive Agents" U.S. Pat. No. 5,177,203; Nicolaou et al., "Total Synthesis Of Rapamycin" J. Am. Chem. Soc. 115: 4419-4420 (1993); Romo et al, "Total Synthesis Of (−) Rapamycin Using An Evans-Tishchenko Fragment Coupling" J. Am. Chem. Soc. 115:7906-7907 (1993); and Hayward et al, "Total Synthesis Of Rapamycin Via A Novel Titanium-Mediated Aldol Macrocyclization Reaction" J. Am. Chem. Soc., 115:9345-9346 (1993), each of which is incorporated herein by reference in its entirety.

The limus family of compounds may be used in the compositions, liquid formulations and methods for the treatment, prevention, inhibition, delaying the onset of, or causing the regression of angiogenesis-mediated diseases and conditions of the eye, including choroidal neovascularization. The limus family of compounds may be used to prevent, treat, inhibit, delay the onset of, or cause regression of AMD, including wet AMD. Rapamycin and rapamycin derivatives and analogs may be used to prevent, treat, inhibit, delay the onset of, or cause regression of angiogenesis-mediated diseases and conditions of the eye, including choroidal neovascularization. Rapamycin may be used to prevent, treat, inhibit, delay the onset of, or cause regression of AMD, including wet AMD. In some variations, a member of the limus family of compounds or rapamycin is used to treat wet AMD or angiogenesis-mediated diseases and conditions of the eye including choroidal neovascularization.

Other therapeutic agents that may be used include those disclosed in the following patents and publications, the contents of each of which is incorporated herein by reference in its entirety: PCT publication WO 2004/027027, published Apr. 1, 2004, titled Method of inhibiting choroidal neovascularization, assigned to Trustees of the University of Pennsylvania; U.S. Pat. No. 5,387,589, issued Feb. 7, 1995, titled Method of Treating Ocular Inflammation, with inventor Prassad Kulkarni, assigned to University of Louisville Research Foundation; U.S. Pat. No. 6,376,517, issued Apr. 23, 2003, titled Pipecolic acid derivatives for vision and memory disorders, assigned to GPI NIL Holdings, Inc; PCT publication WO 2004/028477, published Apr. 8, 2004, titled Method subretinal administration of therapeutics including steroids: method for localizing pharmadynamic action at the choroid and retina; and related methods for treatment and or prevention of retinal diseases, assigned to Innorx, Inc; U.S. Pat. No. 6,416,777, issued Jul. 9, 2002, titled Ophthalmic drug delivery device, assigned to Alcon Universal Ltd; U.S. Pat. No. 6,713,081, issued Mar. 30, 2004, titled Ocular therapeutic agent delivery device and methods for making and using such devices, assigned to Department of Health and Human Services; U.S. Pat. No. 5,100,899, issued Mar. 31, 1992, titled Methods of inhibiting transplant rejection in mammals using rapamycin and derivatives and prodrugs thereof.

Other therapeutic agents that may be used include pyrrolidine, dithiocarbamate (NFκB inhibitor); squalamine; TPN 470 analogue and fumagillin; PKC (protein kinase C) inhibitors; Tie-1 and Tie-2 kinase inhibitors; inhibitors of VEGF receptor kinase; proteosome inhibitors such as Velcade™ (bortezomib, for injection; ranibuzumab (Lucentis™) and other antibodies directed to the same target; pegaptanib (Macugen™); vitronectin receptor antagonists, such as cyclic peptide antagonists of vitronectin receptor-type integrins; α-v/β-3 integrin antagonists; α-v/β-1 integrin antagonists; thiazolidinediones such as rosiglitazone or troglitazone; interferon, including γ-interferon or interferon targeted to CNV by use of dextran and metal coordination; pigment epithelium derived factor (PEDF); endostatin; angiostatin; tumistatin; canstatin; anecortave acetate; acetonide; triamcinolone; tetrathiomolybdate; RNA silencing or RNA interference (RNAi) of angiogenic factors, including ribozymes that target VEGF expression; Accutane™ (13-cis retinoic acid); ACE inhibitors, including but not limited to quinopril, captopril, and perindozril; inhibitors of mTOR (mammalian target of rapamycin); 3-aminothalidomide; pentoxifylline; 2-methoxyestradiol; colchicines; AMG-1470; cyclooxygenase inhibitors such as nepafenac, rofecoxib, diclofenac, rofecoxib, NS398, celecoxib, vioxx, and (E)-2-alkyl-2(4-methanesulfonylphenyl)-1-phenylethene; t-RNA synthase modulator; metalloprotease 13 inhibitor; acetylcholinesterase inhibitor; potassium channel blockers; endorepellin; purine analog of 6-thioguanine; cyclic peroxide ANO-2; (recombinant) arginine deiminase; epigallocatechin-3-gallate; cerivastatin; analogues of suramin; VEGF trap molecules; apoptosis inhibiting agents; Visudyne™, snET2 and other photo sensitizers, which may be used with photodynamic therapy (PDT); inhibitors of hepatocyte growth factor (antibodies to the growth factor or its receptors, small molecular inhibitors of the c-met tyrosine kinase, truncated versions of HGF e.g. NK4).

In some variations the therapeutic agent is a BCR/ABL inhibitor. In some variations the therapeutic agent is a Src family tyrosine kinases inhibitor. In some variations the therapeutic agent is a dual BCR/ABL and Src family tyrosine kinases inhibitor. In some variations the dual BCR/ABL and Src family tyrosine kinases inhibitor is dasatinib (i.e., BMS-354825, Sprycel®, or N-(2-chloro-6-methylphenyl)-2-[[6-[4-(2-hydroxyethyl)-1-piperazinyl]-2-methyl-4-pyrimidinyl]amino]-5-thiazole carboxamide monohydrate) or a derivative, an analog, or a pharmaceutically acceptable salt or ester thereof. In some variations, dasatinib is used to treat, prevent, inhibit, or delay onset or regression of an ocular disease. In some variations, the ocular disease is age-related macular degeneration (AMD). In some variations, the AMD is wet AMD. In some variations, the AMD is dry AMD. In some variations, the ocular disease is macular edema including without limitation diabetic macular edema.

Other therapeutic agents that may be used include anti-inflammatory agents, including, but not limited to nonsteroidal anti-inflammatory agents and steroidal anti-inflammatory agents. In some variations, active agents that may be used in the liquid formulations are ace-inhibitors, endogenous cytokines, agents that influence basement membrane, agents that influence the growth of endothelial cells, adrenergic agonists or blockers, cholinergic agonists or blockers, aldose reductase inhibitors, analgesics, anesthetics, antiallergics, antibacterials, antihypertensives, pressors, antiprotozoal agents, antiviral agents, antifungal agents, anti-infective agents, antitumor agents, antimetabolites, and antiangiogenic agents.

Steroidal therapeutic agents that may be used include but are not limited to 21-acetoxypregnenolone, alclometasone, algestone, amcinonide, beclomethasone, betamethasone, budesonide, chloroprednisone, clobetasol, clobetasone, clocortolone, cloprednol, corticosterone, cortisone, cortivazol, deflazacort, desonide, desoximetasone, dexamethasone, diflorasone, diflucortolone, difluprednate, enoxolone, fluazacort, flucloronide, flumethasone, flunisolide, fluocinolone acetonide, fluocinonide, fluocortin butyl, fluocortolone, fluorometholone, fluperolone acetate, fluprednidene acetate, fluprednisolone, flurandrenolide, fluticasone propionate, formocortal, halcinonide, halobetasol propionate, halometasone, halopredone acetate, hydrocortamate, hydrocortisone, loteprednol etabonate, mazipredone, medrysone, meprednisone, methylprednisolone, mometasone furoate, paramethasone, prednicarbate, prednisolone, prednisolone 25-diethylamino-acetate, prednisolone sodium phosphate, prednisone, prednival, prednylidene, rimexolone, tixocortol, triamcinolone, triamcinolone acetonide, triamcinolone benetonide, triamcinolone hexacetonide, and any of their derivatives.

In some variations, cortisone, dexamethasone, fluocinolone, hydrocortisone, methylprednisolone, prednisolone, prednisone, and triamcinolone, or their derivatives, may be used. The liquid formulation may include a combination of two or more steroidal therapeutic agents.

In one nonlimiting example, the steroidal therapeutic agents may constitute from about 0.05% to about 50% by weight of the liquid formulation. In another nonlimiting example, the steroid constitutes from about 0.05% to about 10%, between about 10% to about 20%; between about 30% to about 40%; or between about 40% to about 50% by weight of the liquid formulation.

Other nonlimiting examples of therapeutic agents that may be used include but are not limited to anaesthetics, analgesics, cell transport/mobility impending agents such as colchicines, vincristine, cytochalasin B and related compounds; carbonic anhydrase inhibitors such as acetazolamide, methazolamide, dichlorphenamide, diamox and neuroprotectants such as nimodipine and related compounds; antibiotics such as tetracycline, chlortetracycline, bacitracin, neomycin, polymyxin, gramicidin, cephalexin, oxytetracycline, chloramphenicol, rifampicin, ciprofloxacin, aminosides, gentamycin, erythromycin and penicillin, quinolone, ceftazidime, vancomycine imipeneme; antifungals such as amphotericin B, fluconazole, ketoconazole and miconazole; antibacterials such as sulfonamides, sulfadiazine, sulfacetamide, sulfamethizole and sulfisoxazole, nitrofurazone and sodium propionate; antivirals, such as idoxuridine, trifluorothymidine, trifluorouridine, acyclovir, ganciclovir, cidofovir, interferon, DDI, AZT, foscarnet, vidarabine, irbavirin, protease inhibitors and anti-cytomegalovirus agents; antiallergenics such as sodium cromoglycate, antazoline, methapyriline, chlorpheniramine, cetirizine, pyrilamine and prophenpyridamine; synthetic gluocorticoids and mineralocorticoids and more generally hormones forms derivating from the cholesterol metabolism (DHEA, progesterone, estrogens); non-steroidal anti-inflammatories such as salicylate, indomethacin, ibuprofen, diclofenac, flurbiprofen, piroxicam and COX2 inhibitors; antineoplastics such as carmustine, cisplatin, fluorouracil; adriamycin, asparaginase, azacitidine, azathioprine, bleomycin, busulfan, carboplatin, carmustine, chlorambucil, cyclophosphamide, cyclosporine, cytarabine, dacarbazine, dactinomycin, daunorubicin, doxorubicin, estramustine, etoposide, etretinate, filgrastin, floxuridine, fludarabine, fluorouracil, florxymesterone, flutamide, goserelin, hydroxyurea, ifosfamide, leuprolide, levamisole, limustine, nitrogen mustard, melphalan, mercaptopurine, methotrexate, mitomycin, mitotane, pentostatin, pipobroman, plicamycin, procarbazine, sargramostin, streptozocin, tamoxifen, taxol, teniposide, thioguanine, uracil mustard, vinblastine, vincristine and vindesine; immunological drugs such as vaccines and immune stimulants; insulin, calcitonin, parathyroid hormone and peptide and vasopressin hypothalamus releasing factor; beta adrenergic blockers such as timolol, levobunolol and betaxolol; cytokines, interleukines and growth factors epidermal growth factor, fibroblast growth factor, platelet derived growth factor, transforming growth factor beta, ciliary neurotrophic growth factor, glial derived neurotrophic factor, NGF, EPO, PLGF, brain nerve growth factor (BNGF), vascular endothelial growth factor (VEGF) and monoclonal antibodies or fragments thereof directed against such growth factors; anti-inflammatories such as hydrocortisone, dexamethasone, fluocinolone, prednisone, prednisolone, methylprednisolone, fluorometholone, betamethasone and triamcinolone; decongestants such as phenylephrine, naphazoline and tetrahydrazoline; miotics and anti-cholinesterases such as pilocarpine, carbachol, di-isopropyl fluorophosphate, phospholine iodine and demecarium bromide; mydriatics such as atropine sulphate, cyclopentolate, homatropine, scopolamine, tropicamide, eucatropine; sympathomimetics such as epinephrine and vasoconstrictors and vasodilators, anticlotting agents such as heparin, antifibrinogen, fibrinolysin, anticlotting activase, antidiabetic agents include acetohexamide, chlorpropamide, glipizide, glyburide, tolazamide, tolbutamide, insulin and aldose reductase inhibitors, hormones, peptides, nucleic acids, saccharides, lipids, glycolipids, glycoproteins and other macromolecules include endocrine hormones such as pituitary, insulin, insulin-related growth factor, thyroid, growth hormones; heat shock proteins; immunological response modifiers such as muramyl dipeptide, cyclosporins, interferons (including alpha-, beta- and gamma-interferons), interleukin-2, cytokines, FK506 (an epoxy-pyridooxaazcyclotricosine-tetrone, also known as Tacrolimus), tumor necrosis factor, pentostatin, thymopentin, transforming factor beta2, erythropoetin; antineogenesis proteins (e.g. anti VEGF, interferons), antibodies (monoclonal, polyclonal, humanized, etc.) or antibodies fragments, oligoaptamers, aptamers and gene fragments (oligonucleotides, plasmids, ribozymes, small interference RNA (SiRNA), nucleic acid fragments, peptides), immunomodulators such as endoxan, thalidomide, tamoxifene; antithrombolytic and vasodilator agents such as rtPA, urokinase, plasmin; nitric oxide donors, nucleic acids, dexamethasone, cyclosporin A, azathioprine, brequinar, gusperimus, 6-mercaptopurine, mizoribine, rapamycin, tacrolimus (FK-506), folic acid analogs (e.g., denopterin, edatrexate, methotrexate, piritrexim, pteropterin, Tomudex®, trimetrexate), purine analogs (e.g., cladribine, fludarabine, 6-mercaptopurine, thiamiprine, thiaguanine), pyrimidine analogs (e.g., ancitabine, azacitidine, 6-azauridine, carmofur, cytarabine, doxifluridine, emitefur, enocitabine, floxuridine, fluorouracil, gemcitabine, tegafur) fluocinolone, triaminolone, anecortave acetate, fluorometholone, medrysone, and prednislone. In some variations the immunosuppressive agent is dexamethasone. In some variations the immunosuppressive agent is cyclosporin A.

In some variations the formulation comprises a combination of one or more therapeutic agents.

Other nonlimiting examples of therapeutic agents that may be used in the formulations described herein include antibacterial antibiotics, aminoglycosides (e.g., amikacin, apramycin, arbekacin, bambermycins, butirosin, dibekacin, dihydrostreptomycin, fortimicin(s), gentamicin, isepamicin, kanamycin, micronomicin, neomycin, neomycin undecylenate, netilmicin, paromomycin, ribostamycin, sisomicin, spectinomycin, streptomycin, tobramycin, trospectomycin), amphenicols (e.g., azidamfenicol, chloramphenicol, florfenicol, thiamphenicol), ansamycins (e.g., rifamide, rifampin, rifamycin sv, rifapentine, rifaximin), P-lactams (e.g., carbacephems (e.g., loracarbef), carbapenems (e.g., biapenem, imipenem, meropenem, panipenem), cephalosporins (e.g., cefaclor, cefadroxil, cefamandole, cefatrizine, cefazedone, cefazolin, cefcapene pivoxil, cefclidin, cefdinir, cefditoren, cefepime, cefetamet, cefixime, cefinenoxime, cefodizime, cefonicid, cefoperazone, ceforanide, cefotaxime, cefotiam, cefozopran, cefpimizole, cefpiramide, cefpirome, cefpodoxime proxetil, cefprozil, cefroxadine, cefsulodin, ceftazidime, cefteram, ceftezole, ceftibuten, ceftizoxime, ceftriaxone, cefuroxime, cefuzonam, cephacetrile sodium, cephalexin, cephaloglycin, cephaloridine, cephalosporin, cephalothin, cephapirin sodium, cephradine, pivcefalexin), cephamycins (e.g., cefbuperazone, cefinetazole, cefminox, cefotetan, cefoxitin), monobactams (e.g., aztreonam, carumonam, tigemonam), oxacephems, flomoxef, moxalactam), penicillins (e.g., amdinocillin, amdinocillin pivoxil, amoxicillin, ampicillin, apalcillin, aspoxicillin, azidocillin, azlocillin, bacampicillin, benzylpenicillinic acid, benzylpenicillin sodium, carbenicillin, carindacillin, clometocillin, cloxacillin, cyclacillin, dicloxacillin, epicillin, fenbenicillin, floxacillin, hetacillin, lenampicillin, metampicillin, methicillin sodium, mezlocillin, nafcillin sodium, oxacillin, penamecillin, penethamate hydriodide, penicillin g benethamine, penicillin g benzathine, penicillin g benzhydrylamine, penicillin g calcium, penicillin g hydrabamine, penicillin g potassium, penicillin g procaine, penicillin n, penicillin o, penicillin v, penicillin v benzathine, penicillin v hydrabamine, penimepicycline, phenethicillin potassium, piperacillin, pivampicillin, propicillin, quinacillin, sulbenicillin, sultamicillin, talampicillin, temocillin, ticarcillin), ritipenem, lincosamides (e.g., clindamycin, lincomycin), macrolides (e.g., azithromycin, carbomycin, clarithromycin, dirithromycin, erythromycin, erythromycin acistrate, erythromycin estolate, erythromycin glucoheptonate, erythromycin lactobionate, erythromycin propionate, erythromycin stearate, josamycin, leucomycins, midecamycins, miokamycin, oleandomycin, primycin, rokitamycin, rosaramicin, roxithromycin, spiramycin, troleandomycin), polypeptides (e.g., amphomycin, bacitracin, capreomycin, colistin, enduracidin, enviomycin, fusafungine, gramicidin s, gramicidin(s), mikamycin, polymyxin, pristinamycin, ristocetin, teicoplanin, thiostrepton, tuberactinomycin, tyrocidine, tyrothricin, vancomycin, viomycin, virginiamycin, zinc bacitracin), tetracyclines (e.g., apicycline, chlortetracycline, clomocycline, demeclocycline, doxycycline, guamecycline, lymecycline, meclocycline, methacycline, minocycline, oxytetracycline, penimepicycline, pipacycline, rolitetracycline, sancycline, tetracycline), and others (e.g., cycloserine, mupirocin, tuberin); synthetic antibacterials, 2,4-Diaminopyrimidines (e.g., brodimoprim, tetroxoprim, trimethoprim), nitrofurans (e.g., furaltadone, furazolium chloride, nifuradene, nifuratel, nifurfoline, nifurpirinol, nifurprazine, nifurtoinol, nitrofurantoin), quinolones and analogs (e.g., cinoxacin, ciprofloxacin, clinafloxacin, difloxacin, enoxacin, fleroxacin, flumequine, grepafloxacin, lomefloxacin, miloxacin, nadifloxacin, nalidixic acid, norfloxacin, ofloxacin, oxolinic acid, pazufloxacin, pefloxacin, pipemidic acid, piromidic acid, rosoxacin, rufloxacin, sparfloxacin, temafloxacin, tosufloxacin, trovafloxacin), sulfonamides (e.g., acetyl sulfamethoxypyrazine, benzylsulfamide, chloramine-b, chloramine-t, dichloramine t, n2-formylsulfisomidine, n4-β-d-glucosylsulfanilamide, mafenide, 4'-(methylsulfamoyl)sulfanilanilide, noprylsulfamide, phthalylsulfacetamide, phthalylsulfathiazole, salazosulfadimidine, succinylsulfathiazole, sulfabenzamide, sulfacetamide, sulfachlorpyridazine, sulfachrysoidine, sulfacytine, sulfadiazine, sulfadicramide, sulfadimethoxine, sulfadoxine, sulfaethidole, sulfaguanidine, sulfaguanol, sulfalene, sulfaloxic acid, sulfamerazine, sulfameter, sulfamethazine, sulfamethizole, sulfamethomidine, sulfamethoxazole, sulfamethoxypyridazine, sulfametrole, sulfamidochrysoidine, sulfamoxole, sulfanilamide, 4-sulfanilamidosalicylic acid, n4-sulfanilylsulfanilamide, sulfanilylurea, n-sulfanilyl-3,4-xylamide, sulfanitran, sulfaperine, sulfaphenazole, sulfaproxyline, sulfapyrazine, sulfapyridine, sulfasomizole, sulfasymazine, sulfathiazole, sulfathiourea, sulfatolamide, sulfisomidine, sulfisoxazole) sulfones (e.g., acedapsone, acediasulfone, acetosulfone sodium, dapsone, diathymosulfone, glucosulfone sodium, solasulfone, succisulfone, sulfanilic acid, p-sulfanilylbenzylamine, sulfoxone sodium, thiazolsulfone), and others (e.g., clofoctol, hexedine, methenamine, methenamine anhydromethylene-citrate, methenamine hippurate, methenamine mandelate, methenamine sulfosalicylate, nitroxoline, taurolidine, xibomol), antifungal antibiotics, polyenes (e.g., amphotericin b, candicidin, dermostatin, filipin, fungichromin, hachimycin, hamycin, lucensomycin, mepartricin, natamycin, nystatin, pecilocin, perimycin), azaserine, griseofulvin, oligomycins, neomycin undecylenate, pyrrolnitrin, siccanin, tubercidin, viridin, synthetic antifungals, allylamines (e.g., butenafine, naftifine, terbinafine), imidazoles (e.g., bifonazole, butoconazole, chlordantoin, chlormidazole, cloconazole, clotrimazole, econazole, enilconazole, fenticonazole, flutrimazole, isoconazole, ketoconazole, lanoconazole, miconazole, omoconazole, oxiconazole nitrate, sertaconazole, sulconazole, tioconazole), thiocarbamates (e.g., tolciclate, tolindate, tolnaftate), triazoles (e.g., fluconazole, itraconazole, saperconazole, terconazole), acrisorcin, amorolfine, biphenamine, bromosalicylchloranilide, buclosamide, calcium propionate, chlorphenesin, ciclopirox, cloxyquin, coparaffinate, diamthazole dihydrochloride, exalamide, flucytosine, halethazole, hexetidine, loflucarban, nifuratel, potassium iodide, propionic acid, pyrithione, salicylanilide, sodium propionate, sulbentine, tenonitrozole, triacetin, ujothion, undecylenic acid, zinc propionate, antineoplastics, antibiotics and analogs (e.g., aclacinomycins, actinomycin f1, anthramycin, azaserine, bleomycins, cactinomycin, carubicin, carzinophilin, chromomycins, dactinomycin, daunorubicin, 6-diazo-5-oxo-L-norleucine, doxorubicin, epirubicin, idarubicin, menogaril, mitomycins, mycophenolic acid, nogalamycin, olivomycines, peplomycin, pirarubicin, plicamycin, porfiromycin, puromycin, streptonigrin, streptozocin, tubercidin, zinostatin, zorubicin), antimetabolites (e.g. folic acid analogs (e.g., denopterin, edatrexate, methotrexate, piritrexim, pteropterin, Tomudex®, trimetrexate), purine analogs (e.g., cladribine, fludarabine, 6-mercaptopurine, thiamiprine, thioguanine), pyrimidine analogs (e.g., ancitabine, azacitidine, 6-azauridine, carmofur, cytarabine, doxifluridine, emitefur, enocitabine, floxuridine, fluorouracil, gemcitabine, tagafur), antiinflammatory agents, steroidal antiinflammatory agents, acetoxypregnenolone, alclometasone, algestone, amcinonide, beclomethasone, betamethasone, budesonide, chloroprednisone, clobetasol, clobetasone, clocortolone, cloprednol, corticosterone, cortisone, cortivazol, deflazacort, desonide, desoximetasone, dexamethasone, diflorasone, diflucortolone, difluprednate, enoxolone, fluazacort, flucloronide, flumethasone, flunisolide, fluocinolone acetonide, fluocinonide, fluocortin butyl, fluocortolone, fluorometholone, fluperolone acetate, fluprednidene acetate, fluprednisolone, flurandrenolide, fluticasone propionate, formocortal, halcinonide, halobetasol propionate, halometasone, halopredone acetate, hydrocortamate, hydrocortisone, loteprednol etabonate, mazipredone, medrysone, meprednisone, methylprednisolone, mometasone furoate, paramethasone, prednicarbate, prednisolone, prednisolone 25-diethylamino-acetate, prednisolone sodium phosphate, prednisone, prednival, prednylidene, rimexolone, tixocortol, triamcinolone, triamcinolone acetonide, triamcinolone benetonide, and triamcinolone hexacetonide, non-steroidal antiinflammatory agents, aminoarylcarboxylic acid derivatives (e.g., enfenamic acid, etofenamate, flufenamic acid, isonixin, meclofenamic acid, mefenamic acid, niflumic acid, talniflumate, terofenamate, tolfenamic acid), arylacetic acid derivatives (e.g., aceclofenac, acemetacin, alclofenac, amfenac, amtolmetin guacil, bromfenac, bufexamac, cinmetacin, clopirac, diclofenac sodium, etodolac, felbinac, fenclozic acid, fentiazac, glucametacin, ibufenac, indomethacin, isofezolac, isoxepac, lonazolac, metiazinic acid, mofezolac, oxametacine, pirazolac, proglumetacin, sulindac, tiaramide, tolmetin, tropesin, zomepirac), arylbutyric acid derivatives (e.g., bumadizon, butibufen, fenbufen, xenbucin), arylcarboxylic acids (e.g., clidanac, ketorolac, tinoridine), arylpropionic acid derivatives (e.g., alminoprofen, benoxaprofen, bermoprofen, bucloxic acid, carprofen, fenoprofen, flunoxaprofen, flurbiprofen, ibuprofen, ibuproxam, indoprofen, ketoprofen, loxoprofen, naproxen, oxaprozin, piketoprolen, pirprofen, pranoprofen, protizinic acid, suprofen, tiaprofenic acid, ximoprofen, zaltoprofen), pyrazoles (e.g., difenamizole, epirizole), pyrazolones (e.g., apazone, benzpiperylon, feprazone, mofebutazone, morazone, oxyphenbutazone, phenylbutazone, pipebuzone, propyphenazone, ramifenazone, suxibuzone, thiazolinobutazone), salicylic acid derivatives (e.g., acetaminosalol, aspirin, benorylate, bromosaligenin, calcium acetylsalicylate, diflunisal, etersalate, fendosal, gentisic acid, glycol salicylate, imidazole salicylate, lysine acetylsalicylate, mesalamine, morpholine salicylate, 1-naphthyl salicylate, olsalazine, parsalmide, phenyl acetylsalicylate, phenyl salicylate, salacetamide, salicylamide o-acetic acid, salicylsulfuric acid, salsalate, sulfasalazine), thiazinecarboxamides (e.g., ampiroxicam, droxicam, isoxicam, lomoxicam, piroxicam, tenoxicam), β-acetamidocaproic acid, s-adenosylmethionine, 3-amino-4-hydroxybutyric acid, amixetrine, bendazac, benzydamine, a-bisabolol, bucolome, difenpiramide, ditazol, emorfazone, fepradinol, guaiazulene, nabumetone, nimesulide, oxaceprol, paranyline, perisoxal, proquazone, superoxide dismutase, tenidap, and zileuton.

The therapeutic agents may also be used in combination with other therapeutic agents and therapies, including but not limited to agents and therapies useful for the treatment, prevention, inhibition, delaying onset of, or causing regression of angiogenesis or neovascularization, particularly CNV. In some variations the additional agent or therapy is used to treat regression of angiogenesis or neovascularization, particularly CNV. Non-limiting examples of such additional agents and therapies include pyrrolidine, dithiocarbamate (NFκB inhibitor); squalamine; TPN 470 analogue and fumagillin; PKC (protein kinase C) inhibitors; Tie-1 and Tie-2 kinase inhibitors; inhibitors of VEGF receptor kinase; proteosome inhibitors such as Velcade™ (bortezomib, for injection; ranibuzumab (Lucentis™) and other antibodies directed to the same target; pegaptanib (Macugen™); vitronectin receptor antagonists, such as cyclic peptide antagonists of vitronectin receptor-type integrins; α-v/β-3 integrin antagonists; α-v/β-1 integrin antagonists; thiazolidinediones such as rosiglitazone or troglitazone; interferon, including γ-interferon or interferon targeted to CNV by use of dextran and metal coordination; pigment epithelium derived factor (PEDF); endostatin; angiostatin; tumistatin; canstatin; anecortave acetate; acetonide; triamcinolone; tetrathiomolybdate; RNA silencing or RNA interference (RNAi) of angiogenic factors, including ribozymes that target VEGF expression; Accutane™ (13-cis retinoic acid); ACE inhibitors, including but not limited to quinopril, captopril, and perindozril; inhibitors of mTOR (mammalian target of rapamycin); 3-aminothalidomide; pentoxifylline; 2-methoxyestradiol; colchicines; AMG-1470; cyclooxygenase inhibitors such as nepafenac, rofecoxib, diclofenac, rofecoxib, NS398, celecoxib, vioxx, and (E)-2-alkyl-2(4-methanesulfonylphenyl)-1-phenylethene; t-RNA synthase modulator; metalloprotease 13 inhibitor; acetylcholinesterase inhibitor; potassium channel blockers; endorepellin; purine analog of 6-thioguanine; cyclic peroxide ANO-2; (recombinant) arginine deiminase; epigallocatechin-3-gallate; cerivastatin; analogues of suramin; VEGF trap molecules; inhibitors of hepatocyte growth factor (antibodies to the growth factor or its receptors, small molecular inhibitors of the c-met tyrosine kinase, truncated versions of HGF e.g. NK4); apoptosis inhibiting agents; Visudyne™, snET2 and other photo sensitizers with photodynamic therapy (PDT); and laser photocoagulation.

In some variations, the therapeutic agent is used in combination with other therapeutic agents. In some variations the therapeutic agent is used in combination with verteporfin (Visudyne™). In some variations the therapeutic agent is used in combination with an inhibitor of Vascular Endothelial Growth Factor (VEGF). In some variations the therapeutic agent is used in combination with an inhibitor of Vascular Endothelial Growth Factor-A (VEGF-A). In some variations, the inhibitor of VEGF is a VEGF trap molecule including, without limitation, the VEGF trap under development by Regeneron Pharmaceuticals. In some variations the inhibitor of VEGF is an antibody or fragment thereof directed to VEGF. In some variations the antibody or fragment thereof directed to VEGF is bevacizumab (i.e., Avastin™). In some variations the antibody or fragment thereof directed to VEGF is ranibizumab (i.e., Lucentis™). In some variations, the therapeutic agent may be a limus compound. In some variations, the therapeutic agent may be rapamycin or an analog or derivative thereof including those described in the Therapeutic Agents section. In some variations, the therapeutic agent is rapamycin. In some variations, the therapeutic agent is dasatinib.

In some variations, the therapeutic agent is a limus compound such as rapamycin or an analog or derivative thereof including those described in the Therapeutic Agents section and an other therapeutic agent such as ranibizumab (i.e., Lucentis™), bevacizumab (i.e., Avastin™), or a VEGF trap. In some variations, the therapeutic agent is a limus compound such as rapamycin or an analog or derivative thereof including those described in the Therapeutic Agents section and the other therapeutic agent is ranibizumab (i.e., Lucentis™) or bevacizumab (i.e., Avastin™). Also provided are methods for treating or preventing wet-AMD in a human subject comprising administration of a liquid formulation comprising a therapeutic agent such as rapamycin or an analog or derivative thereof including those described in the Therapeutic Agents section and an other therapeutic agent such as ranibizumab (i.e., Lucentis™), bevacizumab (i.e., Avastin™), or a VEGF trap. In some variations, the methods for treating or preventing wet-AMD in a human subject comprising administration of a liquid formulation comprising rapamycin and ranibizumab (i.e., Lucentis™), bevacizumab (i.e., Avastin™), or a VEGF trap. In some variations, the liquid formulation comprising rapamycin and ranibizumab (i.e., Lucentis™), bevacizumab (i.e., Avastin™), or a VEGF trap is administered intravitreally, subconjunctivally, subtenonally, or topically. In some variations, the liquid formulation is administered intravitreally. In some variations, the total amount of Lucentis or Avastin is any of about 0.1 mg, about 0.2 mg, about 0.3 mg, about 0.4 mg, about 0.5 mg, about 0.6 mg, or about 0.7 mg. In some variations, the total amount of Lucentis or Avastin is 0.3 mg or 0.5 mg.

In some variations the therapeutic agent used in combination with the other therapeutic agent may be administered simultaneously (i.e., simultaneous administration), sequentially (i.e., sequential administration), or independently of the other therapeutic agents. In some variations the therapeutic agent and the other therapeutic agent are administered by the same route of administration. In some variations, the therapeutic agent and other therapeutic agent are both administered during one visit to the physician. In some variations, the therapeutic agent and other therapeutic agent are both administered during the same physician visit. In some variations, the therapeutic agent and other therapeutic agent are administered during more than one visit to the physician.

In some variations the therapeutic agent and the other therapeutic agent are administered by the same route of administration. In some variations the therapeutic agent and the other therapeutic agent are administered by different routes of administration. In some variations the therapeutic agent are administered by subconjunctival administration including, without limitation, subconjunctival injection, and the other therapeutic agent are administered by intravitreal administration including, without limitation, intravitreal injection. In some variations the therapeutic agent are administered by intravitreal administration including, without limitation, intravitreal injection, and the other therapeutic agent are administered by subconjunctival administration including, without limitation, subconjunctival injection. In some variations the therapeutic agent are administered by subconjunctival administration including, without limitation, subconjunctival injection, and the other therapeutic agent are administered by subtenon administration including, without limitation, subtenon injection. In some variations the therapeutic agent are administered by subtenon administration including, without limitation, subtenon injection, and the other therapeutic agent are administered by subconjunctival administration including, without limitation, subconjunctival injection. In some variations the therapeutic agent are administered by intravitreal administration including, without limitation, intravitreal injection, and the other therapeutic agent are administered by subtenon administration including, without limitation, subtenon injection. In some variations the therapeutic agent are administered by subtenon administration including, without limitation, subtenon injection, and the other therapeutic agent are administered by intravitreal administration including, without limitation, intravitreal injection. In some variations, the therapeutic agent is administered topically and the other therapeutic agent is administered by subconjunctival, subtenon, and/or intravitreal administration. In some variations, the other therapeutic agent is administered topically and the therapeutic agent is administered by subconjunctival, subtenon, and/or intravitreal administration. In some variations the formulation of the therapeutic agent and the other therapeutic agent are the same (i.e., identical).

In some variations the combination of administration of therapeutic agent and administration of other therapeutic agent reduces the dose administered (e.g., dose volume, dose concentration, or amount of therapeutic agent) of one or both therapeutic agents. In some variations the combination of therapeutic agent and other therapeutic agent increases or prolongs the time between administrations and/or decreases the frequency of administrations of one or both therapeutic agents.

In some variations, the therapeutic agent is rapamycin. In some variations, the therapeutic agent is dasatinib. In some variations, the other therapeutic agent is verteporfin, bevacizumab, and/or ranibizumab.

By way of non-limiting example, administration of rapamycin may be used to decrease the frequency of administration of bevacizumab or ranibizumab. In one non-limiting example, wet AMD is treated by administering one, two, or three doses of Avastin or Lucentis followed by subsequent doses of rapamycin, alone or in combination with Avastin or Lucentis.

Diseases and Conditions that May be Treated, Prevented, Inhibited, Onset Delayed, or Regression Caused Herein are described diseases and conditions that may be treated, prevented, inhibited, onset delayed, or regression caused using the therapeutic agents and the formulations, liquid formulations, and methods described herein. In some variations, the diseases or conditions are treated using the therapeutic agents and the formulations, liquid formulations, and methods described herein. Unless the context indicates otherwise, it is envisioned that the subjects on whom all of the methods of treatment may be performed include, but are not limited to, human subjects.

Generally, any diseases or condition of the eye susceptible to treatment, prevention, inhibition, delaying the onset of, or causing the regression of using the therapeutic agents and the formulations, liquid formulations and methods described herein may be treated, prevented, inhibited, onset delayed, or regression caused treated or prevented. Examples of diseases or conditions of the eye include, but are not limited to, diseases or conditions associated with neovascularization including retinal and/or choroidal neovascularization.

Diseases or conditions associated with retinal and/or choroidal neovascularization that can be treated, prevented inhibited, have onset delayed, or be caused to regress using the formulations, liquid formulations, and methods described herein include, but are not limited to, diabetic retinopathy, macular degeneration, wet and dry AMD, retinopathy of prematurity (retrolental fibroplasia), infections causing a retinitis or choroiditis, presumed ocular histoplasmosis, myopic degeneration, angioid streaks, and ocular trauma. Other non-limiting examples of diseases and conditions of the eye that may be treated, prevented inhibited, have onset delayed, or be caused to regress using the formulations, liquid formulations, and methods described herein include, but are not limited to, pseudoxanthoma elasticum, vein occlusion, artery occlusion, carotid obstructive disease, Sickle Cell anemia, Eales disease, myopia, chronic retinal detachment, hyperviscosity syndromes, toxoplasmosis, trauma, polypoidal choroidal vasculopathy, post-laser complications, complications of idiopathic central serous chorioretinopathy, complications of choroidal inflammatory conditions, rubeosis, diseases associated with rubeosis (neovascularization of the angle), neovascular glaucoma, uveitis and chronic uveitis, macular edema, proliferative retinopathies and diseases or conditions caused by the abnormal proliferation of fibrovascular or fibrous tissue, including all forms of proliferative vitreoretinopathy (including post-operative proliferative vitreoretinopathy), whether or not associated with diabetes.

In some variations, the formulations and pharmaceutical formulations described herein are used to prevent or delay onset of a disease or condition of the eye where the subject, including but not limited to a human subject, is at heightened risk of developing the disease or condition of the eye. A subject with a heightened risk of developing a disease or condition is a subject with one or more indications that the disease or condition is likely to develop in the particular subject. In some variations the subject with a heightened risk of developing wet AMD is a subject with dry AMD in at least one eye. In some variations the subject with a heightened risk of developing wet AMD in a fellow eye is a subject with wet AMD in the other eye. In some variations, the formulations and pharmaceutical formulations described herein are used to prevent or delay onset of CNV in a subject at heightened risk of developing CNV, including but not limited to prevention or delaying onset of CNV in the fellow eye of a subject, including but not limited to a human subject with AMD in one eye. In some variations, the formulations and pharmaceutical formulations described herein are used to prevent or delay onset of CNV in the fellow eye of a subject with wet AMD in one eye. In some variations, the formulations and pharmaceutical formulations comprise a limus compound, including but not limited to rapamycin. In some variations the formulations and pharmaceutical formulations are administered periocularly, including without limitation subconjunctivally, to a human subject with vision of 20/40 or better. In some variations, the formulations and pharmaceutical formulations are administered periocularly, including without limitation subconjunctivally, to the eye of a human subject where the eye to which the formulation is administered has vision of 20/40 or better.

In some variations, the formulations and pharmaceutical formulations described herein are used to treat, prevent, or delay onset of AMD. In some variations, the formulations and pharmaceutical formulations described herein are used to treat, prevent, or delay onset of dry AMD. In some variations, subjects including but not limited to human subjects with non-central geographic atrophy are administered a formulation or pharmaceutical formulations described herein to treat, prevent, or delay onset of central geographic atrophy. In some variations, the formulations and pharmaceutical formulations comprise a limus compound, including but not limited to rapamycin. In some variations the formulations and pharmaceutical formulations are administered periocularly, including without limitation subconjunctivally, to a human subject with vision of 20/40 or better. In some variations, the formulations and pharmaceutical formulations described herein are administered and the subject, including but not limited to a human subject is also treated with a second therapy for treating the disease or disorder. In some variations, the formulations and pharmaceutical formulations described herein are used to treat, prevent, or delay onset of wet or dry AMD and the subject, including but not limited to a human subject is also treated with laser therapy such as photodynamic laser therapy, either before, during, or after treatment with the formulations or pharmaceutical formulations described herein.

In some variations, the formulations and pharmaceutical formulations described herein are used to treat one or more of uveitis, allergic conjunctivitis, macular edema, glaucoma, or dry eye.

In some variations, a formulations or pharmaceutical formulation comprises a limus compound such as rapamycin, and is administered to treat, prevent, or delay onset of dry eye. In some variations, a formulations or pharmaceutical formulation comprises a limus compound such as rapamycin, and is administered to treat, prevent, or delay onset of allergic conjunctivitis.

In some variations, the formulations and pharmaceutical formulations described herein are used to treat glaucoma. In some variations, the formulations and pharmaceutical formulations described herein for treating glaucoma comprise a limus compound such as rapamycin, and are used as a surgical adjuvant to prevent, reduce or delay surgical complications. In some variations, the formulations and pharmaceutical formulations described herein for treating glaucoma comprise a limus compound such as rapamycin, and are used to improve or prolong surgical implant success. In some variations, the formulations and pharmaceutical formulations described herein for treating glaucoma comprise a limus compound such as rapamycin, and are used to improve or prolong success of an argon laser trabeculectomy or other glaucoma-related surgery. In some variations, the formulations and pharmaceutical formulations described herein have a neuroprotective effect and are used to treat glaucoma.

In some variations, the formulations and pharmaceutical formulations described herein are used to treat retinitis pigmentosa. In some variations, the formulations and pharmaceutical formulations described herein for treating glaucoma comprise a limus compound such as rapamycin, and are used to treat, prevent, or delay onset of retinitis pigmentosa. In some variations, the formulations and pharmaceutical formulations described herein have a neuroprotective effect and are used to treat retinitis pigmentosa.

In some variations, the formulations and pharmaceutical formulations described herein are used to treat one or more of central retinal vein occlusive diseases (CRVO), branch retinal venous occlusion (BRVO), retinal vascular diseases and conditions, macular edema, diabetic macular edema, iris neovascularization, diabetic retinopathy, or corneal graft rejection. In some variations, a formulations or pharmaceutical formulation comprises a limus compound such as rapamycin, and is administered to treat, prevent, or delay onset of one or more of these diseases or conditions. In some variations the formulations and pharmaceutical formulations are administered subconjunctivally to an eye with vision of 20/40 or better.

When used to treat, prevent, inhibit, delay the onset of, or cause regressions of uveitis, the formulations and pharmaceutical formulations described herein may be administered by a variety of routes as is known in the art, including but not limited to by ocular or oral administration. Other routes of administration are known and are routine in the art. In some variations, the formulations described herein comprise rapamycin and are used to treat uveitis.

One disease that may be treated, prevented, inhibited, have onset delayed, or be caused to regress using the formulation, liquid formulations and methods described herein is the wet form of AMD. In some variations wet AMD is treated using the formulations, liquid formulations and methods described herein. The wet form of AMD is characterized by blood vessels growing from their normal location in the choroid into an undesirable position under the retina. Leakage and bleeding from these new blood vessels results in vision loss and possibly blindness.

The formulations, liquid formulations, and methods described herein may also be used to prevent or slow the transition from the dry form of AMD (wherein the retinal pigment epithelium or RPE degenerates and leads to photoreceptor cell death and the formation of yellow deposits called drusen under the retina) to the wet form of AMD.

"Macular degeneration" is characterized by the excessive buildup of fibrous deposits in the macula and retina and the atrophy of the retinal pigment epithelium. As used herein, an eye "afflicted" with macular degeneration is understood to mean that the eye exhibits at least one detectable physical characteristic associated with the disease of macular degeneration. The administration of rapamycin appears to limit and regress angiogenesis, such as choroidal neovascularization in age-related macular degeneration (AMD), which may occur without treatment. As used herein, the term "angiogenesis" means the generation of new blood vessels ("neovascularization") into a tissue or organ. An "angiogenesis-mediated disease or condition" of the eye or retina is one in which new blood vessels are generated in a pathogenic manner in the eye or retina, resulting in diminution or loss of vision or other problem, e.g., choroidal neovascularization associated with AMD.

The formulations and liquid formulations described herein, including but not limited to rapamycin-containing formulations and liquid formulations, may also be used to treat, prevent, inhibit, delay the onset of, or cause regression of various immune-related diseases and conditions, including but not limited to organ transplant rejection in a host, graft vs. host disease, autoimmune diseases, diseases of inflammation, hyperproliferative vascular disorders, solid tumors, and fungal infections. In some variations, the formulations and liquid formulations described herein, including but not limited to rapamycin-containing formulations and liquid formulations, are used to treat various immune-related diseases and conditions, including but not limited to organ transplant rejection in a host, graft vs. host disease, autoimmune diseases, diseases of inflammation, hyperproliferative vascular disorders, solid tumors, and fungal infections. The formulations and liquid formulations described herein, including but not limited to rapamycin-containing formulations and liquid formulations, may be used as immunosuppressants. The formulations and liquid formulations described herein, including but not limited to rapamycin-containing formulations and liquid formulations, may be used to treat, prevent, inhibit, or delay the onset of rejection of transplanted organs or tissues including but not limited to transplanted heart, liver, kidney, spleen, lung, small bowel, pancreas, and bone marrow. In some variations, the formulations and liquid formulations described herein are used to treat the onset of rejection of transplanted organs or tissues including but not limited to transplanted heart, liver, kidney, spleen, lung, small bowel, pancreas, and bone marrow. When used to treat, prevent, inhibit, delay the onset of, or cause regressions of immune-related diseases, including but not limited to transplant rejection, the formulations and liquid formulations described herein may be administered by a variety of routes as is known in the art, including but not limited to by oral administration.

Systemic administration may be achieved by oral administration of the liquid formulation. Other systemic routes of administration are known and are routine in the art. Some examples thereof are listed in the Detailed Description section.

As used herein, to "inhibit" a disease or condition by administration of a therapeutic agent means that the progress of at least one detectable physical characteristic or symptom of the disease or condition is slowed or stopped following administration of the therapeutic agent as compared to the progress of the disease or condition without administration of the therapeutic agent.

As used herein, to "prevent" a disease or condition by administration of a therapeutic agent means that the detectable physical characteristics or symptom of the disease or condition do not develop following administration of the therapeutic agent.

As used herein, to "delay onset of" a disease or condition by administration of a therapeutic agent means that at least one detectable physical characteristic or symptom of the disease or condition develops later in time following administration of the therapeutic agent as compared to the progress of the disease or condition without administration of the therapeutic agent.

As used herein, to "treat" a disease or condition by administration of a therapeutic agent means that the progress of at least one detectable physical characteristic or symptom of the disease or condition is slowed, stopped, or reversed following administration of the therapeutic agent as compared to the progress of the disease or condition without administration of the therapeutic agent.

As used herein, to "cause regression of" a disease or condition by administration of a therapeutic agent means that the progress of at least one detectable physical characteristic or symptom of the disease or condition is reversed to some extent following administration of the therapeutic agent.

A subject, including but not limited to a human subject, having a predisposition for or in need of prevention may be identified by the skilled practitioner by established methods and criteria in the field given the teachings herein. The skilled practitioner may also readily diagnose individuals as in need of inhibition or treatment based upon established criteria in the field for identifying angiogenesis and/or neovascularization given the teachings herein.

As used herein, a "subject" is generally any animal that may benefit from administration of the therapeutic agents described herein. In some variations the therapeutic agents are administered to a mammalian subject. In some variations the therapeutic agents are administered to a human subject. In some variations the therapeutic agents may be administered to a veterinary animal subject. In some variations the therapeutic agents may be administered to a model experimental animal subject.

Other diseases and conditions that may be treated, prevented, inhibited, have the onset delayed, or be caused to regress using the methods described herein include those disclosed in the following patents and publications, the contents of each of which is incorporated herein in its entirety: PCT publication WO 2004/027027, published Apr. 1, 2004, titled Method of inhibiting choroidal neovascularization, assigned to Trustees of the University of Pennsylvania; U.S. Pat. No. 5,387,589, issued Feb. 7, 1995, titled Method of Treating Ocular Inflammation, with inventor Prassad Kulkami, assigned to University of Louisville Research Foundation; U.S. Pat. No. 6,376,517, issued Apr. 23, 2003, titled Pipecolic acid derivatives for vision and memory disorders, assigned to GPI NIL Holdings, Inc; PCT publication WO 2004/028477, published Apr. 8, 2004, titled Method subretinal administration of therapeutics including steroids: method for localizing pharmadynamic action at the choroid and retina; and related methods for treatment and or prevention of retinal diseases, assigned to Innorx, Inc; U.S. Pat. No. 6,416,777, issued Jul. 9, 2002, titled Ophthalmic drug delivery device, assigned to Alcon Universal Ltd; U.S. Pat. No. 6,713,081, issued Mar. 30, 2004, titled Ocular therapeutic agent delivery device and methods for making and using such devices, assigned to Department of Health and Human Services; and U.S. Pat. No. 5,536,729, issued Jul. 16, 1996, titled Rapamycin Formulations for Oral Administration, assigned to American Home Products Corp., and U.S. Pat. App. Nos. 60/503,840 and 10/945,682.

Liquid Formulations

The liquid formulations described herein contain a therapeutic agent and may generally be any liquid formulation, including but not limited to solutions, suspensions, and emulsions. In some variations the liquid formulations form a non-dispersed mass relative to a surrounding medium when placed in the vitreous of a rabbit eye.

When a certain volume of a liquid formulation is administered, it is understood that there is some imprecision in the accuracy of various devices that may be used to administer the liquid formulation. Where a certain volume is specified, it is understood that this is the target volume. However, certain devices such as insulin syringes are inaccurate to greater than 10%, and sometimes inaccurate to greater than 20% or more. Hamilton HPLC type syringes are generally considered precise to within 10%, and are recommended for volumes below 10 µl are to be injected.

In some variations, a volume of a liquid formulation described herein is administered to the vitreous of a rabbit eye or a subject's, including but not limiting a human subject's eye that is less than about 500 µl, less than about 400 µl, less than about 300 µl, less than about 200 µl, less than about 100 µl, less than about 90 µl, less than about 80 µl, less than about 70 µl, less than about 60 µl, less than about 50 µl, less than about 40 µl, less than about 30 µl, less than about 20 µl, less than about 10 µl, less than about 5 µl, less than about 3 µl, or less than about 1 µl. In some variations, a volume of a liquid formulation described herein is administered to the vitreous of a rabbit eye or subject's, including but not limited to a human subject's eye that is less than about 20 µl. In some variations, a volume of a liquid formulation described herein is administered to the vitreous that is less than about 10 µl. In some variations, a volume of a liquid formulation described herein is administered to the vitreous of a rabbit eye or a subject's, including but not limited to a human subject's eye that is between about 0.1 µl and about 200 µl, between about 50 µl and about 200 µl, between about 50 µl and about 150 µl, between about 0.1 µl and about 100 µl, between about 0.1 µl and about 50 µl, between about 1 µl and about 40 µl, between about 1 µl and about 30 µl, between about 1 µl and about 20 µl, between about 1 µl and about 10 µl, or between about 1 µl and about 5 µl. In some variations, a volume of a liquid formulation described herein is administered to the vitreous of a rabbit eye or a subject's, including but not limited to a human subject's eye that is between about 1 µl and about 10 µl. In some variations, a volume of a liquid formulation described herein is administered to the vitreous of a rabbit eye or a subject's, including but not limited to a human subject's eye that is between about 1 µl and about 5 µl. In some variations, a volume of a liquid formulation described herein is administered to the vitreous of a rabbit eye or a subject's eye that is between about 11 and about 5 µl. In some variations, a volume of a liquid formulation described herein is administered to the vitreous of a rabbit eye or a subject's, including but not limited to a human subject's eye that is between about 0.1 µl and about 200 µl.

In some variations, a total volume of a liquid formulation described herein is subconjunctivally administered to a rabbit eye or a subject's, including but not limited to a human subject's eye that is less than about 1000 µl, less than about 900 µl, less than about 800 µl, less than about 700 µl, less than about 600 µl, less than about 500 µl, less than about 400 µl, less than about 300 µl, less than about 200 µl, less than about 100 µl, less than about 90 µl, less than about 80 µl, less than about 70 µl, less than about 60 µl, less than about 50 µl, less than about 40 µl, less than about 30 µl, less than about 20 µl, less than about 10 µl, less than about 5 µl, less than about 3 µl, or less than about 1 µl. In some variations, a volume of a liquid formulation described herein is subconjunctivally administered to a rabbit eye or a subject's, including but not limited to a human subject's eye that is less than about 20 µl. In some variations, a volume of a liquid formulation described herein is subconjunctivally administered to a rabbit eye or a subject's, including but not limited to a human subject's eye that is less than about 10 µl. In some variations, a volume of a liquid formulation described herein is subconjunctivally administered to a rabbit eye or a subject's, including but not limited to a human subject's eye that is between about 0.11 and about 200 µl, between about 50 µl and about 200 µl, between about 200 µl and about 300 µl, between about 300 µl and about 400 µl, between about 400 µl and about 500 µl, between about 600 µl and about 700 µl, between about 700 µl and about 800 µl, between about 800 µl and about 900 µl, between about 900 µl and about 1000 µl, between about 50 µl and about 150 µl, between about 0.1 µl and about 100 µl, between about 0.1 µl and about 50 µl, between about 1 µl and about 40 µl, between about 1 µl and about 30 µl, between about 1 µl and about 20 µl, between about 1 µl and about 10 µl, or between about 1 µl and about 5 µl. In some variations, a volume of a liquid formulation described herein is subconjunctivally administered to a rabbit eye or a subject's, including but not limited to a human subject's eye that is between about 1 µl and about 10 µl. In some variations, a volume of a liquid formulation described herein is subconjunctivally administered to a rabbit eye or a subject's, including but not limited to a human subject's eye that is between about 1 µl and about 5 µl. In some variations, a volume of a liquid formulation described herein is administered to subconjunctivally administered to a rabbit eye or a subject's, including but not limited to a human subject's eye that is between about 1 µl and about 5 µl. In some variations, a volume of a liquid formulation described herein is administered to subconjunctivally administered to a rabbit eye or a subject's, including but not limited to a human subject's eye that is between about 0.1 µl and about 200 µl.

In some variations, a volume of a liquid formulation described herein is administered to the vitreous of a rabbit eye or a subject's, including but not limited to a human subject's eye that is any of about 2 µl, about 4 µl, about 5 µl, about 6 µl, about 8 µl, about 10 µl, about 12 µl, about 14 µl, about 16 µl, about 18 µl, or about 20 µl. In some variations, a volume of a liquid formulation described herein is administered to the vitreous of a rabbit eye or a subject's, including but not limited to a human subject's eye that is about 2 µl. In some variations, a volume of a liquid formulation described herein is administered to the vitreous of a rabbit eye or a subject's, including but not limited to a human subject's eye that is about 5 µl. In some variations, a volume of a liquid formulation described herein is administered to the vitreous of a rabbit eye or a subject's, including but not limited to a human subject's eye that is about 8 µl.

In some variations, a total volume of a liquid formulation is subconjunctivally administered to a rabbit eye or a subject's, including but not limited to a human subject's eye that is less than about 150 µl. In some variations, a volume of a liquid formulation described herein is subconjunctivally administered to a rabbit eye or a subject's, including but not limited to a human subject's eye that is any of about 10 µl, about 20 µl, about 30 µl, about 40 µl, about 50 µl, about 60 µl, about 70 µl, about 80 µl, about 90 µl, or about 100 µl. In some variations, a volume of a liquid formulation described herein is subconjunctively administered to a rabbit eye or a subject's, including but not limited to a human subject's eye that is about 10 µl. In some variations, a volume of a liquid formulation described herein is subconjunctivally administered to a rabbit eye or a subject's, including but not limited to a human subject's eye that is about 20 µl. In some variations, a volume of a liquid formulation described herein is subconjunctivally administered to a rabbit eye or a subject's, including but not limited to a human subject's eye that is about 30 µl. In some variations, a volume of a liquid formulation described herein is subconjunctivally administered to a rabbit eye or a subject's, including but not limited to a human subject's eye that is 40 µl. In some variations, a volume of a liquid formulation described herein is subconjunctivally administered to a rabbit eye or a subject's, including but not limited to a human subject's eye that is any of between about 10 µl and about 50 µl, between about 15 µl and about 45 µl, between about 20 µl and about 40 µl, or between about 25 µl and about 35 µl.

In some variations, a total volume of a liquid formulation described herein is subtenonally administered to a rabbit eye or a subject's, including but not limited to a human subject's eye that is less than about 1000 µl, less than about 900 µl, less than about 800 µl, less than about 700 µl, less than about 600 µl, less than about 500 µl, less than about 400 µl, less than about 300 µl, less than about 200 µl, less than about 150 µl, less than about 100 µl, less than about 90 µl, less than about 80 µl, less than about 70 µl, less than about 60 µl, less than about 50 µl, less than about 40 µl, less than about 30 µl, less than about 20 µl, less than about 10 µl, less than about 5 µl, less than about 3 µl, or less than about 1 µl. In some variations, a volume of a liquid formulation described herein is subtenonally administered to a rabbit eye or a subject's, including but not limited to a human subject's eye that is less than about 200 µl. In some variations, a volume of a liquid formulation described herein is subtenonally administered to a rabbit eye or a subject's, including but not limited to a human subject's eye that is less than about 100 µl. In some variations, a volume of a liquid formulation described herein is subtenonally administered to a rabbit eye or a subject's, including but not limited to a human subject's eye that is between about 0.1 µl and about 200 pt, between about 50 µl and about 200 µl, between about 200 µl and about 300 µl, between about 300 µl and about 400 µl, between about 400 µl and about 500 µl, between about 600 µl and about 700 µl, between about 700 µl and about 800 µl, between about 800 µl and about 900 µl, between about 900 µl and about 1000 µl, between about 50 µl and about 150 µl, between about 0.1 µl and about 100 µl, between about 0.1 µl and about 50 µl, between about 1 µl and about 40 µl, between about 1 µl and about 30 µl, between about 1 µl and about 20 µl, between about 1 µl and about 10 µl, or between about 1 µl and about 5 µl. In some variations, a volume of a liquid formulation described herein is subtenonally administered to a rabbit eye or a subject's, including but not limited to a human subject's eye that is between about 10 µl and about 200 µl. In some variations, a volume of a liquid formulation described herein is administered subtenonally to a rabbit eye or a subject's, including but not limited to a human subject's eye that is between about 0.1 µl and about 200 µl. In some variations, a volume of a liquid formulation described herein is subtenonally administered to a rabbit eye or a subject's, including but not limited to a human subject's eye that is between about 50 µl and about 150 µl. In some variations, a volume of a liquid formulation described herein is subtenonally administered to a rabbit eye or a subject's, including but not limited to a human subject's eye that is about 30 µl. In some variations, a volume of a liquid formulation described herein is subtenonally administered to a rabbit eye or a subject's, including but not limited to a human subject's eye that is about 120 µl.

In some variations, a total amount of therapeutic agent less than about 5 mg is administered subtenonally. In some variations, a total amount of therapeutic agent less than about 5.0 mg is administered subtenonally. In some variations, a total amount of therapeutic agent less than about 4.5 mg is administered subtenonally. In some variations, a total amount of therapeutic agent less than about 4.0 mg is administered subtenonally. In some variations, a total amount of therapeutic agent less than about 3.5 mg is administered subtenonally. In some variations, a total amount of therapeutic agent less than about 3.0 mg is administered subtenonally. In some variations, a total amount of therapeutic agent less than about 2.5 mg is administered subtenonally. In some variations, a total amount of therapeutic agent less than about 2 mg is administered subtenonally. In some variations, a total amount of therapeutic agent less than about 1.2 mg is administered subtenonally. In some variations, a total amount of therapeutic agent less than about 1.0 mg is administered subtenonally. In some variations, a total amount of therapeutic agent less than about 0.8 mg is administered subtenonally. In some variations, a total amount of therapeutic agent less than about 0.6 mg is administered subtenonally. In some variations, a total amount of therapeutic agent less than about 0.4 mg is administered subtenonally. In some variations, a volume of a formulation is administered that contains an amount of therapeutic agent described herein.

In some variations, a total amount of therapeutic agent less than about 5 mg is administered subconjunctivally. In some variations, a total amount of therapeutic agent less than about 5.0 mg is administered subconjunctivally. In some variations, a total amount of therapeutic agent less than about 4.5 mg is administered subconjunctivally. In some variations, a total amount of therapeutic agent less than about 4.0 mg is administered subconjunctivally. In some variations, a total amount of therapeutic agent less than about 3.5 mg is administered subconjunctivally. In some variations, a total amount of therapeutic agent less than about 3.0 mg is administered subconjunctivally. In some variations, a total amount of therapeutic agent less than about 2.5 mg is administered subconjunctivally. In some variations, a total amount of therapeutic agent less than about 2 mg is administered subconjunctivally. In some variations, a total amount of therapeutic agent less than about 1.2 mg is administered subconjunctivally. In some variations, a total amount of therapeutic agent less than about 1.0 mg is administered subconjunctivally. In some variations, a total amount of therapeutic agent less than about 0.8 mg is administered subconjunctivally. In some variations, a total amount of therapeutic agent less than about 0.6 mg is administered subconjunctivally. In some variations, a total amount of therapeutic agent less than about 0.4 mg is administered subconjunctivally. In some variations, a volume of a formulation is administered that contains an amount of therapeutic agent described herein.

In some variations, a total amount of therapeutic agent less than about 200 µg is administered intravitreally. In some variations, a total amount of therapeutic agent less than about 200 µg is administered intravitreally. In some variations, a total amount of therapeutic agent less than about 300 µg is administered intravitreally. In some variations, a total amount of therapeutic agent less than about 400 µg is administered intravitreally. In some variations, a total amount of therapeutic agent less than about 500 µg is administered intravitreally. In some variations, a total amount of therapeutic agent less than about 600 µg is administered intravitreally. In some variations, a total amount of therapeutic agent less than about 800 µg is administered intravitreally. In some variations, a total amount of therapeutic agent less than about 1 mg is administered intravitreally. In some variations, a total amount of therapeutic agent less than about 2 mg is administered intravitreally. In some variations, a total amount of therapeutic agent less than about 2.5 mg is administered intravitreally. In some variations, a total amount of therapeutic agent less than about 3 mg is administered intravitreally. In some variations, a total amount of therapeutic agent less than about 3.5 mg is administered intravitreally. In some variations, a total amount of therapeutic agent less than about 4 mg is administered intravitreally. In some variations, a volume of a formulation is administered that contains an amount of therapeutic agent described herein.

In some variations, a total amount of therapeutic agent administered subconjunctivally is any of between about 50 µg and about 3 mg, between about 150 µg and about 750 µg, between about 300 µg and about 1000 µg, between about 300 µg and about 950 µg, between about 400 µg and about 900 µg, between about 450 µg and about 850 µg, between about 500 µg and about 800 µg, between about 550 µg and about 750 µg, or between about 600 µg and about 700 µg. In some variations, a total amount of therapeutic agent administered subconjunctivally is any of about 220 µg, about 440 µg, about 587 µg, about 630 µg, about 660 µg, about 880 µg, about 1320 µg, about 1760 µg, or about 2200 µg. In some variations, a total amount of therapeutic agent administered subconjunctivally is about 220 µg. In some variations, a total amount of therapeutic agent administered subconjunctivally is about 440 µg. In some variations, a total amount of therapeutic agent administered subconjunctivally is about 660 µg. In some variations, a total amount of therapeutic agent administered subconjunctivally is about 880 µg. In some variations, a liquid formulation containing an amount of therapeutic agent of 220 µg is subconjunctivally administered to a human subject by administering about 10 µl of a liquid formulation described herein. In some variations, a liquid formulation containing an amount of therapeutic agent of 440 µg is subconjunctivally administered to a human subject by administering about 20 µl of a liquid formulation described herein. In some variations, a liquid formulation containing an amount of therapeutic agent of 660 µg is subconjunctivally administered to a human subject by administering about 30 µl of a liquid formulation described herein. In some variations, a liquid formulation containing an amount of therapeutic agent of 880 µg is subconjunctivally administered to a human subject by administering about 40 µl of a liquid formulation described herein.

In some variations, a total amount of therapeutic agent administered intravitreally is any of between about 20 µg and about 750 µg, between about 20 µg and about 500 µg, or between about 30 µg and about 200 µg. In some variations, a total amount of therapeutic agent administered intravitreally is any of about 44 µg, about 110 µg, about 132 µg, about 133.5 µg, about 176 µg, about 264 µg, about 352 µg, about 440 µg or about 976 µg. In some variations, a total amount of therapeutic agent administered intravitreally is about 44 µg. In some variations, a total amount of therapeutic agent administered intravitreally is about 110 µg. In some variations, a total amount of therapeutic agent administered intravitreally is about 967 µg. In some variations, a liquid formulation containing an amount of therapeutic agent of 44 µg is intravitreally administered to a human subject by administering about 2 µl of a liquid formulation described herein. In some variations, a liquid formulation containing an amount of therapeutic agent of 110 µg is intravitreally administered to a human subject by administering about 5 µl of a liquid formulation described herein. In some variations, a liquid formulation containing an amount of therapeutic agent of 176 µg is intravitreally administered to a human subject by administering about 8 µl of a liquid formulation described herein.

In some variations, a total volume of a liquid formulation described herein is topically administered to a rabbit eye or a subject's, including but not limited to a human subject's eye that is less than about 1000 µl, less than about 900 µl, less than about 800 µl, less than about 700 µl, less than about 600 µl, less than about 500 µl, less than about 400 µl, less than about 300 µl, less than about 200 µl, less than about 150 µl, less than about 100 µl, less than about 90 µl, less than about 80 µl, less than about 70 µl, less than about 60 µl, less than about 50 µl, less than about 40 µl, less than about 30 µl, less than about 20 µl, less than about 10 µl, less than about 5 µl, less than about 3 µl, or less than about 1 µl. In some variations, a volume of a liquid formulation described herein is topically administered to a rabbit eye or a subject's, including but not limited to a human subject's eye that is less than about 200 µl. In some variations, a volume of a liquid formulation described herein is topically administered to a rabbit eye or a subject's, including but not limited to a human subject's eye that is less than about 100 µl. In some variations, a volume of a liquid formulation described herein is topically administered to a rabbit eye or a subject's, including but not limited to a human subject's eye that is between about 0.1 µl and about 200 µl, between about 50 µl and about 200 µl, between about 200 µl and about 300 µl, between about 300 µl and about 400 µl, between about 400 µl and about 500 µl, between about 600 µl and about 700 µl, between about 700 µl and about 800 µl, between about 800 µl and about 900 µl, between about 900 µl and about 1000 µl, between about 50 µl and about 150 µl, between about 0.1 µl and about 100 µl, between about 0.1 µl and about 50 µl, between about 1 µl and about 40 µl, between about 1 µl and about 30 µl, between about 1 µl and about 20 µl, between about 1 µl and about 10 µl, or between about 1 µl and about 5 µl. In some variations, a total volume of a liquid formulation described herein is topically administered to a rabbit eye or a subject's, including but not limited to a human subject's eye that is between about 10 µl and about 200 µl. In some variations, a total volume of a liquid formulation described herein is administered topically to a rabbit eye or a subject's, including but not limited to a human subject's eye that is between about 0.1 µl and about 200 µl. In some variations, a total volume of a liquid formulation described herein is topically administered to a rabbit eye or a subject's, including but not limited to a human subject's eye that is between about 40 µl and about 160 µl. In some variations, a total volume of a liquid formulation described herein is topically administered to a rabbit eye or a subject's, including but not limited to a human subject's eye that is about 40 µl. In some variations, a total volume of a liquid formulation described herein is topically administered to a rabbit eye or a subject's, including but not limited to a human subject's eye that is about 80 µl.

In some variations, a total amount of therapeutic agent less than about 5 mg is administered topically. In some variations, a total amount of therapeutic agent less than about 5.0 mg is administered topically. In some variations, a total amount of therapeutic agent less than about 4.5 mg is administered topically. In some variations, a total amount of therapeutic agent less than about 4.0 mg is administered topically. In some variations, a total amount of therapeutic agent less than about 3.5 mg is administered topically. In some variations, a total amount of therapeutic agent less than about 3.0 mg is administered topically. In some variations, a total amount of therapeutic agent less than about 2.5 mg is administered topically. In some variations, a total amount of therapeutic agent less than about 2 mg is administered topically. In some variations, a total amount of therapeutic agent less than about 1.2 mg is administered topically. In some variations, a total amount of therapeutic agent less than about 1.0 mg is administered topically. In some variations, a total amount of therapeutic agent less than about 0.8 mg is administered topically. In some variations, a total amount of therapeutic agent less than about 0.6 mg is administered topically. In some variations, a total amount of therapeutic agent less than about 0.4 mg is administered topically. In some variations, a volume of a formulation is administered that contains an amount of therapeutic agent described herein. In some variations, a total amount of therapeutic agent administered topically is any of between about 20 µg and about 4000 µg, between about 10 µg and about 2000 µg, between about 10 µg and 1750 µg, between about 1500 µg and 1000 µg, or between about 10 µg and 1000 µg. In some variations, a total amount of therapeutic agent administered topically is about 1660 µg. In some variations, a total amount of therapeutic agent administered topically is about 880 µg. In some variations, a total amount of therapeutic agent administered topically is 40 µg. In some variations, a total amount of therapeutic agent administered topically is about 28 µg.

In some variations, the therapeutic agent may be a limus compound. In some variations, the therapeutic agent may be rapamycin or an analog or derivative thereof including those described in the Therapeutic Agents section. In some variations, the therapeutic agent is rapamycin. In some variations, the therapeutic agent is dasatinib.

"Total amount of a therapeutic agent" as used herein refers to the total amount of a therapeutic agent administered during a single administration session by a patient and/or physician and/or other medical professional. In some variations, a single administration session will involve a single administration of the therapeutic agent. In some variations, one administration session will include more than one administration of the therapeutic agent. In some variations, one administration session will include a single route of administration. In some variations, one administration session will include multiple routes of administration. Thus, in some variations, portions of the total amount of the therapeutic agent are administered separately during a single administration session. In such variations, the portions of the total amount that are administered separately may be administered by the same and/or different routes of administration. In addition, in some variations, portions of the total amount that are administered separately may be administered in the same and/or different formulations.

"Total volume of a liquid formulation" as used herein refers to the total volume of a liquid formulation administered during a single administration session by a patient and/or physician and/or other medical professional. In some variations, a single administration session will involve a single administration of the liquid formulation. In some variations, one administration session will include more than one administration of the liquid formulation. In some variations, one administration session will include a single route of administration. In some variations, one administration session will include multiple, different routes of administration. Thus, in some variations, portions of the total volume are administered separately during a single administration session. In such variations, the portions of the total volume that are administered separately may be administered by the same and/or by different routes of administration.

In some variations, the liquid formulation is administered in multiple ocular locations. In some variations, the liquid formulation is administered intravitreally and subconjunctivally. In some variations, the liquid formulation is administered intravitreally and subtenonally. In some variations, the liquid formulation is administered subtenonally and subconjunctively. In some variations, the liquid formulation is first administered intravitreally and at least one subsequent administration is administered subconjunctivally. In some variations, the liquid formulation is first administered subconjunctivally and at least one subsequent administration is administered intravitreally. In some variations, the liquid formulation is first administered intravitreally and at least one subsequent administration is administered subtenonally. In some variations, the liquid formulation is first administered subconjunctivally and at least one subsequent administration is administered subtenonally. In some variations, the liquid formulation is first administered subtenonally and at least one subsequent administration is administered subconjunctivally. In some variations, the liquid formulation is first administered subtenonally and at least one subsequent administration is administered intravitreally. In some variations, the liquid formulation is first administered intravitrealy, subconjunctivally, or subtenonally and at least on subsequent administration is topically. In some variations, the first administration induces a drug response, and subsequent administrations maintain the drug response. In some variations, the same (i.e., identical) liquid formulation is used for the different routes of administration, as a nonlimiting example for intravitreal and subconjunctival administration. In some variations, administration to multiple ocular locations occurs during one visit to the physician. In some variations, administration to multiple ocular locations occurs during separate visits to the physician.

In some variations, a therapeutic agent is administered in multiple ocular locations. In some variations, a therapeutic agent is administered intravitreally and subconjunctivally. In some variations, a therapeutic agent is first administered intravitreally and at least one subsequent administration is administered subconjunctivally. In some variations, a therapeutic agent is first administered subconjunctivally and at least one subsequent administration is administered intravitreally. In some variations, a therapeutic agent is first administered intravitreally, subconjunctivally, or subtenonally and at least on subsequent administration is topically. In some variations, the same (i.e., identical) liquid formulation of the therapeutic agent is used for the first and subsequent administrations. In some variations, a different liquid formulation is used for intravitreal and subconjunctival administration for the first and subsequent administrations. In some variations, administration to multiple ocular locations occurs during one visit to the physician. In some variations, administration to multiple ocular locations occurs during separate visits to the physician.

In some variations the liquid formulations described herein are administered in multiple subconjunctival locations within a period of time, including without limitation within an hour of one another. Without being bound by theory, it is thought that such multiple administrations, such as multiple injections, allow for a greater total dose to be administered subconjunctivally than a single dose due to a potentially limited ability of the local ocular tissues to absorb larger volumes.

One liquid formulation described herein is an in situ gelling formulation. In situ gelling formulations, as described herein, comprise a therapeutic agent and a plurality of polymers which give a formulation that forms a gel or a gel-like substance when placed in an aqueous medium, including but not limited to an aqueous medium of the eye.

In some variations of the liquid formulations described herein, the therapeutic agent is a solution or suspension of rapamycin in a liquid medium. Liquid media include but are not limited to solvents, including but not limited to those in the Solubilization of Therapeutic Agents section.

The liquid formulations described herein may comprise a solubilizing agent component. In some variations the solubilizing agent component is a surfactant. Note that there is some overlap between components that may be solvents and solubilizing agents, and therefore the same component may in some systems be used as either a solvent or a solubilizing agent. A liquid formulation that comprises a therapeutic agent and a component that may be considered either a solvent or a solubilizing agent or surfactant will be considered a solvent if it is playing the role of a solvent; if the component is not playing the role of the solvent, the component may be considered a solubilizing agent or surfactant.

Liquid formulations may optionally further comprise stabilizers, excipients, gelling agents, adjuvants, antioxidants, and/or other components as described herein.

In some variations all components in the liquid formulation, other than the therapeutic agent, are liquid at room temperature.

In some variations, the liquid formulation comprises a release modifying agent. In some variations, the release modifying agent is a film-forming polymer component. The film-forming polymer component may comprise one or more film-forming polymers. Any film-forming polymer may be used in the excipient component. In some variations, the film-forming polymer component comprises a water insoluble film forming polymer. In some variations, the release modifying agent component comprises an acrylic polymer, including but not limited to polymethacrylate, including but not limited to Eudragit RL.

Described herein are compositions and liquid formulations for delivery of the therapeutic agents described in the Therapeutic Agents section. Delivery of therapeutic agents using the compositions and liquid formulations described herein may be used to treat, prevent, inhibit, delay the onset of, or cause the regression of the diseases and conditions described in the Diseases and Conditions section. The compositions and liquid formulations described herein may comprise any of the therapeutic agents described in the Therapeutic Agents section, including but not limited to rapamycin. The compositions and liquid formulations described herein may comprise one or more than one therapeutic agent. Other compositions and liquid formulations in addition to those explicitly described herein may be used.

When the therapeutic agent is rapamycin, the compositions and liquid formulations may be used to maintain an amount of rapamycin in the vitreous effective to treat wet AMD. In one nonlimiting example, it is believed that a liquid formulation delivering rapamycin to maintain a concentration of rapamycin of about 10 pg/ml to about 2 µg/ml in the vitreous over a period of time may be used for the treatment of wet AMD. When the rapamycin is in a liquid formulation that forms a non-dispersed mass, the stated concentration of rapamycin represents the amount that is effectively treating the disease or condition of the eye, and not merely present in the form of the non-dispersed mass. In another nonlimiting example, it is believed that a delivery system delivering rapamycin to maintain a concentration of rapamycin of about 0.01 µg/mg to about 10 ng/mg in the retina choroid tissues over a period of time may be used for treatment of wet AMD. Other therapeutically effective amounts of therapeutic agent are also possible, and can be readily determined by one of skill in the art given the teachings herein.

When the therapeutic agent is rapamycin, the compositions and liquid formulations described herein may be used to deliver a dose of rapamycin to a subject, including but not limited to a human subject or to the eye of a subject. In one nonlimiting example, it is believed that a liquid formulation containing a dose of about 20 µg to about 4 mg may be used for the treatment of wet AMD.

In some variations the therapeutic agent in the liquid formulation comprises between about 0.01 to about 30% of the total weight of the composition; between about 0.05 to about 15%; between about 0.1 to about 10%; between about 1 to about 5%; or between about 5 to about 15%; between about 8 to about 10%; between about 0.01 to about 1%; between about 0.05 to about 5%; between about 0.1 to about 0.2%; between about 0.2 to about 0.3%; between about 0.3 to about 0.4%; between about 0.4 to about 0.5%; between about 0.5 to about 0.6%; between about 0.6 to about 0.7%; between about 0.7 to about 1%; between about 1 to about 5%; between about 5 to about 10%; between about 15 to about 30%, between about 20 to about 30%; or between about 25 to about 30%.

In some variations the therapeutic agent in the liquid formulation comprises between about 0.001 to about 1.00% of the total weight of the composition. In some variations the therapeutic agent in the liquid formulation comprises any of about 0.07%, about 0.08%, 0.09%, 0.17%, 1.38%, 1.47%, 2%, 4%, 4.84%, or 5% of the total weight of the composition. In some variations, the therapeutic agent may be a limus compound. In some variations, the therapeutic agent may be rapamycin or an analog or derivative thereof including those described in the Therapeutic Agents section. In some variations, the therapeutic agent is rapamycin. In some variations, the therapeutic agent is dasatinib.

Those of skill in the art, based on the teachings herein can determine what amount or concentration of a given therapeutic agent is equivalent to an amount or concentration of rapamycin by, for example, administering the therapeutic agent at various amounts or concentrations to a disease model system, such as an in vivo or in vivo model system, and comparing the results in the model system relative to the results of various amounts or concentrations of rapamycin. Those of skill in the art, based on the teachings herein can also determine what amount or concentration of a given therapeutic agent is equivalent to an amount or concentration of rapamycin by reviewing the scientific literature for experiments performed comparing rapamycin to other therapeutic agents. It is understood that even the same therapeutic agent may have a different equivalent level of rapamycin when, for example, a different disease or disorder is being evaluated, or a different type of formulation is used. Nonlimiting examples of scientific references with comparative studies of rapamycin and other therapeutic agents on ocular disease are Ohia et al., *Effects of steroids and immunosuppressive drugs on endotoxin-uveitis in rabbits*, J. Ocul. Pharmacol. 8(4):295-307 (1992); Kulkami, *Steroidal and nonsteroidal drugs in endotoxin-induced uveitis*, J. Ocul. Pharmacol. 10(1):329-34 (1994); Hafizi et al., *Differential effects of rapamycin, cyclosporine A, and FK506 on human coronary artery smooth muscle cell proliferation and signaling*, Vascul Pharmacol. 41(4-5):167-76 (2004); and US 2005/0187241.

For example, in a model for wet AMD, if a therapeutic agent is found to be approximately 10-fold less potent or efficacious than rapamycin in the treatment of wet AMD, a concentration of 10 ng/ml of the therapeutic agent would be equivalent to a 1 ng/ml concentration of rapamycin. Or if a therapeutic agent is found to be approximately 10-fold less potent or efficacious than rapamycin in the treatment of wet AMD, a 10-fold amount of the therapeutic agent would be administered relative to the amount of rapamycin.

The solvent component may comprise, for instance, between about 0.01 to about 99.9% of the total weight of the composition; between about 0.1 to about 99%; between about 25 to about 55%; between about 30 to about 50%; or between about 35 to about 45%; between about 0.1 to about 10%; between about 10 to about 20%; between about 20 to about 30%; between about 30 to about 40%; between about 40 to about 45%; between about 40 to about 45%; between about 45 to about 50%; between about 50 to about 60%; between about 50 to about 70%; between about 70 to about 80%; between about 80 to about 90%; or between about 90 to about 100%.

The solubilizing agent component may comprise, for instance, between about 0.01 to about 30% of the total weight of the composition; between about 0.1 to about 20%; between about 2.5 to about 15%; between about 10 to about 15%; or between about 5 to about 10%; between about 8 to about 12%; between about 10 to about 20%; between about 20 to about 30%.

In some variations, the liquid formulations described herein have a viscosity of between 40% and 120% centipoise. In some variations the liquid formulations described herein have a viscosity of between 60% and 80% centipoise.

In some variations the liquid formulations described herein comprise a therapeutic agent and a solvent component. The solvent component may comprise a single solvent or a combination of solvents. The therapeutic agent component may comprise a single therapeutic agent or a combination of therapeutic agents. In some variations, the solvent is glycerin, dimethylsulfoxide, N-methylpyrrolidone, dimethyl acetamide (DMA), dimethyl formamide, glycerol formal, ethoxy diglycol, triethylene glycol dimethyl ether, triacetin, diacetin, corn oil, acetyl triethyl citrate (ATC), ethyl lactate, polyglycolated capryl glyceride, γ butyrolactone, dimethyl isosorbide, benzyl alcohol, ethanol, isopropyl alcohol, polyethylene glycol of various molecular weights, including but not limited to PEG 300 and PEG 400, or propylene glycol, or a mixture of one or more thereof.

In some variations the liquid formulations described herein are solutions, and comprise a therapeutic agent and a solvent component. In some variations the solvent component comprises ethanol. In some variations the solvent component comprises ethanol and a polyethylene glycol, including but not limited to a liquid polyethylene glycol, including but not limited to one or more of PEG 300 or PEG 400.

In some variations the liquid formulations described herein contain no greater than about 250 µl of polyethylene glycol. In some variations the liquid formulations described herein contain no greater than about 250 µl, no greater than about 200 µl, no greater than about 150 µl, no greater than about 125 µl, no greater than about 100 µl, no greater than about 75 µl, no greater than about 50 µl, no greater than about 25 µl, no greater than about 20 µl, no greater than about 15 µl, no greater than about 10 µl, no greater than about 7.5 µl, no greater than about 5 µl, no greater than about 2.5 µl, no greater than about 1.0 µl, or no greater than about 0.5 µl of polyethylene glycol. Formulations containing polyethylene glycol may contain, for example, PEG 300 or PEG 400.

In some variations, the liquid formulations described herein are suspensions, and comprise a therapeutic agent and a diluent component. In some variations, the diluent component comprises one or more components listed herein as solvents or solubilizing agents, wherein the resulting mixture is a suspension.

In some variations the liquid formulation is partly a solution and partly a suspension.

In some variations the liquid formulation is an in situ gelling formulation, and comprises a therapeutic agent and a polymer component, wherein the polymer component may comprise a plurality of polymers. In some variations, the liquid formulation comprises a polymethacrylate polymer. In some variations, the liquid formulation comprises a polyvinylpyrrolidone polymer.

Some variations of liquid formulations include a therapeutic agent or agents such as but not limited to rapamycin between about 0.01% and about 20% by weight of the total, a solvent between about 5% and about 15% by weight of the total, a solubilizing agent including but not limited to a surfactant between about 5% and about 15% by weight of the total, with water as the primary remaining component. In some variations the formulations further comprise stabilizing agents, excipients, adjuvants, or antioxidants, between about 0 and about 40% by weight of the total.

In some variations, a liquid formulation comprises up to about 5% therapeutic agent, including but not limited to rapamycin, per weight of the total; and up to about 99.9% of a solvent component, by weight of the total. In some variations the liquid formulation comprises up to about 5% therapeutic agent, including but not limited to rapamycin, per weight of the total; and up to about 99.9% of a diluent component.

In some variations, a liquid formulation may comprise up to about 5% therapeutic agent, including but not limited to rapamycin, per weight of the total; up to about 10% solvent by weight of the total; and up to about 85% of a solubilizing component, by weight of the total. In some variations the solubilizing component is an aqueous solution of a surfactant.

A plurality of polymers component may comprise, for instance, between about 0.01 to about 30% of the total weight of the composition; between about 0.1 to about 20%; between about 2.5 to about 15%; between about 10 to about 15%; between about 3 to about 5%; between about 5 to about 10%; between about 8 to about 12%; between about 10 to about 20%; or between about 20 to about 30%.

Some variations of liquid formulations includes a therapeutic agent or agents such as but not limited to rapamycin between about 0.01% and about 20% by weight of the total, a solvent component between about 60% and about 98% by weight of the total, and a plurality of polymers, whose combined percentage is between about 0.1% and about 15% by weight of the total. In some variations the formulations further comprise stabilizing agents, excipients, adjuvants, or antioxidants, between about 0 and about 40% by weight of the total.

In some variations, a liquid formulation may comprise about 4% therapeutic agent, including but not limited to rapamycin, per weight of the total; about 91% solvent by weight of the total; and about 5% polymeric component, per weight of the total.

In some variations, the liquid formulation comprises about 2% (w/w) rapamycin, about 4% (w/w) ethanol, and about 94% (w/w) PEG 400. In some variations, liquid formulation is administered by subconjunctival, subtenon, and/or intravitreal injection. In some variations, the liquid formulation is used to treat or prevent an ocular disease. In some variations, the ocular disease is wet AMD. In some variations, the ocular disease is dry AMD. In some variations, the ocular disease is macular edema.

In some variations, the liquid formulation comprises about 1.69% (w/w) rapamycin, about 3.39% (w/w) ethanol, about 79.54% (w/w) PEG 400, and about 15.38% (w/w) aqueous liquid (e.g., water or saline). In some variations, liquid formulation is administered by subconjunctival, subtenon, and/or intravitreal injection. In some variations, the liquid formulation is used to treat or prevent an ocular disease. In some variations, the ocular disease is wet AMD. In some variations, the ocular disease is dry AMD. In some variations, the ocular disease is macular edema.

In some variations, the liquid formulation comprises about 1.47% (w/w) rapamycin, about 2.93% (w/w) ethanol, about 94% (w/w) PEG 400, and about 26.6% (w/w) aqueous liquid (e.g., water or saline). In some variations, liquid formulation is administered by subconjunctival, subtenon, and/or intravitreal injection. In some variations, the liquid formulation is used to treat or prevent an ocular disease. In some variations, the ocular disease is wet AMD. In some variations, the ocular disease is dry AMD. In some variations, the ocular disease is macular edema.

In some variations, the liquid formulation comprises about 1.38% (w/w) rapamycin, about 2.75% (w/w) ethanol, about 64.62% (w/w) PEG 400, and about 31.25% (w/w) aqueous liquid (e.g., water or saline). In some variations, liquid formulation is administered by subconjunctival, subtenon, and/or intravitreal injection. In some variations, the liquid formulation is used to treat or prevent an ocular disease. In some variations, the ocular disease is wet AMD. In some variations, the ocular disease is dry AMD. In some variations, the ocular disease is macular edema.

In some variations the liquid formulations described herein comprise a therapeutic agent and a solvent component. In some variations, the solvent component may comprise a solvent having a hygroscopicity that is equal to or greater than that of polyethylene glycol 400 (PEG 400). In some variations, the solvent component may comprise a solvent having a hygroscopicity that is greater than that of polyethylene glycol 400 (PEG 400). In some variations, the solvent component may comprise a solvent having a hygroscopicity that is about equal to that of polyethylene glycol 400 (PEG 400). In some variations, the solvent component may comprise a solvent having a hygroscopicity that is less than that of polyethylene glycol 400 (PEG 400). In some variations, the liquid formulation is about as hygroscopic as a liquid formulation consisting of 2% rapamycin, 4% ethanol, and 94% PEG 400. In some variations, the liquid formulation is less hygroscopic as a liquid formulation consisting of 2% rapamycin, 4% ethanol, and 94% PEG 400.

In some variations, parameters are used to measure hygroscopicity of a material include, but are not limited to, critical relative humidity (which may be measured by "moisture meters" (e.g., Hygrometers (i.e., Thermo Hygrometer Model 625, manufactured by BK Precision))), hygroscopicity potential, hygroscopicity coefficient, or heats of absorption (which may be measured by a Differential Scanning Calorimetry (DSC). Those of ordinary skill in the art will find it routine to identify solvents having a hygroscopicity that is about equal to, less than, or greater than that of polyethylene glycol 400 (PEG 400) given the teachings herein.

The solvent component may comprise a single solvent or a combination of solvents. The therapeutic agent component may comprise a single therapeutic agent or a combination of therapeutic agents. In some variations, the solvent is N-methylpyrrolidone (NMP), dimethyl-acetamine (DMA), dimethyl sulfoxide (DMSO), propylene glycol (PG), polyethylene glycol 600 (PEG 600), polyethylene glycol 400 (PEG 400), ethanol, or a mixture of one or more thereof. In some variations, the solvent component comprises a combination of solvents including N-methylpyrrolidone (NMP), dimethyl-acetamine (DMA), or dimethyl sulfoxide (DMSO). In some variations, the solvent component comprises a combination of solvents including propylene glycol (PG), polyethylene glycol 600 (PEG 600), or polyethylene glycol 400 (PEG 400). In some variation, the solvent component may comprise a combination of at least two solvents. In some variations, the at least two solvents comprising a first solvent such as N-methylpyrrolidone (NMP), dimethyl-acetamine (DMA), or dimethyl sulfoxide (DMSO) and a second solvent such as propylene glycol (PG), polyethylene glycol 600 (PEG 600), or polyethylene glycol 400 (PEG 400). In some variations, the solvent component may comprise N-methylpyrrolidone (NMP) and propylene glycol (PG). In some variations, the solvent component may comprise N-methylpyrrolidone (NMP) and polyethylene glycol 600 (PEG 600). In some variations, the solvent component may comprise dimethylacetamine (DMA) and propylene glycol (PG). In some variations, the solvent component may comprise dimethyl-acetamine (DMA) and polyethylene glycol 400 (PEG 400). In some variations, the solvent component may comprise dimethyl sulfoxide (DMSO) and propylene glycol (PG). In some variations, the solvent component may comprise N-methylpyrrolidone (NMP) and polyethylene glycol 400 (PEG 400). In some variations, the solvent component may further comprise ethanol. In some variations, the solvent component may further comprise water. In some variations, the solvent component may have a hygroscopicity that is about equal to, less than, or greater than that of polyethylene glycol 400 (PEG 400). In some variations, liquid formulation is administered by subconjunctival, subtenon, and/or intravitreal injection. In some variations, the liquid formulation is used to treat or prevent an ocular disease. In some variations, the ocular disease is wet AMD. In some variations, the ocular disease is dry AMD. In some variations, the ocular disease is macular edema.

In some variations, the solvent is polyethoxylated castor oil (e.g., Cremophor (PEG 35 castor oil)), monoglycerides and/or diglycerides of caprylic acid (e.g., Capmul MCM (C8)), nonionic polymer of the alkyl aryl polyether alcohol (e.g., tyloxapol (ethoxylated p-tert-octylphenol formaldehyde polymer)), 50% phosphatidylcholine in propylene glycol/ethanol carrier (e.g., Phosal® 50PG), propylene glycol monolaurate, propylene glycol dicaprylate/dicaprate, macrogol 15 hydroxystearate, ethanol, or a mixture of one or more thereof. In some variation, the solvent may comprise a combination of at least two solvents. In some variations, the at least two solvents comprising a first solvent such as polyethoxylated castor oil (e.g., Cremophor (PEG 35 castor oil)), propylene glycol monolaurate, propylene glycol dicaprylate/dicaprate, macrogol 15 hydroxystearate, or nonionic polymer of the alkyl aryl polyether alcohol (e.g., tyloxapol (ethoxylated p-tert-octylphenol formaldehyde polymer)) and a second solvent such as monoglycerides and/or diglycerides of caprylic acid (e.g., Capmul MCM (C8)). In some variations, the solvent may further comprise ethanol. In some variations, the solvent may further comprise water. In some variations, liquid formulation is topically administered. In some variations, the liquid formulation is administered as eye drops. In some variations, the liquid formulation is used to treat or prevent an ocular disease. In some variations, the ocular disease is wet AMD. In some variations, the ocular disease is dry AMD. In some variations, the ocular disease is macular edema.

The solvent component may comprise water, for instance, between about 0.01 to about 99.9% of the total weight of the composition; between about 0.1 to about 99%; between about 25 to about 55%; between about 30 to about 50%; or between about 35 to about 45%; between about 0.1 to about 10%; between about 10 to about 20%; between about 20 to about 30%; between about 30 to about 40%; between about 40 to about 45%; between about 40 to about 45%; between about 45 to about 50%; between about 50 to about 60%; between about 50 to about 70%; between about 70 to about 80%; between about 80 to about 90%; or between about 90 to about 100%. In some variations, water comprises between about 15 to about 30% (w/w) of the liquid formulation. In some variations, water comprises between about 80 to about 90% (w/w) of the liquid formulation. In some variations, water comprises at least 15% (w/w). In some variations, water comprises at least 20% (w/w) of the liquid formulation. In some variations, water comprises at least 25% (w/w) of the liquid formulation. In some variations, water comprises at least about 5 percent (w/w) of the liquid formulation. In some variations, water comprises about 16% (w/w) of the liquid formulation. In some variations, water comprises about 22% (w/w). In some variations, water comprises about 28% (w/w) of the liquid formulation. In some variations, water comprises about 83% (w/w) of the liquid formulation.

In some variations the liquid formulations described herein contain no greater than about 250 µl of water. In some variations the liquid formulations described herein contain no greater than about 250 µl, no greater than about 200 µl, no greater than about 150 µl, no greater than about 125 µl, no greater than about 100 µl, no greater than about 75 µl, no greater than about 50 µl, no greater than about 25 µl, no greater than about 20 µl, no greater than about 15 µl, no greater than about 10 µl, no greater than about 7.5 µl, no greater than about 5 µl, no greater than about 2.5 µl, no greater than about 1.0 µl, or no greater than about 0.5 µl of water.

In some variations, the liquid formulations described herein contain no greater than about 250 mg, no greater than about 200 mg, no greater than about 150 mg, no greater than about 125 mg, no greater than about 100 mg, no greater than about 75 mg, no greater than about 50 mg, no greater than about 25 mg, no greater than about 20 mg, no greater than about 15 mg, no greater than about 10 mg, no greater than about 7.5 mg, no greater than about 5 mg, no greater than about 2.5 mg, no greater than about 1.0 mg, or no greater than about 0.5 mg of water.

The solvent component may comprise N-methylpyrrolidone (NMP), for instance, between about 0.01 to about 99.9% of the total weight of the composition; between about 0.1 to about 99%; between about 25 to about 55%; between about 30 to about 50%; or between about 35 to about 45%; between about 0.1 to about 10%; between about 10 to about 20%; between about 20 to about 30%; between about 30 to about 40%; between about 40 to about 45%; between about 40 to about 45%; between about 45 to about 50%; between about 50 to about 60%; between about 50 to about 70%; between about 70 to about 80%; between about 80 to about 90%; or between about 90 to about 100%. In some variations, NMP comprises between about 10 to about 40% (w/w) of the liquid formulation. In some variations, NMP comprises at least 10% (w/w) of the liquid formulation. In some variations, NMP comprises at least 11% (w/w) of the liquid formulation. In some variations, NMP comprises at least 25% (w/w) of the liquid formulation. In some variations, NMP comprises at least 35% (w/w) of the liquid formulation. In some variations, NMP comprises about 10% (w/w) of the liquid formulation. In some variations, NMP comprises about 28% (w/w) of the liquid formulation. In some variations, NMP comprises about 39% (w/w) of the liquid formulation.

In some variations the liquid formulations described herein contain no greater than about 250 µl of N-methylpyrrolidone (NMP). In some variations the liquid formulations described herein contain no greater than about 250 µl, no greater than about 200 µl, no greater than about 150 µl, no greater than about 125 µl, no greater than about 100 µl, no greater than about 75 µl, no greater than about 50 µl, no greater than about 25 µl, no greater than about 20 µl, no greater than about 15 µl, no greater than about 10 µl, no greater than about 7.5 µl, no greater than about 5 µl, no greater than about 2.5 µl, no greater than about 1.0 µl, or no greater than about 0.5 µl of N-methylpyrrolidone (NMP).

In some variations, the liquid formulations described herein contain no greater than about 250 mg, no greater than about 200 mg, no greater than about 150 mg, no greater than about 125 mg, no greater than about 100 mg, no greater than about 75 mg, no greater than about 50 mg, no greater than about 25 mg, no greater than about 20 mg, no greater than about 15 mg, no greater than about 10 mg, no greater than about 7.5 mg, no greater than about 5 mg, no greater than about 2.5 mg, no greater than about 1.0 mg, or no greater than about 0.5 mg of N-methylpyrrolidone (NMP).

The solvent component may comprise dimethyl-acetamine (DMA), for instance, between about 0.01 to about 99.9% of the total weight of the composition; between about 0.1 to about 99%; between about 25 to about 55%; between about 30 to about 50%; or between about 35 to about 45%; between about 0.1 to about 10%; between about 10 to about 20%; between about 20 to about 30%; between about 30 to about 40%; between about 40 to about 45%; between about 40 to about 45%; between about 45 to about 50%; between about 50 to about 60%; between about 50 to about 70%; between about 70 to about 80%; between about 80 to about 90%; or between about 90 to about 100%. In some variations, DMA comprises between about 10 to about 40% (w/w) of the liquid formulation. In some variations, DMA comprises at least 10% (w/w) of the liquid formulation. In some variations, DMA comprises about 15% (w/w) of the liquid formulation. In some variations, DMA comprises about 11% (w/w) of the liquid formulation. In some variations, DMA comprises about 10% (w/w) of the liquid formulation.

In some variations the liquid formulations described herein contain no greater than about 250 µl of dimethyl-acetamine (DMA). In some variations the liquid formulations described herein contain no greater than about 250 µl, no greater than about 200 µl, no greater than about 150 µl, no greater than about 125 µl, no greater than about 100 µl, no greater than about 75 µl, no greater than about 50 µl, no greater than about 25 µl, no greater than about 20 µl, no greater than about 15 µl, no greater than about 10 µl, no greater than about 7.5 µl, no greater than about 5 µl, no greater than about 2.5 µl, no greater than about 1.0 µl, or no greater than about 0.5 µl of dimethyl-acetamine (DMA).

In some variations, the liquid formulations described herein contain no greater than about 250 mg, no greater than about 200 mg, no greater than about 150 mg, no greater than about 125 mg, no greater than about 100 mg, no greater than about 75 mg, no greater than about 50 mg, no greater than about 25 mg, no greater than about 20 mg, no greater than about 15 mg, no greater than about 10 mg, no greater than about 7.5 mg, no greater than about 5 mg, no greater than about 2.5 mg, no greater than about 1.0 mg, or no greater than about 0.5 mg of dimethyl-acetamine (DMA).

The solvent component may comprise dimethyl sulfoxide (DMSO), for instance, between about 0.01 to about 99.9% of the total weight of the composition; between about 0.1 to about 99%; between about 25 to about 55%; between about 30 to about 50%; or between about 35 to about 45%; between about 0.1 to about 10%; between about 10 to about 20%; between about 20 to about 30%; between about 30 to about 40%; between about 40 to about 45%; between about 40 to about 45%; between about 45 to about 50%; between about 50 to about 60%; between about 50 to about 70%; between about 70 to about 80%; between about 80 to about 90%; or between about 90 to about 100%. In some variations, DMSO comprises between about 10 to about 40% (w/w) of the liquid formulation. In some variations, DMSO comprises at least 10% (w/w) of the liquid formulation. In some variations, DMSO comprises at least 11% (w/w) of the liquid formulation. In some variations, DMSO comprises about 10% (w/w) of the liquid formulation.

In some variations the liquid formulations described herein contain no greater than about 250 µl of dimethyl sulfoxide (DMSO). In some variations the liquid formulations described herein contain no greater than about 250 µl, no greater than about 200 µl, no greater than about 150 µl, no greater than about 125 µl, no greater than about 100 µl, no greater than about 75 µl, no greater than about 50 µl, no greater than about 25 µl, no greater than about 20 µl, no greater than about 15 µl, no greater than about 10 µl, no greater than about 7.5 µl, no greater than about 5 µl, no greater than about 2.5 µl, no greater than about 1.0 µl, or no greater than about 0.5 µl of dimethyl sulfoxide (DMSO).

In some variations, the liquid formulations described herein contain no greater than about 250 mg, no greater than about 200 mg, no greater than about 150 mg, no greater than about 125 mg, no greater than about 100 mg, no greater than about 75 mg, no greater than about 50 mg, no greater than about 25 mg, no greater than about 20 mg, no greater than about 15 mg, no greater than about 10 mg, no greater than about 7.5 mg, no greater than about 5 mg, no greater than about 2.5 mg, no greater than about 1.0 mg, or no greater than about 0.5 mg of dimethyl sulfoxide (DMSO).

The solvent component may comprise propylene glycol (PG), for instance, between about 0.01 to about 99.9% of the total weight of the composition; between about 0.1 to about 99%; between about 25 to about 55%; between about 30 to about 50%; or between about 35 to about 45%; between about 0.1 to about 10%; between about 10 to about 20%; between about 20 to about 30%; between about 30 to about 40%; between about 40 to about 45%; between about 40 to about 45%; between about 45 to about 50%; between about 50 to about 60%; between about 50 to about 70%; between about 70 to about 80%; between about 80 to about 90%; or between about 90 to about 100%. In some variations, PG comprises between about 35 to about 75% (w/w) of the liquid formulation. In some variations, PG comprises at least 35% (w/w) of the liquid formulation. In some variations, PG comprises at least 70% (w/w) of the liquid formulation. In some variations, PG comprises less than about 90% (w/w) of the liquid formulation. In some variations, PG comprises about 39% (w/w) of the liquid formulation. In some variations, PG comprises about 74% (w/w) of the liquid formulation.

In some variations the liquid formulations described herein contain no greater than about 250 µl of propylene glycol (PG). In some variations the liquid formulations described herein contain no greater than about 250 µl, no greater than about 200 µl, no greater than about 150 µl, no greater than about 125 µl, no greater than about 100 µl, no greater than about 75 µl, no greater than about 50 µl, no greater than about 25 µl, no greater than about 20 µl, no greater than about 15 µl, no greater than about 10 µl, no greater than about 7.5 µl, no greater than about 5 µl, no greater than about 2.5 µl, no greater than about 1.0 µl, or no greater than about 0.5 µl of propylene glycol (PG).

In some variations, the liquid formulations described herein contain no greater than about 250 mg, no greater than about 200 mg, no greater than about 150 mg, no greater than about 125 mg, no greater than about 100 mg, no greater than about 75 mg, no greater than about 50 mg, no greater than about 25 mg, no greater than about 20 mg, no greater than about 15 mg, no greater than about 10 mg, no greater than about 7.5 mg, no greater than about 5 mg, no greater than about 2.5 mg, no greater than about 1.0 mg, or no greater than about 0.5 mg of propylene glycol (PG).

The solvent component may comprise polyethylene glycol (PEG), for instance, between about 0.01 to about 99.9% of the total weight of the composition; between about 0.1 to about 99%; between about 25 to about 55%; between about 30 to about 50%; or between about 35 to about 45%; between about 0.1 to about 10%; between about 10 to about 20%; between about 20 to about 30%; between about 30 to about 40%; between about 40 to about 45%; between about 40 to about 45%; between about 45 to about 50%; between about 50 to about 60%; between about 50 to about 70%; between about 70 to about 80%; between about 80 to about 90%; or between about 90 to about 100%. In some variations, PEG comprises between about 35 to about 75% (w/w) of the liquid formulation. In some variations, PEG comprises at least 35% (w/w) of the liquid formulation. In some variations, PEG comprises at least 70% (w/w) of the liquid formulation. In some variations, PEG comprises less than about 90% (w/w) of the liquid formulation. In some variations, PEG comprises about 39% (w/w) of the liquid formulation. In some variations, PEG comprises about 74% (w/w) of the liquid formulation. In some variations, PEG comprises about 80% (w/w) of the liquid formulation. In some variations, the PEG is polyethylene glycol 400. In some variations, the PEG is polyethylene glycol 600.

In some variations the liquid formulations described herein contain no greater than about 250 µl of polyethylene glycol. In some variations the liquid formulations described herein contain no greater than about 250 µl, no greater than about 200 µl, no greater than about 150 µl, no greater than about 125 µl, no greater than about 100 µl, no greater than about 75 µl, no greater than about 50 µl, no greater than about 25 µl, no greater than about 20 µl, no greater than about 15 µl, no greater than about 10 µl, no greater than about 7.5 µl, no greater than about 5 µl, no greater than about 2.5 µl, no greater than about 1.0 µl, or no greater than about 0.5 µl of polyethylene glycol. In some variations, the PEG is polyethylene glycol 400. In some variations, the PEG is polyethylene glycol 600.

In some variations, the liquid formulations described herein contain no greater than about 250 mg, no greater than about 200 mg, no greater than about 150 mg, no greater than about 125 mg, no greater than about 100 mg, no greater than about 75 mg, no greater than about 50 mg, no greater than about 25 mg, no greater than about 20 mg, no greater than about 15 mg, no greater than about 10 mg, no greater than about 7.5 mg, no greater than about 5 mg, no greater than about 2.5 mg, no greater than about 1.0 mg, or no greater than about 0.5 mg of polyethylene glycol. In some variations, the PEG is polyethylene glycol 400. In some variations, the PEG is polyethylene glycol 600.

The solvent component may comprise ethanol, for instance, between about 0.01 to about 99.9% of the total weight of the composition; between about 0.1 to about 99%; between about 25 to about 55%; between about 30 to about 50%; or between about 35 to about 45%; between about 0.1 to about 10%; between about 10 to about 20%; between about 20 to about 30%; between about 30 to about 40%; between about 40 to about 45%; between about 40 to about 45%; between about 45 to about 50%; between about 50 to about 60%; between about 50 to about 70%; between about 70 to about 80%; between about 80 to about 90%; or between about 90 to about 100%. In some variations, ethanol comprises less than about 10% (w/w) of the liquid formulation. In some variations, ethanol comprises less than about 5% (w/w) of the liquid formulation. In some variations, ethanol comprises less than about 1% (w/w) of the liquid formulation. In some variations, ethanol comprises less than about 0.5% (w/w) of the liquid formulation. In some variations, ethanol comprises about 5% (w/w) of the liquid formulation. In some variations, ethanol comprises about 2.9% (w/w) of the liquid formulation. In some variations, ethanol comprises about 0.35% (w/w) of the liquid formulation.

In some variations the liquid formulations described herein contain no greater than about 250 µl of ethanol. In some variations the liquid formulations described herein contain no greater than about 250 µl, no greater than about 200 µl, no greater than about 150 µl, no greater than about 125 µl, no greater than about 100 µl, no greater than about 75 µl, no greater than about 50 µl, no greater than about 25 µl, no greater than about 20 µl, no greater than about 15 µl, no greater than about 10 µl, no greater than about 7.5 µl, no greater than about 5 µl, no greater than about 2.5 µl, no greater than about 1.0 µl, or no greater than about 0.5 µl of ethanol.

In some variations, the liquid formulations described herein contain no greater than about 250 mg, no greater than about 200 mg, no greater than about 150 mg, no greater than about 125 mg, no greater than about 100 mg, no greater than about 75 mg, no greater than about 50 mg, no greater than about 25 mg, no greater than about 20 mg, no greater than about 15 mg, no greater than about 10 mg, no greater than about 7.5 mg, no greater than about 5 mg, no greater than about 2.5 mg, no greater than about 1.0 mg, or no greater than about 0.5 mg of ethanol.

The solvent component may comprise polyethoxylated castor oil (e.g., Cremophor (PEG 35 castor oil)), for instance, between about 0.01 to about 99.9% of the total weight of the composition; between about 0.1 to about 99%; between about 25 to about 55%; between about 30 to about 50%; or between about 35 to about 45%; between about 0.1 to about 10%; between about 10 to about 20%; between about 20 to about 30%; between about 30 to about 40%; between about 40 to about 45%; between about 40 to about 45%; between about 45 to about 50%; between about 50 to about 60%; between about 50 to about 70%; between about 70 to about 80%; between about 80 to about 90%; or between about 90 to about 100%. In some variations, polyethoxylated castor oil (e.g., Cremophor (PEG 35 castor oil)) comprises less than about 10% (w/w) of the liquid formulation. In some variations, polyethoxylated castor oil (e.g., Cremophor (PEG 35 castor oil)) comprises about 8.35% (w/w) of the liquid formulation.

In some variations, polyethoxylated castor oil (e.g., Cremophor (PEG 35 castor oil)) comprises about 7.18% (w/w) of the liquid formulation.

In some variations the liquid formulations described herein contain no greater than about 250 µl of polyethoxylated castor oil (e.g., Cremophor (PEG 35 castor oil)). In some variations the liquid formulations described herein contain no greater than about 250 µl, no greater than about 200 µl, no greater than about 150 µl, no greater than about 125 µl, no greater than about 100 µl, no greater than about 75 µl, no greater than about 50 µl, no greater than about 25 µl, no greater than about 20 µl, no greater than about 15 µl, no greater than about 10 µl, no greater than about 7.5 µl, no greater than about 5 µl, no greater than about 2.5 µl, no greater than about 1.0 µl, or no greater than about 0.5 µl of polyethoxylated castor oil (e.g., Cremophor (PEG 35 castor oil)).

In some variations, the liquid formulations described herein contain no greater than about 250 mg, no greater than about 200 mg, no greater than about 150 mg, no greater than about 125 mg, no greater than about 100 mg, no greater than about 75 mg, no greater than about 50 mg, no greater than about 25 mg, no greater than about 20 mg, no greater than about 15 mg, no greater than about 10 mg, no greater than about 7.5 mg, no greater than about 5 mg, no greater than about 2.5 mg, no greater than about 1.0 mg, or no greater than about 0.5 mg of polyethoxylated castor oil (e.g., Cremophor (PEG 35 castor oil)).

The solvent component may comprise monoglycerides and/or diglycerides of caprylic acid (e.g., Capmul MCM (C8)), for instance, between about 0.01 to about 99.9% of the total weight of the composition; between about 0.1 to about 99%; between about 25 to about 55%; between about 30 to about 50%; or between about 35 to about 45%; between about 0.1 to about 10%; between about 10 to about 20%; between about 20 to about 30%; between about 30 to about 40%; between about 40 to about 45%; between about 40 to about 45%; between about 45 to about 50%; between about 50 to about 60%; between about 50 to about 70%; between about 70 to about 80%; between about 80 to about 90%; or between about 90 to about 100%. In some variations, monoglycerides and/or diglycerides of caprylic acid (e.g., Capmul MCM (C8)) comprises less than about 10% (w/w) of the liquid formulation. In some variations, monoglycerides and/or diglycerides of caprylic acid (e.g., Capmul MCM (C8)) comprises about 9.47% (w/w) of the liquid formulation. In some variations, monoglycerides and/or diglycerides of caprylic acid (e.g., Capmul MCM (C8)) comprises about 8.37% (w/w) of the liquid formulation. In some variations, monoglycerides and/or diglycerides of caprylic acid (e.g., Capmul MCM (C8)) comprises about 8.15% (w/w) of the liquid formulation. In some variations, monoglycerides and/or diglycerides of caprylic acid (e.g., Capmul MCM (C8)) comprises about 6.81% (w/w) of the liquid formulation.

In some variations the liquid formulations described herein contain no greater than about 250 µl of monoglycerides and/or diglycerides of caprylic acid (e.g., Capmul MCM (C8)). In some variations the liquid formulations described herein contain no greater than about 250 µl, no greater than about 200 µl, no greater than about 150 µl, no greater than about 125 µl, no greater than about 100 µl, no greater than about 75 µl, no greater than about 50 µl, no greater than about 25 µl, no greater than about 20 µl, no greater than about 15 µl, no greater than about 10 µl, no greater than about 7.5 µl, no greater than about 5 µl, no greater than about 2.5 µl, no greater than about 1.0 µl, or no greater than about 0.5 µl of monoglycerides and/or diglycerides of caprylic acid (e.g., Capmul MCM (C8)).

In some variations, the liquid formulations described herein contain no greater than about 250 mg, no greater than about 200 mg, no greater than about 150 mg, no greater than about 125 mg, no greater than about 100 mg, no greater than about 75 mg, no greater than about 50 mg, no greater than about 25 mg, no greater than about 20 mg, no greater than about 15 mg, no greater than about 10 mg, no greater than about 7.5 mg, no greater than about 5 mg, no greater than about 2.5 mg, no greater than about 1.0 mg, or no greater than about 0.5 mg of monoglycerides and/or diglycerides of caprylic acid (e.g., Capmul MCM (C8)).

The solvent component may comprise nonionic polymer of the alkyl aryl polyether alcohol (e.g., tyloxapol (ethoxylated p-tert-octylphenol formaldehyde polymer)), for instance, between about 0.01 to about 99.9% of the total weight of the composition; between about 0.1 to about 99%; between about 25 to about 55%; between about 30 to about 50%; or between about 35 to about 45%; between about 0.1 to about 10%; between about 10 to about 20%; between about 20 to about 30%; between about 30 to about 40%; between about 40 to about 45%; between about 40 to about 45%; between about 45 to about 50%; between about 50 to about 60%; between about 50 to about 70%; between about 70 to about 80%; between about 80 to about 90%; or between about 90 to about 100%. In some variations, nonionic polymer of the alkyl aryl polyether alcohol (e.g., tyloxapol (ethoxylated p-tert-octylphenol formaldehyde polymer)) comprises less than about 10% (w/w) of the liquid formulation. In some variations, nonionic polymer of the alkyl aryl polyether alcohol (e.g., tyloxapol (ethoxylated p-tert-octylphenol formaldehyde polymer)) comprises about 8.12% (w/w) of the liquid formulation. In some variations, nonionic polymer of the alkyl aryl polyether alcohol (e.g., tyloxapol (ethoxylated p-tert-octylphenol formaldehyde polymer)) comprises about 6.81% (w/w) of the liquid formulation.

In some variations the liquid formulations described herein contain no greater than about 250 µl of nonionic polymer of the alkyl aryl polyether alcohol (e.g., tyloxapol (ethoxylated p-tert-octylphenol formaldehyde polymer)). In some variations the liquid formulations described herein contain no greater than about 250 µl, no greater than about 200 µl, no greater than about 150 µl, no greater than about 125 µl, no greater than about 100 µl, no greater than about 75 µl, no greater than about 50 µl, no greater than about 25 µl, no greater than about 20 µl, no greater than about 15 µl, no greater than about 10 µl, no greater than about 7.5 µl, no greater than about 5 µl, no greater than about 2.5 µl, no greater than about 1.0 µl, or no greater than about 0.5 µl of nonionic polymer of the alkyl aryl polyether alcohol (e.g., tyloxapol (ethoxylated p-tert-octylphenol formaldehyde polymer)).

In some variations, the liquid formulations described herein contain no greater than about 250 mg, no greater than about 200 mg, no greater than about 150 mg, no greater than about 125 mg, no greater than about 100 mg, no greater than about 75 mg, no greater than about 50 mg, no greater than about 25 mg, no greater than about 20 mg, no greater than about 15 mg, no greater than about 10 mg, no greater than about 7.5 mg, no greater than about 5 mg, no greater than about 2.5 mg, no greater than about 1.0 mg, or no greater than about 0.5 mg of nonionic polymer of the alkyl aryl polyether alcohol (e.g., tyloxapol (ethoxylated p-tert-octylphenol formaldehyde polymer)).

The solvent component may comprise 50% phosphatidylcholine in propylene glycol/ethanol carrier (e.g., Phosal® 50PG), for instance, between about 0.01 to about 99.9% of the total weight of the composition; between about 0.1 to about 99%; between about 25 to about 55%; between about 30 to about 50%; or between about 35 to about 45%; between about 0.1 to about 10%; between about 10 to about 20%; between about 20 to about 30%; between about 30 to about 40%; between about 40 to about 45%; between about 40 to about 45%; between about 45 to about 50%; between about 50 to about 60%; between about 50 to about 70%; between about 70 to about 80%; between about 80 to about 90%; or between about 90 to about 100%. In some variations, 50% phosphatidylcholine in propylene glycol/ethanol carrier (e.g., Phosal® 50PG) comprises less than about 10% (w/w) of the liquid formulation. In some variations, 50% phosphatidylcholine in propylene glycol/ethanol carrier (e.g., Phosal® 50PG) comprises less than about 5% (w/w) of the liquid formulation. In some variations, 50% phosphatidylcholine in propylene glycol/ethanol carrier (e.g., Phosal® 50PG) comprises about 3.12% (w/w) of the liquid formulation.

In some variations the liquid formulations described herein contain no greater than about 250 µl of 50% phosphatidylcholine in propylene glycol/ethanol carrier (e.g., Phosal® 50PG). In some variations the liquid formulations described herein contain no greater than about 250 µl, no greater than about 200 µl, no greater than about 150 µl, no greater than about 125 µl, no greater than about 100 µl, no greater than about 75 µl, no greater than about 50 µl, no greater than about 25 µl, no greater than about 20 µl, no greater than about 15 µl, no greater than about 10 µl, no greater than about 7.5 µl, no greater than about 5 µl, no greater than about 2.5 µl, no greater than about 1.0 µl, or no greater than about 0.5 µl of 50% phosphatidylcholine in propylene glycol/ethanol carrier (e.g., Phosal® 50PG).

In some variations, the liquid formulations described herein contain no greater than about 250 mg, no greater than about 200 mg, no greater than about 150 mg, no greater than about 125 mg, no greater than about 100 mg, no greater than about 75 mg, no greater than about 50 mg, no greater than about 25 mg, no greater than about 20 mg, no greater than about 15 mg, no greater than about 10 mg, no greater than about 7.5 mg, no greater than about 5 mg, no greater than about 2.5 mg, no greater than about 1.0 mg, or no greater than about 0.5 mg of 50% phosphatidylcholine in propylene glycol/ethanol carrier (e.g., Phosal® 50PG).

The solvent component may comprise propylene glycol monolaurate, for instance, between about 0.01 to about 99.9% of the total weight of the composition; between about 0.1 to about 99%; between about 25 to about 55%; between about 30 to about 50%; or between about 35 to about 45%; between about 0.1 to about 10%; between about 10 to about 20%; between about 20 to about 30%; between about 30 to about 40%; between about 40 to about 45%; between about 40 to about 45%; between about 45 to about 50%; between about 50 to about 60%; between about 50 to about 70%; between about 70 to about 80%; between about 80 to about 90%; or between about 90 to about 100%. In some variations, propylene glycol monolaurate comprises less than about 10% (w/w) of the liquid formulation. In some variations, propylene glycol monolaurate comprises less than about 5% (w/w) of the liquid formulation. In some variations, propylene glycol monolaurate comprises about 3.12% (w/w) of the liquid formulation.

In some variations the liquid formulations described herein contain no greater than about 250 µl of propylene glycol monolaurate. In some variations the liquid formulations described herein contain no greater than about 250 µl, no greater than about 200 µl, no greater than about 150 µl, no greater than about 125 µl, no greater than about 100 µl, no greater than about 75 µl, no greater than about 50 µl, no greater than about 25 µl, no greater than about 20 µl, no greater than about 15 µl, no greater than about 10 µl, no greater than about 7.5 µl, no greater than about 5 µl, no greater than about 2.5 µl, no greater than about 1.0 µl, or no greater than about 0.5 µl of propylene glycol monolaurate.

In some variations, the liquid formulations described herein contain no greater than about 250 mg, no greater than about 200 mg, no greater than about 150 mg, no greater than about 125 mg, no greater than about 100 mg, no greater than about 75 mg, no greater than about 50 mg, no greater than about 25 mg, no greater than about 20 mg, no greater than about 15 mg, no greater than about 10 mg, no greater than about 7.5 mg, no greater than about 5 mg, no greater than about 2.5 mg, no greater than about 1.0 mg, or no greater than about 0.5 mg of propylene glycol monolaurate.

The solvent component may comprise propylene glycol dicaprylate/dicaprate, for instance, between about 0.01 to about 99.9% of the total weight of the composition; between about 0.1 to about 99%; between about 25 to about 55%; between about 30 to about 50%; or between about 35 to about 45%; between about 0.1 to about 10%; between about 10 to about 20%; between about 20 to about 30%; between about 30 to about 40%; between about 40 to about 45%; between about 40 to about 45%; between about 45 to about 50%; between about 50 to about 60%; between about 50 to about 70%; between about 70 to about 80%; between about 80 to about 90%; or between about 90 to about 100%. In some variations, propylene glycol dicaprylate/dicaprate comprises less than about 10% (w/w) of the liquid formulation. In some variations, propylene glycol dicaprylate/dicaprate comprises less than about 5% (w/w) of the liquid formulation. In some variations, propylene glycol dicaprylate/dicaprate comprises about 3.12% (w/w) of the liquid formulation.

In some variations the liquid formulations described herein contain no greater than about 250 µl of propylene glycol dicaprylate/dicaprate. In some variations the liquid formulations described herein contain no greater than about 250 µl, no greater than about 200 µl, no greater than about 150 µl, no greater than about 125 µl, no greater than about 100 µl, no greater than about 75 µl, no greater than about 50 µl, no greater than about 25 µl, no greater than about 20 µl, no greater than about 15 µl, no greater than about 10 µl, no greater than about 7.5 µl, no greater than about 5 µl, no greater than about 2.5 µl, no greater than about 1.0 µl, or no greater than about 0.5 µl of propylene glycol dicaprylate/dicaprate.

In some variations, the liquid formulations described herein contain no greater than about 250 mg, no greater than about 200 mg, no greater than about 150 mg, no greater than about 125 mg, no greater than about 100 mg, no greater than about 75 mg, no greater than about 50 mg, no greater than about 25 mg, no greater than about 20 mg, no greater than about 15 mg, no greater than about 10 mg, no greater than about 7.5 mg, no greater than about 5 mg, no greater than about 2.5 mg, no greater than about 1.0 mg, or no greater than about 0.5 mg of propylene glycol dicaprylate/dicaprate.

The solvent component may comprise macrogol 15 hydroxystearate, for instance, between about 0.01 to about 99.9% of the total weight of the composition; between about 0.1 to about 99%; between about 25 to about 55%; between about 30 to about 50%; or between about 35 to about 45%; between about 0.1 to about 10%; between about 10 to about 20%; between about 20 to about 30%; between about 30 to about 40%; between about 40 to about 45%; between about 40 to about 45%; between about 45 to about 50%; between about 50 to about 60%; between about 50 to about 70%; between about 70 to about 80%; between about 80 to about 90%; or between about 90 to about 100%. In some variations, macrogol 15 hydroxystearate comprises less than about 10%

(w/w) of the liquid formulation. In some variations, macrogol 15 hydroxystearate comprises less than about 5% (w/w) of the liquid formulation. In some variations, macrogol 15 hydroxystearate comprises about 3.12% (w/w) of the liquid formulation.

In some variations the liquid formulations described herein contain no greater than about 250 µl of macrogol 15 hydroxystearate. In some variations the liquid formulations described herein contain no greater than about 250 µl, no greater than about 200 µl, no greater than about 150 µl, no greater than about 125 µl, no greater than about 100 µl, no greater than about 75 µl, no greater than about 50 µl, no greater than about 25 µl, no greater than about 20 µl, no greater than about 15 µl, no greater than about 10 µl, no greater than about 7.5 µl, no greater than about 5 µl, no greater than about 2.5 µl, no greater than about 1.0 µl, or no greater than about 0.5 µl of macrogol 15 hydroxystearate.

In some variations, the liquid formulations described herein contain no greater than about 250 mg, no greater than about 200 mg, no greater than about 150 mg, no greater than about 125 mg, no greater than about 100 mg, no greater than about 75 mg, no greater than about 50 mg, no greater than about 25 mg, no greater than about 20 mg, no greater than about 15 mg, no greater than about 10 mg, no greater than about 7.5 mg, no greater than about 5 mg, no greater than about 2.5 mg, no greater than about 1.0 mg, or no greater than about 0.5 mg of macrogol 15 hydroxystearate.

In some variations, the liquid formulation contains a solvent component comprising about 10.5% of NMP, about 73.7% of propylene glycol, and about 15.8% of water. In some variations, the liquid formulation contains a solvent component comprising about 38.9% of NMP, about 38.9% of propylene glycol, and about 22.2% of water. In some variations, the liquid formulation contains a solvent component comprising about 10.5% of NMP, about 73.7% of PEG600, and about 15.8% of water. In some variations, the liquid formulation contains a solvent component comprising about 10.5% of DMA, about 73.7% of propylene glycol, and about 15.8% of water. In some variations, the liquid formulation contains a solvent component comprising about 10.5% of DMSO, about 73.7% of propylene glycol, and about of 15.8% water. In some variations, the liquid formulation contains a solvent component comprising about 27.9% of NMP, about 39% of PEG400, and about 28.4% of water. In some variations, the liquid formulation further contains a therapeutic agent. In some variations, the therapeutic agent is less than or equal to about 5% of the total weight of the liquid formulation. In some variations, the therapeutic agent is less than any of about 5%, 4%, 3%, 2%, or 1% of the total weight of the liquid formulation. In some variations, liquid formulation is administered by subconjunctival, subtenon, and/or intravitreal injection. In some variations, the liquid formulation is used to treat or prevent an ocular disease. In some variations, the ocular disease is wet AMD. In some variations, the ocular disease is dry AMD. In some variations, the ocular disease is macular edema.

In some variations, the liquid formulation contains about 8.35% of polyethoxylated castor oil (e.g., Cremophor (PEG 35 castor oil)), about 8.37% of monoglycerides and/or diglycerides of caprylic acid (e.g., Capmul MCM (C8)), about 0.07% of therapeutic agent, and about 83.21% of aqueous liquid (e.g., water or saline). In some variations, the liquid formulation contains about 8.15% of monoglycerides and/or diglycerides of caprylic acid (e.g., Capmul MCM (C8)), about 8.12% of nonionic polymer of the alkyl aryl polyether alcohol (e.g., tyloxapol (ethoxylated p-tert-octylphenol formaldehyde polymer)), about 0.09% of therapeutic agent, about 0.35% of Ethanol, and about 83.29% of aqueous liquid (e.g., water or saline). In some variations, the liquid formulation contains about 6.81% of nonionic polymer of the alkyl aryl polyether alcohol (e.g., tyloxapol (ethoxylated p-tert-octylphenol formaldehyde polymer)), about 6.81% of monoglycerides and/or diglycerides of caprylic acid (e.g., Capmul MCM (C8)), about 0.08% therapeutic agent, about 3.12% of 50% phosphatidylcholine in propylene glycol/ethanol carrier (e.g., Phosal® 50PG), and about 83.21% aqueous liquid (e.g., water or saline). In some variations, the liquid formulation contains about 7.18% of polyethoxylated castor oil (e.g., Cremophor (PEG 35 castor oil)), about 9.47% of monoglycerides and/or diglycerides of caprylic acid (e.g., Capmul MCM (C8)), about 0.17% of therapeutic agent, and about 83.18% of aqueous liquid (e.g., water or saline). In some variations the therapeutic agent is rapamycin. In some variations, the therapeutic agent is dasatinib. In some variations, liquid formulation is topically administered. In some variations, the liquid formulation is administered as eye drops. In some variations, the liquid formulation is used to treat or prevent an ocular disease. In some variations, the ocular disease is wet AMD. In some variations, the ocular disease is dry AMD. In some variations, the ocular disease is macular edema.

In some variations, any of the liquid formulation described herein may be diluted. In some variations, the liquid formulation may be diluted any of about 5, about 4, about 3, about 2, about 1.9, about 1.8, about 1.7, about 1.6, about 1.5, about 1.4, about 1.3, about 1.2, about 1.1 fold. In some variations, the liquid formulation is diluted 1.5 fold. In some variations, the liquid formulation is dilute about 1.4 fold. In some variations, the liquid formulation is diluted with an aqueous liquid (including, but not limited to, water or saline). In some variations, the liquid formulation is diluted with saline. In some variations, the liquid formulation is diluted with water. Fold dilution, as used herein, refers to the final total volume of the diluted liquid formulation divided by the total volume of undiluted liquid formulation added to make the dilution. For example, a 1.5 fold dilution would result if 500 µl of an undiluted liquid formulation was added to 250 µl of saline to result in a final total volume of the diluted liquid formulation of 750 µl (750 µl of final total volume of the diluted liquid formulation/500 µl of the total volume of undiluted liquid formulation=1.5). In some variations, the dilution is a solution. In some variations, the solution is a clear solution. In some variations, the dilution is a suspension. In some variations, the suspension is a milky suspension. In some variations, the dilution is made prior to distribution to the patient or physician. In some variations, the dilution is made by the patient or physician. In some variations, the dilution is made prior to administration. In some variations, the entire diluted liquid formulation is administered to the subject. In some variations, a portion of the diluted liquid formulation is administered to the subject. In some variations, a portion of the diluted liquid formulation equal to the volume of the undiluted liquid formulation is administered to the subject.

Some examples and variations of liquid formulations described herein were prepared and are listed in Table 1. Depending on their type, the listed formulations are denoted one or more of solutions ("S"), suspensions ("SP"), emulsions ("E") or in situ gelling ("ISG"). Median particle size is listed for some of the suspensions. As described herein, some liquid formulations form a non-dispersed mass after, for example, injection into an aqueous environment such as the vitreous of an eye. For those formulations injected into the vitreous of a rabbit eye, the right-hand column of Table 1 indicates whether or not a non-dispersed mass (NDM) formed after a specified volume was injected into the vitreous of the rabbit eye.

The following references, each of which is incorporated herein by reference in its entirety, show one or more formulations, including but not limited to rapamycin formulations, and which describe use of rapamycin at various doses and other therapeutic agents for treating various diseases or conditions: U.S. 60/651,790, filed Feb. 9, 2005, titled FORMULATIONS FOR OCULAR TREATMENT; U.S. 60/664,040, filed Feb. 9, 2005, titled LIQUID FORMULATIONS FOR TREATMENT OF DISEASES OR CONDITIONS; U.S. 60/664,119, filed Mar. 21, 2005, titled DRUG DELIVERY SYSTEMS FOR TREATMENT OF DISEASES OR CONDITIONS; U.S. 60/664,306, filed Mar. 21, 2005, titled IN SITU GELLING FORMULATIONS AND LIQUID FORMULATIONS FOR TREATMENT OF DISEASES OR CONDITIONS; U.S. Ser. No. 11/351,844, filed Feb. 9, 2006, titled FORMULATIONS FOR OCULAR TREATMENT; U.S. Ser. No. 11/351,761, filed Feb. 9, 2006, titled LIQUID FORMULATIONS FOR TREATMENT OF DISEASES OR CONDITIONS; US 2005/0187241, and US 2005/0064010.

Liquid Formulations which Form a Non-Dispersed Mass

One class of liquid formulations described herein forms a non-dispersed mass when placed in an aqueous medium. As used herein, a "non-dispersed mass" refers to the structure formed or shape assumed when the liquid formulation is placed into an environment, relative to the environment in which it is placed. Generally, a non-dispersed mass of a liquid formulation is anything other than a homogeneous distribution of the liquid formulation in the surrounding medium. The non-dispersed mass may, for instance, be indicated by visually inspecting the administered liquid formulation and characterizing its appearance relative to the surrounding medium.

In some variations, the aqueous medium is water. In some variations, the water is deionized, distilled, sterile, or tap water, including but not limited to tap water available at the place of business of MacuSight in Union City, Calif.

In some variations, the aqueous medium is an aqueous medium of a subject. In some variations the aqueous medium is an aqueous medium of the eye of a subject, including but not limited to the vitreous of an eye of a subject. In some variations the subject is a human subject. In some variations the subject is a rabbit.

In some variations the liquid formulation forms a non-dispersed mass when exposed to a certain temperature or range of temperatures, including but not limited to about room temperature, about ambient temperature, about 30° C., about 37° C., or about the temperature of the aqueous medium of the subject.

In some variations the liquid formulation forms a non-dispersed mass when exposed to a certain pH or range of pH, including but not limited to a pH between about 6 and about 8.

In some variations, the non-dispersed mass comprises a gel or gel-like substance.

In some variations, the non-dispersed mass comprises a polymer matrix. In some variations, the non-dispersed mass comprises a polymer matrix in which a therapeutic agent is dispersed.

The liquid formulations described herein may generally be of any geometry or shape after administration to a subject or the eye of a subject, including but not limited to a human subject. In some variations, the non-dispersed mass is between about 0.1 and about 5 mm. In some variations, the non-dispersed mass is between about 1 and about 3 mm. The non-dispersed mass-forming liquid formulations may, for instance, appear as a compact spherical mass when administered to the vitreous. In some instances, the liquid formulation may appear as a non-dispersed mass relative to the surrounding medium, wherein the non-dispersed mass is less clearly defined and the geometry is more amorphous than spherical.

The non-dispersed mass-forming liquid formulations described herein may form a non-dispersed mass immediately upon placement in the medium or the non-dispersed mass may form some period of time after placement of the liquid formulation. In some variations the non-dispersed mass forms over the course of about 1, about 2, about 3, about 4, about 5, about 6, or about 7 days. In some variations the non-dispersed mass forms over the course of about 1 week, about 2 weeks, or about 3 weeks.

In some variations, the liquid formulations described herein that form a non-dispersed mass appear as a milky or whitish colored semi-contiguous or semi-solid non-dispersed mass relative to the medium in which it is placed.

One liquid formulation described herein forms a non-dispersed mass which has the form of a solid depot when the formulation is injected into any or all of water, the vitreous of a rabbit eye, or between the sclera and the conjunctiva of a rabbit eye. One liquid formulation described herein forms a non-dispersed mass which has the form of a semi-solid when the formulation is injected into any or all of water, the vitreous of a rabbit eye, or between the sclera and the conjunctiva of a rabbit eye. One liquid formulation described herein forms a non-dispersed mass which has the form of a polymeric matrix when the formulation is injected into any or all of water, the vitreous of a rabbit eye, or between the sclera and the conjunctiva of a rabbit eye. One liquid formulation described herein forms a non-dispersed mass which has the form of a gel, a hydrogel, or a gel-like substance when the formulation is injected into any or all of water, the vitreous of a rabbit eye, or between the sclera and the conjunctiva of a rabbit eye.

In some variations described herein the liquid formulation forms a non-dispersed mass relative to a surrounding medium where the surrounding medium is aqueous. An "aqueous medium" or "aqueous environment" is one that contains at least about 50% water. Examples of aqueous media include but are not limited to water, the vitreous, extracellular fluid, conjunctiva, sclera, between the sclera and the conjunctiva, aqueous humor, gastric fluid, and any tissue or body fluid comprised of at least about 50% of water. Aqueous media include but are not limited to gel structures, including but not limited to those of the conjunctiva and sclera.

In some variations, the liquid formulations described herein form a non-dispersed mass when a test volume of the liquid formulation is placed in the vitreous of a rabbit eye. In some variations the test volume administered to a rabbit eye, and the test volume is equal to the volume of the liquid formulation administered to a subject's, including but not limited to a human subject's eye.

In some variations, the test volume administered to a rabbit eye is equal to the volume administered to the subject's eye multiplied by a scale factor, and the scale factor is equal to the average volume of a rabbit eye divided by the average volume of a subject eye. The "average volume" of an eye, as used herein, refers to the average volume of an eye of a member of similar age of the species under consideration generally, as opposed to the average volume of any particular individual's eye.

In some variations, the test volume administered to the rabbit eye is between about 10 µl and about 50 µl. In some variations, the test volume administered to the rabbit eye is between about 1 µl and about 30 µl. In some variations, the test volume administered to the rabbit eye is between about 50

μl and about 100 μl. In some variations, the test volume administered to the rabbit eye is between about 25 μl and about 75 μl. In some variations, the test volume administered to the rabbit eye is about 30 μl.

In some variations, the liquid formulation that forms a non-dispersed mass when placed in the medium may comprises a therapeutic agent or agents with a concentration of between about 0.01% and about 10% by weight of the total, and a solvent between about 10% and about 99% by weight of the total. In some variations the formulation further comprises a solubilizing agent including but not limited to a surfactant. In some variations the liquid formulation further comprises a stabilizing agent, excipient, adjuvant, or antioxidant, etc., between about 0 and about 40% by weight of the total. In some variations, the therapeutic agent is about 5% by weight of the total, and the solvent component is about 95% by weight of the total.

Whether a liquid formulation exhibits a non-dispersed mass relative to a surrounding medium when present in a subject, including but not limited to a human subject or the eye of a subject may be determined by, for instance, mixing a therapeutic agent with a solvent, administering it to the vitreous of an eye of a subject, including but not limited to a human subject, and comparing the liquid formulation to the surrounding medium.

One liquid formulation that may be used for treating, preventing, inhibiting, delaying the onset of, or causing the regression of the diseases and conditions of a subject, including but not limited to a human subject, is a liquid formulation that forms a non-dispersed mass when placed into the vitreous of a rabbit eye. When used for treating, preventing, inhibiting, delaying the onset of, or causing the regression of the disease or condition of the subject, the liquid formulation is administered to the subject. The liquid formulation may or may not form a non-dispersed mass in the subject. One liquid formulation described herein forms a non-dispersed mass when administered to a subject and forms a non-dispersed mass when administered to a rabbit eye.

Without being bound by theory, it is believed that the low solubility of rapamycin in the vitreous contributes to the formation of a non-dispersed mass by some rapamycin-containing liquid formulations described herein. The vitreous is a clear gel composed almost entirely of water (up to 99%). Without being bound by theory, it is believed that as rapamycin in an injected formulation contacts the vitreous, the rapamycin precipitates.

Without being bound by theory, factors believed to affect the formation of and geometry of a non-dispersed mass include the concentration of rapamycin in the formulation, the viscosity of the formulation, ethanol content of the formulation, and the volume of injection. It is believed that maintaining a higher local concentration of rapamycin after injection of the formulation favors formation of a non-dispersed mass, as opposed to a lower local concentration of rapamycin after injection of the formulation. As volume is increased for a given dose, formation of a non-dispersed mass may become less favorable. Formation of a non-dispersed mass may become more favorable as rapamycin concentration is increased and/or as viscosity is increased. Ethanol content affects both the solubility of the rapamycin in the formulation and the viscosity of the formulation.

In one comparison, 100 μl of a solution of 0.4% rapamycin, 4.0% ethanol, and 95.6% PEG 400 (a 400 μg dose) did not form a non-dispersed mass after injection into a rabbit eye. In contrast, 20 μl of a solution of 2.00% rapamycin, 4.0% ethanol, and 94% PEG 400 (also a 400 μg dose) formed a compact spherical non-dispersed mass after injection into a rabbit eye.

Without being bound by theory, in the latter example, it is hypothesized that formation of the non-dispersed mass occurred as depicted in FIGS. 1A-1C and described as follows. Upon injection, due to its viscosity the liquid formulation formed a spherical globule 100 within the vitreous 110. Ethanol then diffused out of this globule, resulting in localized precipitation 120 of the rapamycin within the globule. Eventually, the polyethylene glycol also diffused out of the globule to leave a solid, compact non-dispersed mass of rapamycin 130.

In some variations, the non-dispersed masses described herein consists of at least about 20%, at least about 30%, at least about 40%, at least about 50%, at least about 60%, at least about 70%, at least about 80%, at least about 90%, or at least about 95% by volume of therapeutic agent when injected into the vitreous of a rabbit eye.

In some variations, upon formation a non-dispersed mass comprising rapamycin, for example, delivers the drug continuously at approximately a constant rate for an extended period of time. Without being bound by theory, it is believed that delivery of rapamycin from a non-dispersed mass in the vitreous depends on dissolution of the rapamycin in the vitreous, which depends in turn on clearance of the drug from the vitreous to other tissues. Without being bound by theory, this release process is believed to maintain a steady-state concentration of rapamycin in the vitreous.

In some variations, formation of a non-dispersed mass reduces the toxicity of the injected liquid formulation compared to an equivalent dose that did not form a non-dispersed mass. In variations in which a liquid formulation injected into the vitreous does not form a non-dispersed mass, the drug (e.g., rapamycin) appears to disperse in the vitreous body. In some variations this may interfere with vision.

In some variations, liquid formulations that are suspensions form a non-dispersed mass upon injection into the vitreous. Formation of a non-dispersed mass from an injected suspension may become more favorable as the suspension particle size increases.

In some variations, it is believed that the liquid formulations will form a visually observable non-dispersed mass when injected into the eye of a subject, including but not limited to a human subject.

In some variations, liquid formulations are believed to form non-dispersed masses when injected subconjunctivally. In some variations it is believed that when subconjunctivally administered the liquid formulation forms a depot in the scleral tissue. That is, it is believed that the therapeutic agent is absorbed into the sclera proximate to the injection site and forms a local concentration of drug in the sclera.

In Situ Gelling Formulations

Described herein are non-dispersed mass-forming liquid formulations which form a gel or gel-like substance when placed in an aqueous medium. In some variations, the non-dispersed mass comprises a gel; in some variations the gel is a hydrogel.

An "in situ gelling formulation," as used herein, refers to a liquid formulation which forms a gel-like non-dispersed mass when the liquid formulation is placed in an aqueous medium, including but not limited to aqueous media that are water, the vitreous of a rabbit eye, and between the sclera and the conjunctiva of a rabbit eye. In some variations, an in situ gelling formulation forms a gel-like non-dispersed mass when placed in tap water.

In some variations, the in situ gelling formulation is a suspension prior to placement in an aqueous medium, and forms a gel in situ upon placement in an aqueous medium. In some variations, the in situ gelling formulation is a solution prior to placement in an aqueous medium, and forms a gel in situ upon placement in an aqueous medium. In some variations, the in situ gelling formulation is an emulsion prior to placement in an aqueous medium, and forms a gel in situ upon placement in an aqueous medium. In some variations a gel-like non-dispersed mass forms after placement of the in situ gelling formulation into an aqueous medium, including but not limited to any or all of water, the vitreous, or between the sclera and the conjunctiva of an eye. In some variations, the in situ gel is formed of a polymer matrix. In some variations a therapeutic agent is dispersed in the polymer matrix.

Described herein are in situ gelling formulations which may be used for treating, preventing, inhibiting, delaying the onset of, or causing the regression of the diseases and conditions of a subject including but not limited to a human subject. When used for treating, preventing, inhibiting, delaying the onset of, or causing the regression of the disease or condition of the subject, the in situ gelling formulation is administered to the subject. One liquid formulation described herein comprises an in situ gelling formulation which forms a non-dispersed mass when administered to a subject and forms a non-dispersed mass when administered to a rabbit eye.

In some variations, the in situ gelling formulation comprises one or more polymers. Described herein are various types of polymers, including polymers which are solvents, polymers which are solubilizing agents, polymers which are release modifying agents, polymers which are stabilizing agents, etc. In some variations, any combination of polymers is used wherein the polymers when combined with the therapeutic agent form any or all of a non-dispersed mass, a gel, a hydrogel, or polymeric matrix when placed in an aqueous medium, including but not limited to any or all of water, the vitreous, or between the sclera and the conjunctiva.

In some variations, the in situ gelling formulation delivers extended release of therapeutic agents to a subject when administered to the subject.

In some variations, the liquid formulation comprises a therapeutic agent and a plurality of polymers, wherein one of the polymers is a polymethacrylate. Polymethacrylates are known by various names and are available in various preparations, including but not limited to polymeric methacrylates, methacrylic acid-ethyl acrylate copolymer (1:1), methacrylic acid-ethyl acrylate copolymer (1:1) dispersion 30 percent, methacrylic acid-methyl methacrylate copolymer (1:1), methacrylic acid-methyl methacrylate copolymer (1:2), acidum methacrylicum et ethylis acrylas polymerisatum 1:1, acidum methacrylicum et ethylis acrylas polymerisatum 1:1 dispersio 30 per centum, acidum methacrylicum et methylis methacrylas polymerisatum 1:1, acidum methacrylicum et methylis methacrylas polymerisatum 1:2, USPNF: ammonio methacrylate copolymer, methacrylic acid copolymer, methacrylic acid copolymer dispersion.

In some variations, one of the polymers is polyvinylpyrrolidone. Polyvinylpyrrolidone is known by various names and is available in various preparations, including but not limited to povidone, povidonum, kollidon; plasdone; poly[1-(2-oxo-1-pyrrolidinyl)ethylene]; polyvidone; PVP; 1-vinyl-2-pyrrolidinone polymer, and 1-Ethenyl-2-pyrrolidinone homopolymer.

One liquid formulation described herein comprises a therapeutic agent and a solvent component. The solvent component may comprise a single solvent or a combination of solvents.

In some variations, the solvent is glycerin, dimethylsulfoxide, N-methylpyrrolidone, ethanol, isopropyl alcohol, polyethylene glycol of various molecular weights, including but not limited to PEG 300 and PEG 400, or propylene glycol, or a mixture of one or more thereof.

In some variations, the solvent is polyethylene glycol. Polyethylene glycol is known by various names and is available in various preparations, including but not limited to macrogels, macrogel 400, macrogel 1500, macrogel 4000, macrogel 6000, macrogel 20000, macrogola, breox PEG; carbowax; carbowax sentry; Hodag PEG; Lipo; Lipoxol; Lutrol E; PEG; Pluriol E; polyoxyethylene glycol, and α-Hydro-ω-hydroxy-poly(oxy-1,2-ethanediyl).

Compositions and Liquid Formulations for Delivery of Therapeutic Agents

The compositions and liquid formulations described herein may be used to deliver amounts of the therapeutic agents effective for treating, preventing, inhibiting, delaying on set of, or causing the regression of the diseases and conditions described in the Diseases and Conditions section. In some variations the compositions and liquid formulations described herein deliver one or more therapeutic agents over an extended period of time.

An "effective amount," which is also referred to herein as a "therapeutically effective amount," of a therapeutic agent for administration as described herein is that amount of the therapeutic agent that provides the therapeutic effect sought when administered to the subject, including but not limited to a human subject. The achieving of different therapeutic effects may require different effective amounts of therapeutic agent. For example, the therapeutically effective amount of a therapeutic agent used for preventing a disease or condition may be different from the therapeutically effective amount used for treating, inhibiting, delaying the onset of, or causing the regression of the disease or condition. In addition, the therapeutically effective amount may depend on the age, weight, and other health conditions of the subject as is well know to those versed in the disease or condition being addressed. Thus, the therapeutically effective amount may not be the same in every subject to which the therapeutic agent is administered.

An effective amount of a therapeutic agent for treating, preventing, inhibiting, delaying the onset of, or causing the regression of a specific disease or condition is also referred to herein as the amount of therapeutic agent effective to treat, prevent, inhibit, delay the onset of, or cause the regression of the disease or condition.

To determine whether a level of therapeutic agent is a "therapeutically effective amount" to treat, prevent, inhibit, delay on set of, or cause the regression of the diseases and conditions described in the Diseases and Conditions section, liquid formulations may be administered in animal models for the diseases or conditions of interest, and the effects may be observed. In addition, dose ranging human clinical trials may be conducted to determine the therapeutically effective amount of a therapeutic agent.

Generally, the therapeutic agent may be formulated in any composition or liquid formulation capable of delivery of a therapeutically effective amount of the therapeutic agent to a subject or to the eye of a subject for the required delivery period. Compositions include liquid formulations.

Solubilization of Therapeutic Agents

One composition or liquid formulation that may be used is a composition or liquid formulation in which the therapeutic agent is dissolved in a solvent component. Generally, any solvent which has the desired effect may be used in which the therapeutic agent dissolves. In some variations the solvent is aqueous. In some variations the solvent is non-aqueous. An "aqueous solvent" is a solvent that contains at least about 50% water.

Generally, any concentration of solubilized therapeutic agent that has the desired effect can be used. The solvent component may be a single solvent or may be a mixture of solvents. The solvent component may be a single solvent or may be a mixture of solvents. Solvents and types of solutions are well known to those versed in such drug delivery technologies. See for example, Remington: The Science and Practice of Pharmacy, Twentieth Edition, Lippincott Williams & Wilkins; 20th edition (Dec. 15, 2000); Ansel's Pharmaceutical Dosage Forms and Drug Delivery Systems, Eighth Edition, Lippincott Williams & Wilkins (August 2004); Handbook Of Pharmaceutical Excipients 2003, American Pharmaceutical Association, Washington, D.C., USA and Pharmaceutical Press, London, UK; and Strickley, solubilizing Excipients in Oral and Injectable Formulations, Pharmaceutical Research, Vol. 21, No. 2, February 2004.

As noted previously, some solvents may also serve as solubilizing agents.

Solvents that may be used include but are not limited to DMSO, ethanol, methanol, isopropyl alcohol; castor oil, propylene glycol, glycerin, polysorbate 80, benzyl alcohol, dimethyl acetamide (DMA), dimethyl formamide (DMF), triacetin, diacetin, corn oil, acetyl triethyl citrate (ATC), ethyl lactate, glycerol formal, ethoxy diglycol (Transcutol, Gattefosse), tryethylene glycol dimethyl ether (Triglyme), dimethyl isosorbide (DMI), γ-butyrolactone, N-Methyl-2-pyrrolidinone (NMP), polyethylene glycol of various molecular weights, including but not limited to PEG 300 and PEG 400, and polyglycolated capryl glyceride (Labrasol, Gattefosse), combinations of any one or more of the foregoing, or analogs or derivatives of any one or more of the foregoing.

In some variations, the solvent is a polyethylene glycol. Polyethylene glycol is known by various names and is available in various preparations, including but not limited to macrogels, macrogel 400, macrogel 1500, macrogel 4000, macrogel 6000, macrogel 20000, macrogola, breox PEG; carbowax; carbowax sentry; Hodag PEG; Lipo; Lipoxol; Lutrol E; PEG; Pluriol E; polyoxyethylene glycol, and α-Hydro-ω-hydroxy-poly(oxy-1,2-ethanediyl).

In some variations the polyethylene glycol is a liquid PEG, and is one or more of PEG 300 or PEG 400.

Other solvents include an amount of a $C_6$-$C_{24}$ fatty acid sufficient to solubilize a therapeutic agent.

Phospholipid solvents may also be used, such as lecithin, phosphatidylcholine, or a mixture of various diglycerides of stearic, palmitic, and oleic acids, linked to the choline ester of phosphoric acid; hydrogenated soy phosphatidylcholine (HSPC), distearoylphosphatidylglycerol (DSPG), L-α-dimyristoylphosphatidylcholine (DMPC), L-α-dimyristoylphosphatidylglycerol (DMPG).

Further examples of solvents include, for example, components such as alcohols, propylene glycol, polyethylene glycol of various molecular weights, propylene glycol esters, propylene glycol esterified with fatty acids such as oleic, stearic, palmic, capric, linoleic, etc; medium chain mono-, di-, or triglycerides, long chain fatty acids, naturally occurring oils, and a mixture thereof. The oily components for the solvent system include commercially available oils as well as naturally occurring oils. The oils may further be vegetable oils or mineral oils. The oils can be characterized as non-surface active oils, which typically have no hydrophile lipophile balance value. Commercially available substances comprising medium chain triglycerides include, but are not limited to, Captex 100, Captex 300, Captex 355, Miglyol 810, Miglyol 812, Miglyol 818, Miglyol 829, and Dynacerin 660. Propylene glycol ester compositions that are commercially available encompass Captex 200 and Miglyol 840, and the like. The commercial product, Capmul MCM, comprises one of many possible medium chain mixtures comprising monoglycerides and diglycerides.

Other solvents include naturally occurring oils such as peppermint oil, and seed oils. Exemplary natural oils include oleic acid, castor oil, safflower seed oil, soybean oil, olive oil, sunflower seed oil, sesame oil, and peanut oil. Soy fatty acids may also be used. Examples of fully saturated non-aqueous solvents include, but are not limited to, esters of medium to long chain fatty acids (such as fatty acid triglycerides with a chain length of about $C_6$ to about $C_{24}$). Hydrogenated soybean oil and other vegetable oils may also be used. Mixtures of fatty acids may be split from the natural oil (for example coconut oil, palm kernel oil, babassu oil, or the like) and refined. In some embodiments, medium chain (about $C_8$ to about $C_{12}$) triglycerides, such as caprilyic/capric triglycerides derived from coconut oil or palm seed oil, may be used. Medium chain mono- and diglycerides may also be used. Other fully saturated non-aqueous solvents include, but are not limited to, saturated coconut oil (which typically includes a mixture of lauric, myristic, palmitic, capric and caproic acids), including those sold under the Miglyol™ trademark from Huls and bearing trade designations 810, 812, 829 and 840). Also noted are the NeoBee™ products sold by Drew Chemicals. Non-aqueous solvents include isopropyl myristate. Examples of synthetic oils include triglycerides and propylene glycol diesters of saturated or unsaturated fatty acids having 6 to 24 carbon atoms such as, for example hexanoic acid, octanoic (caprylic), nonanoic (pelargonic), decanoic (capric), undecanoic, lauric, tridecanoic, tetradecanoic (myristic), pentadecanoic, hexadecanoic (palmitic), heptadecanoic, octadecanoic (stearic), nonadecanoic, heptadecanoic, eicosanoic, heneicosanoic, docosanoic and lignoceric acids, and the like. Examples of unsaturated carboxylic acids include oleic, linoleic and linolenic acids, and the like. The non-aqueous solvent can comprise the mono-, di- and triglyceryl esters of fatty acids or mixed glycerides and/or propylene glycol mono- or diesters wherein at least one molecule of glycerol has been esterified with fatty acids of varying carbon atom length. A non-limiting example of a "non-oil" useful as a solvent is polyethylene glycol.

Exemplary vegetable oils include cottonseed oil, corn oil, sesame oil, soybean oil, olive oil, fractionated coconut oil, peanut oil, sunflower oil, safflower oil, almond oil, avocado oil, palm oil, palm kernel oil, babassu oil, beechnut oil, linseed oil, rape oil and the like. Mono-, di-, and triglycerides of vegetable oils, including but not limited to corn, may also be used.

Polyvinyl pyrrolidone (PVP), cross-linked or not, may also be used as a solvent. Further solvents include but are not limited to $C_6$-$C_{24}$ fatty acids, oleic acid, Imwitor 742, Capmul, F68, F68 (Lutrol), PLURONICS including but not limited to PLURONICS F108, F127, and F68, Poloxamers, Jeffamines), Tetronics, F127; cyclodextrins such as α-cyclodextrin, β-cyclodextrin, hydroxypropyl-β-cyclodextrin, sulfobutylether-β-cyclodextrin (Captisol); CMC, polysorbitan 20, Cavitron, polyethylene glycol of various molecular weights including but not limited to PEG 300 and PEG 400.

Beeswax and d-α-tocopherol (Vitamin E) may also be used as solvents.

In some variations, the solvent is N-methylpyrrolidone (NMP), dimethyl-acetamine (DMA), dimethyl sulfoxide (DMSO), propylene glycol (PG), polyethylene glycol 600 (PEG 600), polyethylene glycol 400 (PEG 400), ethanol, or a mixture of one or more thereof. In some variations, the solvent comprises a combination of solvents including N-methyl pyrrolidone (NMP), dimethyl-acetamine (DMA), or dimethyl sulfoxide (DMSO). In some variations, the solvent comprises a combination of solvents including propylene glycol (PG), polyethylene glycol 600 (PEG 600), or polyethylene glycol 400 (PEG 400). In some variation, the solvent may comprise a combination of at least two solvents. In some variations, the at least two solvents comprising a first solvent such as N-methylpyrrolidone (NMP), dimethyl-acetamine (DMA), or dimethyl sulfoxide (DMSO) and a second solvent such as propylene glycol (PG), polyethylene glycol 600 (PEG 600), or polyethylene glycol 400 (PEG 400). In some variations, the solvent may comprise N-methylpyrrolidone (NMP) and propylene glycol (PG). In some variations, the solvent may comprise N-methylpyrrolidone (NMP) and polyethylene glycol 600 (PEG 600). In some variations, the solvent may comprise dimethyl-acetamine (DMA) and propylene glycol (PG). In some variations, the solvent component may comprise dimethyl-acetamine (DMA) and polyethylene glycol 400 (PEG 400). In some variations, the solvent may comprise dimethyl sulfoxide (DMSO) and propylene glycol (PG). In some variations, the solvent may comprise N-methylpyrrolidone (NMP) and polyethylene glycol 400 (PEG 400). In some variations, the solvent may further comprise ethanol. In some variations, the solvent may further comprise water. In some variations, the solvent may have a hygroscopicity that is about equal to, less than, or greater than that of polyethylene glycol 400 (PEG 400).

In some variations, the solvent is polyethoxylated castor oil (e.g., Cremophor (PEG 35 castor oil)), monoglycerides and/or diglycerides of caprylic acid (e.g., Capmul MCM (C8)), nonionic polymer of the alkyl aryl polyether alcohol (e.g., tyloxapol (ethoxylated p-tert-octylphenol formaldehyde polymer)), Phosal® 50PG, ethanol, or a mixture of one or more thereof. In some variation, the solvent may comprise a combination of at least two solvents. In some variations, the at least two solvents comprising a first solvent such as polyethoxylated castor oil (e.g., Cremophor (PEG 35 castor oil)) or nonionic polymer of the alkyl aryl polyether alcohol (e.g., tyloxapol (ethoxylated p-tert-octylphenol formaldehyde polymer)) and a second solvent such as monoglycerides and/or diglycerides of caprylic acid (e.g., Capmul MCM (C8)). In some variations, the solvent may further comprise 50% phosphatidylcholine in propylene glycol/ethanol carrier (e.g., Phosal® 50PG).

Solvents for use in the liquid formulations can be determined by a variety of methods known in the art, including but not limited to (1) theoretically estimating their solubility parameter values and choosing the ones that match with the therapeutic agent, using standard equations in the field; and (2) experimentally determining the saturation solubility of therapeutic agent in the solvents, and choosing the ones that exhibit the desired solubility.

Solubilization of Rapamycin

Where the therapeutic agent is rapamycin, solvents that may be used for making solutions or suspensions of rapamycin include but are not limited to any solvent described herein, including but not limited to any one or more of DMSO, glycerin, ethanol, methanol, isopropyl alcohol; castor oil, propylene glycol, polyvinylpropylene, glycerin, polysorbate 80, benzyl alcohol, dimethyl acetamide (DMA), dimethyl formamide (DMF), glycerol formal, ethoxy diglycol (Transcutol, Gattefosse), tryethylene glycol dimethyl ether (Triglyme), dimethyl isosorbide (DMI), γ-butyrolactone, N-Methyl-2-pyrrolidinone (NMP), polyethylene glycol of various molecular weights, including but not limited to PEG 300 and PEG 400, and polyglycolated capryl glyceride (Labrasol, Gattefosse).

Further solvents include but are not limited to $C_6$-$C_{24}$ fatty acids, oleic acid, Imwitor 742, Capmul, F68, F68 (Lutrol), PLURONICS including but not limited to PLURONICS F108, F127, and F68, Poloxamers, Jeffamines), Tetronics, F127, beta-cyclodextrin, CMC, polysorbitan 20, Cavitron, softigen 767, captisol, and sesame oil.

Other methods that may be used to dissolve rapamycin are described in Solubilization of Rapamycin, P. Simamora et al. Int'l J. Pharma 213 (2001) 25-29, the contents of which is incorporated herein in its entirety.

As a nonlimiting example, rapamycin can be dissolved in 5% DMSO or methanol in a balanced salt solution. The rapamycin solution can be unsaturated, a saturated or a supersaturated solution of rapamycin. The rapamycin solution can be in contact with solid rapamycin. In one nonlimiting example, rapamycin can be dissolved in a concentration of up to about 400 mg/ml. Rapamycin can also, for example, be dissolved in propylene glycol esterified with fatty acids such as oleic, stearic, palmic, capric, linoleic, etc.

In some variations, the solvent is N-methylpyrrolidone (NMP), dimethyl-acetamine (DMA), dimethyl sulfoxide (DMSO), propylene glycol (PG), polyethylene glycol 600 (PEG 600), polyethylene glycol 400 (PEG 400), ethanol, or a mixture of one or more thereof. In some variations, the solvent comprises a combination of solvents including N-methyl pyrrolidone (NMP), dimethyl-acetamine (DMA), or dimethyl sulfoxide (DMSO). In some variations, the solvent comprises a combination of solvents including propylene glycol (PG), polyethylene glycol 600 (PEG 600), or polyethylene glycol 400 (PEG 400). In some variation, the solvent may comprise a combination of at least two solvents. In some variations, the at least two solvents comprising a first solvent such as N-methylpyrrolidone (NMP), dimethyl-acetamine (DMA), or dimethyl sulfoxide (DMSO) and a second solvent such as propylene glycol (PG), polyethylene glycol 600 (PEG 600), or polyethylene glycol 400 (PEG 400). In some variations, the solvent may comprise N-methylpyrrolidone (NMP) and propylene glycol (PG). In some variations, the solvent may comprise N-methylpyrrolidone (NMP) and polyethylene glycol 600 (PEG 600). In some variations, the solvent may comprise dimethyl-acetamine (DMA) and propylene glycol (PG). In some variations, the solvent component may comprise dimethyl-acetamine (DMA) and polyethylene glycol 400 (PEG 400). In some variations, the solvent may comprise dimethyl sulfoxide (DMSO) and propylene glycol (PG). In some variations, the solvent may comprise N-methylpyrrolidone (NMP) and polyethylene glycol 400 (PEG 400). In some variations, the solvent may further comprise ethanol. In some variations, the solvent may further comprise water. In some variations, the solvent may have a hygroscopicity that is about equal to, less than, or greater than that of polyethylene glycol 400 (PEG 400).

In some variations, the solvent is polyethoxylated castor oil (e.g., Cremophor (PEG 35 castor oil)), monoglycerides and/or diglycerides of caprylic acid (e.g., Capmul MCM (C8)), nonionic polymer of the alkyl aryl polyether alcohol (e.g., tyloxapol (ethoxylated p-tert-octylphenol formaldehyde polymer)), Phosal® 50PG, ethanol, or a mixture of one or more thereof. In some variation, the solvent may comprise a combination of at least two solvents. In some variations, the at least two solvents comprising a first solvent such as polyethoxylated castor oil (e.g., Cremophor (PEG 35 castor oil)) or nonionic polymer of the alkyl aryl polyether alcohol (e.g., tyloxapol (ethoxylated p-tert-octylphenol formaldehyde polymer)) and a second solvent such as monoglycerides and/or diglycerides of caprylic acid (e.g., Capmul MCM (C8)). In some variations, the solvent may further comprise 50% phosphatidylcholine in propylene glycol/ethanol carrier (e.g., Phosal® 50PG). In some variations, the solvent may further comprise ethanol. In some variations, the solvent may further comprise water.

Many other solvents are possible. Those of ordinary skill in the art will find it routine to identify solvents for rapamycin given the teachings herein.

Solubilizing Agents

Generally, any solubilizing agent or combination of solubilizing agents may be used in the liquid formulations described herein.

In some variations, the solubilizing agent is a surfactant or combination of surfactants. Many surfactants are possible. Combinations of surfactants, including combinations of various types of surfactants, may also be used. For instance, surfactants which are nonionic, anionic (i.e. soaps, sulfonates), cationic (i.e. CTAB), zwitterionic, polymeric or amphoteric may be used.

Surfactants that can be used may be determined by mixing a therapeutic agent of interest with a putative solvent and a putative surfactant, and observing the characteristics of the formulation after exposure to a medium.

Examples of surfactants include but are not limited to fatty acid esters or amides or ether analogues, or hydrophilic derivatives thereof; monoesters or diesters, or hydrophilic derivatives thereof; or mixtures thereof; monoglycerides or diglycerides, or hydrophilic derivatives thereof; or mixtures thereof; mixtures having enriched mono- or/and diglycerides, or hydrophilic derivatives thereof; surfactants with a partially derivatized with a hydrophilic moiety; monoesters or diesters or multiple-esters of other alcohols, polyols, saccharides or oligosaccharides or polysaccharides, oxyalkylene oligomers or polymers or block polymers, or hydrophilic derivatives thereof, or the amide analogues thereof; fatty acid derivatives of amines, polyamines, polyimines, aminoalcohols, aminosugars, hydroxyalkylamines, hydroxypolyimines, peptides, polypeptides, or the ether analogues thereof.

Hydrophilic Lipophilic Balance ("HLB") is an expression of the relative simultaneous attraction of a surfactant for water and oil (or for the two phases of the emulsion system being considered).

Surfactants are characterized according to the balance between the hydrophilic and lipophilic portions of their molecules. The hydrophilic-lipophilic balance (HLB) number indicates the polarity of the molecule in an arbitrary range of 1-40, with the most commonly used emulsifiers having a value between 1-20. The HLB increases with increasing hydrophilicity.

Surfactants that may be used include but are not limited to those with an HLB greater than 10, 11, 12, 13 or 14. Examples of surfactants include polyoxyethylene products of hydrogenated vegetable oils, polyethoxylated castor oils or polyethoxylated hydrogenated castor oil, polyoxyethylene-sorbitan-fatty acid esters, polyoxyethylene castor oil derivatives and the like, for example, Nikkol HCO-50, Nikkol HCO-35, Nikkol HCO-40, Nikkol HCO-60 (from Nikko Chemicals Co. Ltd.); Cremophor (from BASF) such as Cremophor RH40, Cremophor RH60, Cremophor EL, TWEENs (from ICI Chemicals) e.g., TWEEN 20, TWEEN 21, TWEEN 40, TWEEN 60, TWEEN 80, TWEEN 81, Cremophor RH 410, Cremophor RH 455 and the like.

The surfactant component may be selected from compounds having at least one ether formed from at least about 1 to 100 ethylene oxide units and at least one fatty alcohol chain having from at least about 12 to 22 carbon atoms; compounds having at least one ester formed from at least about 1 to 100 ethylene oxide units and at least one fatty acid chain having from at least about 12 to 22 carbon atoms; compounds having at least one ether, ester or amide formed from at least about 1 to 100 ethylene oxide units and at least one vitamin or vitamin derivative; and combinations thereof consisting of no more than two surfactants.

Other examples of surfactants include Lumulse GRH-40, TGPS, Polysorbate-80 (TWEEN-80), Polysorbate-20 (TWEEN-20), polyoxyethylene (20) sorbitan mono-oleate), glyceryl glycol esters, polyethylene glycol esters, polyglycolyzed glycerides, and the like, or mixtures thereof; polyethylene sorbitan fatty acid esters, polyoxyethylene glycerol esters, such as Tagat TO, Tagat L, Tagat I, tagat I2 and Tagat 0 (commercially available from Goldschmidt Chemical Co., Essen, Germany); ethylene glycol esters, such as glycol stearate and distearate; propylene glycol esters, such as propylene glycol myristate; glyceryl esters of fatty acids, such as glyceryl stearates and monostearates; sorbitan esters, such as spans and TWEENs; polyglyceryl esters, such as polyglyceryl 4-oleate; fatty alcohol ethoxylates, such as Brij type emulsifiers; ethoxylated propoxylated block copolymers, such as poloxamers; polyethylene glycol esters of fatty acids, such as PEG 300 linoleic glycerides or Labrafil 2125 CS, PEG 300 oleic glycerides or Labrafil M 1944 CS, PEG 400 caprylic/capric glycerides or Labrasol, and PEG 300 caprylic/capric glycerides or Softigen 767; cremophors, such as Cremophor E, polyoxyl 35 castor oil or Cremophor EL, Cremophor EL-P, Cremophor RH 40P, polyoxyl 40 hydrogenated castor oil, Cremophor RH40; polyoxyl 60 hydrogenated castor oil or Cremophor RH 60, glycerol monocaprylate/caprate, such as Campmul CM 10; polyoxyethylated fatty acids (PEG-stearates, PED-laurates, Brij®), polyoxylated glycerides of fatty acid, polyoxylated glycerol fatty acid esters i.e. Solutol HS-15; PEG-ethers (Mirj®), sorbitan derivatives (TWEENs), sorbitan monooleate or Span 20, aromatic compounds (Tritons®), PEG-glycerides (PECEOL™), PEG-PPG (polypropylene glycol) copolymers (PLURONICS including but not limited to PLURONICS F108, F127, and F68, Poloxamers, Jeffamines), Tetronics, Polyglycerines, PEG-tocopherols, PEG-LICOL 6-oleate; propylene glycol derivatives, sugar and polysaccharide alkyl and acyl derivatives (octylsucrose, sucrose stearate, laurolydextran etc.) and/or a mixture thereof; surfactants based on an oleate or laureate ester of a polyalcohol copolymerized with ethylene oxide; Labrasol Gelucire 44/14; polyoxytheylene stearates; saturated polyglycolyzed glycerides; or poloxamers; all of which are commercially available. Polyoxyethylene sorbitan fatty acid esters can include polysorbates, for example, polysorbate 20, polysorbate 40, polysorbate 60, and polysorbate 80. Polyoxyethylene stearates can include polyoxyl 6 stearate, polyoxyl 8 stearate, polyoxyl 12 stearate and polyoxyl 20 stearate. Saturated polyglycolyzed glycerides are, for example, GELUCIRE 44/14 or GELUCIRE™ 50/13 (Gattefosse, Westwood, N.J., U.S.A.). Poloxamers used herein include poloxamer 124 and poloxamer 188.

Surfactants include d-α-tocopheryl polyethylene glycol 1000 succinate (TPGS), polyoxyl 8 stearate (PEG 400 monostearate), polyoxyl 40 stearate (PEG 1750 monostearate) and peppermint oil.

In some variations, the surfactant is polyethoxylated castor oil (e.g., Cremophor (PEG 35 castor oil)).

In some variations, surfactants having an HLB lower than 10 are used. Such surfactants may optionally be used in combination with other surfactants as co-surfactants. Examples of some surfactants, mixtures, and other equivalent compositions having an HLB less than or equal to 10 are propylene glycols, glyceryl fatty acids, glyceryl fatty acid esters, polyethylene glycol esters, glyceryl glycol esters, polyglycolyzed glycerides and polyoxyethyl steryl ethers. Propylene glycol esters or partial esters form the composition of commercial products, such as Lauroglycol FCC, which contains propylene glycol laureate. The commercially available excipient Maisine 35-1 comprises long chain fatty acids, for example glyceryl linoleate. Products, such as Acconon E, which comprise polyoxyethylene stearyl ethers, may also be used. Labrafil M 1944 CS is one example of a surfactant wherein the composition contains a mixture of glyceryl glycol esters and polyethylene glycol esters.

Solubilizing Agents for Rapamycin

Many solubilizing agents may be used for rapamycin, including but not limited to those in the solubilizing agents section above.

In some variations the solubilizing agent is a surfactant. Nonlimiting examples of surfactants that may be used for rapamycin include but are not limited to surfactants with an HLB greater than 10, 11, 12, 13 or 14. One nonlimiting example is Cremophor EL. In some variations, the surfactant is polyethoxylated castor oil (e.g., Cremophor (PEG 35 castor oil)). In some variations, the surfactant may be a polymeric surfactant including but not limited to PLURONICS F108, F127, and F68, and Tetronics. As noted herein, some solvents may also serve as surfactants. Those of ordinary skill in the art will find it routine to identify which solubilizing agents and surfactants may be used for rapamycin given the teachings herein.

Viscosity Modifying Agents

The liquid formulations described herein may be administered with or further comprise a viscosity modifying agent.

One exemplary viscosity modifying agent that may be used is hyaluronic acid. Hyaluronic acid is a glycosaminoglycan. It is made of a repetitive sequence of glucuronic acid and glucosamine. Hyaluronic acid is present in many tissues and organs of the body, and contributes to the viscosity and consistency of such tissues and organs. Hyaluronic acid is present in the eye, including the vitreous of the eye, and along with collagen contributes to the viscosity thereof. The liquid formulations described herein may further comprise or be administered with hyaluronic acid.

Other nonlimiting examples of viscosity modifying agents include polyalkylene oxides, glycerol, carboxymethyl cellulose, sodium alginate, chitosan, dextran, dextran sulfate and collagen. These viscosity modifying agents can be chemically modified.

Other viscosity modifying agents that may be used include but are not limited to carrageenan, cellulose gel, colloidal silicon dioxide, gelatin, propylene carbonate, carbonic acid, alginic acid, agar, carboxyvinyl polymers or carbomers and polyacrylamides, acacia, ester gum, guar gum, gum arabic, ghatti, gum karaya, tragacanth, terra, pectin, tamarind seed, larch arabinogalactan, alginates, locust bean, xanthan gum, starch, veegum, tragacanth, polyvinyl alcohol, gellan gum, hydrocolloid blends, and povidone. Other viscosity modifying agents known in the art can also be used, including but not limited to sodium carboxymethyl cellulose, algin, carageenans, galactomannans, hydropropyl methyl cellulose, hydroxypropyl cellulose, polyethylene glycol, polyvinylpyrrolidone, sodium carboxymethyl chitin, sodium carboxymethyl dextran, sodium carboxymethyl starch, xanthan gum, and zein.

Other Components of Liquid Formulations

The formulations described herein may further comprise various other components such as stabilizers, for example. Stabilizers that may be used in the formulations described herein include but are not limited to agents that will (1) improve the compatibility of excipients with the encapsulating materials such as gelatin, (2) improve the stability (e.g. prevent crystal growth of a therapeutic agent such as rapamycin) of a therapeutic agent such as rapamycin and/or rapamycin derivatives, and/or (3) improve formulation stability. Note that there is overlap between components that are stabilizers and those that are solvents, solubilizing agents or surfactants, and the same component can carry out more than one role.

Stabilizers may be selected from fatty acids, fatty alcohols, alcohols, long chain fatty acid esters, long chain ethers, hydrophilic derivatives of fatty acids, polyvinylpyrrolidones, polyvinylethers, polyvinyl alcohols, hydrocarbons, hydrophobic polymers, moisture-absorbing polymers, and combinations thereof. Amide analogues of the above stabilizers can also be used. The chosen stabilizer may change the hydrophobicity of the formulation (e.g. oleic acid, waxes), or improve the mixing of various components in the formulation (e.g. ethanol), control the moisture level in the formula (e.g. PVP), control the mobility of the phase (substances with melting points higher than room temperature such as long chain fatty acids, alcohols, esters, ethers, amides etc. or mixtures thereof; waxes), and/or improve the compatibility of the formula with encapsulating materials (e.g. oleic acid or wax). Some of these stabilizers may be used as solvents/co-solvents (e.g. ethanol). Stabilizers may be present in sufficient amount to inhibit the therapeutic agent's (such as rapamycin's) crystallization.

Examples of stabilizers include, but are not limited to, saturated, monoenoic, polyenoic, branched, ring-containing, acetylenic, dicarboxylic and functional-group-containing fatty acids such as oleic acid, caprylic acid, capric acid, caproic acid, lauric acid, myristic acid, palmitic acid, stearic acid, behenic acid, linoleic acid, linolenic acid, eicosapentaenoic acid (EPA), DHA; fatty alcohols such as stearyl alcohol, cetyl alcohol, ceteryl alcohol; other alcohols such as ethanol, isopropyl alcohol, butanol; long chain fatty acid esters, ethers or amides such as glyceryl stearate, cetyl stearate, oleyl ethers, stearyl ethers, cetyl ethers, oleyl amides, stearyl amides; hydrophilic derivatives of fatty acids such as polyglyceryl fatty acids, polyethylene glycol fatty acid esters; polyvinylpyrrolidones, polyvinylalcohols (PVAs), waxes, docosahexaenoic acid and de-hydroabietic acid etc.

The formulations described may further contain a gelling agent that alters the texture of the final formulation through formation of a gel.

The therapeutic agents for use as described herein, such as rapamycin, may be subjected to conventional pharmaceutical operations, such as sterilization and compositions containing the therapeutic agent may also contain conventional adjuvants, such as preservatives, stabilizers, wetting agents, emulsifiers, buffers etc. The therapeutic agents may also be formulated with pharmaceutically acceptable excipients for clinical use to produce a pharmaceutical composition. Formulations for ocular administration may be presented as a solution, suspension, particles of solid material, a discrete mass of solid material, incorporated within a polymer matrix, liquid formulations or in any other form for ocular administration. The therapeutic agents may be used to prepare a medicament to treat, prevent, inhibit, delay onset, or cause regression of any of the conditions described herein. In some variations, the therapeutic agents may be used to prepare a medicament to treat any of the conditions described herein.

A composition containing a therapeutic agent such as rapamycin may contain one or more adjuvants appropriate for the indicated route of administration. Adjuvants with which the therapeutic agent may be admixed with include but are not limited to lactose, sucrose, starch powder, cellulose esters of alkanoic acids, stearic acid, talc, magnesium stearate, magnesium oxide, sodium and calcium salts of phosphoric and sulphuric acids, acacia, gelatin, sodium alginate, polyvinylpyrrolidine, and/or polyvinyl alcohol. When a solubilized formulation is required the therapeutic agent may be in a solvent including but not limited to polyethylene glycol of various molecular weights, propylene glycol, carboxymethyl cellulose colloidal solutions, methanol, ethanol, DMSO, corn oil, peanut oil, cottonseed oil, sesame oil, tragacanth gum, and/or various buffers. Other adjuvants and modes of administration are well known in the pharmaceutical art and may be used in the practice of the methods, compositions and liquid formulations described herein. The carrier or diluent may include time delay material, such as glyceryl monostearate or glyceryl distearate alone or with a wax, or other materials well known in the art. The formulations for use as described herein may also include gel formulations, erodible and non-erodible polymers, microspheres, and liposomes.

Other adjuvants and excipients that may be used include but are not limited to $C_8$-$C_{10}$ fatty acid esters such as softigen 767, polysorbate 80, PLURONICS, Tetronics, Miglyol, and Transcutol.

Additives and diluents normally utilized in the pharmaceutical arts can optionally be added to the pharmaceutical composition and the liquid formulation. These include thickening, granulating, dispersing, flavoring, sweetening, coloring, and stabilizing agents, including pH stabilizers, other excipients, anti-oxidants (e.g., tocopherol, BHA, BHT, TBHQ, tocopherol acetate, ascorbyl palmitate, ascorbic acid propyl gallate, and the like), preservatives (e.g., parabens), and the like. Exemplary preservatives include, but are not limited to, benzylalcohol, ethylalcohol, benzalkonium chloride, phenol, chlorobutanol, and the like. Some useful antioxidants provide oxygen or peroxide inhibiting agents for the formulation and include, but are not limited to, butylated hydroxytoluene, butylhydroxyanisole, propyl gallate, ascorbic acid palmitate, α-tocopherol, and the like. Thickening agents, such as lecithin, hydroxypropylcellulose, aluminum stearate, and the like, may improve the texture of the formulation.

In some variations, the therapeutic agent is rapamycin, and the rapamycin is formulated as rapamune in solid or liquid form. In some variations, the rapamune is formulated as an oral dosage.

In addition, a viscous polymer may be added to the suspension, assisting the localization and ease of placement and handling. In some uses of the liquid formulation, a pocket in the sclera may be surgically formed to receive an injection of the liquid formulations. The hydrogel structure of the sclera can act as a rate-controlling membrane. Particles of therapeutic agent substance for forming a suspension can be produced by known methods including but not limited to via ball milling, for example by using ceramic beads. For example, a Cole Parmer ball mill such as Labmill 8000 may be used with 0.8 mm YTZ ceramic beads available from Tosoh or Norstone Inc.

The formulations may conveniently be presented in unit dosage form and may be prepared by conventional pharmaceutical techniques. Such techniques include the step of bringing into association the therapeutic agent and the pharmaceutical carrier(s) or excipient(s). The formulations may be prepared by uniformly and intimately bringing into associate the active ingredient with liquid carriers or finely divided solid carriers or both, and then, if necessary, shaping the product.

In some variations, the formulations described herein are provided in one or more unit dose forms, wherein the unit dose form contains an amount of a liquid formulation described herein that is effective to treat or prevent the disease or condition for which it is being administered. In some variations, the formulations described herein are provided in one or more unit dose forms, wherein the unit dose form contains an amount of a liquid rapamycin formulation described herein that is effective to treat or prevent the disease or condition for which it is being administered.

In some embodiments, the unit dose form is prepared in the concentration at which it will be administered. In some variations, the unit dose form is diluted prior to administration to a subject. In some variations, a liquid formulation described herein is diluted in an aqueous medium prior to administration to a subject. In some variations the aqueous medium is an isotonic medium. In some variations, a liquid formulation described herein is diluted in an non-aqueous medium prior to administration to a subject.

In a further aspect, provided herein are kits comprising one or more unit dose forms as described herein. In some embodiments, the kit comprises one or more of packaging and instructions for use to treat one or more diseases or conditions. In some embodiments, the kit comprises a diluent which is not in physical contact with the formulation or pharmaceutical formulation. In some embodiments, the kit comprises any of one or more unit dose forms described herein in one or more sealed vessels. In some embodiments, the kit comprises any of one or more sterile unit dose forms.

In some variations, the unit dose form is in a container, including but not limited to a sterile sealed container. In some variations the container is a vial, ampule, or low volume applicator, including but not limited to a syringe. In some variations, a low-volume applicator is pre-filled with rapamycin for treatment of an ophthalmic disease or condition, including but not limited to a limus compound for treatment of age-related macular degeneration. Described herein is a pre-filled low-volume applicator pre-filled with a formulation comprising a therapeutic agent, including but not limited to rapamycin. In some variations a low-volume applicator is pre-filled with a solution comprising a therapeutic agent, including but not limited to rapamycin and a polyethylene glycol, and optionally further comprises one or more additional components including but not limited to ethanol. In some variations a pre-filled low-volume applicator is pre-filled with a solution comprising about 2% rapamycin, about 94% PEG-400, about 4% ethanol.

Described herein are kits comprising one or more containers. In some variations a kit comprises one or more low-volume applicators is pre-filled with a formulation described herein comprising a therapeutic agent, including but not limited to formulations comprising rapamycin, formulations comprising rapamycin and a polyethylene glycol, and optionally further comprises one or more additional components including but not limited to ethanol, and formulations in liquid form comprising about 2% rapamycin, about 94% PEG-400, about 4% ethanol. In some variations the kit comprises one or more containers, including but not limited to pre-filled low-volume applicators, with instructions for its use. In a further variation a kit comprises one or more low-volume applicators pre-filled with rapamycin, with instructions for its use in treating a disease or condition of the eye. In some variations, the containers described herein are in a secondary packaging.

Routes of Administration

The compositions, methods, and liquid formulations described herein deliver one or more therapeutic agents to a subject, including but not limited to a human subject.

In some variations, the compositions, methods, and liquid formulations described herein deliver one or more therapeutic agents to an aqueous medium of a human subject.

In some variations, the compositions, methods, and liquid formulations described herein deliver one or more therapeutic agents to an aqueous medium in or proximal to an area where a disease or condition is to be treated, prevented, inhibited, onset delayed, or regression caused.

In some variations, the compositions, methods, and liquid formulations described herein deliver one or more therapeutic agents to an eye of a subject, including the macula and the retina choroid tissues, in an amount and for a duration effective to treat, prevent, inhibit, delay the onset of, or cause the regression of the diseases and conditions described in the Diseases and Conditions section.

"Retina choroid" and "retina choroid tissues," as used herein, are synonymous and refer to the combined retina and choroid tissues of the eye.

As a non-limiting example, the compositions, liquid formulations, and methods described in herein may be administered to the vitreous, aqueous humor, sclera, conjunctiva, between the sclera and conjunctiva, the retina choroid tissues, macula, or other area in or proximate to the eye of a subject, either by direct administration to these tissues or by periocular routes, in amounts and for a duration effective to treat, prevent, inhibit, delay the onset of, or cause the regression of CNV and wet AMD. The effective amounts and durations may be different for each of treating, preventing, inhibiting, delaying the onset of, or causing the regression of CNV and wet AMD, and for each of the different sites of delivery.

Intravitreal administration is more invasive than some other types of ocular procedures. Because of the potential risks of adverse effects, intravitreal administration may not be optimal for treatment of relatively healthy eyes. By contrast, periocular administration, such as subconjunctival administration, is much less invasive than intravitreal administration. When a therapeutic agent is delivered by a periocular route, it may be possible to treat patients with healthier eyes than could be treated using intravitreal administration. In some variations, subconjunctival injection is used to prevent or delay onset of a disease or condition of the eye, where the eye of the subject has visual acuity of 20/40 or better.

"Subconjunctival" placement or injection, as used herein, refers to placement or injection between the sclera and conjunctiva. Subconjunctival is sometimes referred to herein as "sub-conj" administration.

Routes of administration that may be used to administer a liquid formulation include but are not limited to placement of the liquid formulation, for example by injection, into an aqueous medium in the subject, including but not limited to placement, including but not limited to by injection, into the eye of a subject, including but not limited to a human subject. The liquid formulation may be administered systemically, including but not limited to the following delivery routes: rectal, vaginal, infusion, intramuscular, intraperitoneal, intraarterial, intrathecal, intrabronchial, intracisternal, cutaneous, subcutaneous, intradermal, transdermal, intravenous, intracervical, intraabdominal, intracranial, intraocular, intrapulmonary, intrathoracic, intratracheal, nasal, buccal, sublingual, oral, parenteral, or nebulised or aerosolized using aerosol propellants.

Compositions and liquid formulations comprising therapeutic agent can be administered directly to the eye using a variety of procedures, including but not limited to procedures in which (1) the therapeutic agent is administered by injection using a syringe and hypodermic needle, (2) a specially designed device is used to inject the therapeutic agent, (3) prior to injection of the therapeutic agent, a pocket is surgically formed within the sclera to serve as a receptacle for the therapeutic agent or therapeutic agent composition. For example, in one administration procedure a surgeon forms a pocket within the sclera of the eye followed by injection of a solution or liquid formulation comprising the therapeutic agent into the pocket.

Other administration procedures include, but are not limited to procedures in which (1) a formulation of the therapeutic agent is injected through a specially designed curved cannula to place the therapeutic agent directly against a portion of the eye, (2) a compressed form of the therapeutic agent is placed directly against a portion of the eye, (3) the therapeutic agent is inserted into the sclera by a specially designed injector or inserter, (4) the liquid formulation comprising the therapeutic agent is incorporated within a polymer, (5) a surgeon makes a small conjunctival incision through which to pass a suture and any therapeutic agent delivery structure so as to secure the structure adjacent to the sclera, (6) a needle is used for injection directly into the vitreous of an eye, or into any other site described.

The liquid formulations described herein may be used directly, for example, by injection, as an elixir, for topical administration including but not limited to via eye drops, or in hard or soft gelatin or starch capsules. The capsules may be banded to prevent leakage.

In some variations, the liquid formulations described herein may be administered by topical administration. In some variations, the topical administration is ocular topical administration. In some variations, the ocular topical administration includes, but is not limited to, administration via eye drops, contacts, punctual plugs, or other ocular devices. In some variations, the liquid formulation is applied topically, including topically to the eye, any of about 1, 2, 3, 4, or 5 times per day. In some variations, the liquid formulation is applied topically, including topically to the eye, about once or less any of about every 1, 2, 3, 4, 5, 6, 7, 10, 14, 21, or 28 day(s). In some variations, the liquid formulation is applied topically, including topically to the eye, about once or less a day. In some variations, the liquid formulation is applied topically, including topically to the eye, about once or less every 5 days. In some variations, the liquid formulation is applied topically, including topically to the eye, about once or less of every 10 days.

Delivery by Injection

One method that may be used to deliver the compositions and liquid formulations described herein is delivery by injection. In this method compositions and liquid formulations may be injected into a subject, including but not limited to a human subject, or into a position in or proximate to an eye of the subject for delivery to a subject or to the eye of a subject. Injection includes but is not limited to intraocular and periocular injection. Nonlimiting examples of positions that are in or proximate to an eye of a subject are as follows.

Injection of therapeutic agent into the vitreous may provide a high local concentration of therapeutic agent in the vitreous and retina. Further, it has been found that in the vitreous the clearance half-lives of drugs increases with molecular weight.

Intracameral injection, or injection into the anterior chamber of they eye, may also be used. In one example, up to about 100 µl may be injected intracamerally.

Periocular routes of delivery may deliver therapeutic agent to the retina without some of the risks of intravitreal delivery. Periocular routes include but are not limited to subconjunctival, subtenon, retrobulbar, peribulbar and posterior juxtascleral delivery. A "periocular" route of administration means placement near or around the eye. For a description of exemplary periocular routes for retinal drug delivery, see *Periocular routes for retinal drug delivery*, Raghava et al. (2004), Expert Opin. Drug Deliv. 1(1):99-114, which is incorporated herein by reference in its entirety.

In some variations the liquid formulations described herein are administered intraocularly. Intraocular administration includes placement or injection within the eye, including in the vitreous.

Subconjunctival injection may be by injection of therapeutic agent underneath the conjunctiva, or between the sclera and conjunctiva. In one example, up to about 500 µl may be injected subconjunctivally. As one nonlimiting example, a needle of up to about 25 to about 30 gauge and about 30 mm long may be used. Local pressure to the subconjunctival site of therapeutic agent administration may elevate delivery of the therapeutic agent to the posterior segment by reducing local choroidal blood flow.

Subtenon injection may be by injection of therapeutic agent into the tenon's capsule around the upper portion of the eye and into the "belly" of the superior rectus muscle. In one example, up to about 4 ml may be injected subtenon. As one nonlimiting example, a blunt-tipped cannula about 2.5 cm long may be used.

Retrobulbar injection refers to injection into the conical compartment of the four rectus muscles and their intermuscular septa, behind the globe of the eye. In one example, up to about 5 ml may be injected retrobulbarly. As one nonlimiting example, a blunt needle of about 25- or about 27-gauge may be used.

Peribulbar injection may be at a location external to the confines of the four rectus muscles and their intramuscular septa, i.e., outside of the muscle cone. A volume of, for example, up to about 10 ml may be injected peribulbarly. As one nonlimiting example, a blunt-tipped cannula about 1.25 inches long and about 25-gauge may be used.

Posterior juxtascleral delivery refers to placement of a therapeutic agent near and above the macula, in direct contact with the outer surface of the sclera, and without puncturing the eyeball. In one example, up to about 500 ml may be injected posterior juxtasclerally. As one nonlimiting example, a blunt-tipped curved cannula, specially designed at 56°, is used to place the therapeutic agent in an incision in the sclera.

In some variations the liquid formulations described herein are injected intraocularly. Intraocular injection includes injection within the eye.

Sites to which the compositions and liquid formulations may be administered include but are not limited to the vitreous, aqueous humor, sclera, conjunctiva, between the sclera and conjunctiva, the retina choroid tissues, macula, or other area in or proximate to the eye of a subject. Methods that may be used for placement of the compositions and liquid formulations include but are not limited to injection.

In one method that may be used, the therapeutic agent is dissolved in an solvent or solvent mixture and then injected into or proximate to the vitreous, aqueous humor, sclera, conjunctiva, between the sclera and conjunctiva, the retina choroid tissues, macula, other area in or proximate to the eye of a subject, or other medium of a subject, according to any of the procedures mentioned above. In one such method that may be used, the therapeutic agent is rapamycin in a liquid formulation.

When the therapeutic agent is rapamycin, the compositions and liquid formulations may be used to deliver or maintain an amount of rapamycin in tissues of the eye, including without limitation retina, choroid, or the vitreous, which amount is effective to treat AMD. In one nonlimiting example, it is believed that a liquid formulation delivering rapamycin in an amount capable of providing a concentration of rapamycin of about 0.1 pg/ml to about 2 µg/ml in the vitreous may be used for treatment of wet AMD. In some nonlimiting examples, it is believed that a liquid formulation delivering a concentration of rapamycin of about 0.1 µg/mg to about 1 µg/mg in the retina choroid tissues may be used for treatment of wet AMD. Other effective concentrations are readily ascertainable by those of skill in the art based on the teachings described herein.

"Subtenonally administered", as used herein, means administration to the subtenon. In some variations, a therapeutic agent or liquid formulation is subtenonally administered by subtenon injection. In some variations, a therapeutic agent or liquid formulation is subtenonally administered by a means other than subtenon injection.

Method of Preparing Liquid Formulations

One nonlimiting method that may be used for preparing the liquid formulations described herein, including but not limited to liquid formulations comprising rapamycin, is by mixing a solvent and a therapeutic agent together at room temperature or at slightly elevated temperature until a solution or suspension is obtained, with optional use of a sonicator, and then cooling the formulation. Other components including but not limited to those described above may then be mixed with the formulation. Other preparation methods that may be used are described herein including in the examples, and those of skill in the art will be able to select other preparation methods based on the teachings herein.

Extended Delivery of Therapeutic Agents

Described herein are compositions and liquid formulations showing in vivo delivery or clearance profiles with one or more of the following characteristics. The delivery or clearance profiles are for clearance of the therapeutic agent in vivo after injection of the composition or liquid formulations subconjunctivally or into the vitreous of a rabbit eye. In some variations, the delivery or clearance profiles are for clearance of rapamycin in vivo after injection of the composition or liquid formulations subconjunctivally or into the vitreous of a rabbit eye. The volume of the rabbit vitreous is approximately 30-40% of the volume of the human vitreous. The amount of therapeutic agent is measured using techniques as described in Example 2, but without limitation to the formulation and therapeutic agent described in Example 2.

In some variations, the therapeutic agents with the in vivo delivery or clearance profiles described herein include but are not limited to those described in the Therapeutic Agents section. In some variations the therapeutic agent is rapamycin. In some variations, the liquid formulations described herein are used to deliver therapeutic agents in a concentration equivalent to rapamycin. The liquid formulations described herein may comprise any therapeutic agent including but not limited to those in the Therapeutic Agents section, in a concentration equivalent to rapamycin including but not limited to those concentrations described herein including in the examples.

"Average percentage in vivo" level means that an average concentration of therapeutic agent is obtained across multiple rabbit eyes for a given timepoint, and the average concentration of therapeutic agent at one timepoint is divided by the average concentration of therapeutic agent at another timepoint. In some variations of the average percentage in vivo levels, the therapeutic agent is rapamycin.

The average concentration of a therapeutic agent in the tissue of a rabbit eye at a given time after administration of a formulation containing the therapeutic agent may be measured according to the following method. Where volumes below 10 µl are to be injected, a Hamilton syringe is used.

The liquid formulations are stored at a temperature of 2-8° C. prior to use.

The experimental animals are specific pathogen free (SPF) New Zealand White rabbits. A mixed population of about 50% male, about 50% female is used. The rabbits are at least 12 weeks of age, usually at least 14 weeks of age, at the time of dosing. The rabbits each weigh at least 2.2 kg, usually at least 2.5 kg, at the time of dosing. Prior to the study, the animals are quarantined for at least one week and examined for general health parameters. Any unhealthy animals are not used in the study. At least 6 eyes are measured and averaged for a given timepoint.

Housing and sanitation are performed according to standard procedures used in the industry. The animals are provided approximately 150 grams of Teklad Certified Hi-Fiber Rabbit Diet daily, and are provided tap water ad libitum. No contaminants are known to exist in the water and no additional analysis outside that provided by the local water district is performed. Environmental Conditions are monitored.

Each animal undergoes a pre-treatment ophthalmic examination (slit lamp and opthalmoscopy), performed by a board certified veterinary ophthalmologist. Ocular findings are scored according to the McDonald and Shadduck scoring system as described in Dermatoxicology, F. N. Marzulli and H. I. Maibach, 1977 "Eye Irritation," T. O. McDonald and J. A. Shadduck (pages 579-582). Observations are recorded using a standardized data collection sheet. Acceptance criteria for placement on study are as follows: scores of <1 for conjunctival congestion and swelling; scores of 0 for all other observation variables.

Gentamicin ophthalmic drops are placed into both eyes of each animal twice daily on the day prior to dosing, on the day of dosing (Day 1), and on the day after dosing (Day 2). Dosing is performed in two phases, the first including one set of animals and the second including the other animals. Animals are randomized separately into masked treatment groups prior to each phase of dosing according to modified Latin squares. Animals are fasted at least 8 hours prior to injection. The start time of the fast and time of injection are recorded.

Animals are weighed and anesthetized with an intravenous injection of a ketamine/xylazine cocktail (87 mg/mL ketamine, 13 mg/mL xylazine) at a volume of 0.1-0.2 mL/kg. Both eyes of each animal are prepared for injection as follows: approximately five minutes prior to injection, eyes are moistened with an ophthalmic Betadine solution. After five minutes, the Betadine is washed out of the eyes with sterile saline. Proparacaine hydrochloride 0.5% (1-2 drops) is delivered to each eye. For eyes to be intravitreally injected, 1% Tropicamide (1 drop) is delivered to each eye.

On Day 1, both eyes of each animal receive an injection of test or control article. Animals in selected groups are dosed a second time on Day 90±1. Dosing is subconjunctival or intravitreal. Actual treatments, injection locations, and dose volumes are masked and revealed at the end of the study.

Subconjunctival injections are given using an insulin syringe and 30 gauge×½-inch needle. The bulbar conjunctiva in the dorsotemporal quadrant is elevated using forceps. Test article is injected into the subconjunctival space.

Intravitreal injections are given using an Insulin syringe and 30 gauge×½-inch needle. For each injection, the needle is introduced through the ventral-nasal quadrant of the eye, approximately 2-3 mm posterior to the limbus, with the bevel of the needle directed downward and posteriorly to avoid the lens. Test article is injected in a single bolus in the vitreous near the retina.

Animals are observed for mortality/morbidity twice daily. An animal determined to be moribund is euthanized with an intravenous injection of commercial euthanasia solution. Both eyes are removed and stored frozen at −70° C. for possible future evaluation. If an animal is found dead prior to onset of rigor mortis, both eyes are removed and stored frozen at −70° C. for possible future evaluation. Animals found after the onset of rigor mortis are not necropsied.

Animals are weighed at randomization, on Day 1 prior to dosing, and prior to euthanasia.

Ophthalmic observations (slit lamp and indirect opthalmoscopy) are performed on all animals on Days 5±1, 30±1, 60±1, 90±1, and at later dates in some variations. Observations are performed by a board certified veterinary ophthalmologist. For animals to be dosed on Day 90±1, ophthalmic observations are performed prior to dosing. Ocular findings are scored according to the McDonald and Shadduck scoring system as described in Dermatoxicology, F. N. Marzulli and H. I. Maibach, 1977 "Eye Irritation", T. O. McDonald and J. A. Shadduck (pages 579-582), and observations are recorded using a standardized data collection sheet.

Whole blood samples (1-3 mL per sample) are collected from each animal prior to necropsy in vacutainer tubes containing EDTA. Each tube is filled at least ⅔ full and thoroughly mixed for at least 30 seconds. Tubes are stored frozen until shipped on dry ice.

Animals are euthanized with an intravenous injection of commercial euthanasia solution. Euthanasia is performed according to standard procedures used in the industry.

For treatment groups dosed intravitreally or subconjunctivally with placebo, all eyes from each of these groups are placed into Davidsons solution for approximately 24 hours. Following the 24-hour period, the eyes are transferred to 70% ethanol; these globes are submitted for masked histopathological evaluation by a board certified veterinary pathologist. The time that eyes are placed into Davidsons and the time of removal are recorded.

For treatment groups dosed intravitreally or subconjunctivally with test article, some eyes from each of these groups are frozen at −70° C. and submitted for pharmacokinetic analysis. The remaining eyes from each of these groups are placed into Davidsons solution for approximately 24 hours. Following the 24-hour period, the eyes are transferred to 70% ethanol; these globes are submitted for masked histopathological evaluation by a board certified veterinary pathologist. The time that eyes are placed into Davidsons and the time of removal are recorded.

Frozen samples submitted for pharmacokinetic analysis are dissected with disposable instruments. One set of instruments is used per eye, and then discarded. The samples are thawed at room temperature for 1 to 2 minutes to ensure that the frost around the tissue has been removed. The sclera is dissected into 4 quadrants, and the vitreous is removed. If a non-dispersed mass (NDM) is clearly visible within the vitreous, the vitreous is separated into two sections. The section with the NDM is approximately two-thirds of the vitreous. The section without the NDM is the portion of the vitreous that is the most distant from the NDM. The aqueous humor, lens, iris, and cornea are separated. The retina choroid tissue is removed using a forceps and collected for analysis. The conjunctiva is separated from the sclera.

The various tissue types are collected into separate individual pre-weighed vials which are then capped and weighed. The vials of tissue are stored at −80° C. until analyzed.

The sirolimus content of the retina choroid, sclera, vitreous humor, and whole anti-coagulated blood is determined by high-pressure liquid chromatography/tandem mass spectroscopy (HPLC/MS/MS) using 32-O-desmethoxyrapamycin as an internal standard. Where an NDM was observed in the vitreous, the section of the vitreous containing the NDM and the section of the vitreous not containing the NDM are analyzed separately.

The average concentration of a therapeutic agent over a period of time means for representative timepoints over the period of time the average concentration at each time point. For example, if the time period is 30 days, the average concentration may be measured at 5 day intervals: for the average concentration at day 5, the average of a number of measurements of concentration at day 5 would be calculated; for the average concentration at day 10, the average of a number of measurements of the concentration at day 10 would be calculated, etc.

Figure 2:
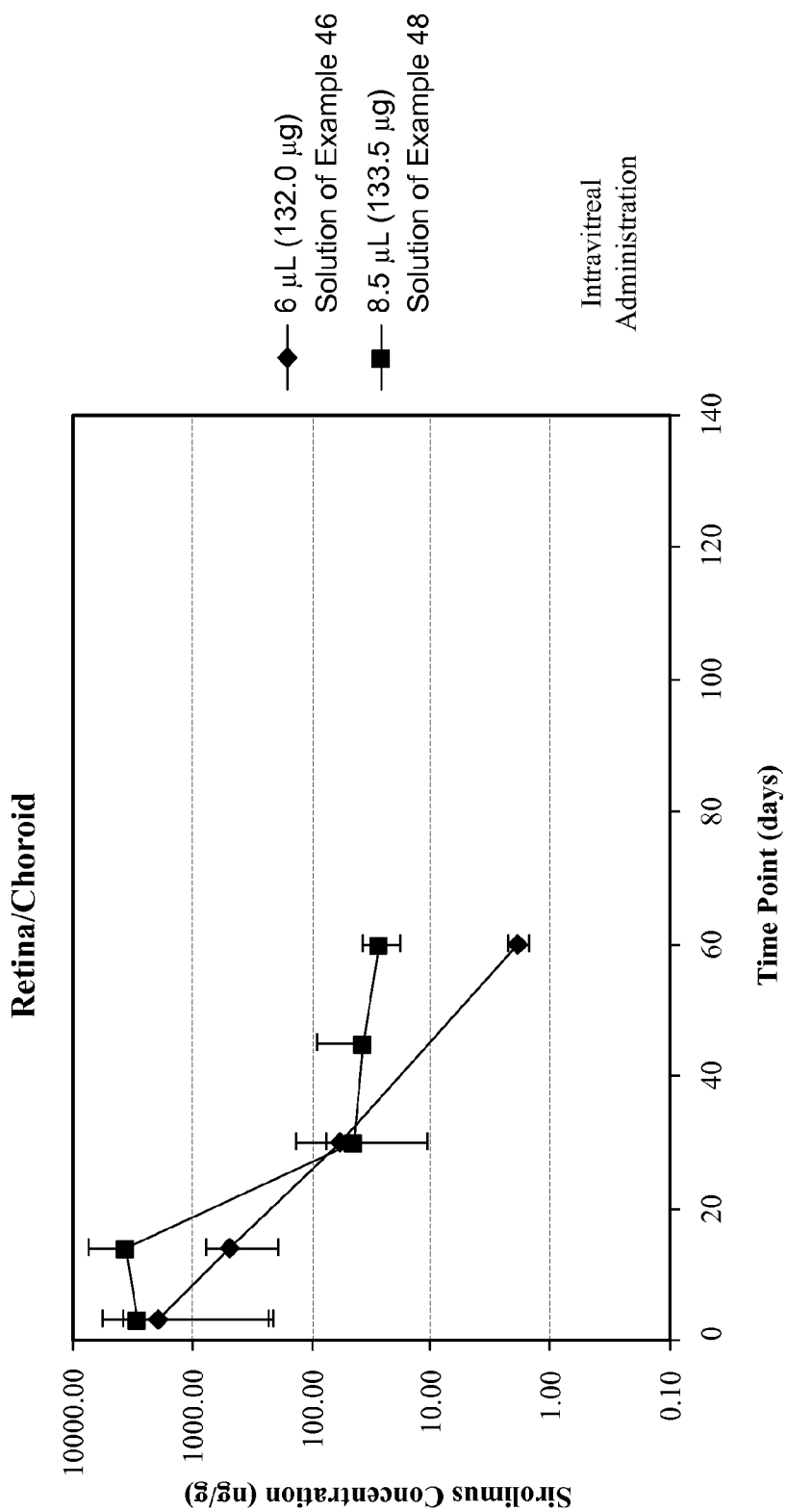
FIG. 2 depicts the level of rapamycin in the retina choroid tissue (ng/g) of rabbit eyes at 3, 14, 30, 45, and 60 days after intravitreal injection of 6 µl of 2% solution of rapamycin in ethanol and PEG 400 or 8.5 µl of 1.47% solution of rapamycin in ethanol and PEG 400.

In some variations, the liquid formulations described herein may have in vivo delivery to the vitreous profiles with the following described characteristics, where the delivery profiles are for delivery of therapeutic agent in vivo after injection of the liquid formulation between the sclera and the conjunctiva of a rabbit eye. One nonlimiting variation of in vivo delivery to the vitreous profiles is shown in FIG. 2.

At day 40 after injection, the average percentage in vivo vitreal level may be between about 70% and about 100%, and more usually between about 80% and about 90%, relative to the level present at day 20 after injection. At day 40 after injection, the average percentage in vivo vitreal level may be greater than about 70%, and more usually greater than about 80%, relative to the level present at day 20 after injection.

At day 67 after injection, the average percentage in vivo vitreal level may be between about 75% and about 115%, and more usually between about 85% and about 105%, relative to the level present at day 20 after injection. At day 67 after injection, the average percentage in vivo vitreal level may be greater than about 75%, and more usually greater than about 85%, relative to the level present at day 20 after injection.

At day 90 after injection, the average percentage in vivo vitreal level may be between about 20% and about 50%, and more usually between about 30% and about 40%, relative to the level present at day 20 after injection. At day 90 after injection, the average percentage in vivo vitreal level may be greater than about 20%, and more usually greater than about 30%, relative to the level present at day 20 after injection.

In some variations, the average percentage in vivo vitreal level has the following characteristics relative to the level present at day 20 after injection: at 40 days after injection it is less than about 100%; at 67 days after injection it is less than about 115%; and 90 days after injection it is less than about 50%.

In some variations, the liquid formulation when injected between the sclera and conjunctiva of a rabbit eye delivers therapeutic agent giving an average concentration of therapeutic agent in the vitreous of the rabbit eye of at least about 0.01 ng/mL for at least about 30, at least about 60, or at least about 90 days after administration of the liquid formulation to the rabbit eyes. In some variations, the liquid formulation when injected between the sclera and conjunctiva of a rabbit eye delivers therapeutic agent giving an average concentration of therapeutic agent in the vitreous of the rabbit eye of at least about 0.1 ng/mL for at least about 30, at least about 60, or at least about 90 days after administration of the liquid formulation to the rabbit eyes. In some variations, the liquid formulation when injected between the sclera and conjunctiva of a rabbit eye delivers therapeutic agent giving an average concentration of therapeutic agent in the vitreous of the rabbit eye of at least about 1 ng/mL for at least about 30, at least about 60, or at least about 90 days after administration of the liquid formulation to the rabbit eyes.

In some variations, the liquid formulations described herein may have in vivo delivery to the retina choroid profiles with the following described characteristics, where the delivery profiles are for delivery of therapeutic agent in vivo after injection of the liquid formulation between the sclera and the conjunctiva of a rabbit eye.

At day 40 after injection, the average percentage in vivo retina choroid level may be between about 350% and about 410%, and more usually between about 360% and about 400%, relative to the level present at day 20 after injection. At day 40 after injection, the average percentage in vivo retina choroid level may be greater than about 350%, and more usually greater than about 360%, relative to the level present at day 20 after injection.

At day 67 after injection, the average percentage in vivo retina choroid level may be between about 125% and about 165%, and more usually between about 135% and about 155%, relative to the level present at day 20 after injection. At day 67 after injection, the average percentage in vivo retina choroid level may be greater than about 125%, and more usually greater than about 135%, relative to the level present at day 20 after injection.

At day 90 after injection, the average percentage in vivo retina choroid level may be between about 10% and about 50%, and more usually between about 20% and about 40%, relative to the level present at day 20 after injection. At day 90 after injection, the average percentage in vivo retina choroid level may be greater than about 10%, and more usually greater than about 20%, relative to the level present at day 20 after injection.

In some variations, the average percentage in vivo retina choroid level has the following characteristics relative to the level present at day 20 after injection: at 40 days after injection it is less than about 410%; at 67 days after injection it is less than about 165%; and 90 days after injection it is less than about 50%.

In some variations, the liquid formulation when injected between the sclera and conjunctiva of a rabbit eye delivers therapeutic agent giving an average concentration of therapeutic agent in the retina choroid tissues of the rabbit eye of at least about 0.001 ng/mg for at least about 30, at least about 60, or at least about 90 days after administration of the liquid formulation to the rabbit eyes. In some variations, the liquid formulation when injected between the sclera and conjunctiva of a rabbit eye delivers therapeutic agent giving an average concentration of therapeutic agent in the retina choroid tissues of the rabbit eye of at least about 0.01 ng/mg for at least about 30, at least about 60, or at least about 90 days after administration of the liquid formulation to the rabbit eyes.

In some variations, the level of therapeutic agent present in the retina choroid first increases, then peaks and decreases. The peak may, for instance, occur at about day 40 after injection.

In some variations, the liquid formulations described herein may have in vivo clearance from the sclera profiles with the following described characteristics, where the clearance profiles are for clearance of therapeutic agent in vivo after injection of the liquid formulation between the sclera and the conjunctiva of a rabbit eye. Where injection is between the sclera and the conjunctiva, the scleral level is thought to include the injected liquid formulation.

At day 40 after injection, the average percentage in vivo scleral level may be between about 150% and about 230%, and more usually between about 170% and about 210%, relative to the level present at day 20 after injection. At day 40 after injection, the average percentage in vivo scleral level may be greater than about 150%, and more usually greater than about 170%, relative to the level present at day 20 after injection.

At day 67 after injection, the average percentage in vivo scleral level may be between about 30% and about 70%, and more usually between about 40% and about 60%, relative to the level present at day 20 after injection. At day 67 after injection, the average percentage in vivo scleral level may be greater than about 30%, and more usually greater than about 40%, relative to the level present at day 20 after injection.

At day 90 after injection, the average percentage in vivo scleral level may be between about 110% and about 160%, and more usually between about 125% and about 145%, relative to the level present at day 20 after injection. At day 90 after injection, the average percentage in vivo scleral level may be greater than about 110%, and more usually greater than about 125%, relative to the level present at day 20 after injection.

In some variations, the average percentage in vivo scleral level has the following characteristics relative to the level present at day 20 after injection: at 40 days after injection it is less than about 230%; at 67 days after injection it is less than about 70%; and 90 days after injection it is less than about 160%.

In some variations, the level of therapeutic agent present in the sclera first increases, then peaks and decreases. The peak may, for instance, occur at about day 40 after injection.

In some variations, the liquid formulations described herein may have in vivo delivery to the vitreous profiles with the following described characteristics, where the delivery profiles are for delivery of therapeutic agent in vivo after injection of the liquid formulation between the sclera and the conjunctiva of a rabbit eye.

At day 14 after injection, the average percentage in vivo vitreal level may be between about 1350% and about 1650%, and more usually between about 1450% and about 1550%, relative to the level present at day 2 after injection. At day 14 after injection, the average percentage in vivo vitreal level may be greater than about 1350%, and more usually greater than about 1450%, relative to the level present at day 2 after injection.

At day 35 after injection, the average percentage in vivo vitreal level may be between about 200% and about 300%, and more usually between about 225% and about 275%, relative to the level present at day 2 after injection. At day 35 after injection, the average percentage in vivo vitreal level may be greater than about 200%, and more usually greater than about 225%, relative to the level present at day 2 after injection.

At day 62 after injection, the average percentage in vivo vitreal level may be between about 100% and about 160%, and more usually between about 115% and about 145%, relative to the level present at day 2 after injection. At day 62 after injection, the average percentage in vivo vitreal level may be greater than about 100%, and more usually greater than about 115%, relative to the level present at day 2 after injection.

At day 85 after injection, the average percentage in vivo vitreal level may be between about 5% and about 30%, and more usually between about 10% and about 25%, relative to the level present at day 2 after injection. At day 85 after injection, the average percentage in vivo vitreal level may be greater than about 5%, and more usually greater than about 10%, relative to the level present at day 2 after injection.

In some variations, the average percentage in vivo vitreal level has the following characteristics relative to the level present at day 2 after injection: at 14 days after injection it is less than about 1600%; at 35 days after injection it is less than about 300%; at 62 days after injection it is less than about 160% and 85 days after injection it is less than about 30%.

In some variations, the liquid formulation when injected between the sclera and conjunctiva of a rabbit eye delivers therapeutic agent giving an average concentration of therapeutic agent in the vitreous of the rabbit eye of at least about 0.01 ng/mL for at least about 30, at least about 60, or at least about 85 days after administration of the liquid formulation to the rabbit eyes. In some variations, the liquid formulation when injected between the sclera and conjunctiva of a rabbit eye delivers therapeutic agent giving an average concentration of therapeutic agent in the vitreous of the rabbit eye of at least about 0.1 ng/mL for at least about 30, at least about 60, or at least about 85 days after administration of the liquid formulation to the rabbit eyes. In some variations, the liquid formulation when injected between the sclera and conjunctiva of a rabbit eye delivers therapeutic agent giving an average concentration of therapeutic agent in the vitreous of the rabbit eye of at least about 1 ng/mL for at least about 30, or at least about 60 days after administration of the liquid formulation to the rabbit eyes.

In some variations, the level of therapeutic agent present in the vitreous first increases, then peaks and decreases. The peak may, for instance, occur at about day 14 after injection.

In some variations, the liquid formulations described herein may have in vivo delivery to the retina choroid profiles with the following described characteristics, where the delivery profiles are for delivery of therapeutic agent in vivo after injection of the liquid formulation between the sclera and the conjunctiva of a rabbit eye.

At day 35 after injection, the average percentage in vivo retina choroid level may be between about 320% and about 400%, and more usually between about 340% and about 380%, relative to the level present at day 14 after injection. At day 35 after injection, the average percentage in vivo retina choroid level may be greater than about 320%, and more usually greater than about 340%, relative to the level present at day 14 after injection.

At day 62 after injection, the average percentage in vivo retina choroid level may be between about 3% and about 25%, and more usually between about 6% and about 20%, relative to the level present at day 14 after injection. At day 62 after injection, the average percentage in vivo retina choroid level may be greater than about 3%, and more usually greater than about 6%, relative to the level present at day 14 after injection.

At day 85 after injection, the average percentage in vivo retina choroid level may be between about 0.1% and about 6%, and more usually between about 0.5% and about 4%, relative to the level present at day 14 after injection. At day 85 after injection, the average percentage in vivo retina choroid level may be greater than about 0.1%, and more usually greater than about 0.5%, relative to the level present at day 14 after injection.

In some variations, the average percentage in vivo retina choroid level has the following characteristics relative to the level present at day 14 after injection: at 35 days after injection it is less than about 400%; at 62 days after injection it is less than about 25%; and 85 days after injection it is less than about 6%.

In some variations, the liquid formulation when injected between the sclera and conjunctiva of a rabbit eye delivers therapeutic agent giving an average concentration of therapeutic agent in the retina choroid tissues of the rabbit eye of at least about 0.001 ng/mg for at least about 30, at least about 60, or at least about 85 days after administration of the liquid formulation to the rabbit eyes. In some variations, the liquid formulation when injected between the sclera and conjunctiva of a rabbit eye delivers therapeutic agent giving an average concentration of therapeutic agent in the retina choroid tissues of the rabbit eye of at least about 0.01 ng/mg for at least about 30, at least about 60, or at least about 85 days after administration of the liquid formulation to the rabbit eyes.

In some variations, the liquid formulations described herein may have in vivo clearance from the sclera profiles with the following described characteristics, where the clearance profiles are for clearance of therapeutic agent in vivo after injection of the liquid formulation between the sclera and the conjunctiva of a rabbit eye. For injection between the sclera and conjunctiva, the scleral level is thought to include the injected liquid formulation.

At day 35 after injection, the average percentage in vivo scleral level may be between about 0.1% and about 0.7%, and more usually between about 0.2% and about 0.6%, relative to the level present at day 14 after injection. At day 35 after injection, the average percentage in vivo scleral level may be greater than about 0.1%, and more usually greater than about 0.2%, relative to the level present at day 14 after injection.

At day 62 after injection, the average percentage in vivo scleral level may be between about 0.05% and about 0.35%, and more usually between about 0.07% and about 0.3%, relative to the level present at day 14 after injection. At day 62 after injection, the average percentage in vivo scleral level may be greater than about 0.05%, and more usually greater than about 0.07%, relative to the level present at day 14 after injection.

At day 85 after injection, the average percentage in vivo scleral level may be between about 0.1% and about 0.9%, and more usually between about 0.3% and about 0.7%, relative to the level present at day 14 after injection. At day 85 after injection, the average percentage in vivo scleral level may be greater than about 0.1%, and more usually greater than about 0.3%, relative to the level present at day 14 after injection.

In some variations, the average percentage in vivo scleral level has the following characteristics relative to the level present at day 14 after injection: at 35 days after injection it is less than about 0.7%; at 62 days after injection it is less than about 0.35%; and 85 days after injection it is less than about 0.9%.

In some variations, the liquid formulations described herein may have in vivo clearance from the vitreous profiles with the following described characteristics, where the clearance profiles are for clearance of therapeutic agent in vivo after injection of the liquid formulation into the vitreous of a rabbit eye. Where injection is into the vitreous, the measured vitreous level is thought to include the injected formulation.

At day 35 after injection, the average percentage in vivo vitreal level may be between about 1% and about 40%, and more usually between about 1% and about 10%, relative to the level present at day 14 after injection. At day 35 after injection, the average percentage in vivo vitreal level may be greater than about 1% relative to the level present at day 14 after injection.

At day 62 after injection, the average percentage in vivo vitreal level may be between about 1% and about 40%, and more usually between about 5% and about 25%, relative to the level present at day 14 after injection. At day 62 after injection, the average percentage in vivo vitreal level may be greater than about 1% relative to the level present at day 14 after injection, and more usually greater than about 5% relative to the level present at day 14 after injection.

At day 90 after injection, the average percentage in vivo vitreal level may be between about 1% and about 40%, and more usually between about 10% and about 30%, relative to the level present at day 14 after injection. At day 90 after injection, the average percentage in vivo vitreal level may be greater than about 1% relative to the level present at day 14 after injection, and more usually greater than about 10% relative to the level present at day 14 after injection.

In some variations, the level of therapeutic agent present in the vitreous first increases, then peaks and decreases. The peak may, for instance, occur at about day 14 after injection.

In some variations, the liquid formulations described herein may have in vivo delivery to the retina choroid profiles with the following described characteristics, where the delivery profiles are for delivery of therapeutic agent in vivo after injection of the liquid formulation into the vitreous of a rabbit eye.

At day 35 after injection, the average percentage in vivo retina choroid level may be between about 3400% and about 5100%, and more usually between about 3750% and about 4750%, relative to the level present at day 14 after injection. At day 35 after injection, the average percentage in vivo retina choroid level may be greater than about 3400%, and more usually greater than about 3750%, relative to the level present at day 14 after injection.

At day 62 after injection, the average percentage in vivo retina choroid level may be between about 0.1% and about 5%, and more usually between about 1% and about 3%, relative to the level present at day 14 after injection. At day 62 after injection, the average percentage in vivo retina choroid level may be greater than about 0.1%, and more usually greater than about 1%, relative to the level present at day 14 after injection.

At day 90 after injection, the average percentage in vivo retina choroid level may be between about 10% and about 50%, and more usually between about 20% and about 40%, relative to the level present at day 14 after injection. At day 90 after injection, the average percentage in vivo retina choroid level may be greater than about 10%, and more usually greater than about 20%, relative to the level present at day 14 after injection.

In some variations, the average percentage in vivo retina choroid level has the following characteristics relative to the level present at day 14 after injection: at 35 days after injection it is less than about 5100%; at 62 days after injection it is less than about 5%; and 90 days after injection it is less than about 50%.

In some variations, the liquid formulations described herein may have in vivo delivery to the sclera profiles with the following described characteristics, where the delivery profiles are for delivery of therapeutic agent in vivo after injection of the liquid formulation into the vitreous of a rabbit eye.

At day 35 after injection, the average percentage in vivo scleral level may be between about 1700% and about 2600%, and more usually between about 1900% and about 2400%, relative to the level present at day 14 after injection. At day 35 after injection, the average percentage in vivo scleral level may be greater than about 1700%, and more usually greater than about 1900%, relative to the level present at day 14 after injection.

At day 62 after injection, the average percentage in vivo scleral level may be between about 120% and about 180%, and more usually between about 140% and about 160%, relative to the level present at day 14 after injection. At day 62 after injection, the average percentage in vivo scleral level may be greater than about 120%, and more usually greater than about 140%, relative to the level present at day 14 after injection.

At day 90 after injection, the average percentage in vivo scleral level may be between about 95% and about 155%, and more usually between about 115% and about 135%, relative to the level present at day 14 after injection. At day 90 after injection, the average percentage in vivo scleral level may be greater than about 95%, and more usually greater than about 115%, relative to the level present at day 14 after injection.

In some variations, the average percentage in vivo scleral level has the following characteristics relative to the level present at day 14 after injection: at 35 days after injection it is less than about 2600%; at 62 days after injection it is less than about 180%; and 90 days after injection it is less than about 155%.

In some variations, the liquid formulation when injected into the vitreous of a rabbit eye delivers therapeutic agent giving an average concentration of therapeutic agent in the sclera of the rabbit eye of at least about 0.001 ng/mg for at least about 30, at least about 60, or at least about 90 days after administration of the liquid formulation to the rabbit eyes. In some variations, the liquid formulation when injected into the vitreous of a rabbit eye delivers therapeutic agent giving an average concentration of therapeutic agent in the sclera of the rabbit eye of at least about 0.01 ng/mg for at least about 30, at least about 60, or at least about 90 days after administration of the liquid formulation to the rabbit eyes. In some variations, the liquid formulation when injected into the vitreous of a rabbit eye delivers therapeutic agent giving an average concentration of therapeutic agent in the sclera of the rabbit eye of at least about 0.1 ng/mg for at least about 30, at least about 60, or at least about 90 days after administration of the liquid formulation to the rabbit eyes.

In some variations, the level of therapeutic agent present in the vitreous first increases, then peaks and decreases. The peak may, for instance, occur at about day 35 after injection.

In some variations, in situ gelling liquid formulations described herein may have in vivo delivery to the vitreous profiles with the following described characteristics, where the delivery profiles are for delivery of therapeutic agent in vivo after injection of the liquid formulation between the sclera and the conjunctiva of a rabbit eye.

At day 32 after injection, the average percentage in vivo vitreal level may be between about 25% and about 85%, and more usually between about 45% and about 65%, relative to the level present at day 7 after injection. At day 40 after injection, the average percentage in vivo vitreal level may be greater than about 25%, and more usually greater than about 45%, relative to the level present at day 7 after injection.

At day 45 after injection, the average percentage in vivo vitreal level may be between about 2% and about 50%, and more usually between about 8% and about 20%, relative to the level present at day 7 after injection. At day 67 after injection, the average percentage in vivo vitreal level may be greater than about 2%, and more usually greater than about 5%, relative to the level present at day 7 after injection.

At day 90 after injection, the average percentage in vivo vitreal level may be between about 40% and about 100%, and more usually between about 60% and about 80%, relative to the level present at day 7 after injection. At day 90 after injection, the average percentage in vivo vitreal level may be greater than about 40%, and more usually greater than about 60%, relative to the level present at day 7 after injection.

In some variations, the average percentage in vivo vitreal level has the following characteristics relative to the level present at day 7 after injection: at 32 days after injection it is less than about 80%; at 45 days after injection it is less than about 30%; and 90 days after injection it is less than about 100%.

In some variations, the liquid formulation when injected between the sclera and conjunctiva of a rabbit eye delivers therapeutic agent giving an average concentration of therapeutic agent in the vitreous of the rabbit eye of at least about 0.1 µg/mL for at least about 30, at least about 60, or at least about 90 days after administration of the liquid formulation to the rabbit eye. In some variations, the liquid formulation when injected between the sclera and conjunctiva of a rabbit eye delivers therapeutic agent giving an average concentration of therapeutic agent in the vitreous of the rabbit eye of at least about 0.01 ng/mL for at least about 30, at least about 60, or at least about 90 days after administration of the liquid formulation to the rabbit eye. In some variations, the liquid formulation when injected between the sclera and conjunctiva of a rabbit eye delivers therapeutic agent giving an average concentration of therapeutic agent in the vitreous of the rabbit eye of at least about 0.1 ng/mL for at least about 30, at least about 60, or at least about 90 days after administration of the liquid formulation to the rabbit eye. In some variations, the liquid formulation when injected between the sclera and conjunctiva of a rabbit eye delivers therapeutic agent giving an average concentration of therapeutic agent in the vitreous of the rabbit eye of at least about 1 ng/mL for at least about 30, at least about 60, or at least about 90 days after administration of the liquid formulation to the rabbit eye. In some variations, the liquid formulation when injected between the sclera and conjunctiva of a rabbit eye delivers therapeutic agent giving an average concentration of therapeutic agent in the vitreous of the rabbit eye of at least about 10 ng/mL for at least about 30, at least about 60, or at least about 90 days after administration of the liquid formulation to the rabbit eye.

In some variations, the liquid formulation when injected between the sclera and conjunctiva of a rabbit eye delivers therapeutic agent giving an average concentration of therapeutic agent in the vitreous of the rabbit eye of at least 0.001 ng/mL for at least 30, at least 60, at least 90, or at least 120 days after administration of the liquid formulation to the rabbit eyes. In some variations, the liquid formulation when injected between the sclera and conjunctiva of a rabbit eye delivers therapeutic agent giving an average concentration of therapeutic agent in the vitreous of the rabbit eye of at least 0.01 ng/mL for at least 30, at least 60, at least 90, or at least 120 days after administration of the liquid formulation to the rabbit eyes. In some variations, the liquid formulation when injected between the sclera and conjunctiva of a rabbit eye delivers therapeutic agent giving an average concentration of therapeutic agent in the vitreous of the rabbit eye of at least 0.1 ng/mL for at least 30, at least 60, at least 90, or at least 120 days after administration of the liquid formulation to the rabbit eyes. In some variations, the liquid formulation when injected between the sclera and conjunctiva of a rabbit eye delivers therapeutic agent giving an average concentration of therapeutic agent in the vitreous of the rabbit eye of at least 0.5 ng/mL for at least 30, at least 60, at least 90, or at least 120 days after administration of the liquid formulation to the rabbit eyes.

In some variations, the liquid formulation when injected between the sclera and conjunctiva of a rabbit eye delivers therapeutic agent giving an average concentration of therapeutic agent in the vitreous of the rabbit eye of between 0.001 ng/mL and 10.0 ng/mL for at least 30, at least 60, at least 90, or at least 120 days after administration of the liquid formulation to the rabbit eyes. In some variations, the liquid formulation when injected between the sclera and conjunctiva of a rabbit eye delivers therapeutic agent giving an average concentration of therapeutic agent in the vitreous of the rabbit eye of between 0.01 ng/mL and 10 ng/mL for at least 30, at least 60, at least 90, or at least 120 days after administration of the liquid formulation to the rabbit eyes. In some variations, the liquid formulation when injected between the sclera and conjunctiva of a rabbit eye delivers therapeutic agent giving an average concentration of therapeutic agent in the vitreous of the rabbit eye of between 0.1 ng/mL and 10 ng/mL for at least 30, at least 60, at least 90, or at least 120 days after administration of the liquid formulation to the rabbit eyes.

In some variations, the liquid formulation when injected between the sclera and conjunctiva of a rabbit eye delivers therapeutic agent giving an average concentration of therapeutic agent in the vitreous of the rabbit eye of between 0.5 ng/mL and 10.0 ng/mL for at least 30, at least 60, at least 90, or at least 120 days after administration of the liquid formulation to the rabbit eyes.

In some variations, the liquid formulation when injected between the sclera and conjunctiva of a rabbit eye delivers therapeutic agent giving a ratio of a maximum average concentration of therapeutic agent in the vitreous of a rabbit eye to a minimum average concentration of therapeutic agent in the vitreous of a rabbit eye less than 100 for days 30 to at least 60, at least 90, or at least 120 days after administration of the liquid formulation to the rabbit eyes. In some variations, the liquid formulation when injected between the sclera and conjunctiva of a rabbit eye delivers therapeutic agent giving a ratio of a maximum average concentration of therapeutic agent in the vitreous of a rabbit eye to a minimum average concentration of therapeutic agent in the vitreous of a rabbit eye less than 50 for days 30 to at least 60, at least 90, or at least 120 days after administration of the liquid formulation to the rabbit eyes. In some variations, the liquid formulation when injected between the sclera and conjunctiva of a rabbit eye delivers therapeutic agent giving a ratio of a maximum average concentration of therapeutic agent in the vitreous of a rabbit eye to a minimum average concentration of therapeutic agent in the vitreous of a rabbit eye less than 10 for days 30 to at least 60, at least 90, or at least 120 days after administration of the liquid formulation to the rabbit eyes. In some variations, the liquid formulation when injected between the sclera and conjunctiva of a rabbit eye delivers therapeutic agent giving a ratio of a maximum average concentration of therapeutic agent in the vitreous of a rabbit eye to a minimum average concentration of therapeutic agent in the vitreous of a rabbit eye less than 5 for days 30 to at least 60, at least 90, or at least 120 days after administration of the liquid formulation to the rabbit eyes.

"Approximately constant," as used herein, means that the average level does not vary by more than one order of magnitude over the extended period of time, i.e., the difference between the maximum and minimum is less than a 10-fold difference for measurements of the average concentration at times in the relevant period of time.

In some variations, the liquid formulation when injected between the sclera and conjunctiva of a rabbit eye delivers therapeutic agent giving an average concentration of therapeutic agent in the vitreous of a rabbit eye that is approximately constant at a value greater than 0.001 ng/mL for days 30 to at least 60, at least 90, or at least 120 days after administration of the solution to the rabbit eyes. In some variations, the liquid formulation when injected between the sclera and conjunctiva of a rabbit eye delivers therapeutic agent giving an average concentration of therapeutic agent in the vitreous of a rabbit eye that is approximately constant at a value greater than 0.01 ng/mL for days 30 to at least 60, at least 90, or at least 120 days after administration of the liquid formulation to the rabbit eyes. In some variations, the liquid formulation when injected between the sclera and conjunctiva of a rabbit eye delivers therapeutic agent giving an average concentration of therapeutic agent in the vitreous of a rabbit eye that is approximately constant at a value greater than 0.1 ng/mL for days 30 to at least 60, at least 90, or at least 120 days after administration of the liquid formulation to the rabbit eyes. In some variations, the liquid formulation when injected between the sclera and conjunctiva of a rabbit eye delivers therapeutic agent giving an average concentration of therapeutic agent in the vitreous of a rabbit eye that is approximately constant at a value of 1.0 ng/mL for days 30 to at least 60, at least 90, or at least 120 days after administration of the liquid formulation to the rabbit eyes.

In some variations, the liquid formulation when injected between the sclera and conjunctiva of a rabbit eye delivers therapeutic agent giving an average concentration of therapeutic agent in the retina choroid tissues of the rabbit eye of at least 0.001 ng/mg for at least 30, at least 60, at least 90, or at least 120 days after administration of the liquid formulation to the rabbit eyes. In some variations, the liquid formulation when injected between the sclera and conjunctiva of a rabbit eye delivers therapeutic agent giving an average concentration of therapeutic agent in the retina choroid tissues of the rabbit eye of at least 0.005 ng/mg for at least 30, at least 60, at least 90, or at least 120 days after administration of the liquid formulation to the rabbit eyes. In some variations, the liquid formulation when injected between the sclera and conjunctiva of a rabbit eye delivers therapeutic agent giving an average concentration of therapeutic agent in the retina choroid tissues of the rabbit eye of at least 0.01 ng/mg for at least 30, at least 60, at least 90, or at least 120 days after administration of the liquid formulation to the rabbit eyes.

In some variations, the liquid formulation when injected between the sclera and conjunctiva of a rabbit eye delivers therapeutic agent giving an average concentration of therapeutic agent in the retina choroid tissues of the rabbit eye of between 0.001 ng/mg and 1.0 ng/mg for at least 30, at least 60, at least 90, or at least 120 days after administration of the liquid formulation to the rabbit eyes. In some variations, the liquid formulation when injected between the sclera and conjunctiva of a rabbit eye delivers therapeutic agent giving an average concentration of therapeutic agent in the retina choroid tissues of the rabbit eye of between 0.001 ng/mg and 0.50 ng/mg for at least 30, at least 60, at least 90, or at least 120 days after administration of the liquid formulation to the rabbit eyes. In some variations, the liquid formulation when injected between the sclera and conjunctiva of a rabbit eye delivers therapeutic agent giving an average concentration of therapeutic agent in the retina choroid tissues of the rabbit eye of between 0.001 ng/mg and 0.15 ng/mg for at least 30, at least 60, at least 90, or at least 120 days after administration of the liquid formulation to the rabbit eyes. In some variations, the liquid formulation when injected between the sclera and conjunctiva of a rabbit eye delivers therapeutic agent giving an average concentration of therapeutic agent in the retina choroid tissues of the rabbit eye of between 0.001 ng/mg and 0.1 ng/mg for at least 30, at least 60, at least 90, or at least 120 days after administration of the liquid formulation to the rabbit eyes.

In some variations, the liquid formulation when injected between the sclera and conjunctiva of a rabbit eye delivers therapeutic agent giving an average concentration of therapeutic agent in the retina choroid tissues of the rabbit eye of between 0.005 ng/mg and 1.0 ng/mg for at least 30, at least 60, at least 90, or at least 120 days after administration of the liquid formulation to the rabbit eyes. In some variations, the liquid formulation when injected between the sclera and conjunctiva of a rabbit eye delivers therapeutic agent giving an average concentration of therapeutic agent in the retina choroid tissues of the rabbit eye of between 0.005 ng/mg and 0.50 ng/mg for at least 30, at least 60, at least 90, or at least 120 days after administration of the liquid formulation to the rabbit eyes. In some variations, the liquid formulation when injected between the sclera and conjunctiva of a rabbit eye delivers therapeutic agent giving an average concentration of therapeutic agent in the retina choroid tissues of the rabbit eye of between 0.005 ng/mg and 0.15 ng/mg for at least 30, at least 60, at least 90, or at least 120 days after administration of the liquid formulation to the rabbit eyes. In some variations, the liquid formulation when injected between the sclera and conjunctiva of a rabbit eye delivers therapeutic agent giving an average concentration of therapeutic agent in the retina choroid tissues of the rabbit eye of between 0.005 ng/mg and 0.1 ng/mg for at least 30, at least 60, at least 90, or at least 120 days after administration of the liquid formulation to the rabbit eyes.

In some variations, the liquid formulation when injected between the sclera and conjunctiva of a rabbit eye delivers therapeutic agent giving an average concentration of therapeutic agent in the retina choroid tissues of the rabbit eye of between 0.01 ng/mg and 1.0 ng/mg for at least 30, at least 60, at least 90, or at least 120 days after administration of the liquid formulation to the rabbit eyes. In some variations, the liquid formulation when injected between the sclera and conjunctiva of a rabbit eye delivers therapeutic agent giving an average concentration of therapeutic agent in the retina choroid tissues of the rabbit eye of between 0.01 ng/mg and 0.50 ng/mg for at least 30, at least 60, at least 90, or at least 120 days after administration of the liquid formulation to the rabbit eyes. In some variations, the liquid formulation when injected between the sclera and conjunctiva of a rabbit eye delivers therapeutic agent giving an average concentration of therapeutic agent in the retina choroid tissues of the rabbit eye of between 0.01 ng/mg and 0.15 ng/mg for at least 30, at least 60, at least 90, or at least 120 days after administration of the liquid formulation to the rabbit eyes. In some variations, the liquid formulation when injected between the sclera and conjunctiva of a rabbit eye delivers therapeutic agent giving an average concentration of therapeutic agent in the retina choroid tissues of the rabbit eye of between 0.01 ng/mg and 0.1 ng/mg for at least 30, at least 60, at least 90, or at least 120 days after administration of the liquid formulation to the rabbit eyes.

In some variations, the liquid formulation when injected between the sclera and conjunctiva of a rabbit eye delivers therapeutic agent giving a ratio of a maximum average concentration of therapeutic agent in the retina choroid tissues of a rabbit eye to a minimum average concentration of therapeutic agent in the retina choroid tissues of a rabbit eye less than 100 for days 30 to at least 60, at least 90, or at least 120 days after administration of the liquid formulation to the rabbit eyes. In some variations, the liquid formulation when injected between the sclera and conjunctiva of a rabbit eye delivers therapeutic agent giving a ratio of a maximum average concentration of therapeutic agent in the retina choroid tissues of a rabbit eye to a minimum average concentration of therapeutic agent in the retina choroid tissues of a rabbit eye less than 50 for days 30 to at least 60, at least 90, or at least 120 days after administration of the liquid formulation to the rabbit eyes. In some variations, the liquid formulation when injected between the sclera and conjunctiva of a rabbit eye delivers therapeutic agent giving a ratio of a maximum average concentration of therapeutic agent in the retina choroid tissues of a rabbit eye to a minimum average concentration of therapeutic agent in the retina choroid tissues of a rabbit eye less than 10 for days 30 to at least 60, at least 90, or at least 120 days after administration of the liquid formulation to the rabbit eyes. In some variations, the liquid formulation when injected between the sclera and conjunctiva of a rabbit eye delivers therapeutic agent giving a ratio of a maximum average concentration of therapeutic agent in the retina choroid tissues of a rabbit eye to a minimum average concentration of therapeutic agent in the retina choroid tissues of a rabbit eye less than 5 for days 30 to at least 60, at least 90, or at least 120 days after administration of the liquid formulation to the rabbit eyes.

In some variations, the liquid formulation when injected between the sclera and conjunctiva of a rabbit eye delivers therapeutic agent giving an average concentration of therapeutic agent in the retina choroid tissues of a rabbit eye that is approximately constant at a value greater than 0.001 ng/mg for days 30 to at least 60, at least 90, or at least 120 days after administration of the liquid formulation to the rabbit eyes. In some variations, the liquid formulation when injected between the sclera and conjunctiva of a rabbit eye delivers therapeutic agent giving an average concentration of therapeutic agent in the retina choroid tissues of a rabbit eye that is approximately constant at a value greater than 0.005 ng/mg for days 30 to at least 60, at least 90, or at least 120 days after administration of the liquid formulation to the rabbit eyes. In some variations, the liquid formulation when injected between the sclera and conjunctiva of a rabbit eye delivers therapeutic agent giving an average concentration of therapeutic agent in the retina choroid tissues of a rabbit eye that is approximately constant at a value greater than 0.01 ng/mg for days 30 to at least 60, at least 90, or at least 120 days after administration of the liquid formulation to the rabbit eyes.

In some variations, the liquid formulation when injected into the vitreous of a rabbit eye delivers therapeutic agent giving an average concentration of therapeutic agent in the vitreous of the rabbit eye of at least 100 ng/mL for at least 30, at least 60, at least 90, or at least 120 days after administration of the liquid formulation to the rabbit eyes. In some variations, the liquid formulation when injected into the vitreous of a rabbit eye delivers therapeutic agent giving an average concentration of therapeutic agent in the vitreous of the rabbit eye of at least 1000 ng/mL for at least 30, at least 60, at least 90, or at least 120 days after administration of the liquid formulation to the rabbit eyes. In some variations, the liquid formulation when injected into the vitreous of a rabbit eye delivers therapeutic agent giving an average concentration of therapeutic agent in the vitreous of the rabbit eye of at least 10,000 ng/mL for at least 30, at least 60, at least 90, or at least 120 days after administration of the liquid formulation to the rabbit eyes.

In some variations, the liquid formulation when injected into the vitreous of a rabbit eye delivers therapeutic agent giving an average concentration of therapeutic agent in the vitreous of the rabbit eye between 100 ng/mL and 100,000 ng/mL for day 30 to at least 60, at least 90, or at least 120 days after administration of the liquid formulation to the rabbit eyes. In some variations, the liquid formulation when injected into the vitreous of a rabbit eye delivers therapeutic agent giving an average concentration of therapeutic agent in the vitreous of the rabbit eye between 100 ng/mL and 50,000 ng/mL for day 30 to at least 60, at least 90, or at least 120 days after administration of the liquid formulation to the rabbit eyes.

In some variations, the liquid formulation when injected into the vitreous of a rabbit eye delivers therapeutic agent giving an average concentration of therapeutic agent in the vitreous of the rabbit eye between 1000 ng/mL and 100,000 ng/mL for day 30 to at least 60, at least 90, or at least 120 days after administration of the liquid formulation to the rabbit eyes. In some variations, the liquid formulation when injected into the vitreous of a rabbit eye delivers therapeutic agent giving an average concentration of therapeutic agent in the vitreous of the rabbit eye between 1000 ng/mL and 50,000 ng/mL for day 30 to at least 60, at least 90, or at least 120 days after administration of the liquid formulation to the rabbit eyes.

In some variations, the liquid formulation when injected into the vitreous of a rabbit eye delivers therapeutic agent giving a ratio of a maximum average concentration of therapeutic agent in the vitreous of the rabbit eye to a minimum average concentration of therapeutic agent in the vitreous of the rabbit eye less than 100 for days 30 to at least 60, at least 90, or at least 120 days after administration of the liquid formulation to the rabbit eyes. In some variations, the liquid formulation when injected into the vitreous of a rabbit eye delivers therapeutic agent giving a ratio of a maximum average concentration of therapeutic agent in the vitreous of the rabbit eye to a minimum average concentration of therapeutic agent in the vitreous of the rabbit eye less than 50 for days 30 to at least 60, at least 90, or at least 120 days after administration of the liquid formulation to the rabbit eyes. In some variations, the liquid formulation when injected into the vitreous of a rabbit eye delivers therapeutic agent giving a ratio of a maximum average concentration of therapeutic agent in the vitreous of the rabbit eye to a minimum average concentration of therapeutic agent in the vitreous of the rabbit eye less than 10 for days 30 to at least 60, at least 90, or at least 120 days after administration of the liquid formulation to the rabbit eyes.

In some variations, the liquid formulation when injected into the vitreous of a rabbit eye delivers therapeutic agent giving an average concentration of therapeutic agent in the vitreous of the rabbit eye that is approximately constant at a value greater than 100 ng/mL for days 30 to at least 60, at least 90, or at least 120 days after administration of the liquid formulation to the rabbit eyes. In some variations, the liquid formulation when injected into the vitreous of a rabbit eye delivers therapeutic agent giving an average concentration of therapeutic agent in the vitreous of the rabbit eye that is approximately constant at a value greater than 1000 ng/mL for days 30 to at least 60, at least 90, or at least 120 days after administration of the liquid formulation to the rabbit eyes. In some variations, the liquid formulation when injected into the vitreous of a rabbit eye delivers therapeutic agent giving an average concentration of therapeutic agent in the vitreous of the rabbit eye that is approximately constant at a value greater than 10,000 ng/mL for days 30 to at least 60, at least 90, or at least 120 days after administration of the liquid formulation to the rabbit eyes.

In some variations, the liquid formulation when injected into the vitreous of a rabbit eye delivers therapeutic agent giving an average concentration of therapeutic agent in the retina choroid tissues of the rabbit eye of at least 0.001 ng/mg for at least 30, at least 60, at least 90, or at least 120 days after administration of the liquid formulation to the rabbit eyes. In some variations, the liquid formulation when injected into the vitreous of a rabbit eye delivers therapeutic agent giving an average concentration of therapeutic agent in the retina choroid tissues of the rabbit eye of at least 0.01 ng/mg for at least 30, at least 60, at least 90, or at least 120 days after administration of the liquid formulation to the rabbit eyes. In some variations, the liquid formulation when injected into the vitreous of a rabbit eye delivers therapeutic agent giving an average concentration of therapeutic agent in the retina choroid tissues of the rabbit eye of at least 0.05 ng/mg for at least 30, at least 60, at least 90, or at least 120 days after administration of the liquid formulation to the rabbit eyes. In some variations, the liquid formulation when injected into the vitreous of a rabbit eye delivers therapeutic agent giving an average concentration of therapeutic agent in the retina choroid tissues of the rabbit eye of at least 0.10 ng/mg for at least 30, at least 60, at least 90, or at least 120 days after administration of the liquid formulation to the rabbit eyes.

In some variations, the liquid formulation when injected into the vitreous of a rabbit eye delivers therapeutic agent giving an average concentration of therapeutic agent in the retina choroid tissues of the rabbit eye between 0.001 ng/mg and 10.00 ng/mg for at least 30, at least 60, at least 90, or at least 120 days after administration of the liquid formulation to the rabbit eyes. In some variations, the liquid formulation when injected into the vitreous of a rabbit eye delivers therapeutic agent giving an average concentration of therapeutic agent in the retina choroid tissues of the rabbit eye between 0.001 ng/mg and 5.00 ng/mg for at least 30, at least 60, at least 90, or at least 120 days after administration of the liquid formulation to the rabbit eyes. In some variations, the liquid formulation when injected into the vitreous of a rabbit eye delivers therapeutic agent giving an average concentration of therapeutic agent in the retina choroid tissues of the rabbit eye between 0.001 ng/mg and 1.00 ng/mg for at least 30, at least 60, at least 90, or at least 120 days after administration of the liquid formulation to the rabbit eyes.

In some variations, the liquid formulation when injected into the vitreous of a rabbit eye delivers therapeutic agent giving an average concentration of therapeutic agent in the retina choroid tissues of the rabbit eye between 0.01 ng/mg and 10.00 ng/mg for at least 30, at least 60, at least 90, or at least 120 days after administration of the liquid formulation to the rabbit eyes. In some variations, the liquid formulation when injected into the vitreous of a rabbit eye delivers therapeutic agent giving an average concentration of therapeutic agent in the retina choroid tissues of the rabbit eye between 0.01 ng/mg and 5.00 ng/mg for at least 30, at least 60, at least 90, or at least 120 days after administration of the liquid formulation to the rabbit eyes. In some variations, the liquid formulation when injected into the vitreous of a rabbit eye delivers therapeutic agent giving an average concentration of therapeutic agent in the retina choroid tissues of the rabbit eye between 0.01 ng/mg and 1.00 ng/mg for at least 30, at least 60, at least 90, or at least 120 days after administration of the liquid formulation to the rabbit eyes.

In some variations, the liquid formulation when injected into the vitreous of a rabbit eye delivers therapeutic agent giving an average concentration of therapeutic agent in the retina choroid tissues of the rabbit eye between 0.05 ng/mg and 10.00 ng/mg for at least 30, at least 60, at least 90, or at least 120 days after administration of the liquid formulation to the rabbit eyes. In some variations, the liquid formulation when injected into the vitreous of a rabbit eye delivers therapeutic agent giving an average concentration of therapeutic agent in the retina choroid tissues of the rabbit eye between 0.05 ng/mg and 5.00 ng/mg for at least 30, at least 60, at least 90, or at least 120 days after administration of the liquid formulation to the rabbit eyes. In some variations, the liquid formulation when injected into the vitreous of a rabbit eye delivers therapeutic agent giving an average concentration of therapeutic agent in the retina choroid tissues of the rabbit eye between 0.05 ng/mg and 1.00 ng/mg for at least 30, at least 60, at least 90, or at least 120 days after administration of the liquid formulation to the rabbit eyes.

In some variations, the liquid formulation when injected into the vitreous of a rabbit eye delivers therapeutic agent giving an average concentration of therapeutic agent in the retina choroid tissues of the rabbit eye between 0.10 ng/mg and 10.00 ng/mg for at least 30, at least 60, at least 90, or at least 120 days after administration of the liquid formulation to the rabbit eyes. In some variations, the liquid formulation when injected into the vitreous of a rabbit eye delivers therapeutic agent giving an average concentration of therapeutic agent in the retina choroid tissues of the rabbit eye between 0.10 ng/mg and 5.00 ng/mg for at least 30, at least 60, at least 90, or at least 120 days after administration of the liquid formulation to the rabbit eyes. In some variations, the liquid formulation when injected into the vitreous of a rabbit eye delivers therapeutic agent giving an average concentration of therapeutic agent in the retina choroid tissues of the rabbit eye between 0.10 ng/mg and 1.00 ng/mg for at least 30, at least 60, at least 90, or at least 120 days after administration of the liquid formulation to the rabbit eyes.

In some variations, the liquid formulation when injected into the vitreous of a rabbit eye delivers therapeutic agent giving a ratio of a maximum average concentration of therapeutic agent in the retina choroid tissues of the rabbit eye to a minimum average concentration of therapeutic agent in the retina choroid tissues of the rabbit eye less than 100 for days 30 to at least 60, at least 90, or at least 120 days after administration of the liquid formulation to the rabbit eyes. In some variations, the liquid formulation when injected into the vitreous of a rabbit eye delivers therapeutic agent giving a ratio of a maximum average concentration of therapeutic agent in the retina choroid tissues of the rabbit eye to a minimum average concentration of therapeutic agent in the retina choroid tissues of the rabbit eye less than 50 for days 30 to at least 60, at least 90, or at least 120 days after administration of the liquid formulation to the rabbit eyes.

In some variations, in situ gelling liquid formulations described herein may have in vivo delivery to the retina choroid tissue profiles with the following described characteristics, where the delivery profiles are for delivery of therapeutic agent in vivo after injection of the liquid formulation between the sclera and the conjunctiva of a rabbit eye.

At day 32 after injection, the percentage in vivo vitreal level may be between about 20% and about 80%, and more usually between about 40% and about 60%, relative to the level present at day 7 after injection. At day 40 after injection, the percentage in vivo vitreal level may be greater than about 20%, and more usually greater than about 40%, relative to the level present at day 7 after injection.

At day 45 after injection, the percentage in vivo vitreal level may be between about 15% and about 55%, and more usually between about 25% and about 45%, relative to the level present at day 7 after injection. At day 67 after injection, the percentage in vivo vitreal level may be greater than about 15%, and more usually greater than about 25%, relative to the level present at day 7 after injection.

At day 90 after injection, the percentage in vivo vitreal level may be between about 60% and about 100%, and more usually between about 70% and about 90%, relative to the level present at day 7 after injection. At day 90 after injection, the percentage in vivo vitreal level may be greater than about 60%, and more usually greater than about 70%, relative to the level present at day 7 after injection.

In some variations, the percentage in vivo vitreal level has the following characteristics relative to the level present at day 7 after injection: at 32 days after injection it is less than about 80%; at 45 days after injection it is less than about 60%; and 90 days after injection it is less than about 100%.

In some variations, the liquid formulation when injected between the sclera and conjunctiva of a rabbit eye delivers therapeutic agent giving an average concentration of therapeutic agent in the retina choroid tissues of the rabbit eye of at least about 0.1 µg/mg for at least about 30, at least about 60, or at least about 90 days after administration of the liquid formulation to the rabbit eye. In some variations, the liquid formulation when injected between the sclera and conjunctiva of a rabbit eye delivers therapeutic agent giving an average concentration of therapeutic agent in the vitreous of the rabbit eye of at least about 0.01 ng/mg for at least about 30, at least about 60, or at least about 90 days after administration of the liquid formulation to the rabbit eye. In some variations, the liquid formulation when injected between the sclera and conjunctiva of a rabbit eye delivers therapeutic agent giving an average concentration of therapeutic agent in the vitreous of the rabbit eye of at least about 0.1 ng/mg for at least about 30, at least about 60, or at least about 90 days after administration of the liquid formulation to the rabbit eye. In some variations, the liquid formulation when injected between the sclera and conjunctiva of a rabbit eye delivers therapeutic agent giving an average concentration of therapeutic agent in the vitreous of the rabbit eye of at least about 1 ng/mL for at least about 30, at least about 60, or at least about 90 days after administration of the liquid formulation to the rabbit eye.

In some variations, the ratio of the base ten logarithms of the average levels of a therapeutic agent in two or more of the retina choroid tissues, the sclera, and the vitreous is approximately constant over an extended period of time after placement of the in situ gelling formulation in or proximate to the eye. In some variations, the ratio of the base ten logarithms of the average levels of a therapeutic agent in two or more of the retina choroid tissues, the sclera, and the vitreous is approximately constant over an extended period of time after placement of the in situ gelling formulation between the sclera and the conjunctiva of an eye. In some variations, the ratio of the base ten logarithms of the average levels of a therapeutic agent in the vitreous and the sclera is approximately constant over an extended period of time after placement of the in situ gelling formulation between the sclera and the conjunctiva of an eye.

In some variations, the ratio of the base ten logarithms of the average levels of a therapeutic agent in the vitreous and the retina choroid tissues is approximately constant over an extended period of time. Put another way, as the level of therapeutic agent in the vitreous rises, the level of therapeutic agent in the retina choroid tissues rises to a similar degree when considered on the logarithmic scale, and vice versa.

In some variations, the ratio of the base ten logarithms of the average levels of a therapeutic agent in the vitreous versus the retina choroid tissues is approximately constant over an extended period of time of about 7, about 30, about 60, or about 90 days. In some variations, the ratio of the average level of therapeutic agent in the vitreous relative to the level of therapeutic agent in the retina choroid tissues after placement of the in situ gelling formulation between the sclera and the conjunctiva of an eye is constant at about 37:1 at day 7, about 40:1 at day 32, about 10:1 at day 45, and about 34:1 at day 90.

In some variations, the ratio of the average level of therapeutic agent in the vitreous relative to the level of therapeutic agent in the retina choroid tissues is constant at about 40:1 over a period of about 7, about 32, about 45, or about 90 days.

In some variations, the average level of the therapeutic agent in any or all of the retina choroid tissues, the sclera, and the vitreous is approximately constant over an extended period of time after placement of the in situ gelling formulation in or proximate to the eye.

In some variations, after placement of an in situ gelling formulation between the sclera and the conjunctiva, the average level of therapeutic agent in the vitreous is approximately constant at about 8.1 ng/ml. In some variations, after placement of an in situ gelling formulation between the sclera and the conjunctiva, the average level of therapeutic agent in the retina choroid tissues is approximately constant at about 0.25 ng/mg. In some variations, after placement of an in situ gelling formulation between the sclera and the conjunctiva, the average level of therapeutic agent in the sclera is approximately constant at about 1930 ng/mg.

In some variations, the in situ gelling formulation when injected between the sclera and conjunctiva of a rabbit eye maintains an average level of therapeutic agent in the vitreous that is approximately constant at about 0.1 µg/mL for at least about 30, at least about 60, or at least about 90 days after administration of the liquid formulation to the rabbit eye. In some variations, the in situ gelling formulation when injected between the sclera and conjunctiva of a rabbit eye maintains an average level of therapeutic agent in the vitreous that is approximately constant at about 0.001 ng/mL for at least about 30, at least about 60, or at least about 90 days after administration of the liquid formulation to the rabbit eye. In some variations, the in situ gelling formulation when injected between the sclera and conjunctiva of a rabbit eye maintains an average level of therapeutic agent in the vitreous that is approximately constant at about 0.01 ng/mL for at least about 30, at least about 60, or at least about 90 days after administration of the liquid formulation to the rabbit eye. In some variations, the in situ gelling formulation when injected between the sclera and conjunctiva of a rabbit eye maintains an average level of therapeutic agent in the vitreous that is approximately constant at about 0.1 ng/mL for at least about 30, at least about 60, or at least about 90 days after administration of the liquid formulation to the rabbit eye. In some variations, the in situ gelling formulation when injected between the sclera and conjunctiva of a rabbit eye maintains an average level of therapeutic agent in the vitreous that is approximately constant at about 1 ng/mL for at least about 30, at least about 60, or at least about 90 days after administration of the liquid formulation to the rabbit eye. In some variations, the in situ gelling formulation when injected between the sclera and conjunctiva of a rabbit eye maintains an average level of therapeutic agent in the vitreous that is approximately constant at about 10 ng/mL for at least about 30, at least about 60, or at least about 90 days after administration of the liquid formulation to the rabbit eye. In some variations, the in situ gelling formulation when injected between the sclera and conjunctiva of a rabbit eye maintains an average level of therapeutic agent in the vitreous that is approximately constant at about 100 ng/mL for at least about 30, at least about 60, or at least about 90 days after administration of the liquid formulation to the rabbit eye.

In some variations, the in situ gelling formulation when injected between the sclera and conjunctiva of a rabbit eye maintains an average level of therapeutic agent in the retina choroid tissues that is approximately constant at about 0.1 µg/mg for at least about 30, at least about 60, or at least about 90 days after administration of the liquid formulation to the rabbit eye. In some variations, the in situ gelling formulation when injected between the sclera and conjunctiva of a rabbit eye maintains an average level of therapeutic agent in the retina choroid tissues that is approximately constant at about 0.001 ng/mg for at least about 30, at least about 60, or at least about 90 days after administration of the liquid formulation to the rabbit eye. In some variations, the in situ gelling formulation when injected between the sclera and conjunctiva of a rabbit eye maintains an average level of therapeutic agent in the retina choroid tissues that is approximately constant at about 0.01 ng/mg for at least about 30, at least about 60, or at least about 90 days after administration of the liquid formulation to the rabbit eye. In some variations, the in situ gelling formulation when injected between the sclera and conjunctiva of a rabbit eye maintains an average level of therapeutic agent in the retina choroid tissues that is approximately constant at about 0.1 ng/mg for at least about 30, at least about 60, or at least about 90 days after administration of the liquid formulation to the rabbit eye. In some variations, the in situ gelling formulation when injected between the sclera and conjunctiva of a rabbit eye maintains an average level of therapeutic agent in the retina choroid tissues that is approximately constant at about 1 ng/mg for at least about 30, at least about 60, or at least about 90 days after administration of the liquid formulation to the rabbit eye. In some variations, the in situ gelling formulation when injected between the sclera and conjunctiva of a rabbit eye maintains an average level of therapeutic agent in the retina choroid tissues that is approximately constant at about 10 ng/mg for at least about 30, at least about 60, or at least about 90 days after administration of the liquid formulation to the rabbit eye.

In some variations, the in situ gelling formulation when injected between the sclera and conjunctiva of a rabbit eye maintains an average level of therapeutic agent in the sclera that is approximately constant at about 0.1 µg/mg for at least about 30, at least about 60, or at least about 90 days after administration of the liquid formulation to the rabbit eye. In some variations, the in situ gelling formulation when injected between the sclera and conjunctiva of a rabbit eye maintains an average level of therapeutic agent in the sclera that is approximately constant at about 0.001 ng/mg for at least about 30, at least about 60, or at least about 90 days after administration of the liquid formulation to the rabbit eye. In some variations, the in situ gelling formulation when injected between the sclera and conjunctiva of a rabbit eye maintains an average level of therapeutic agent in the sclera that is approximately constant at about 0.01 ng/mg for at least about 30, at least about 60, or at least about 90 days after administration of the liquid formulation to the rabbit eye. In some variations, the in situ gelling formulation when injected between the sclera and conjunctiva of a rabbit eye maintains an average level of therapeutic agent in the sclera that is approximately constant at about 0.1 ng/mg for at least about 30, at least about 60, or at least about 90 days after administration of the liquid formulation to the rabbit eye. In some variations, the in situ gelling formulation when injected between the sclera and conjunctiva of a rabbit eye maintains an average level of therapeutic agent in the sclera that is approximately constant at about 1 ng/mg for at least about 30, at least about 60, or at least about 90 days after administration of the liquid formulation to the rabbit eye. In some variations, the in situ gelling formulation when injected between the sclera and conjunctiva of a rabbit eye maintains an average level of therapeutic agent in the sclera that is approximately constant at about 10 ng/mg for at least about 30, at least about 60, or at least about 90 days after administration of the liquid formulation to the rabbit eye. In some variations, the in situ gelling formulation when injected between the sclera and conjunctiva of a rabbit eye maintains an average level of therapeutic agent in the sclera that is approximately constant at about 100 ng/mg for at least about 30, at least about 60, or at least about 90 days after administration of the liquid formulation to the rabbit eye. In some variations, the in situ gelling formulation when injected between the sclera and conjunctiva of a rabbit eye maintains an average level of therapeutic agent in the sclera that is approximately constant at about 1 µg/mg for at least about 30, at least about 60, or at least about 90 days after administration of the liquid formulation to the rabbit eye. In some variations, the in situ gelling formulation when injected between the sclera and conjunctiva of a rabbit eye maintains an average level of therapeutic agent in the sclera that is approximately constant at about 10 µg/mg for at least about 30, at least about 60, or at least about 90 days after administration of the liquid formulation to the rabbit eye.

For treatment, prevention, inhibition, delaying the onset of, or causing the regression of certain diseases or conditions, it may be desirable to maintain delivery of a therapeutically effective amount of the therapeutic agent for an extended period of time. Depending on the disease or condition being treated, prevented, inhibited, having onset delayed, or being caused to regress this extended period of time may be at least about 1 week, at least about 2 weeks, at least about 3 weeks, at least about 1 month, at least about 3 months, at least about 6 months, at least about 9 months, or at least about 1 year. Generally, however, any extended period of delivery may be possible. A therapeutically effective amount of agent may be delivered for an extended period by a liquid formulation or composition that maintains for the extended period a concentration of agent in a subject or an eye of a subject sufficient to deliver a therapeutically effective amount of agent for the extended time.

Delivery of a therapeutically effective amount of the therapeutic agent for an extended period may be achieved via placement of one composition or liquid formulation or may be achieved by application of two or more doses of composition or liquid formulations. As a non-limiting example of such multiple applications, maintenance of the therapeutic amount of rapamycin for 3 months for treatment, prevention, inhibition, delay of onset, or cause of regression of wet AMD may be achieved by application of one liquid formulation or composition delivering a therapeutic amount for 3 months or by sequential application of a plurality of liquid formulations or compositions. The optimal dosage regime will depend on the therapeutic amount of the therapeutic agent needing to be delivered, and the period over which it need be delivered. Those versed in such extended therapeutic agent delivery dosing will understand how to identify dosing regimes that may be used based on the teachings provided herein.

When using certain therapeutic agents or for the treatment, prevention, inhibition, delaying the onset of, or causing the regression of certain diseases, it may be desirable for delivery of the therapeutic agent not to commence immediately upon placement of the liquid formulation or composition into the eye region, but for delivery to commence after some delay. For example, but in no way limiting, such delayed release may be useful where the therapeutic agent inhibits or delays wound healing and delayed release is desirable to allow healing of any wounds occurring upon placement of the liquid formulation or composition. Depending on the therapeutic agent being delivered and/or the diseases and conditions being treated, prevented, inhibited, onset delayed, and regression caused this period of delay before delivery of the therapeutic agent commences may be about 1 hour, about 6 hours, about 12 hours, about 18 hours, about 1 day, about 2 days, about 3 days, about 4 days, about 5 days, about 6 days, about 7 days, about 8 days, about 9 days, about 10 days, about 11 days, about 12 days, about 13 days, about 14 days, about 21 days, about 28 days, about 35 days, or about 42 days. Other delay periods may be possible. Delayed release formulations that may be used are known to people versed in the technology.

Intravitreal, Subconjunctival, Subtenonal, and Topical Delivery of Rapamycin for Treatment, Prevention, Inhibition, Delay of Onset, or Cause of Regression of AMD In one method described herein, a liquid formulation comprising rapamycin is delivered subconjunctivally or to the vitreous of an eye to prevent, treat, inhibit, delay onset of, or cause regression of angiogenesis in the eye, including but not limited to treating CNV as observed, for example, in AMD. In some variations, the liquid formulation is used to treat angiogenesis in the eye, including but not limited to treating CNV as observed, for example, in AMD. Rapamycin has been shown to inhibit CNV in rat and mice models, as described in U.S. application Ser. No. 10/665,203, which is incorporated herein by reference in its entirety. Rapamycin has been observed to inhibit Matrigel™ and laser-induced CNV when administered systemically and subretinally. Also, periocular injection of rapamycin inhibits laser-induced CNV.

Other therapeutic agents that may be delivered to the eye, particularly the vitreous of an eye, for treatment, prevention, inhibition, delaying onset, or causing regression of angiogenesis in the eye (such as CNV) are members of the limus family of compounds other than rapamycin including but not limited to everolimus and tacrolimus (FK-506).

As described herein, the dosage of the therapeutic agent will depend on the condition being addressed, whether the condition is to be treated, prevented, inhibited, have onset delayed, or be caused to regress, the particular therapeutic agent, and other clinical factors such as weight and condition of the subject and the route of administration of the therapeutic agent. It is to be understood that the methods, liquid formulations, and compositions described herein have application for both human and veterinary use, as well as uses in other possible animals. As described herein, tissue concentrations of therapeutic agents expressed in units of mass per volume generally refer to tissues that are primarily aqueous such as the vitreous, for example. Tissue concentrations of therapeutic agents expressed in unit of mass per mass generally refer to other tissues such as the sclera or retina choroid tissues, for example.

One concentration of rapamycin that may be used in the methods described herein is one that provides about 0.01 pg/ml or pg/mg or more of rapamycin at the tissue level. Another concentration that may be used is one that provides about 0.1 pg/ml or ng/mg or more at the tissue level. Another concentration that may be used is one that provides about 1 pg/ml or ng/mg or more at the tissue level. Another concentration that may be used is one that provides about 0.01 ng/ml or ng/mg or more at the tissue level. Another concentration that may be used is one that provides about 0.1 ng/ml or ng/mg or more at the tissue level. Another concentration that may be used is one that provides about 0.5 ng/ml or ng/mg or more at the tissue level. Another concentration that may be used is one that provides about 1 ng/ml or more at the tissue level. Another concentration that may be used is one that provides about 2 ng/ml or more at the tissue level. Another concentration that may be used is one that provides about 3 ng/ml or more at the tissue level. Another concentration that may be used is one that provides about 5 ng/ml or more at the tissue level. Another concentration that may be used is one that provides about 10 ng/ml or more at the tissue level. Another concentration that may be used is one that provides about 15 ng/ml or more at the tissue level. Another concentration that may be used is one that provides about 20 ng/ml or more at the tissue level. Another concentration that may be used is one that provides about 30 ng/ml or more at the tissue level. Another concentration that may be used is one that provides about 50 ng/ml or more at the tissue level. One of ordinary skill in the art would know how to arrive at an appropriate concentration depending on the route and duration of administration utilized, given the teachings herein.

Generally, the amount of rapamycin administered in a liquid formulation is an amount sufficient to treat, prevent, inhibit, delay the onset, or cause regression of the disease or condition of the eye for the required amount of time. In some variations the amount of rapamycin administered in the liquid formulation is an amount sufficient to treat the disease or condition of the eye for the required amount of time.

In some variations, a total amount of rapamycin less than about 5 mg is administered subconjunctivally. In some variations, a total amount of rapamycin less than about 5.0 mg is administered subconjunctivally. In some variations, a total amount of rapamycin less than about 4.5 mg is administered subconjunctivally. In some variations, a total amount of rapamycin less than about 4.0 mg is administered subconjunctivally. In some variations, a total amount of rapamycin less than about 3.5 mg is administered subconjunctivally. In some variations, a total amount of rapamycin less than about 3.0 mg is administered subconjunctivally. In some variations, a total amount of rapamycin less than about 2.5 mg is administered subconjunctivally. In some variations, a total amount of rapamycin less than about 2 mg is administered subconjunctivally. In some variations, a total amount of rapamycin less than about 1.2 mg is administered subconjunctivally. In some variations, a total amount of rapamycin less than about 1.0 mg is administered subconjunctivally. In some variations, a total amount of rapamycin less than about 0.8 mg is administered subconjunctivally. In some variations, a total amount of rapamycin less than about 0.6 mg is administered subconjunctivally. In some variations, a total amount of rapamycin less than about 0.4 mg is administered subconjunctivally. In some variations, a volume of a formulation is administered that contains an amount of rapamycin described herein.

In some variations, a liquid formulation containing a concentration of rapamycin by weight of the total of between about 0.5% and about 6% is subconjunctivally administered to a human subject by administering between about 0.1 µl and about 200 µl of a liquid formulation described herein. In some variations, a liquid formulation containing a concentration of rapamycin by weight of the total of between about 0.5% and about 4% is subconjunctivally administered to a human subject by administering between about 1 µl and about 50 µl of a liquid formulation described herein. In some variations, a liquid formulation containing a concentration of rapamycin by weight of the total of between about 1.5% and about 3.5% is subconjunctivally administered to a human subject by administering between about 1 µl and about 15 µl of a liquid formulation described herein. In some variations, a liquid formulation containing a concentration of rapamycin by weight of the total of about 2% is subconjunctivally administered to a human subject by administering between about 1 µl and about 15 µl of a liquid formulation described herein.

In some variations, a liquid formulation containing an amount of rapamycin of between about 0.2 µg and about 4 mg is subconjunctivally administered to a human subject by administering between about 0.1 µl and about 200 µl of a liquid formulation described herein. In some variations, a liquid formulation containing an amount of rapamycin of between about 20 µg and about 2 mg is subconjunctivally administered to a human subject by administering between about 1 µl and about 100 µl of a liquid formulation described herein. In some variations, a liquid formulation containing an amount of rapamycin of between about 20 µg and about 1 mg is subconjunctivally administered to a human subject by administering between about 1 µl and about 50 µl of a liquid formulation described herein. In some variations, a liquid formulation containing an amount of rapamycin of between about 20 µg and about 500 µg is subconjunctivally administered to a human subject by administering between about 1 µl and about 25 µl of a liquid formulation described herein. In some variations, a liquid formulation containing an amount of rapamycin of between about 20 µg and about 300 µg is subconjunctivally administered to a human subject by administering between about 1 µl and about 15 µl of a liquid formulation described herein.

In some variations, a total amount of rapamycin less than about 200 µg is administered intravitreally. In some variations, a total amount of rapamycin less than about 200 µg is administered intravitreally. In some variations, a total amount of rapamycin less than about 300 µg is administered intravitreally. In some variations, a total amount of rapamycin less than about 400 µg is administered intravitreally. In some variations, a total amount of rapamycin less than about 500 µg is administered intravitreally. In some variations, a total amount of rapamycin less than about 600 µg is administered intravitreally. In some variations, a total amount of rapamycin less than about 800 µg is administered intravitreally. In some variations, a total amount of rapamycin less than about 1 mg is administered intravitreally. In some variations, a total amount of rapamycin less than about 2 mg is administered intravitreally. In some variations, a total amount of rapamycin less than about 2.5 mg is administered intravitreally. In some variations, a total amount of rapamycin less than about 3 mg is administered intravitreally. In some variations, a total amount of rapamycin less than about 3.5 mg is administered intravitreally. In some variations, a total amount of rapamycin less than about 4 mg is administered intravitreally. In some variations, a volume of a formulation is administered that contains an amount of rapamycin described herein.

In some variations, a liquid formulation containing a concentration of rapamycin by weight of the total of between about 0.5% and about 6% is intravitreally administered to a human subject by administering between about 0.1 µl and about 200 µl of a liquid formulation described herein. In some variations, a liquid formulation containing a concentration of rapamycin by weight of the total of between about 0.5% and about 4% is intravitreally administered to a human subject by administering between about 1 µl and about 50 µl of a liquid formulation described herein. In some variations, a liquid formulation containing a concentration of rapamycin by weight of the total of between about 1.5% and about 3.5% is intravitreally administered to a human subject by administering between about 1 µl and about 15 µl of a liquid formulation described herein. In some variations, a liquid formulation containing a concentration of rapamycin by weight of the total of about 2% is intravitreally administered to a human subject by administering between about 1 µl and about 15 µl of a liquid formulation described herein.

In some variations, a liquid formulation containing an amount of rapamycin of between about 0.2 µg and about 4 mg is intravitreally administered to a human subject by administering between about 0.1 µl and about 200 µl of a liquid formulation described herein. In some variations, a liquid formulation containing an amount of rapamycin of between about 20 µg and about 2 mg is intravitreally administered to a human subject by administering between about 1 µl and about 100 µl of a liquid formulation described herein. In some variations, a liquid formulation containing an amount of rapamycin of between about 20 µg and about 1 mg is intravitreally administered to a human subject by administering between about 1 µl and about 50 µl of a liquid formulation described herein. In some variations, a liquid formulation containing an amount of rapamycin of between about 20 µg and about 500 µg is intravitreally administered to a human subject by administering between about 1 µl and about 25 µl of a liquid formulation described herein. In some variations, a liquid formulation containing an amount of rapamycin of between about 20 µg and about 300 µg is intravitreally administered to a human subject by administering between about 1 µl and about 15 µl of a liquid formulation described herein.

In some variations, a total amount of rapamycin less than about 5 mg is administered subtenonally. In some variations, a total amount of rapamycin less than about 5.0 mg is administered subtenonally. In some variations, a total amount of rapamycin less than about 4.5 mg is administered subtenonally. In some variations, a total amount of rapamycin less than about 4.0 mg is administered subtenonally. In some variations, a total amount of rapamycin less than about 3.5 mg is administered subtenonally. In some variations, a total amount of rapamycin less than about 3.0 mg is administered subtenonally. In some variations, a total amount of rapamycin less than about 2.5 mg is administered subtenonally. In some variations, a total amount of rapamycin less than about 2 mg is administered subtenonally. In some variations, a total amount of rapamycin less than about 1.2 mg is administered subtenonally. In some variations, a total amount of rapamycin less than about 1.0 mg is administered subtenonally. In some variations, a total amount of rapamycin less than about 0.8 mg is administered subtenonally. In some variations, a total amount of rapamycin less than about 0.6 mg is administered subtenonally. In some variations, a total amount of rapamycin less than about 0.4 mg is administered subtenonally. In some variations, a volume of a formulation is administered that contains an amount of therapeutic agent described herein.

In some variations, a total amount of rapamycin less than about 5 mg is administered topically. In some variations, a total amount of rapamycin less than about 5.0 mg is administered topically. In some variations, a total amount of rapamycin less than about 4.5 mg is administered topically. In some variations, a total amount of rapamycin less than about 4.0 mg is administered topically. In some variations, a total amount of rapamycin less than about 3.5 mg is administered topically. In some variations, a total amount of rapamycin less than about 3.0 mg is administered topically. In some variations, a total amount of rapamycin less than about 2.5 mg is administered topically. In some variations, a total amount of rapamycin less than about 2 mg is administered topically. In some variations, a total amount of rapamycin less than about 1.2 mg is administered topically. In some variations, a total amount of rapamycin less than about 1.0 mg is administered topically. In some variations, a total amount of rapamycin less than about 0.8 mg is administered topically. In some variations, a total amount of rapamycin less than about 0.6 mg is administered topically. In some variations, a total amount of rapamycin less than about 0.4 mg is administered topically. In some variations, a volume of a formulation is administered that contains an amount of rapamycin described herein. In some variations, a total amount of therapeutic agent administered topically is any of between about 20 µg and about 4000 µg, between about 10 µg and about 2000 µg, between about 10 µg and 1750 µg, between about 1500 µg and 1000 µg, or between about 10 µg and 1000 µg. In some variations, a total amount of therapeutic agent administered topically is about 1660 µg. In some variations, a total amount of therapeutic agent administered topically is about 880 µg. In some variations, a total amount of therapeutic agent administered topically is 40 µg. In some variations, a total amount of therapeutic agent administered topically is about 28 µg.

In some variations, the liquid formulation when topically administered to a rabbit eye delivers therapeutic agent giving an average concentration of therapeutic agent in the cornea of the rabbit eye of at least any of about 0.001 ng/mg, 0.01 ng/mg, 0.1 ng/mg, or 1 ng/mg. In some variations, the liquid formulation when topically administered to a rabbit eye delivers therapeutic agent giving an average concentration of therapeutic agent in the cornea of the rabbit eye of at least 0.01 ng/mg. In some variations, the liquid formulation when topically administered to a rabbit eye delivers therapeutic agent giving an average concentration of therapeutic agent in the retina choroid tissues of the rabbit eye of at least any of about 0.0001 ng/mg, 0.001 ng/mg, 0.01 ng/mg, 0.1 ng/mg, or 1 ng/mg. In some variations, the liquid formulation when topically administered to a rabbit eye delivers therapeutic agent giving an average concentration of therapeutic agent in the retina choroid tissues of the rabbit eye of at least 0.001 ng/mg.

In some variations, a total amount of rapamycin administered subconjunctivally is any of between about 50 µg and about 3 mg, between about 150 µg and about 750 µg, between about 300 µg and about 1000 µg, between about 300 µg and about 950 µg, between about 400 µg and about 900 µg, between about 450 µg and about 850 µg, between about 500 µg and about 800 µg, between about 550 µg and about 750 µg, or between about 600 µg and about 700 µg. In some variations, a total amount of rapamycin administered subconjunctivally is any of about 220 µg, about 440 µg, about 587 µg, about 630 µg, about 660 µg, about 880 µg, about 1320 µg, about 1760 µg, or about 2200 µg. In some variations, a total amount of rapamycin administered subconjunctivally is about 220 µg. In some variations, a total amount of rapamycin administered subconjunctivally is about 440 µg. In some variations, a total amount of rapamycin administered subconjunctivally is about 660 µg. In some variations, a total amount of rapamycin administered subconjunctivally is about 880 µg. In some variations, a liquid formulation containing an amount of rapamycin of 220 µg is subconjunctivally administered to a human subject by administering about 10 µl of a liquid formulation described herein. In some variations, a liquid formulation containing an amount of rapamycin of 440 µg is subconjunctivally administered to a human subject by administering about 20 µl of a liquid formulation described herein. In some variations, a liquid formulation containing an amount of rapamycin of 660 µg is subconjunctivally administered to a human subject by administering about 30 µl of a liquid formulation described herein. In some variations, a liquid formulation containing an amount of rapamycin of 880 µg is subconjunctivally administered to a human subject by administering about 40 µl of a liquid formulation described herein.

In some variations, a total amount of rapamycin administered intravitreally is any of between about 20 µg and about 750 µg, between about 20 µg and about 500 µg, or between about 30 µg and about 200 µg. In some variations, a total amount of rapamycin administered intravitreally is any of about 44 µg, about 110 µg, about 132 µg, about 133.5 µg, about 176 µg, about 264 µg, about 352 µg, or about 440 µg. In some variations, a total amount of rapamycin administered intravitreally is about 44 µg. In some variations, a total amount of rapamycin administered intravitreally is about 110 µg. In some variations, a liquid formulation containing an amount of rapamycin of 44 µg is intravitreally administered to a human subject by administering about 2 µl of a liquid formulation described herein. In some variations, a liquid formulation containing an amount of rapamycin of 110 µg is intravitreally administered to a human subject by administering about 5 µl of a liquid formulation described herein. In some variations, a liquid formulation containing an amount of rapamycin of 176 µg is intravitreally administered to a human subject by administering about 8 µl of a liquid formulation described herein.

In some variations a liquid formulation as described herein containing an amount of rapamycin of between about 1 µg and about 5 mg is administered to a human subject for treatment of wet AMD. In some variations a liquid formulation as described herein containing an amount of rapamycin of between about 20 µg and about 4 mg is administered to a human subject for treatment of wet AMD. In some variations a liquid formulation as described herein containing an amount of rapamycin of between about 20 µg and about 1.2 mg is administered to a human subject for treatment of wet AMD. In some variations an amount of rapamycin of between about 10 µg and about 0.5 mg is administered to a human subject for treatment of wet AMD. In some variations an amount of rapamycin of between about 10 µg and 90 µg is administered to a human subject for treatment of wet AMD. In some variations an amount of rapamycin of between about 60 µg and about 120 µg is administered to a human subject for treatment of wet AMD. In some variations an amount of rapamycin of between about 100 µg and about 400 µg is administered to a human subject for treatment of wet AMD. In some variations an amount of rapamycin of between about 400 µg and about 1 mg is administered to a human subject for treatment of wet AMD. In some variations an amount of rapamycin of between about 1 mg and about 5 mg is administered to a human subject for treatment of wet AMD. In some variations, an amount of rapamycin of between about 3 mg and about 7 mg is administered to a human subject for treatment of wet AMD. In some variations, an amount of rapamycin of between about 5 mg and about 10 mg is administered to a human subject for treatment of wet AMD.

In some variations a liquid formulation as described herein containing an amount of rapamycin of between about 1 µg and about 5 mg is administered to a human subject for prevention of wet AMD. In some variations a liquid formulation as described herein containing an amount of rapamycin of between about 20 µg and about 4 mg is administered to a human subject for prevention of wet AMD. In some variations a liquid formulation as described herein containing an amount of rapamycin of between about 20 µg and about 1.2 mg is administered to a human subject for prevention of wet AMD. In some variations an amount of rapamycin of between about 10 µg and about 0.5 mg is administered to a human subject for prevention of wet AMD. In some variations an amount of rapamycin of between about 10 µg and 90 µg is administered to a human subject for prevention of wet AMD. In some variations an amount of rapamycin of between about 60 µg and about 120 µg is administered to a human subject for prevention of wet AMD. In some variations an amount of rapamycin of between about 100 µg and about 400 µg is administered to a human subject for prevention of wet AMD. In some variations an amount of rapamycin of between about 400 µg and about 1 mg is administered to a human subject for prevention of wet AMD. In some variations an amount of rapamycin of between about 1 mg and about 5 mg is administered to a human subject for prevention of wet AMD. In some variations, an amount of rapamycin of between about 3 mg and about 7 mg is administered to a human subject for prevention of wet AMD. In some variations, an amount of rapamycin of between about 5 mg and about 10 mg is administered to a human subject for prevention of wet AMD.

In some variations a liquid formulation as described herein containing an amount of rapamycin of between about 1 µg and about 5 mg is administered to a human subject for treatment of dry AMD. In some variations a liquid formulation as described herein containing an amount of rapamycin of between about 20 µg and about 4 mg is administered to a human subject for treatment of dry AMD. In some variations a liquid formulation as described herein containing an amount of rapamycin of between about 20 µg and about 1.2 mg is administered to a human subject for treatment of dry AMD. In some variations an amount of rapamycin of between about 10 µg and about 0.5 mg is administered to a human subject for treatment of dry AMD. In some variations an amount of rapamycin of between about 10 µg and 90 µg is administered to a human subject for treatment of dry AMD. In some variations an amount of rapamycin of between about 60 µg and about 120 µg is administered to a human subject for treatment of dry AMD. In some variations an amount of rapamycin of between about 100 µg and about 400 µg is administered to a human subject for treatment of dry AMD. In some variations an amount of rapamycin of between about 400 µg and about 1 mg is administered to a human subject for treatment of dry AMD. In some variations an amount of rapamycin of between about 1 mg and about 5 mg is administered to a human subject for treatment of dry AMD. In some variations, an amount of rapamycin of between about 3 mg and about 7 mg is administered to a human subject for treatment of dry AMD. In some variations, an amount of rapamycin of between about 5 mg and about 10 mg is administered to a human subject for treatment of dry AMD.

In some variations, a liquid formulation as described herein containing an amount of rapamycin of between about 1 µg and about 5 mg is administered to a human subject for treatment of angiogenesis, including but not limited to choroidal neovascularization. In some variations, an amount of rapamycin of between about 20 µg and about 4 mg is administered to the human subject; between about 20 µg and about 1.2 mg; between about 10 µg and about 0.5 mg is administered to a human subject for treatment of wet AMD, between about 10 µg and 90 µg, between about 60 µg and 120 µg is administered to the human subject; between about 100 µg and 400 µg, between about 400 µg and 1 mg is administered to the human subject; in some variations, an amount of rapamycin of between about 1 mg and 5 mg is administered to the human subject; in some variations, an amount of rapamycin of between about 3 mg and 7 mg is administered to the human subject; in some variations, an amount of rapamycin of between about 5 mg and 10 mg is administered to the human subject for treatment of angiogenesis, including but not limited to choroidal neovascularization.

In one method, a liquid formulation as described herein contains an amount of a therapeutic agent equivalent to an amount of rapamycin.

In one method, a liquid formulation as described herein containing an amount of a therapeutic agent equivalent to an amount of rapamycin of between about 1 µg and about 5 mg is administered to a human subject for treatment of wet AMD. In some variations, an amount of a therapeutic agent equivalent to an amount of rapamycin of between about 1 µg and about 5 mg is administered to the human subject; between about 20 µg and about 1.2 mg; between about 10 µg and about 0.5 mg is administered to a human subject for treatment of wet AMD, between about 10 µg and 90 µg, between about 60 µg and 120 µg is administered to the human subject; between about 100 µg and 400 µg, between about 400 µg and 1 mg is administered to the human subject is administered to the human subject; in some variations, an amount of a therapeutic agent equivalent to an amount of rapamycin of between about 1 mg and 5 mg is administered to the human subject; in some variations, an amount of a therapeutic agent equivalent to an amount of rapamycin of between about 3 mg and 7 mg is administered to the human subject; in some variations, an amount of a therapeutic agent equivalent to an amount of rapamycin of between about 5 mg and 10 mg is administered to the human subject.

In some variations, a liquid formulation as described herein containing an amount of a therapeutic agent equivalent to an amount of rapamycin of between about 1 µg and about 5 mg is administered to a human subject for treatment of dry AMD. In some variations, an amount of a therapeutic agent equivalent to an amount of rapamycin of between about 20 µg and about 4 mg is administered to the human subject; between about 20 µg and about 1.2 mg; between about 10 µg and about 0.5 mg is administered to a human subject for treatment of wet AMD, between about 10 µg and 90 µg, between about 60 µg and 120 µg is administered to the human subject; between about 100 µg and 400 µg, between about 400 µg and 1 mg is administered to the human subject; in some variations, an amount of a therapeutic agent equivalent to an amount of rapamycin of between about 400 µg and 1 mg is administered to the human subject; in some variations, an amount of a therapeutic agent equivalent to an amount of rapamycin of between about 1 mg and 5 mg is administered to the human subject; in some variations, an amount of a therapeutic agent equivalent to an amount of rapamycin of between about 3 mg and 7 mg is administered to the human subject; in some variations, an amount of a therapeutic agent equivalent to an amount of rapamycin of between about 5 mg and 10 mg is administered to the human subject to treat dry AMD.

In some variations, a liquid formulation as described herein containing an amount of a therapeutic agent equivalent to an amount of rapamycin of between about 1 µg and about 5 mg is administered to a human subject for prevention of wet AMD. In some variations, an amount of a therapeutic agent equivalent to an amount of rapamycin of between about 20 µg and about 4 mg is administered to the human subject; between about 20 µg and about 1.2 mg; between about 10 µg and about 0.5 mg is administered to a human subject for prevention of wet AMD, between about 10 µg and 90 µg, between about 60 µg and 120 µg is administered to the human subject; between about 100 µg and 400 µg, between about 400 µg and 1 mg is administered to the human subject; in some variations, an amount of a therapeutic agent equivalent to an amount of rapamycin of between about 400 µg and 1 mg is administered to the human subject; in some variations, an amount of a therapeutic agent equivalent to an amount of rapamycin of between about 1 mg and 5 mg is administered to the human subject; in some variations, an amount of a therapeutic agent equivalent to an amount of rapamycin of between about 3 mg and 7 mg is administered to the human subject; in some variations, an amount of a therapeutic agent equivalent to an amount of rapamycin of between about 5 mg and 10 mg is administered to the human subject to prevent wet AMD.

In some variations, any one or more of the formulations described herein are administered intravitreally every 3 or more months, every 6 or more months, every 9 or more months, or every 12 or more months, or longer, to treat one or more of choroidal neovascularization, wet AMD, dry AMD, to prevent wet AMD, or to prevent progression of dry AMD to wet AMD. In some variations, any one or more of the formulations described herein are administered subconjunctivally every 3 or more months, every 6 or more months, every 9 or more months, or every 12 or more months, or longer, to treat one or more of choroidal neovascularization, wet AMD, dry AMD, or to prevent wet AMD.

In some variations, any one or more of the rapamycin formulations described herein are administered intravitreally every 3 or more months, every 6 or more months, every 9 or more months, or every 12 or more months, or longer, to treat one or more of choroidal neovascularization, wet AMD, dry AMD, to prevent wet AMD, or to prevent progression of dry AMD to wet AMD. In some variations, any one or more of the rapamycin formulations described herein are administered subconjunctivally every 3 or more months, every 6 or more months, every 9 or more months, or every 12 or more months, or longer, to treat one or more of choroidal neovascularization, wet AMD, dry AMD, or to prevent wet AMD. In some variations, the effect of the rapamycin persists beyond the period during which it is present in the ocular tissues.

Delivery of the therapeutic agents described herein may, for example, be delivered at a dosage range between about 1 ng/day and about 100 µg/day, or at dosages higher or lower than this range, depending on the route and duration of administration. In some variations of liquid formulation or composition used in the methods described herein, the therapeutic agents are delivered at a dosage range of between about 0.1 µg/day and about 10 µg/day. In some variations of liquid formulation or composition used in the methods described herein, the therapeutic agents are delivered at a dosage range of between about 1 µg/day and about 5 µg/day. Dosages of various therapeutic agents for treatment, prevention, inhibition, delay of onset, or cause of regression of various diseases and conditions described herein can be refined by the use of clinical trials.

The liquid formulations, including but not limited to solutions, suspensions, emulsions and situ gelling formulations, and compositions described herein may be used for delivery to the eye, as one nonlimiting example by ocular or periocular administration, of therapeutically effective amounts of rapamycin for extended periods of time to treat, prevent, inhibit, delay the onset of, or cause regression of CNV, and thus may be used to treat, prevent, inhibit, delay the onset of, or cause regression of wet AMD, or transition of dry AMD to wet AMD. It is believed that by changing certain characteristics of the liquid formulations described herein, including but not limited to the components of the liquid formulations, the location in the eye to which the liquid formulation is delivered, including without limitation subconjunctival or intravitreal placement, the liquid formulations may be used to deliver therapeutically effective amounts of rapamycin to the eye for a variety of extended time periods including delivery of therapeutic amounts for greater than about 1 week, for greater than about 2 weeks, for greater than about 3 weeks, for greater than about 1 month, for greater than about 3 months, for greater than about 6 months, for greater than about 9 months, for greater than about 1 year.

When a therapeutically effective amount of rapamycin is administered to a subject suffering from wet AMD, the rapamycin may treat, inhibit, or cause regression of the wet AMD. Different therapeutically effective amounts may be required for treatment, inhibition or causing regression. A subject suffering from wet AMD may have CNV lesions, and it is believed that administration of a therapeutically effective amount of rapamycin may have a variety of effects, including but not limited to causing regression of the CNV lesions, stabilizing the CNV lesion, and preventing progression of an active CNV lesion.

When a therapeutically effective amount of rapamycin is administered to a subject suffering from dry AMD, it is believed that the rapamycin may prevent or slow the progression of dry AMD to wet AMD.

EXAMPLES

Unless the context indicates otherwise, the error bars in the charts show one standard deviation. Where ethanol is used, it is 200 proof ethanol from Gold Shield Distributors, Hayward, Calif. Where rapamycin is used, it is from LC laboratories, Woburn, Mass., or Chunghwa Chemical Synthesis & Biotech Co., LTD (CCSB), Taipei Hsien, Taiwan, ROC. Where PEG 400 is used, it is from The Dow Chemical Company, New Milford, Conn. Some of the graphs use the expression "uL" or "ug" to refer to μL or μg, respectively. Where a volume of 10 μL or less is administered, Hamilton HPLC syringes were used.

Examples 1-45

Preparation and Administration of Rapamycin-Containing Compositions

Preparation and characterization of exemplary rapamycin-containing compositions, and administration thereof to New Zealand white rabbits is described in US 2006/0258698 A1 and WO 2006/102378A2 of Mudumba et al. (Examples 1-45 and associated figures herein incorporated by reference).

Example 46

Preparation and Characterization of a Rapamycin-Containing Solution

About 320 g of ethanol was sparged with $N_2$ for about 10 minutes, and then about 40 g of sirolimus was added to the ethanol. The mixture was sonicated for about 20 minutes, by the end of which all of the sirolimus had gone into solution to form a sirolimus stock solution. A diluent solvent was prepared by sonicating about 1880 g of PEG 400 for about 60 minutes, and then sparging the solvent with nitrogen for about 10 minutes.

The sirolimus stock solution and the PEG 400 were then rotated at room temperature in a rotary evaporator for about 10 minutes to mix the stock solution with the diluent solvent. After mixing, the solution was sparged with nitrogen for about 10 minutes and blanketed with nitrogen for about 5 minutes. After the solution was sparged and filled with nitrogen, about 240 g of excess ethanol was evaporated from the solution by increasing the solution temperature, maintaining a temperature that did not exceed 40° C. for an extended period of time and continuing to rotate the solution for about 2.5 hours.

The resulting solution comprised about 40 g of sirolimus (about 2% by weight), about 80 g of ethanol (about 4% by weight), and about 1880 g of PEG 400 (about 94% by weight). This solution was sparged with nitrogen for about 10 minutes and blanketed with nitrogen for about 5 minutes. The solution was then filtered through a 0.2 micron filter. USP type I glass vials were filled with 0.5 ml each of the filtered solution to leave a head space in each container of about 2 ml. This head space was filled with nitrogen gas and capped. This solution is listed as formulation #340 in Table 1.

Example 47

Preparation and Characterization of a Rapamycin-Containing Solution

About 32 g of ethanol was sparged with $N_2$ for about 10 minutes, and then about 4 g of sirolimus was added to the ethanol. The mixture was sonicated for about 20 minutes, by the end of which all of the sirolimus had gone into solution to form a sirolimus stock solution. A diluent solvent was prepared by sonicating about 92 g of PEG 400 for about 60 minutes, and then sparging the solvent with Nitrogen for about 10 minutes.

The sirolimus stock solution and the PEG 400 were then rotated at about room temperature in a rotary evaporator for about 10 minutes to mix the stock solution with the diluent solvent. After mixing, the solution was sparged with nitrogen for about 10 minutes and blanketed with nitrogen for about 5 minutes. After the solution was sparged and filled with nitrogen, about 28 g of excess ethanol was evaporated from the solution by increasing the solution temperature, maintaining a temperature that did not exceed 40° C. for an extended period of time and continuing to rotate the solution for about 2.5 hours.

The resulting solution comprised about 4 g of sirolimus (about 4% by weight), about 4 g of ethanol (about 4% by weight), and about 92 g of PEG 400 (about 92% by weight). This solution was sparged with nitrogen for about 10 minutes and blanketed with nitrogen for about 5 minutes. The solution was then filtered through a 0.2 micron filter. USP type I glass vials were filled with 0.5 ml each of the filtered solution to leave a head space in each container of about 2 ml. This head space was filled with nitrogen gas and capped. This solution is listed as formulation #326 in Table 1.

Example 48

Preparation and Characterization of a Rapamycin-Containing Solution

About 200 μL of normal saline (sodium chloride, 0.9%) was added to 0.5 mL of the solution of Example 46 (previously filled in 2 mL USP type I glass vials) using a 0.5 cc insulin syringe, and mixed by gently swirling. The resulting mixture is a clear solution and has an approximate composition of 1.47% (w/w) of sirolimus, 2.93% (w/w) of ethanol, 26.6% (w/w) of normal saline, and 69% (w/w) of PEG 400. This solution is listed as formulation #327 in Table 1.

Example 49

Preparation and Characterization of a Rapamycin-Containing Solution

About 250 μL of normal saline (sodium chloride, 0.9%) was added to 0.5 mL of the solution of Example 46 (previously filled in 2 mL USP type I glass vials) using a 0.5 cc insulin syringe, and mixed by gently swirling. The resulting mixture is a dispersed form and has an approximate composition of 1.38% (w/w) of sirolimus, 2.75% (w/w) of ethanol, 31.25% (w/w) of normal saline, and 64.62% (w/w) of PEG 400. This solution is listed as formulation #328 in Table 1.

Example 50

Subconjunctival Injection of a Rapamycin-Containing Solution

Either 40 μl of the solution described in Example 46, Example 48, or Example 49, or 20 μL of the solution described in Example 47 was injected between the sclera and the conjunctiva of the eye of New Zealand White rabbits. FIG. 1 depicts the average concentration of rapamycin present in the retina choroid (ng/g) on a logarithmic scale at 14, 30, 60, and 90 days after injection.

The analysis was by liquid chromatography mass spectroscopy (LCMS) using an internal standard. At each time point, the average concentration of rapamycin was calculated by adding the concentrations of rapamycin obtained for each eye from each rabbit, and dividing the total by the number of eyes analyzed. In this experiment, each time point represents the average of either two eyes of each of two rabbits (four eyes at that time point).

The full retina choroid was homogenized and analyzed. The average concentration of the retina choroid was calculated by dividing the mass of rapamycin measured by the mass of retina choroid analyzed. The sample did not include the site of administration; thus, this measurement indicated the level of rapamycin delivered to the retina choroid via test article (in this case, the solutions of Examples 46, 47, 48, and 49).

The average level of rapamycin in the retina choroid at 14, 30, 60, and 90 days after subconjunctival injection of the solution of Example 46 was about 56.94, 9.79, 2.26, and 0.00 ng/g, respectively. The average level of rapamycin in the retina choroid at 14, 30, 60, and 90 days after subconjunctival injection of the solution of Example 47 was about 90.19, 6.0, 5.72, and 0.98 ng/g, respectively. The average level of rapamycin in the retina choroid at 14, 30, 60, and 90 days after subconjunctival injection of the solution of Example 48 was about 103.86, 20.54, 6.07, and 12.76 ng/g, respectively. The average level of rapamycin in the retina choroid at 14, 30, 60, and 90 days after subconjunctival injection of the solution of Example 49 was about 70.12, 27.83, 3.99, and 5.94 ng/g, respectively.

Example 51

Intravitreal Injection of a Rapamycin-Containing Solution

6 µl of the solution of Example 46 or 8.5 µL of the solution of Example 48 was injected into the vitreous of the eye of New Zealand White rabbits using a 10 µL Hamilton syringe. FIG. 2 depicts the level of rapamycin present in the retina choroid (ng/g) on a logarithmic scale at 3, 14, 30, 45 and 60 days after injection.

Full vitreous of each eye was homogenized and analyzed by liquid chromatography tandem mass spectrometry (LC/MS/MS). The average level of rapamycin in the vitreous at 3, 14, 30 and 60 days after intravitreal injection of the solution of Example 46 was about 63,064.3, 6,095.56, 58.21, and 0.15 ng/ml, respectively. The average level of rapamycin in the vitreous at 3, 14, 30, 45 and 60 days after intravitreal injection of the solution of Example 48 was about 58,930.4, 18,573.1, 6,793.21, 799.18, and 4116.17 ng/ml, respectively.

The full retina choroid was homogenized and analyzed. The average concentration of the retina choroid was calculated by dividing the mass of rapamycin measured by the mass of retina choroid analyzed. The sample did not include the site of administration; thus, this measurement indicated the level of rapamycin delivered to the retina choroid via test article (in this case, the solution of Example 46 or 48). The average level of rapamycin in the retina choroid at 3, 14, 30, and 60 days after intravitreal injection of the solution of Example 46 was about 1971.84, 478.02, 57.70, and 1.90 ng/g, respectively. The average level of rapamycin in the retina choroid at 3, 14, 30, 45 and 60 days after intravitreal injection of the solution of Example 48 was about 2869.05, 3633.64, 43.38, 37.09 and 27.36 ng/g, respectively.

Example 52

Intravitreal and Subtenon Injection of a Rapamycin-Containing Solution

Figure 3:
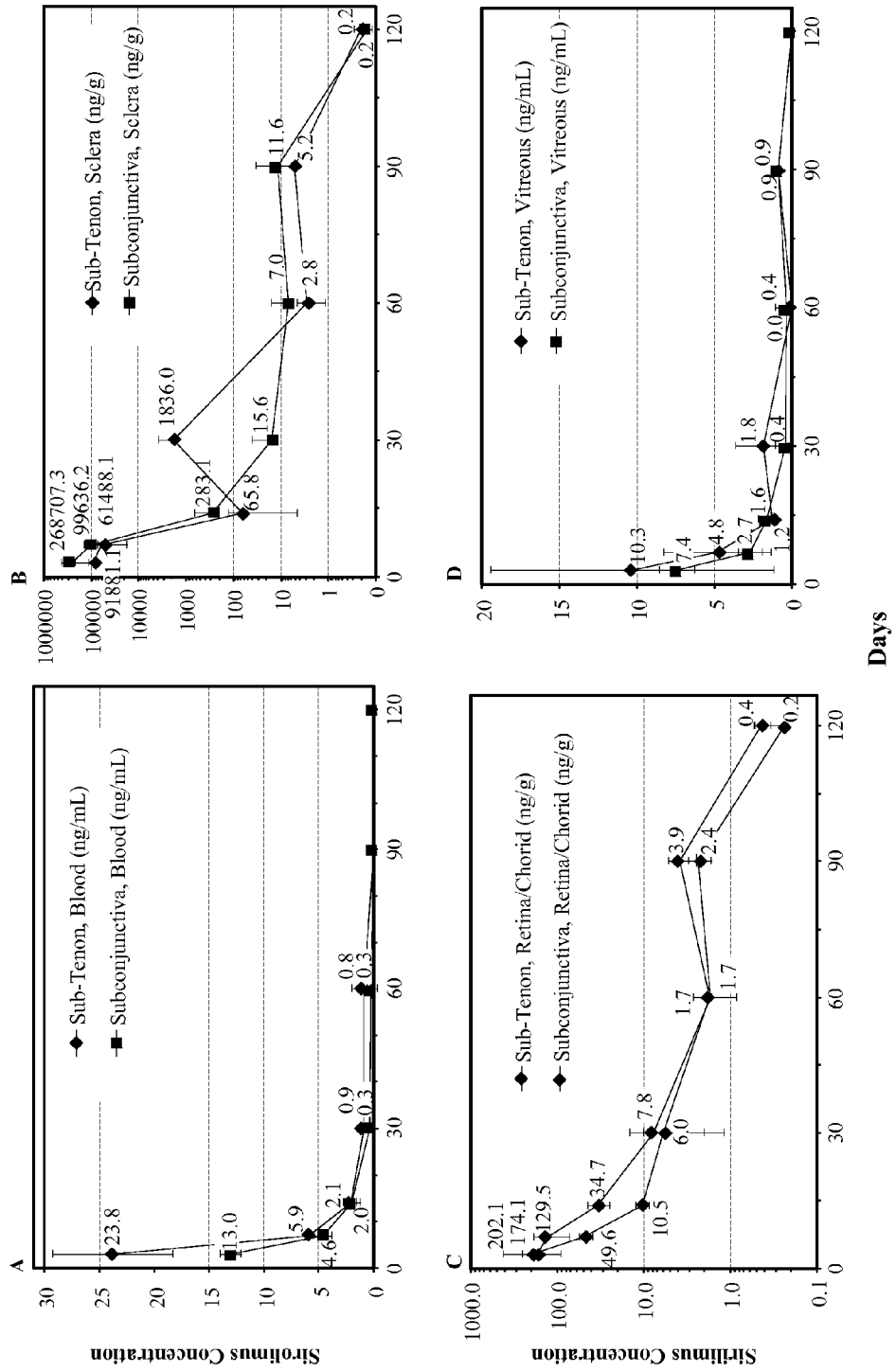
FIGS. 3A-3D depict the concentration of rapamycin present in (A) whole blood (ng/ml), (B) sclera (ng/g), (C) retina choroid (ng/g), and (D) vitreous fluid (ng/mL) at 3, 7, 14, 30, 60, and 90 days after either subconjunctival or subtenous injection of 30 µl of 2% solution of rapamycin in ethanol and PEG 400.

30 µl of the solution of Example 46 was injected between the sclera and the conjunctiva of the eye of New Zealand White rabbits. FIG. 3 depicts the average concentration of rapamycin present in the retina choroid (ng/g) and whole blood (ng/mL) on a logarithmic scale at 3, 7, 14, 30, 60 and 90 days after injection.

The full retina choroid was processed and analyzed as described earlier. The average level of rapamycin in the retina choroid at 3, 7, 14, 30, 60 and 90 days after subconjunctival injection of the solution of Example 46 was about 174.1, 129.5, 34.7, 7.8, 1.7, and 1.7 ng/g, respectively. The whole blood samples are precipitated by addition of known amount organic solvents, homogenized, centrifuged, and supernatant was collected to analyze rapamycin levels using LC/MS/MS. The average level of rapamycin in the blood at 3, 7, 14, 30 and 60 days after subconjunctival injection of the solution of Example 46 was about 13.0, 4.6, 2.0, 0.3, and 0.3 ng/mL, respectively.

For the 30 µL subtenon injections, a guide hole was made by inserting and removing a 20 gauge×½ inch sharp BD needle though the conjunctiva in the dorsotemporal quadrant 3 mm posterior to the limbus and temporal to the dorsal rectus muscle attachment. A 24 G fukasaku anesthesia cannula attached to a sterile 0.5 cc BD syringe was then guided through the guide hole posteriorly into the subtenon space and the solution of Example 46 was injected slowly on the posterior surface of the sclera near the optic nerve. FIG. 3 depicts the average concentration of rapamycin present in the retina choroid (ng/g) and whole blood (ng/mL) on a logarithmic scale at 3, 7, 14, 30, 60 and 90 days after injection.

The full retina choroid was processed and analyzed as described earlier. The average level of rapamycin in the retina choroid at 3, 7, 14, 30, 60 and 90 days after subtenon injection of the solution of Example 46 was about 202.1, 49.6, 10.5, 6.0, 1.7, and 3.9 ng/g, respectively. The whole blood samples are precipitated by addition of known amount organic solvents, homogenized, centrifuged, and supernatant was collected to analyze rapamycin levels using LC/MS/MS. The average level of rapamycin in the blood at 3, 7, 14, 30 and 60 days after subtenon injection of the solution of Example 46 was about 23.8, 5.9, 2.1, 0.4, and 0.8 ng/mL, respectively.

Example 53

Preparation and Characterization of a Rapamycin-Containing Solution

The following solvent preparation allows up to 5% (w/w) of rapamycin. N-methyl pyrrolidone (NMP) and propylene glycol (PG) are mixed in 10.5:73.7 ratio, desired amount of sirolimus (up to 5% w/w of final composition) is dissolved in the mix, and subsequently water (up to 15.8% w/w of final composition) is added slowly to obtain the final solution. This solution is listed as formulation #333 in Table 1.

Example 54

Preparation and Characterization of a Rapamycin-Containing Solution

The following solvent preparation allows up to 5% (w/w) of rapamycin. N-methyl pyrrolidone (NMP) and propylene glycol (PG) are mixed in 38.9:38.9 (1:1) ratio, desired amount of sirolimus (up to 5% w/w of final composition) is dissolved in the mix, and subsequently water (up to 22.2% w/w of final composition) is added slowly to obtain the final solution. This solution is listed as formulation #334 in Table 1.

Example 55

Preparation and Characterization of a Rapamycin-Containing Solution

The following solvent preparation allows up to 5% (w/w) of rapamycin. N-methyl pyrrolidone (NMP) and polyethylene glycol 600 (PEG 600) are mixed in 10.5:73.7 ratio, desired amount of sirolimus (up to 5% w/w of final composition) is dissolved in the mix, and subsequently water (up to 15.8% w/w of final composition) is added slowly to obtain the final solution. This solution is listed as formulation #335 in Table 1.

Example 56

Preparation and Characterization of a Rapamycin-Containing Solution

The following solvent preparation allows up to 5% (w/w) of rapamycin. Dimethyl acetamide (DMA) and propylene glycol (PG) are mixed in 10.5:73.7 ratio, desired amount of sirolimus (up to 5% w/w of final composition) is dissolved in the mix, and subsequently water (up to 15.8% w/w of final composition) is added slowly to obtain the final solution. This solution is listed as formulation #336 in Table 1.

Example 57

Preparation and Characterization of a Rapamycin-Containing Solution

The following solvent preparation allows up to 5% (w/w) of rapamycin. Dimethyl sulfoxide (DMSO) and propylene glycol (PG) are mixed in 10.5:73.7 ratio, desired amount of sirolimus (up to 5% w/w of final composition) is dissolved in the mix, and subsequently water (up to 15.8% w/w of final composition) is added slowly to obtain the final solution. This solution is listed as formulation #337 in Table 1.

Example 58

Preparation and Characterization of a Rapamycin-Containing Solution

N-methylpyrrolidone (NMP), polyethylene glycol 400 (PEG 400) and ethanol are mixed in 27.9:28.4:4.7 ratio (respectively), desired amount of sirolimus (up to 5% w/w of final composition) is dissolved in the mix, and subsequently water (up to 28.4% w/w of final composition) is added slowly to obtain the final solution. This solution is listed as formulation #338 in Table 1.

Example 59

Preparation and Characterization of a Rapamycin-Containing Solution 8.35% of Cremophor (percentage of total weight) is mixed with 8.37% of Capmul MCM (percentage of total weight). 0.07% rapamycin (percentage of the total weight) was dissolved in the Cremophor-Capmul MCM solution using an ultrasound bath. 83.21% (percentage of total weight) of sterile water is added to the former solution and the resulting solution is vortexed creating a milky microemulsion. The solution was placed at 2-8° C. until use. This solution is listed as formulation #329 in Table 1.

Example 60

Preparation and Characterization of a Rapamycin-Containing Solution 8.15% of Capmul MCM (percentage of total weight) is mixed with 8.12% of Tyloxapol (percentage of total weight). 0.09% rapamycin (percentage of the total weight) was dissolved in the Tyloxapol-Capmul MCM solution in which 0.35% of Ethanol was added. The final dissolution is completed by using an ultrasound bath. 83.29% (percentage of total weight) of sterile water is added to the former solution and the resulting solution is vortexed creating a milky microemulsion. The solution was placed at 2-8° C. until use. This solution is listed as formulation #330 in Table 1.

Example 61

Preparation and Characterization of a Rapamycin-Containing Solution 6.81% of Tyloxapol (percentage of total weight) is mixed with 6.81% of Capmul MCM (percentage of total weight) and 3.12% of PHOSAL® 50PG (percentage of total weight). 0.08% rapamycin (percentage of the total weight) was dissolved in the Tyloxapol-Capmul MCM-PHOSAL® 50PG solution using an ultrasound bath. 83.21% (percentage of total weight) of sterile water is added to the former solution and the resulting solution is vortexed creating a milky microemulsion. The solution was placed at 2-8° C. until use. This solution is listed as formulation #331 in Table 1.

Example 62

Preparation and Characterization of a Rapamycin-Containing Solution 7.18% of Cremophor (percentage of total weight) is mixed with 9.47% of Capmul MCM (percentage of total weight). 0.17% rapamycin (percentage of the total weight) was dissolved in the Cremophor-Capmul MCM solution in which 0.35% of Ethanol was added. 83.18% (percentage of total weight) of sterile water was added to the former solution and the resulting solution is vortexed creating a milky microemulsion. The solution was placed at 2-8° C. until use. This solution is listed as formulation #332 in Table 1.

Example 63

Topical Administration of Rapamycin-Containing Formulations

Both eyes (or one eye depending on the study) of each animal received one or two drops (40 µl per drop) of the studied formulations using a calibrated pipette on day 0 (day of dosing). Results are shown in Tables 3-6 and FIGS. 4-9.

Figure 4:
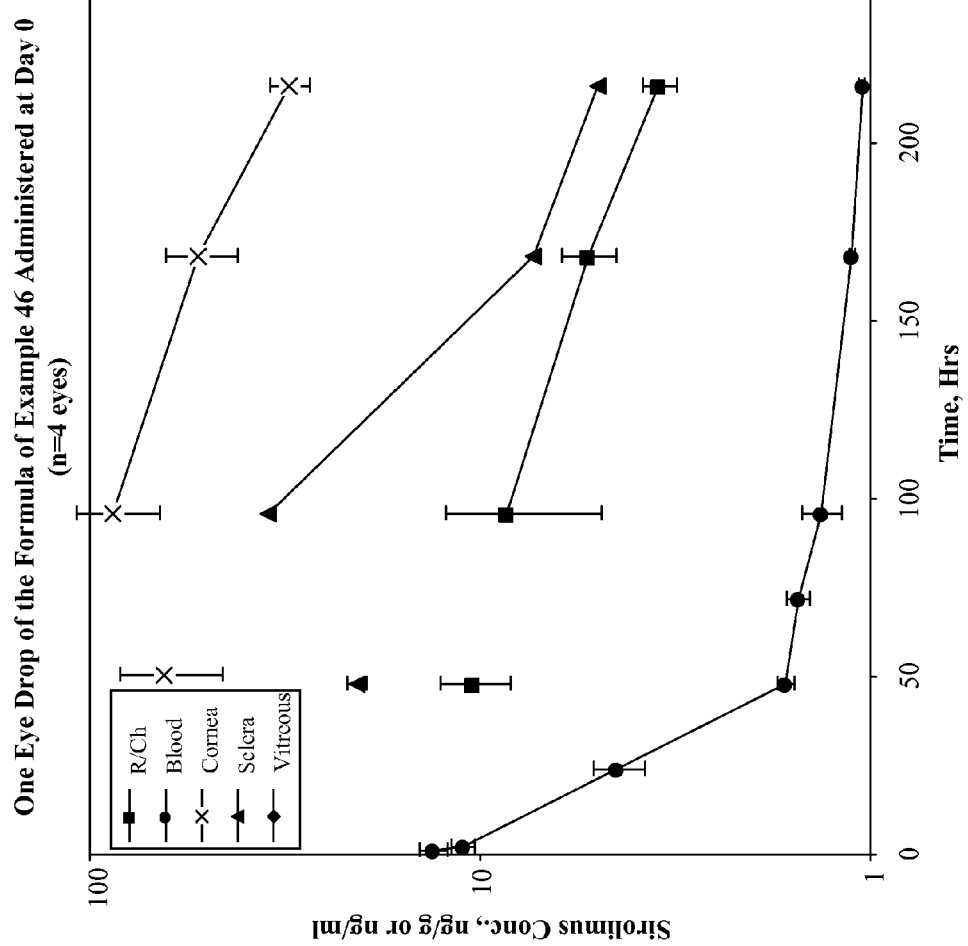
FIG. 4 depicts the concentration of rapamycin present in tissue or fluid of rabbit eyes after topical administration of one eye drop (about 40 µL) of a 2% rapamycin solution.

For Tables 3-6, the solution of Example 46 (formulation #340) was administered two drops twice a day on both eyes, one time for Group I, two drops once a day on one eye, one time for Group II, and two drops once a day on both eyes for 6 days in Group III. In Group II, the right eye (OD) but not the left eye (OS) received eye drops. In a further study, one drop of the formulation #340 (40 µL containing 880 µg rapamycin) was administered on day zero. As shown in FIG. 4, after administration of a single eye drop, the rapamycin concentration in the cornea remained above 0.01 ng/g nine days (e.g., 216 hrs) after administration, while the rapamycin concentration in retina choroid remained above 0.001 ng/g nine days (e.g., 216 hrs) after administration. In fact after administration of a single eye drop, the rapamycin concentration in the cornea remained above 10.0 ng/g (above 0.01 ng/mg) nine days (e.g., 216 hrs) after administration, while the rapamycin concentration in retina choroid remained above 1.0 ng/g (above 0.001 ng/mg) nine days (e.g., 216 hrs) after administration.

Figure 9:
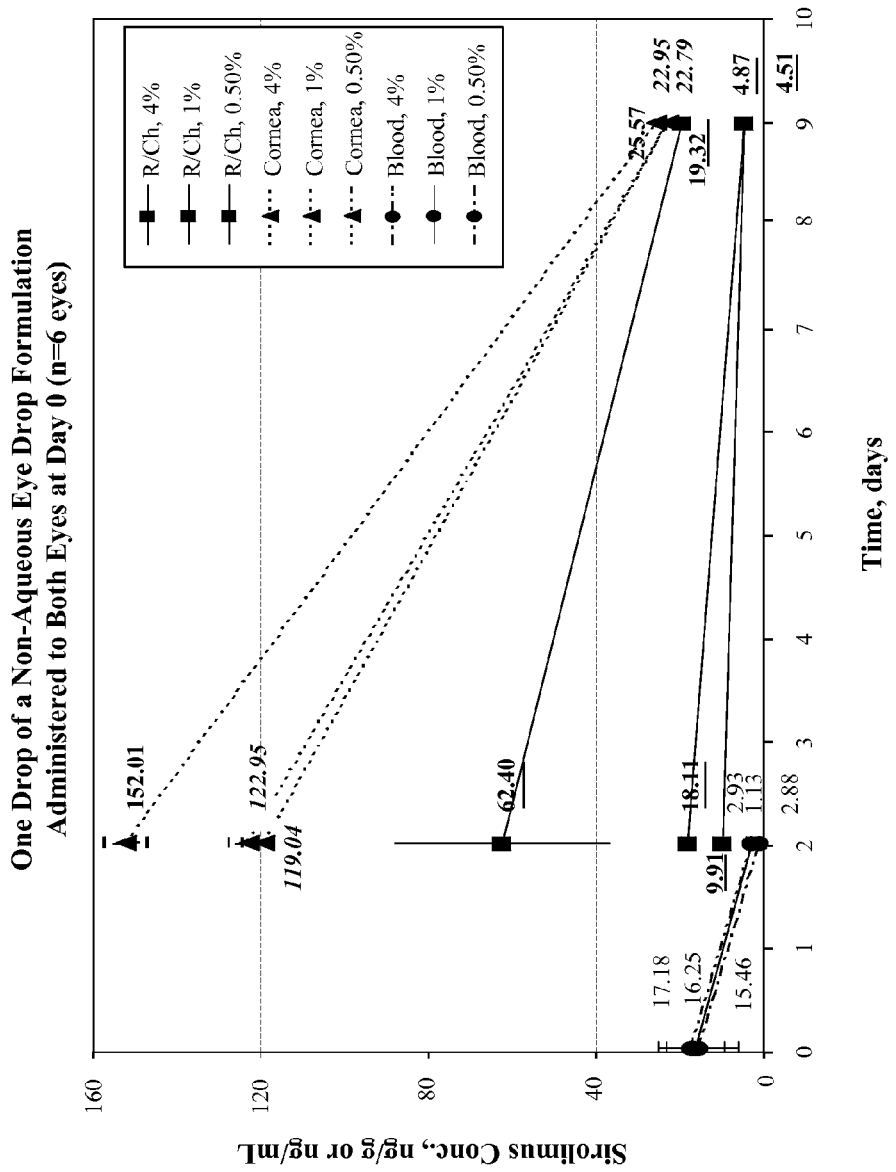
FIG. 9 depicts the concentration of rapamycin present in eye tissue or blood (ng/g or ng/ml) after topical administration by eye drops of a non-aqueous solution comprising 0.5%, 1.0% or 4.0% rapamycin.

Moreover as shown in FIG. 9 in a further study, following administration of a single non-aqueous eye drop formulation containing 4%, 1% or 0.5% rapamycin, sustained levels of rapamycin were detected in the cornea and retina choroid. In particular, after administration of a single eye drop, the rapamycin concentration in the cornea remained above 0.01 ng/g (above 0.01 ng/mg) for at least nine days after administration, while the rapamycin concentration in retina choroid remained above 0.001 ng/g (above 0.001 ng/mg) for at least 9 days after administration. In contrast, the rapamycin concentration in the blood was substantially lower than that observed in the cornea and retina choroid indicating that the non-aqueous eye drop formulations did not result in significant systemic exposure to rapamycin.

Figure 5:
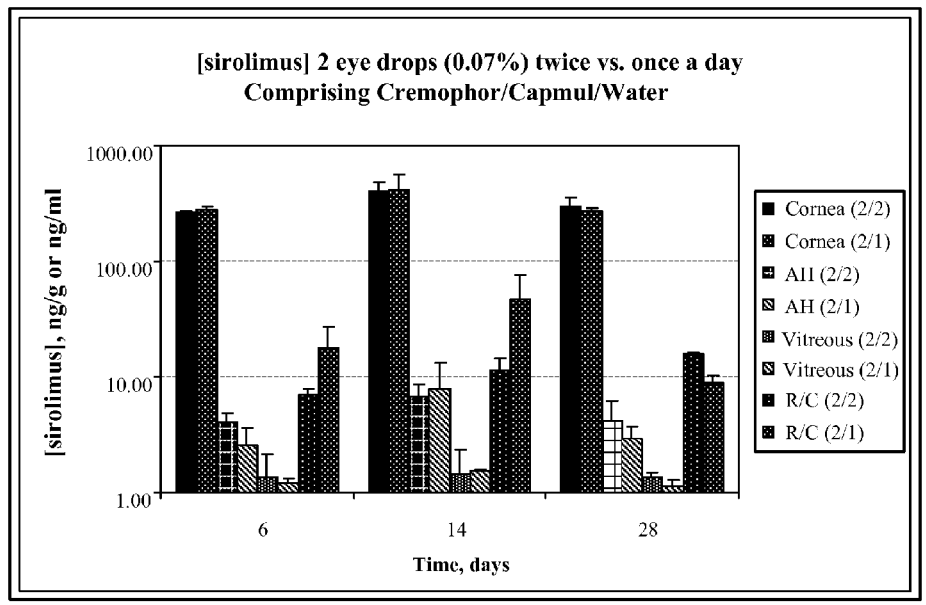
FIG. 5 depicts the concentration of rapamycin present in tissue or fluid of rabbit eyes after topical administration by eye drops of a 0.07% rapamycin solution.
Figure 6:
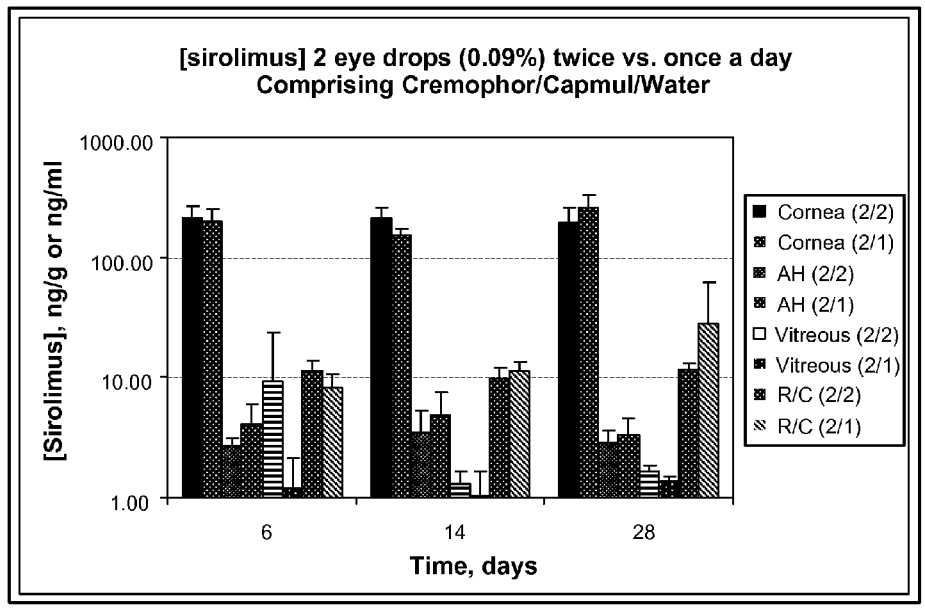
FIG. 6 depicts the concentration of rapamycin present in eye tissue (ng/g) of rabbit eyes after topical administration by eye drops of a 0.09% rapamycin solution.
Figure 7:
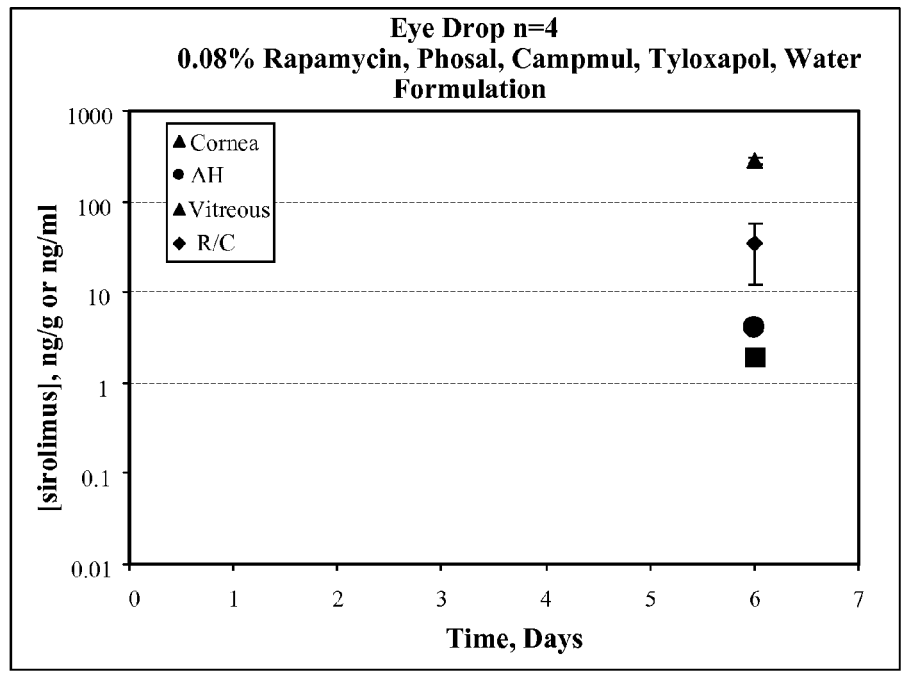
FIG. 7 depicts the concentration of rapamycin present in eye tissue or fluid (ng/g or ng/ml) after topical administration by eye drops of a 0.08% rapamycin solution comprising phosal, capmul, tyloxapol and water.
Figure 8:
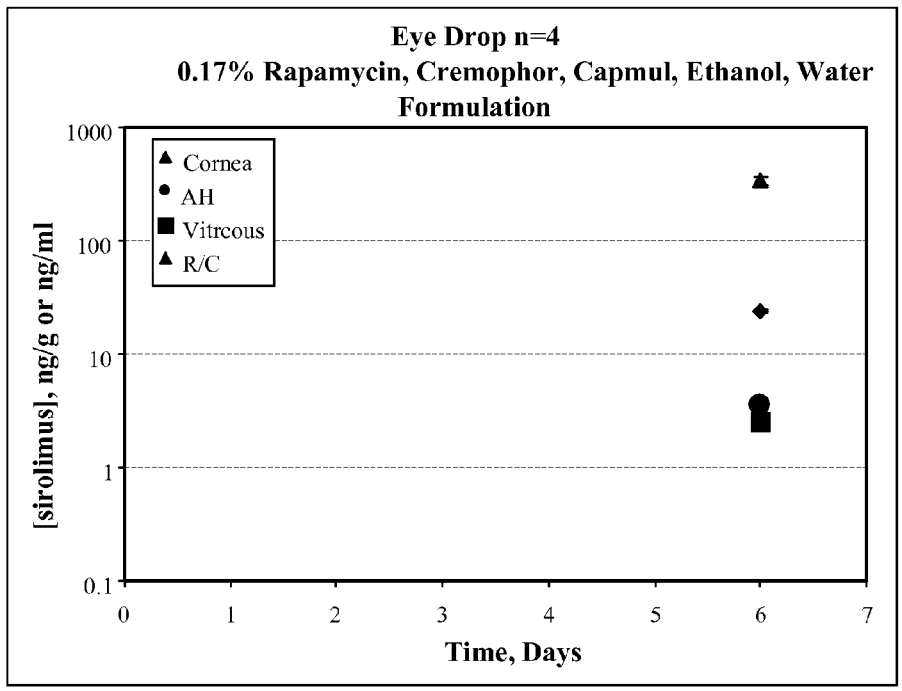
FIG. 8 depicts the concentration of rapamycin present in eye tissue or fluid (ng/g or ng/ml) after topical administration by eye drops of a 0.17% rapamycin solution comprising cremophor, capmul, ethanol, and water.

For FIGS. 5 and 6, the aqueous rapamycin-containing formulations #329 and #330 of Table 1, were administered two drops once or twice a day for up to 28 days. For FIGS. 7 and 8, the aqueous rapamycin-containing formulations #331 and #332 of Table 1 were administered two drops twice a day for 6 days. In short, the aqueous rapamycin-containing formulations tested achieved an average concentration of rapamycin in the cornea of at least 0.01 ng/g (greater than 0.01 ng/mg to 0.1 ng/mg in FIGS. 5-8), in the retina choroid of at least 0.01 ng/g (greater than 0.001 ng/mg to 0.01 ng/mg in some measurements of FIGS. 5-8), in the aqueous humor of at least 0.1 ng/mL (greater than 1.0 ng/mL), and in the vitreous humor of at least 0.1 ng/mL (greater than 1.0 ng/mL).

Figure 10A:
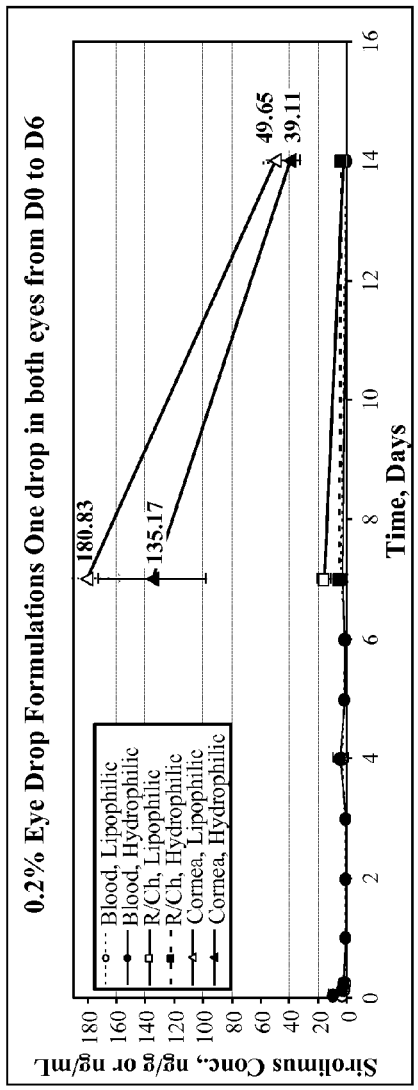
FIGS. 10A-B depict the concentration of rapamycin present in eye tissue or blood (ng/g or ng/ml) after topical administration by eye drops of a non-aqueous solution or an aqueous solution comprising about 0.2% rapamycin.
Figure 10B:
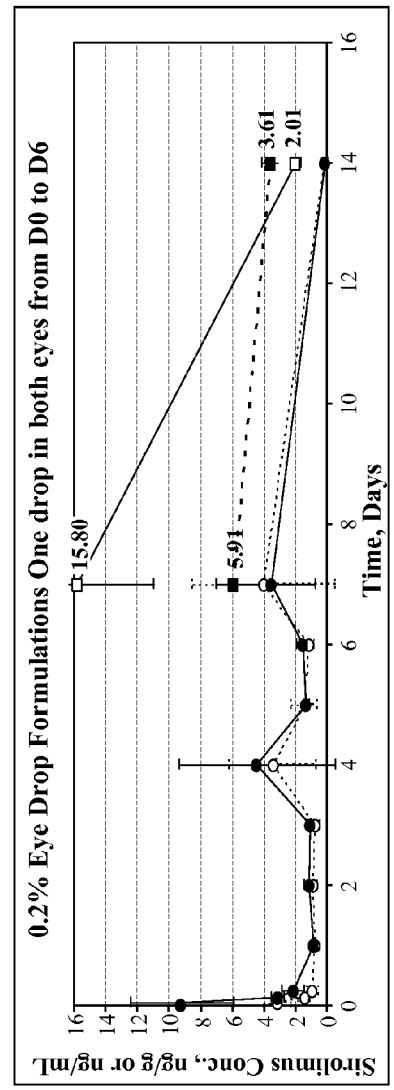

For FIGS. 10A and 10B one drop of an aqueous or a non-aqueous formulation containing about 0.2% rapamycin were administered to both eyes of rabbit subjects once a day for six days (day 0 to day 6). As used herein, the terms "aqueous" and "hydrophilic" refer to formulations in which the dominant component is an aqueous compound such as water (e.g., formulations #342 and #342 of Table 1), while the terms "non-aqueous" and "lipophilic" refer to formulation in which the dominant component is a non-aqueous compound such as PEG 400 (e.g., formulations #344 and #345 of Table 1). Rapamycin concentrations in the cornea, retina choroid and blood were measured at day 7 and day 14. Both formulations tested achieved an average concentration of rapamycin in the cornea of at least 0.01 ng/g (at least 10 ng/g) on days 7 and 14, and in the retina choroid of at least 0.01 ng/g (at least 1 ng/g) on days 7 and 14.

Figure 11:
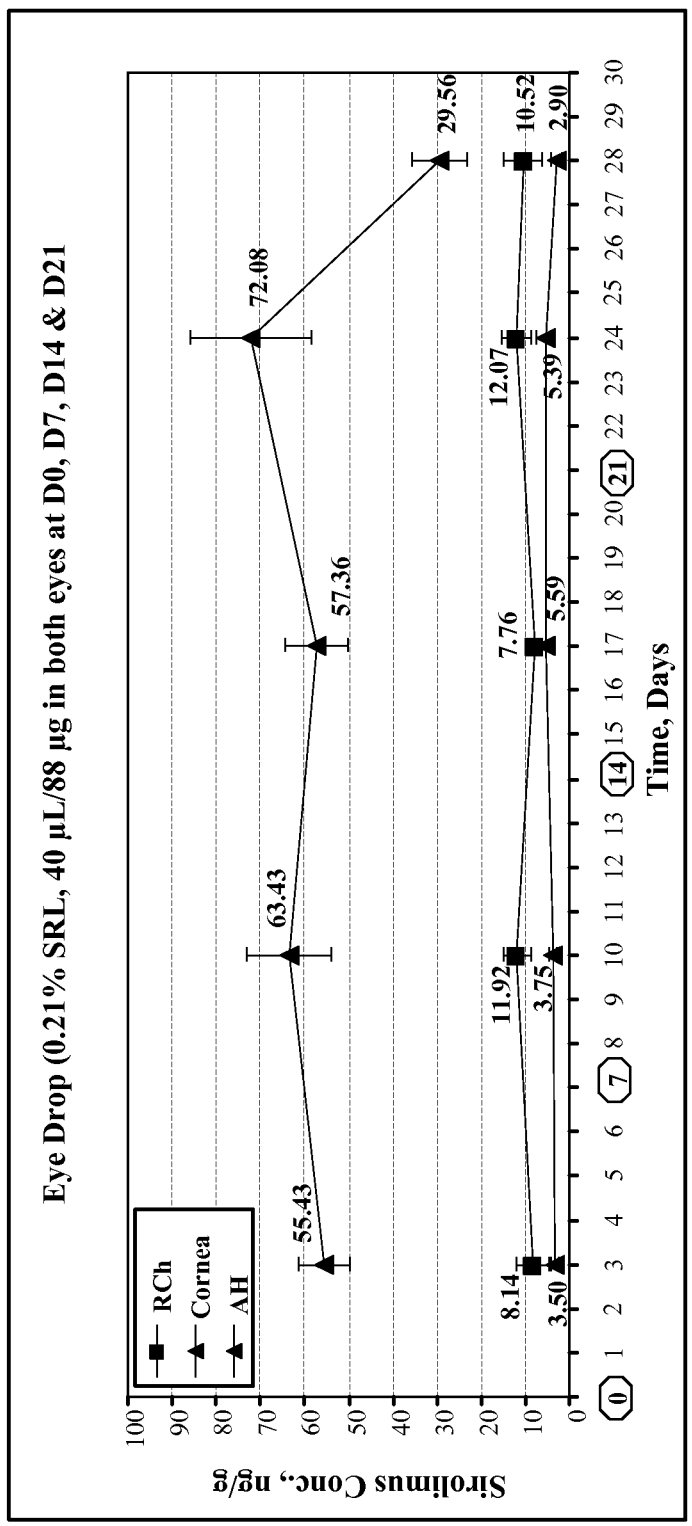
FIG. 11 depicts the concentration of rapamycin present in eye tissue or fluid (ng/g or ng/ml) after topical administration by eye drops of a non-aqueous solution comprising about 0.2% rapamycin.

For FIG. 11 one drop of a non-aqueous formulation containing about 0.2% rapamycin (e.g., formulations #344 or #345) was administered to both eyes of rabbit subjects once a day on day 0, 7, 14 and 21. Rapamycin concentrations in the cornea, retina choroid and aqueous humor were measured on days 3, 10, 17, 24 and 28. Infrequent administration of the non-aqueous eye drops achieved sustained therapeutic levels of rapamycin. In particular a sustained rapamycin concentration was achieved in the cornea of at least 0.01 ng/g (above 10 ng/g) and in the retina choroid and aqueous humor of at least 0.01 ng/mL (above 1 ng/mL).

Example 64

Preparation and Intravitreal Administration of a Rapamycin-Containing Formulation An exemplary rapamycin containing formulation was prepared by adding 0.2003 g rapamycin to 5.9989 g NMP. After mixing, 7.8030 g PG is added, followed by 6.010 g sterile water. This recipe yielded a formulation having final concentrations as a percentage of the total weight of approximately: rapamycin 1.0%, NMP 30.0%, PG 39.0% and sterile water 30.0%. This formulation is listed as #346 in Table 1.

Figure 12:
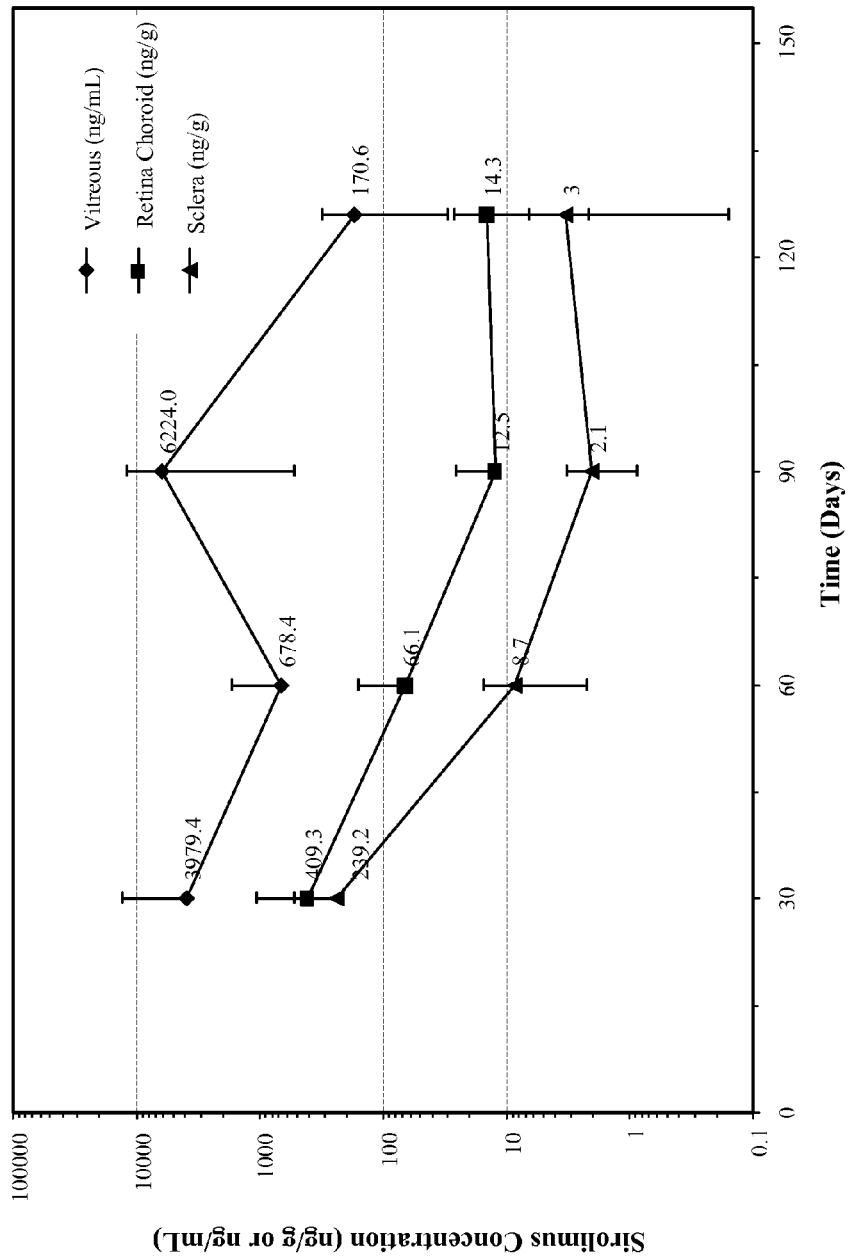
FIG. 12 depicts the concentration of rapamycin present in eye tissue or fluid (ng/g or ng/ml) after intravitreal administration of liquid formulation comprising about 0.6% rapamycin.

The formulation of this example, however, was not stable. As such at the time of the in vivo study (ten days after this preparation was made) the rapamycin potency was determined to be 0.6%. Twenty µl of the 0.6% rapamycin-containing formulation was injected into the vitreous of the eye of New Zealand White rabbits. Rapamycin concentrations in vitreous, retina choroid and sclera were determined as described in Example 51. FIG. 12 depicts the level of rapamycin present in the vitreous, retina choroid and sclera 30 days or more (e.g., 30, 60, 90 and 120 days or more) after injection.

Example 65

Preparation and Subconjunctival Administration of Rapamycin Formulations

An exemplary 2% rapamycin suspension was prepared by dispersing 106.9 mg of rapamycin (2.07% by weight) in 5056.3 mg of 1% carboxymethylcellulose (CMC) low viscosity (97.93% by weight) aqueous solution. Briefly, 106.9 mg of rapamycin and 5056.3 mg of 1% carboxymethylcellulose low viscosity were placed in an amber vial. High wear resistant Ziconia grinding media (beads) of 3 mm diameter were added, up to ¾ of the total volume. The vial was sealed and placed in a Cole-Parmer milling apparatus for at least 24 hrs. The median and mean particle sizes for rapamycin were 3.2957 µm and 3.5487 µm, respectively. The formulation was kept at 4° C. until use. Final concentrations as a percentage of the total weight were approximately: rapamycin: 2.07%, CMC 1%, and sterile water 97.93%. This formulation is listed as #347 in Table 1.

Another exemplary 2% rapamycin in situ gelling formulation was prepared by dissolving 459.9 mg of PLGA (75/25) in 1678.0 mg of NMP overnight. Then 44.8 mg of rapamycin is added until complete dissolution. The formulation was kept at 4° C. until use. Final concentrations as a percentage of the total weight were approximately: rapamycin 2.05%, PLGA 75/25 21.07%, and NMP 76.88%. This formulation is listed as #348 in Table 1.

A further exemplary 2% rapamycin formulation was prepared by dissolving rapamycin in NMP. Then PEG 400 is added under continuous agitation, followed by sterile water also under continuous agitation. The formulation was kept at 4° C. until use. Final concentrations as a percentage of the total weight were approximately: rapamycin 2.02%, NMP 44.47%, PEG 400 29.04%, and sterile water 24.47%. This formulation is listed as #349 in Table 1.

Thirty µl of the 2% rapamycin-containing formulations are injected between the sclera and the conjunctiva of the eye of New Zealand White rabbits. Rapamycin concentrations in vitreous, retina/choroid and sclera are determined as described in Example 50, at days 30, 60 and 90 days post-administration.

Example 66

Preparation and Topical Administration of a Rapamycin-Containing SDF

An exemplary rapamycin-containing solid dosage form (SDF) was prepared using a solvent cast technique. Briefly, the following components were mixed together: 10.0% rapamycin, 57.9% KOLLIDON 90F (PVP 90), 20.0% phosal 50 SD, 10.1% PEG 400, 1.0% vitamin E (gamma tocopherol), and 1.0% ascorbyl palmitate (e.g., equivalent to the formulation #351 in Table 1). A volume of ethanol was added sufficient to obtain 30% total solids (e.g., 70% ethanol) as a final percentage. The mixture was then poured onto a release liner (polyester film with a silicone release coating, and spread to a thickness of 50 mm using a gardner knife. The ethanol was evaporated off in a dark, nitrogen rich environment (i.e., glove box) for about 24 hrs. After drying, the concentration of rapamycin in the SDF was determined by liquid chromatography to be 9.1±0.1% (e.g., 0.9% rapamycin lost). The dried formulation was punched to the desired diameter. The SDF of this example had a diameter of 4 mm, with a thickness of 0.15-0.20 mm, yielding a rapamycin dosage of about 246±21 µg.

Figure 13:
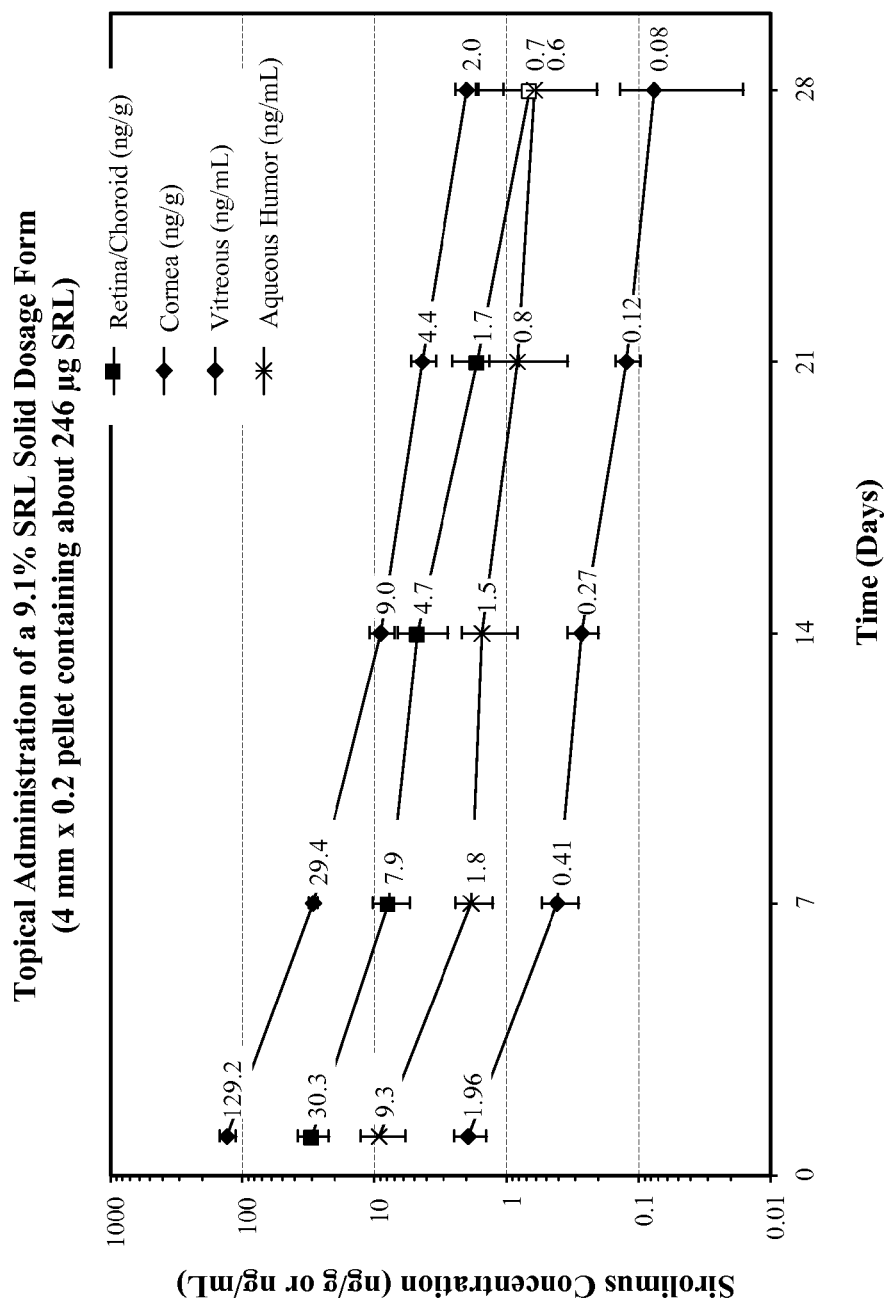
FIG. 13 depicts the concentration of rapamycin present in eye tissue or fluid (ng/g or ng/ml) after periocular administration of solid formulation comprising about 10% rapamycin.

The SDF was administered topically to the eyes of New Zealand White rabbits by placement in the inferior cul-de-sac. Briefly, the lower lid of the eye was pulled out, permitting the placement at the bottom of the cul-de-sac on the inferior side (not sclera side) with a pair of tweezers. Rapamycin concentrations in cornea, retina choroid, vitreous humor, aqueous humor and blood were determined. FIG. 13 depicts the levels of rapamycin in various tissues on days 1, 7, 14, 21 and 28 post-administration.

Example 67

Preparation of a Dexamethasone-Containing SDF

An exemplary dexamethasone-containing solid dosage form (SDF) is prepared using a solvent cast technique. The SDF is prepared with concentrations as a percentage of the total weight of approximately: 25.3% dexamethasone, 33.2% hydroxypropyl cellulose (HPC), 32.0% eudragit RS 30D, and 9.5% xanthan gum. The SDF of less than or equal to 3 mm in diameter is inserted subconjunctivally, for controlled release in the retina/choroid for up to six months (1 to 100 ng/g dexamethasone). This formulation is listed as #352 in Table 1.

Example 68

Preparation and Invitreal Administration of a Dasatanib Formulation

An exemplary dasatanib-containing solution was prepared by dissolving dasatanib in DMA. PEG 400 was then added under continuous agitation. Final concentrations as a percentage of the total weight were approximately: dasatanib 4.8%, dimethylacetamide 16.0%, and PEG 400 79.2% (e.g., equivalent to the formulation #339 in Table 1).

Figure 14:
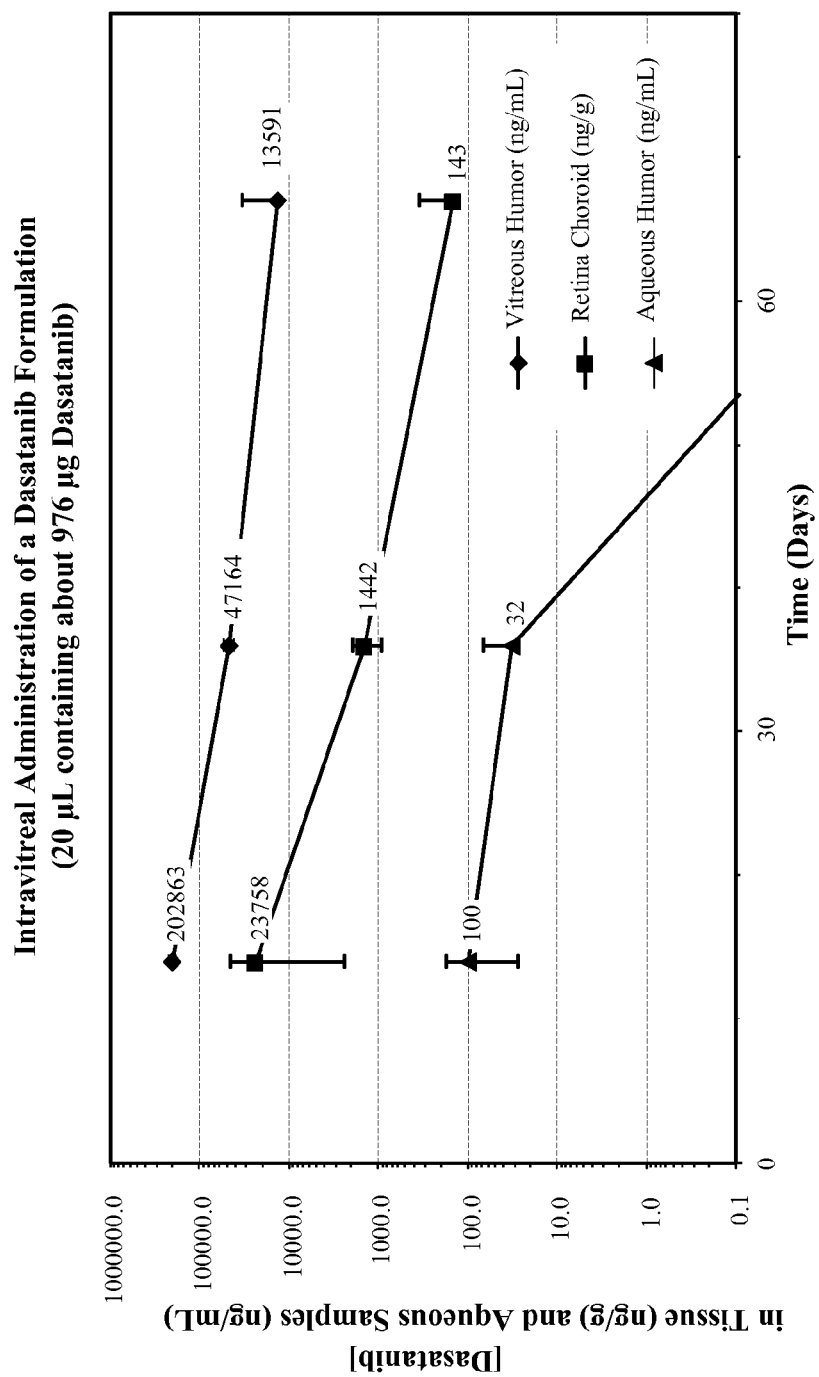
FIG. 14 depicts the concentration of dasatanib present in eye tissue or fluid (ng/g or ng/ml) after intravitreal administration of liquid formulation comprising about 5% dasatanib.

Twenty µl of the 4.84% dasatanib-containing formulation was injected into the vitreous of the eye of New Zealand White rabbits. Dasatanib concentrations in the vitreous and retina choroid were determined. FIG. 14 depicts the level of dasatanib present in the vitreous and retina choroid about 2 weeks, 5 weeks and 10 weeks after injection.

TABLE 1

Formulations

| Form. # | Composition (mg), % (w/w) | Type | Median particle size | NDM, Injection volume |
|---|---|---|---|---|
| 1 | DMSO = 2000 mg (20%)<br>Water = 8000 mg (80%) | S | | |
| 2 | F68 = 1000 mg (10%)<br>Water = 9000 mg (90%) | S | | |
| 3 | F68 = 3000 mg (30%)<br>Water = 7000 mg (70%) | S | | |
| 4 | F127 = 1000 mg (10%)<br>Water = 9000 mg (90%) | S | | |
| 5 | F127 = 1500 mg (15%)<br>Water = 8500 mg (85%) | S | | |
| 6 | Beta-cyclodextrin = 250 mg (2.5%)<br>Water = 9750 mg (97.5%) | S | | |
| 7 | Rapa = 10.2 mg (0.101%)<br>Pluronic, F68 = 1010 mg (9.99%)<br>Water = 9090 mg (89.909%) | S | | No, 50 µL |
| 8 | Rapa = 10.2 mg (0.102%)<br>Pluronic, F68 = 3000 mg (29.969%)<br>Water = 7000 mg (69.929%) | S | | No, 50 µL |
| 9 | Rapa = 10.5 mg (0.104%)<br>Pluronic, F127 = 1010 mg (9.99%)<br>Water = 9090 mg (89.907%) | S | | No, 50 µL |
| 10 | Rapa = 10.5 mg (0.105%)<br>Pluronic, F127 = 1500 mg (14.984%)<br>Water = 8925 mg (84.9%) | S | | No, 50 µL |
| 11 | Rapa = 10.7 mg (0.105%)<br>Beta-cyclodextrin = 255 mg (2.497%)<br>Water = 9945 mg (97.398%) | S | | No, 50 µL |
| 12 | Rapa = 6.4 mg (0.0999%)<br>CMC = 48 mg (0.7493%)<br>Polysorbitan 20 = 2.56 mg (0.04%)<br>Water = 6349.44 mg (99.111%) | SP | | |

TABLE 1-continued

| Form. # | Composition (mg), % (w/w) | Type | Median particle size | NDM, Injection volume |
|---|---|---|---|---|
| 13 | Rapa = 6.5 mg (0.0999%)<br>DMSO = 325 mg (4.995%)<br>Water = 6175 mg (94.905%) | S | | |
| 14 | Rapa = 13.5 mg (0.0999%)<br>CMC = 101.25 mg (0.7493%)<br>Polysorbitan 20 = 5.4 mg (0.04%)<br>Water = 13393.35 mg (99.112%) | SP | | |
| 15 | Rapa = 11.0 mg (0.2%)<br>EtOH = 5500 mg (99.8%) | S | | |
| 16 | Rapa = 6.6 mg (0.1%)<br>EtOH = 1054.6 mg (15.933%)<br>F127 = 833.64 mg (12.595%)<br>Water = 4723.96 mg (71.372%) | S | | |
| 17 | Rapa = 5 mg (0.1%)<br>Cavitron = 0.25 g (5%)<br>Ethanol, 95% = 57 mg (1.1%)<br>Sterile water = 4.753 g (93.8%) | S | | |
| 18 | Rapa = 5 mg (0.1%)<br>Ethanol, 95% = 150 mg (2.9%)<br>PEG400 = 1.0 g (19.4%)<br>Sterile water = 4.01 g (77.6%) | S | | |
| 19 | Rapa = 5 mg (0.1%)<br>Ethanol, 95% = 152 mg (3.2%)<br>PEG400 = 1.5227 g (30.2%)<br>Sterile water = 3.3592 g (66.67%) | S | | Yes, 50 μL |
| 20 | Rapa = 6.6 mg (0.1%)<br>EtOH = 505.1 mg (7.618%)<br>F127 = 917.8 mg (13.843%)<br>Water = 5200.6 mg (78.44%) | S | | |
| 21 | Rapa = 6.6 mg (0.1%)<br>EtOH = 536 mg (7.5%)<br>Pluronic, F127 = 983.75 mg (14.0%)<br>Water = 5574.56 mg (78.4%) | S | | No, 50 μL |
| 22 | Rapa = 5.2 mg (0.1023%)<br>EtOH = 56.6 mg (1.127%)<br>Captisol = 2008.9 mg (39.5%)<br>Water = 3013.3 mg (59.3%) | S | | |
| 23 | Rapa = 6.9 mg (0.201%)<br>EtOH = 3418.0 mg (99.799%) | S | | |
| 24 | Rapa = 9.1 mg (0.491%)<br>EtOH = 90.9 mg (4.908%)<br>F127 = 262.8 mg (14.191%)<br>Water = 1489.1 mg (80.409%) | S | | |
| 25 | Rapa = 0 mg (0%)<br>EtOH = 310.2 mg (5.144%)<br>F127 = 858.1 mg (14.228%)<br>Water = 4862.6 mg (80.628%) | S | | |
| 26 | Rapa = 0 mg (0%)<br>EtOH = 613.1 mg (10.19%)<br>F127 = 810.6 mg (13.471%)<br>Water = 4593.6 mg (76.339%) | S | | |
| 27 | Rapa = 53.5 mg (1.095%)<br>EtOH = 414.8 mg (8.488%)<br>F127 = 662.8 mg (13.563%)<br>Water = 3755.7 mg (76.854%) | S | | Yes, 50 μL |
| 28 | Rapa = 0.3 g (10%)<br>PVP K90 = 0.35 g (12%)<br>Eudragit RS30D = 2.35 g (78%) | ISG, SP | | |
| 29 | Rapa = 0.2154 g (7.31%)<br>PVP K90 = 0.25 g (8.5%)<br>Eudragit RS30D = 2.48 g (84.19%) | ISG, SP | | |
| 30 | Rapa = 53.9 mg (1.103%)<br>EtOH = 413.6 mg (8.463%)<br>Sterile water = 3843.5 mg (78.647%)<br>F127 (Lutrol) = 576.0 mg (11.786%) | S | | No, 50 μL |
| 31 | Rapa = 0 mg (0%)<br>EtOH = 411.9 mg (8.513%)<br>Sterile Water = 3849.3 mg (79.554%)<br>F127(Lutrol) = 577.4 mg (11.933%) | S | | |
| 32 | Rapa = 54.1 mg (1.256%)<br>EtOH = 416.8 mg (9.676%)<br>Sterile Water = 3836.3 mg (78.569%)<br>F127(Lutrol) = 577.5 mg (10.499%) | S | | |

TABLE 1-continued

Formulations

| Form. # | Composition (mg), % (w/w) | Type | Median particle size | NDM, Injection volume |
|---|---|---|---|---|
| 33 | Rapa = 80.7 g (1.964%)<br>EtOH = 65.0 mg (0.158%)<br>PEG400 = 4021.8 mg (97.878%) | S | | |
| 34 | Rapa = 106.9 g (5.233%)<br>EtOH = 129.6 mg (6.344%)<br>PEG400 = 1806.5 mg (88.424%) | S | | Yes, 25 μL |
| 35 | Rapa = 0 mg (0%)<br>PVP K90 = 0.204 g (2.3%)<br>Ethanol, 100% = 0.4 g (4.5%)<br>Eudragit RL100 = 0.201 g (2.3%)<br>PEG 400 = 8.00 g (90.9%) | ISG, SP | | |
| 36 | Rapa = 0 mg (0%)<br>PVP K90 = 0.2 g (2.2%)<br>Ethanol, 100% = 0.4 g (4.4%)<br>PVAP = 0.4 g (4.4%)<br>PEG 400 = 8.00 g (88.9%) | ISG, SP | | |
| 37 | Rapa = 106.1 mg (4.2%)<br>PVP K90 = 55.2 mg (2.2%)<br>Ethanol, 100% = 108 mg (4.3%)<br>Eudragit RL100 = 55 mg (2.2%)<br>PEG 400 = 2.2 g (87.1%) | ISG, SP | | |
| 38 | Rapa = 399.6 mg (9.965%)<br>F68(Lutrol) = 40.6 mg (1.012%)<br>Sterile Water = 3569.7 mg (89.022%) | S | | Yes, 20 μL |
| 39 | Rapa = 53.8 mg (1.1%)<br>EtOH = 415.2 mg (8.489%)<br>Sterile Water = 3844.2 mg (78.594%)<br>F127 = 578.0 mg (11.817%) | S | | |
| 40 | Rapa = 208.1 mg (3.148%)<br>PEG400 = 6403.4 mg (96.852%) | S | | Yes, 20 μL |
| 41 | Rapa = 200.4 mg (5.148%)<br>F68(Lutrol) = 20.8 mg (0.534%)<br>PEG400 = 3569.3 mg (91.697%)<br>EtOH (95%) = 102 mg (2.62%) | SP | | |
| 42 | Rapa = 200.4 g (5.259%)<br>PEG400 = 3561.4 mg (93.46%)<br>Tween 80 = 48.8 mg (1.281%) | SP | | |
| 43 | Rapa = 30.9 mg (1.03%)<br>PEG 400 = 2.9624 g (98.97%) | S | | No, 50 μL |
| 44 | Rapa = 61 mg (1.96%)<br>Ethanol, 100% = 0.1860 g (6%)<br>PEG 400 = 2.8588 g (92.04%) | S | | Yes, 50 μL |
| 45 | Rapa = 90.7 mg (3.02%)<br>Ethanol, 100% = 0.2722 g (9.06%)<br>PEG 400 = 2.6423 g (87.94%) | S | | Yes, 50 μL |
| 46 | Rapa = 101.6 mg (4.997%)<br>EtOH = 331.6 mg (16.308%)<br>PEG400 = 1600.1 mg (78.695%) | S | | |
| 47 | Rapa = 120.9 mg (3.189%)<br>F68(Lutrol) = 42.4 mg (1.118%)<br>Sterile Water = 3627.7 mg (95.692%) | SP | | |
| 48 | Rapa = 100.1 g (1.999%)<br>EtOH = 305.1 mg (6.092%)<br>PEG400 = 4602.9 mg (91.909%) | S | | |
| 49 | Rapa = 150.5 mg (3.004%)<br>PEG400 = 4860.3 mg (96.996%) | SP | | Yes, 20 μL, 40 μL |
| 50 | Rapa = 153.4 mg (3.055%)<br>F68(Pluronic) = 50.6 mg (1.008%)<br>Sterile Water = 4816.6 mg (95.937%) | SP | | No, 20 μL |
| 51 | Rapa = 116.6 mg (2.29%)<br>EtOH = 306.6 mg (6.05%)<br>PEG400 = 4647.5 mg (91.66%) | S | | Yes, 30 μL |
| 52 | Rapa = 150.4 mg (2.994%)<br>F68 Lutrol = 15.4 mg (0.306%)<br>Sterile water = 4859.1 mg (96.7%) | SP | | |
| 53 | Rapa = 306.5 mg (6.088%)<br>PEG 400 = 4727.7 mg (93.912%) | SP | | |
| 54 | Rapa = 309.3 mg (6.146%)<br>PEG 400 = 4723.3 mg (93.854%) | SP | | |
| 55 | Rapa = 303.3 mg (6.061%)<br>PEG 400 = 4700.6 mg (93.939%) | SP | | |
| 56 | Rapa = 305.4 mg (6.088%)<br>PEG 400 = 4711.0 mg (93.912%) | SP | | |
| 57 | Rapa = 306.9 mg (6.098%)<br>PEG 400 = 4725.5 mg (93.902%) | SP | | |

TABLE 1-continued

Formulations

| Form. # | Composition (mg), % (w/w) | Type | Median particle size | NDM, Injection volume |
|---|---|---|---|---|
| 58 | Rapa = 302.5 mg (6.021%)<br>PEG 400 = 4721.6 mg (93.979%) | SP | | |
| 59 | Rapa = 304.5 mg (6.053%)<br>PEG 400 = 4726.4 mg (93.947%) | SP | | |
| 60 | Dexamethasone = 251.4 mg (5.011%)<br>PEG 400 = 4765.2 mg (94.989%) | SP | | |
| 61 | Dexamethasone = 252.4 mg (5%)<br>PEG 400 = 4600 mg (92%)<br>EtOH = 150 mg (3%) | SP | | |
| 62 | Rapa = 32.2 mg (0.641%)<br>PEG 400 = 4677.9 mg (93.096%)<br>EtOH = 314.7 mg (6.263%) | S | | |
| 63 | Rapa = 32.3 mg (0.6%)<br>PEG 400 = 5516.3 mg (93.1%)<br>EtOH = 314.7 mg (6.263%) | S | | |
| 64 | Rapa = 54.4 mg (1.007%)<br>PEG 400 = 4638.9 mg (92.702%)<br>EtOH = 314.8 mg (6.291%) | S | | |
| 65 | Rapa = 50.8 mg (1.013%)<br>PEG 400 = 4963.2 mg (98.987%) | S | | |
| 66 | Rapa = 52.1 mg (1.035%)<br>PEG 400 = 4868.6 mg (96.718%)<br>EtOH = 113.1 mg (2.247%) | S | | |
| 67 | Rapa = 50.5 mg (1.009%)<br>PEG 400 = 4752.8 mg (94.953%)<br>EtOH = 202.1 mg (4.038%) | S | | Yes, 20 μL<br>No, 40 μL, 100 μL |
| 68 | Rapa = 101.8 mg (2.030%)<br>PEG 400 = 4712.4 mg (93.970%)<br>EtOH = 200.6 mg (4.000%) | S | | |
| 69 | Rapa = 102.1 mg (2.036%)<br>PEG 400 = 4605.5 mg (91.847%)<br>EtOH = 306.7 mg (6.117%) | S | | |
| 70 | Rapa = 101.6 mg (2.025%)<br>PEG 400 = 4510.6 mg (89.892%)<br>EtOH = 405.6 mg (8.083%) | S | | |
| 71 | Rapa = 75.9 mg (3.019%)<br>PEG 400 = 2438.4 mg (96.981%) | SP | | |
| 72 | Rapa = 50.9 mg (2.034%)<br>PEG 400 = 2350.1 mg (93.914%)<br>EtOH = 101.4 mg (4.052%) | S | | |
| 73 | Rapa = 12.5 mg (0.620%)<br>PEG 400 = 2004.8 mg (99.380%) | SP | | |
| 74 | Rapa = 1.20949 g (2.0152%)<br>EtOH = 2.401 g (4.000%)<br>PEG 400 = 56.407 g (93.9848%) | S | | |
| 75 | Rapa = 16.0 mg g (0.795%)<br>EtOH = 80.0 mg (3.976%)<br>PEG 400 = 1916.0 mg (95.2298%) | S | | No, 50 μL |
| 76 | Rapa = 8.1 mg (0.400%)<br>PEG 400 = 2014.5 mg (99.600%) | SP | | |
| 77 | Rapa = 8.6 mg (0.428%)<br>PEG 400 = 2002.5 mg (99.572%) | S | | |
| 78 | Rapa = 8.2 mg (0.410%)<br>PEG 400 = 1992.0 mg (99.590%) | S | | |
| 79 | Rapa = 8.7 mg (0.433%)<br>PEG 400 = 1998.8 mg (99.567%) | S | | |
| 80 | Rapa = 8.6 mg (0.427%)<br>PEG 400 = 2003.2 mg (99.573%) | S | | |
| 81 | Rapa = 8.6 mg (0.428%)<br>PEG 400 = 1999.3 mg (99.572%) | S | | |
| 82 | Rapa = 9.0 mg (0.448%)<br>PEG 400 = 2000.8 mg (99.552%) | S | | |
| 83 | Rapa = 8.0 mg (0.397%)<br>PEG 400 = 2008.8 mg (99.603%) | S | | |
| 84 | Rapa = 8.5 mg (0.422%)<br>PEG 400 = 2006.8 mg (99.578%) | S | | |
| 85 | Rapa = 8.0 mg (0.399%)<br>PEG 400 = 1998.2 mg (99.601%) | S | | |
| 86 | Rapa = 8.5 mg (0.422%)<br>PEG 400 = 2004.3 mg (99.578%) | S | | |
| 87 | Rapa = 8.6 mg (0.428%)<br>PEG 400 = 2002.5 mg (99.572%) | S | | |
| 88 | Rapa = 0.7 g (1.983%)<br>EtOH = 1.4 g (3.966%)<br>PEG 400 = 33.2 g (94.051%) | S | | |

TABLE 1-continued

Formulations

| Form. # | Composition (mg), % (w/w) | Type | Median particle size | NDM, Injection volume |
|---|---|---|---|---|
| 89 | Rapa = 0 g (0%)<br>EtOH = 0.574 g (1.995%)<br>PEG 400 = 28.2 g (98.005%) | S | | |
| 90 | Rapa = 1.95 g (1.950%)<br>EtOH = 4.05 g (4.050%)<br>PEG 400 = 94.00 g (94.000%) | S | | |
| 91 | Rapa = 0.0107 g (0.534%)<br>EtOH = 0.0805 g (4.019%)<br>PEG 400 = 1.912 g (95.447%) | S | | No, 80 μL |
| 92 | Rapa = 0.0081 g (0.403%)<br>EtOH = 0.0804 g (4.003%)<br>PEG 400 = 1.920 g (95.594%) | S | | No, 100 μL |
| 93 | Rapa = 1.992 g (2%)<br>EtOH = 3.9419 (4%)<br>PEG 400 = 93.95 g (94%) | S | | |
| 94 | Rapa = 0.405 g (0.4%)<br>EtOH = 4.24 g (4%)<br>PEG 400 = 95.6 g (95.6%) | S | | |
| 95 | PEG 400 = 96 g (96%)<br>EtOH = 3.9027 (4%) | S | | |
| 96 | Rapa = 0.4020 g (0.402%)<br>EtOH = 3.970 g (3.971%)<br>PEG 400 = 95.600 g (95.627%) | S | | |
| 97 | Rapa = 2.000 g (1.990%)<br>EtOH = 4.000 g (3.980%)<br>PEG 400 = 94.500 g (94.030%) | S | | |
| 98 | PEG 400 = 96 g (96%)<br>EtOH = 3.92 g (4%) | S | | |
| 99 | Rapa = 0.4036 g (0.4%)<br>EtOH = 3.9054 g (4%)<br>PEG 400 = 95.6 g (95.6%) | S | | No, 100 μL |
| 100 | Rapa = 2.0025 g (2%)<br>EtOH = 3.98 g (4%)<br>PEG 400 = 94.00 g (94%) | S | | Yes, 1 μL, 3 μL, 20 μL, 40 μL |
| 101 | Rapa = 9.5 mg (0.472%)<br>EtOH = 90.3 mg (4.485%)<br>PEG 600 = 1913.5 mg (95.043%) | S | | |
| 102 | Rapa = 44.6 mg (2.21%)<br>EtOH = 86.1.0 mg (4.26%)<br>PEG 600 = 1891.1 mg (93.53%) | S | | |
| 103 | Rapa = 1.97 g (2%)<br>EtOH = 4.10 g (4%)<br>PEG 400 = 94.15 g (94%) | S | | |
| 104 | Rapa = 1.95 g (2%)<br>EtOH = 4.00 g (4%)<br>PEG 400 = 94.0 g (94%) | S | | |
| 105 | Rapa = 8.00 g (2%)<br>PEG 400 = 376.0 g (94%)<br>EtOH = 16.0 g (4%) | S | | |
| 106 | Rapa = 6.00 g (2%)<br>PEG 400 = 282.0 g (94%)<br>EtOH = 12.0 g (4%) | S | | |
| 107 | Rapa = 8.9 mg (0.4434%)<br>EtOH = 80.3 mg (4.0006%)<br>PEG 300 = 1918.0 mg (95.556%) | S | | |
| 108 | Rapa = 40.8 mg (2.00886%)<br>EtOH = 110.0 mg (5.41605%)<br>PEG 300 = 1880.2 mg (92.57509%) | S | | |
| 109 | Rapa = 9.9 mg (0.488%)<br>EtOH = 86.7 mg (4.277%)<br>PEG 400/300(50/50) = 1930.3 mg (95.235%) | S | | |
| 110 | Dexamethasone = 142.5 mg (4.994%)<br>PEG 400 = 2710.7 mg (95.006%) | SP | 0.3305 μm | Yes, 30 μL |
| 111 | Dexamethasone = 134.3 mg (4.891%)<br>PEG 400 = 2611.4 mg (95.109%) | SP | >10 μm | |
| 112 | Triamcinolone = 139.2 mg (5.087%)<br>PEG 400 = 2597.4 mg (94.913%) | SP | 3.98 μm | Yes, 30 μL |
| 113 | Triamcinolone = 135.3 mg (5.089%)<br>PEG 400 = 2523.5 mg (94.911%) | SP | >10 μm | |
| 114 | EtOH = 206.4 mg (4.121%)<br>PEG 400 = 4801.6 mg (95.879%) | S | | No, 30 μL |
| 115 | Rapa = 43.0 mg (2.144%)<br>PEG 400 = 1962.3 mg (97.8567%) | SP | 61.4390 μm | |
| 116 | Rapa = 40.0 mg (2.001%)<br>PEG 400 = 1959.1 mg (97.999%) | SP | 3.7128 μm | |

TABLE 1-continued

Formulations

| Form. # | Composition (mg), % (w/w) | Type | Median particle size | NDM, Injection volume |
|---|---|---|---|---|
| 117 | Rapa = 42.9 mg (2.142%)<br>PEG 400 = 1959.7 mg (97.858%) | SP | 2.7313 μm | |
| 118 | Rapa = 100.8 mg (2.013%)<br>PEG 400 = 4906.0 mg (97.987%) | SP | 4.1063 μm | |
| 119 | Rapa = 20.9 mg (0.42%)<br>EtOH = 209.1 mg (4.17%)<br>PEG 400 = 4784.9 mg (95.41%) | S | | |
| 120 | Rapa = 20.6 mg (0.41%)<br>EtOH = 211.5 mg (4.22%)<br>Benz. Chl = 19.1 mg (0.38%)<br>PEG 400 = 4762.0 mg (94.99%) | S | | |
| 121 | Rapa = 20.1 mg (0.40%)<br>EtOH = 211.5 mg (4.22%)<br>Benz. Chl = 2.3 mg (0.05%)<br>PEG 400 = 4782.3 mg (95.34%) | S | | |
| 122 | Rapa = 8.0 g (2%)<br>EtOH = 16.0 g (4%)<br>PEG 400 = 376.0 g (94%) | S | | |
| 123 | Rapa = 351.3 mg (2.006%)<br>EtOH = 2353.1 mg (4.093%)<br>PEG 400 = 16448.2 mg (93.901%) | S | | |
| 124 | Rapa = 2.2035 g (2%)<br>EtOH = 4.45 g (4%)<br>PEG 400 = 103.7 g (94%) | S | | |
| 125 | Rapa = 515.5 mg (2.021%)<br>PEG 400 = 24,993.8 mg (97.979%) | SP | 18.1453 μm | |
| 126 | Rapa = 0.3 g (2%)<br>EtOH = 0.6 g (4%)<br>PEG 400 = 14.1 g (94%)<br>BHT = 0.0002 (0.002%) | S | | |
| 127 | Rapa = 0.3 g (2%)<br>EtOH = 0.6 g (4%)<br>PEG 400 = 14.1 g (94%)<br>BHT = 0.00037 (0.004%) | S | | |
| 128 | Rapa = 0.3 g (2%)<br>EtOH = 0.6 g (4%)<br>PEG 400 = 14.1 g (94%)<br>BHT = 0.0081 (0.05%) | S | | |
| 129 | Rapa = 243.2 mg (1.869%)<br>EtOH = 4.88.4 mg (3.753%)<br>PEG 400 = 12283.3 mg (94.378%) | S | | |
| 130 | Rapa = 0.404 g (2%)<br>EtOH = 0.8 g (4%)<br>PEG 400 = 18.8 g (94%)<br>BHT = 0.00051 (0.002%) | S | | |
| 131 | Rapa = 0.6024 g (2%)<br>EtOH = 1.2 g (4%)<br>PEG 400 = 28.25 g (94%) | S | | |
| 132 | Rapa = 2.001 g (2%)<br>EtOH = 4.05 g (4%)<br>PEG 400 = 94.45 g (94%) | S | | |
| 133 | Rapa = 0.5155 g (2.057%)<br>EtOH = 1.0198 g (4.070%)<br>PEG 400 = 23.5225 g (93.873%) | S | | |
| 134 | PEG 400 = 9.6 g (96%)<br>EtOH = 0.4 g (4%) | S | | |
| 135 | Rapa = 0.610 g (2%)<br>EtOH = 1.2 g (4%)<br>PEG 400 = 28.2 g (94%) | S | | |
| 136 | Rapa = 24.6 mg (1.193%)<br>EtOH = 91.1 mg (4.418%)<br>Tyloxapol = 219.6 mg (10.649%)<br>BSS = 1726.8 mg (83.740%) | S | | |
| 137 | Rapa = 100.0 mg (1.993%)<br>PEG 400 = 4916.9 mg (98.007%) | SP | | |
| 138 | Rapa = 201.6 mg (4.005%)<br>PEG 400 = 4831.5 mg (95.995%) | SP | | |
| 139 | Rapa = 102.4 mg (2.036%)<br>EtOH = 209.0 mg (4.154%)<br>PEG 400 = 4719.3 mg (93.810%) | S | | |
| 140 | Rapa = 10.3 mg (0.205%)<br>EtOH = 27.4 mg (0.544%)<br>PEG 400 = 4995.8 mg (99.251%) | S | | Yes, 10 μL |

TABLE 1-continued

Formulations

| Form. # | Composition (mg), % (w/w) | Type | Median particle size | NDM, Injection volume |
|---|---|---|---|---|
| 141 | Rapa = 10.6 mg (0.211%)<br>EtOH = 208.4 mg (4.150%)<br>PEG 400 = 4802.3 mg (95.639%) | S | | No, 10 μL |
| 142 | Rapa = 31.5 mg (0.628%)<br>EtOH = 67.1 mg (1.337%)<br>PEG 400 = 4918.9 mg (98.035%) | S | | Yes, 10 μL |
| 143 | Rapa = 30.8 mg (0.613%)<br>EtOH = 204.5 mg (4.073%)<br>PEG 400 = 4786.1 mg (95.314%) | S | | No, 10 μL, 100 μL |
| 144 | Rapa = 103.5 mg (2.057%)<br>EtOH = 207.1 mg (4.116%)<br>PEG 400 = 4720.8 mg (93.827%) | S | | Yes, 10 μL |
| 145 | Rapa = 283.0 mg (2.020%)<br>EtOH = 566.1 mg (4.041%)<br>PEG 400 = 13,160.8 mg (93.939%) | S | | |
| 146 | Rapa = 280.1 mg (1.998%)<br>EtOH = 565.2 mg (4.033%)<br>PEG 400 = 13,171.7 mg (93.969%) | S | | |
| 147 | Rapa = 201.6 mg (3.000%)<br>PEG 400 = 6518.8 mg (97.000%) | SP | | |
| 148 | Rapa = 31.9 mg (1.019%)<br>Benzyl Alcohol = 1021.9 mg (20.070%)<br>Sesame Oil = 4017.9 mg (78.911%) | S | | |
| 149 | Rapa = 51.5 mg (1.03%)<br>Benzyl Alcohol = 259.9 mg (5.19%)<br>Sesame Oil = 4694.3 mg (93.78%) | S | | |
| 150 | Rapa = 5.96 g (2%)<br>EtOH = 12.0 g (4%)<br>PEG 400 = 282.0 g (94%) | S | | |
| 151 | Rapa = 54.5 mg (1.07%)<br>Benzyl Alcohol = 1014.3 mg (19.95%)<br>Olive Oil = 4014.8 mg (78.98%) | S | | |
| 152 | Rapa = 0 mg (0.00%)<br>Benzyl Alcohol = 269.4 mg (5.421%)<br>Tyloxapol = 608.2 mg (12.238%)<br>Sesame Oil = 4092.2 mg (82.341%) | S | | |
| 153 | Rapa = 76.3 mg (1.75%)<br>Benzyl Alcohol = 307.0 mg (7.06%)<br>Tyloxapol = 607.8 mg (13.97%)<br>Sesame Oil = 3000.5 mg (68.97%)<br>Span 80 = 63.1 mg (1.45%)<br>EtOH = 295.5 mg (6.79%) | S | | |
| 154 | Form. # 150 = 200 g (99.998)<br>BHT = 0.004 g (0.002%) | S | | |
| 155 | Rapa = 51.0 mg (0.87%)<br>EtOH = 642.3 mg (10.93%)<br>Benzyl Alcohol = 431.8 mg (7.34%)<br>Sesame Oil = 4753.7 mg (80.86%) | S | | |
| 156 | Rapa = 51.4 mg (1.03%)<br>Benzyl Alcohol = 518.4 mg (10.34%)<br>Olive Oil = 4444.7 mg (88.64%) | S | | |
| 157 | Rapa = 8.1 g (2%)<br>EtOH = 16.0 g (4%)<br>PEG 400 = 376.0 g (94%) | S | | |
| 158 | Form. # 157 = 225.00 g (99.998%)<br>BHT = 0.0045 g (0.002%) | S | | |
| 159 | Rapa = 8.1 g (2%)<br>EtOH = 16.0 g (4%)<br>PEG 400 = 376 g (94%) | S | | |
| 160 | Form. # 159 = 112.0 g (99.998%)<br>BHT = 0.00224 g (0.002%) | S | | |
| 161 | Form. # 159 = 112.0 g (99.998%)<br>BHT = 0.0019 g (0.002%) | S | | |
| 162 | Rapa = 55.4 mg (1.10%)<br>EtOH = 112.7 mg (2.25%)<br>Benzyl Alcohol = 157.8 mg (3.15%)<br>Cotton Seed Oil = 4688.0 mg (93.50%) | S | | |
| 163 | Rapa = 5.005 g (1%)<br>EtOH = 10.0 g (2%)<br>PEG 400 = 485.5 g (97%) | S | | |
| 164 | PEG 400 = 9.82 g (98%)<br>EtOH = 0.235 g (2%) | S | | |

TABLE 1-continued

Formulations

| Form. # | Composition (mg), % (w/w) | Type | Median particle size | NDM, Injection volume |
|---|---|---|---|---|
| 165 | Form. # 163 = 100.25 g (99.998%)<br>BHT = 0.0026 g (0.002%) | S | | |
| 166 | Rapa = 203.1 mg (2.025%)<br>F68 = 30.3 mg (0.303%)<br>Sterile Water = 9792.6 mg (97.672%) | SP | 2.8651 μm | |
| 167 | Rapa = 201.4 mg (2.0005%)<br>Tween 20 = 43.9 mg (0.436%)<br>Sterile Water = 9822.8 mg (97.564%) | SP | 1.0984 μm | |
| 168 | EtOH = 0.8301 g (4.144%)<br>PEG 400 = 19.2014 g (95.856%) | S | | |
| 169 | Form. # 168 = 300 μl | S | | |
| 170 | Form. # 168 = 250 μl<br>Form. # 154 = 50 μl | S | | |
| 171 | Form. # 168 = 200 μl<br>Form. # 154 = 100 μl | S | | |
| 172 | Form. # 168 = 150 μl<br>Form. # 154 = 150 μl | S | | |
| 173 | Form. # 154 = 300 μl | S | | |
| 174 | Rapa = 102.2 mg (2.041%)<br>F68 = 16.0 mg (0.32%)<br>Sterile Water = 4889.0 mg (97.639%) | SP | 0.4165 μm | |
| 175 | Rapa = 101.1 mg (2.010%)<br>Tween 20 = 27.7 mg (0.551%)<br>Sterile Water = 4901.0 mg (97.439%) | SP | 0.5294 μm | |
| 176 | BSS+ = 0 μl<br>Sterile Water = 0 μl<br>Form. # 154 = 1000 μl | S | | |
| 177 | BSS+ = 200 μl<br>Sterile Water = 0 μl<br>Form. # 154 = 800 μl | SP | | |
| 178 | BSS+ = 400 μl<br>Form. # 154 = 600 μl | SP | | |
| 179 | BSS+ = 500 μl<br>Form. # 154 = 500 μl | SP | | |
| 180 | BSS+ = 600 μl<br>Form. # 154 = 400 μl | SP | | |
| 181 | BSS+ = 800 μl<br>Form. # 154 = 200 μl | SP | | |
| 182 | Sterile Water = 200 μl<br>Form. # 154 = 800 μl | SP | | |
| 183 | Sterile Water = 400 μl<br>Form. # 154 = 600 μl | SP | | |
| 184 | Sterile Water = 500 μl<br>Form. # 154 = 500 μl | SP | | |
| 185 | Sterile Water = 600 μl<br>Form. # 154 = 400 μl | SP | | |
| 186 | Sterile Water = 800 μl<br>Form. # 154 = 200 μl | SP | | |
| 187 | BSS+ = 2536.9 mg (49.98%)<br>Form. # 154 = 2538.7 mg (50.02%) | SP | 60.2075 μm | |
| 188 | Sterile Water = 2515.6 mg (49.84%)<br>Form. # 154 = 2532.2 mg (50.16%) | SP | 617.5157 μm | |
| 189 | F68 = 12.6 mg (0.25%)<br>Sterile Water = 2524.7 mg (49.79%)<br>Form. # 154 = 2533.1 mg (49.96%) | SP | 70.6089 μm | |
| 190 | Rapa = 2.0225 g (2%)<br>EtOH = 3.65 g (4%)<br>PEG 400 = 94.0 g (94%)<br>BHT = 0.002 g (0.002%) | S | | |
| 191 | F68 = 12.1 mg<br>Sterile Water = 2558.9 mg<br>Form. # 154 = 2556.4 mg | SP | | |
| 192 | F68 = 19.8 mg<br>Sterile Water = 2564.1 mg<br>Form. # 154 = 25557.5 mg | SP | | |
| 193 | F68 = 25.3 mg<br>Sterile Water = 2575.1 mg<br>Form. # 154 = 2572.9 mg | SP | | |
| 194 | F68 = 32.4 mg<br>Sterile Water = 2572.1 mg<br>Form. # 154 = 2562.1 mg | SP | | |
| 195 | F68 = 38.3 mg<br>Sterile Water = 2563.2 mg<br>Form. # 154 = 2573.5 mg | SP | | |

TABLE 1-continued

Formulations

| Form. # | Composition (mg), % (w/w) | Type | Median particle size | NDM, Injection volume |
|---|---|---|---|---|
| 196 | F68 = 43.6 mg<br>Sterile Water = 2541.1 mg<br>Form. # 154 = 2556.0 mg | SP | | |
| 197 | F68 = 51.2 mg<br>Sterile Water = 2594.5 mg<br>Form. # 154 = 2594.1 mg | SP | | |
| 198 | PEG 400 = 1920 g (96%)<br>EtOH = 80 g (4%) | S | | |
| 199 | Form. # 168 = 1000 µl | S | | |
| 200 | Form. # 168 = 200 µl<br>Form. # 154 = 800 µl | S | | |
| 201 | Form. # 168 = 400 µl<br>Form. # 154 = 600 µl | S | | |
| 202 | Form. # 168 = 500 µl<br>Form. # 154 = 500 µl | S | | |
| 203 | Form. # 168 = 600 µl<br>Form. # 154 = 400 µl | S | | |
| 204 | Form. # 168 = 800 µl<br>Form. # 154 = 200 µl | S | | |
| 205 | PEG 400 = 200 µl<br>Form. # 154 = 800 µl | S | | |
| 206 | PEG 400 = 400 µl<br>Form. # 154 = 600 µl | S | | |
| 207 | PEG 400 = 500 µl<br>Form. # 154 = 500 µl | S | | |
| 208 | PEG 400 = 600 µl<br>Form. # 154 = 400 µl | S | | |
| 209 | PEG 400 = 800 µl<br>Form. # 154 = 200 µl | S | | |
| 210 | Phosal 50PG = 6735.0 mg (99.002%)<br>Tween 80 = 67.9 mg (0.998%) | S | | |
| 211 | Rapa = 2.0047 g (2%)<br>EtOH = 4.00 g (4%)<br>PEG 400 = 94.05 g (94%) | S | | |
| 212 | Phosal 50PG = 20.0662 g (98.999%)<br>Tween 80 = 0.2029 g (1.001%) | S | | |
| 213 | Form. # 154 = 100 µl<br>Form. # 168 = 900 µl | S | | |
| 214 | Form. # 154 = 100 µl<br>Form. # 168 = 900 µl | S | | |
| 215 | Form. # 154 = 100 µl<br>Form. # 168 = 900 µl | S | | |
| 216 | Form. # 154 = 100 µl<br>PEG 400 = 900 µl | S | | |
| 217 | Form. # 154 = 100 µl<br>PEG 400 = 900 µl | S | | |
| 218 | Form. # 154 = 100 µl<br>PEG 400 = 900 µl | S | | |
| 219 | Form. # 154 = 100 µl<br>BSS+ = 900 µl | SP | | |
| 220 | Form. # 154 = 100 µl<br>BSS+ = 900 µl | SP | | |
| 221 | Form. # 154 = 100 µl<br>BSS+ = 900 µl | SP | | |
| 222 | Form. # 154 = 1000 µl | S | | |
| 223 | Form. # 154 = 1000 µl | S | | |
| 224 | Form. # 154 = 100 µl<br>Form. # 168 = 900 µl | S | | |
| 225 | Form. # 154 = 100 µl<br>Form. # 168 = 900 µl | S | | |
| 226 | Form. # 154 = 100 µl<br>Form. # 168 = 900 µl | S | | |
| 227 | Form. # 154 = 100 µl<br>PEG 400 = 900 µl | S | | |
| 228 | Form. # 154 = 100 µl<br>PEG 400 = 900 µl | S | | |
| 229 | Form. # 154 = 100 µl<br>PEG 400 = 900 µl | S | | |
| 230 | Form. # 154 = 100 µl<br>BSS+ = 900 µl | SP | | |
| 231 | Form. # 154 = 100 µl<br>BSS+ = 900 µl | SP | | |

TABLE 1-continued

Formulations

| Form. # | Composition (mg), % (w/w) | Type | Median particle size | NDM, Injection volume |
|---|---|---|---|---|
| 232 | Form. # 154 = 100 μl<br>BSS+ = 900 μl | SP | | |
| 233 | Form. # 154 = 200 μl<br>Form. # 168 = 800 μl | S | | |
| 234 | Form. # 154 = 200 μl<br>Form. # 168 = 800 μl | S | | |
| 235 | Form. # 154 = 200 μl<br>Form. # 168 = 800 μl | S | | |
| 236 | Form. # 154 = 200 μl<br>Form. # 168 = 800 μl | S | | |
| 237 | Form. # 154 = 200 μl<br>PEG 400 = 800 μl | S | | |
| 238 | Form. # 154 = 200 μl<br>PEG 400 = 800 μl | S | | |
| 239 | Form. # 154 = 200 μl<br>BSS+ = 800 μl | SP | | |
| 240 | Form. # 154 = 200 μl<br>BSS+ = 800 μl | SP | | |
| 241 | Form. # 154 = 200 μl<br>BSS+ = 800 μl | SP | | |
| 242 | Form. # 154 = 100 μl<br>Form. # 168 = 900 μl | S | | No, 10 μL |
| 243 | Form. # 154 = 100 μl<br>PEG 400 = 900 μl | S | | Yes, 10 μL |
| 244 | Form. # 154 = 100 μl<br>BSS+ = 900 μl | SP | | Yes, 10 μL |
| 245 | Form. # 154 = 100 μl<br>BSS+/CMC(0.5%) = 900 μl | SP | | |
| 246 | Form. # 154 = 400 μl<br>Form. # 168 = 900 μl | S | | No, 10 μL |
| 247 | Form. # 154 = 400 μl<br>PEG 400 = 900 μl | S | | Yes, 10 μL |
| 248 | Form. # 154 = 400 μl<br>BSS+ = 900 μl | SP | | Yes, 10 μL |
| 249 | Form. # 154 = 400 μl<br>BSS+/CMC(0.5%) = 900 μl | SP | | |
| 250 | Form. # 154 = 100 μl<br>BSS+/CMC(0.5%) = 900 μl | SP | | |
| 251 | Form. # 154 = 100 μl<br>BSS+/CMC(0.5%) = 900 μl | SP | | |
| 252 | Form. # 154 = 100 μl<br>BSS+/CMC(0.5%) = 900 μl | SP | | |
| 253 | Form. # 154 = 200 μl<br>BSS+/CMC(0.5%) = 800 μl | SP | | |
| 254 | Form. # 154 = 200 μl<br>BSS+/CMC(0.5%) = 800 μl | SP | | |
| 255 | Form. # 154 = 200 μl<br>BSS+/CMC(0.5%) = 800 μl | SP | | |
| 256 | Form. # 154 = 400 μl<br>BSS+/CMC(0.5%) = 900 μl | SP | | |
| 257 | Form. # 154 = 400 μl<br>BSS+/CMC(0.5%) = 900 μl | SP | | |
| 258 | Form. # 154 = 400 μl<br>BSS+/CMC(0.5%) = 900 μl | SP | | |
| 259 | EtOH = 17.1 mg (0.57%)<br>PEG 400 = 2997.3 mg (99.43%) | S | | |
| 260 | EtOH = 40.8 mg (1.35%)<br>PEG 400 = 2980.2 mg (98.65%) | S | | |
| 261 | EtOH = 47.1 mg (1.57%)<br>PEG 400 = 2950.1 mg (98.43%) | S | | |
| 262 | Rapa = 2.0032 g (2%)<br>EtOH = 3.92 g (4%)<br>PEG 400 = 94.00 g (94%) | S | | |
| 263 | Triamcinolone acetomide = 80.8 mg (4.04%)<br>PEG 400 = 1920.8 mg (95.96%) | SP | | |
| 264 | NFF-0007 filled in glove box | S | | |
| 265 | PEG 400 = 9.598 g (96%)<br>EtOH = 0.4052 (4%) | S | | |
| 266 | Triamcinolone acetomide = 42.2 mg (4.123%)<br>PEG 400 = 981.3 mg (95.877%) | SP | | |
| 267 | Phosal 50PG = 20.0783 g (99.00835%)<br>Tween 80 = 0.2011 g (0.99165%) | S | | |

TABLE 1-continued

| Form. # | Composition (mg), % (w/w) | Type | Median particle size | NDM, Injection volume |
|---|---|---|---|---|
| 268 | PEG 400 = 96.1 g (96%)<br>EtOH = 4.00 g (4%) | S | | |
| 269 | Rapa = 0.4001 g (2%)<br>EtOH = 0.80 g (4%)<br>PEG 400 = 18.8 g (94%) | S | | |
| 270 | Sterile Water = 9955.8 mg (99.27%)<br>CMC High visc. = 47.8 mg (0.48%)<br>Tween 80 = 25.4 mg (0.25%) | S | | |
| 271 | Sterile Water = 9947.5 mg (99.00%)<br>CMC Medium visc. = 75 mg (0.75%)<br>Tween 80 = 25.1 mg (0.25%) | S | | |
| 272 | Rapa = 41 mg (2.01%)<br>Form. # 270 = 2000 mg (97.99%) | SP | | |
| 273 | Rapa = 40.2 mg (1.97%)<br>MSF-03-172-07E = 2000 mg (98.03%) | SP | | |
| 274 | NMP (Pharmasolve ®) = 1280.5 mg (65.89%)<br>PLGA 75/25 = 662.9 mg (34.11%) | S | | |
| 275 | NMP (Pharmasolve ®) = 1573.3 mg (80.50%)<br>PLGA 75/25 = 381.0 mg (19.50%) | S | | |
| 276 | NMP (Pharmasolve ®) = 1009.7 mg 49.8%)<br>PLGA 75/25 = 1001.6 mg (50.20%) | S | | Yes, 10 µL |
| 277 | Sterile Water = 14934.0 mg (99.25%)<br>CMC Medium visc. = 112.4 mg (0.75%) | S | | |
| 278 | Propylene Glycol = 1893.7 mg (93.85%)<br>EtOH = 83.8 mg (4.16%)<br>Rapa = 40.2 mg (1.99%) | S | | Yes, 10 µL |
| 279 | Propylene Glycol = 1946.2 mg (95.68%)<br>Benzyl Alcohol = 47.1 mg (2.31%)<br>Rapa = 40.8 mg (2.01%) | S | | Yes, 10 µL |
| 280 | PEG 300 = 1894.1 mg (93.74%)<br>EtOH = 40.1 mg (1.98%)<br>Rapa = 86.4 mg (4.28%) | S | | Yes, 10 µL |
| 281 | PEG 300 = 1925.5 mg (95.88%)<br>EtOH = 39.8 mg (1.98%)<br>Rapa = 43.0 mg (2.14%) | S | | Yes, 10 µL, 30 µL |
| 282 | Rapa = 100.6 mg (2.01%)<br>MSF-03-176-02 = 4910.8 mg (97.99%) | SP | | Yes, 10 µL, 30 µL |
| 283 | Rapa = 11.5 mg (0.57%)<br>PEG 300 = 2012.5 mg (99.43%) | S | | |
| 284 | Rapa = 10.3 mg (0.51%)<br>PEG 400 = 2017.2 mg (99.49%) | S | | |
| 285 | Rapa = 9.8 mg (0.486%)<br>PEG 600 = 2005.9 mg (99.51%) | S | | |
| 286 | Tacrolimus = 42.7 mg (2.11%)<br>EtOH = 46.0 mg (2.27%)<br>PG = 1938.7 mg (95.62%) | S | | |
| 287 | Tacrolimus = 40.7 mg (2.01%)<br>EtOH = 43.0 mg (2.12%)<br>PEG 300 = 1942.1 mg (95.87%) | S | | |
| 288 | Tacrolimus = 40.3 mg (1.99%)<br>EtOH = 43.8 mg (2.16%)<br>PEG 400 = 1942.3 mg (95.85%) | S | | |
| 289 | Tacrolimus = 40.8 mg (2.03%)<br>EtOH = 44.5 mg (2.21%)<br>PEG 600 = 1924.0 mg (95.76%) | S | | |
| 290 | Rapa = 61.0 mg (3.17%)<br>NMP = 1226.54 mg (63.80%)<br>PLGA 75/25 = 634.96 mg (33.03%) | S | | |
| 291 | Rapa = 100.2 mg (5.13%)<br>NMP = 1492.95 mg (76.37%)<br>PLGA 75/25 = 361.65 mg (18.50%) | S | | |
| 292 | Rapa = 62.9 mg (3.04%)<br>NMP = 1103.8 g mg (53.40%)<br>PLGA 75/25 = 900.2 mg (43.56%) | S | | |
| 293 | Rapa = 62.4 mg (3.00%)<br>NMP = 1205.1 mg (58.11%)<br>PLGA 75/25 = 806.4 mg (38.89%) | S | | |
| 294 | Water + 1% CMC Med. = 4909.1 mg (97.99%)<br>Rapa = 100.5 mg (2.01%) | SP | | |
| 295 | Water + 1% CMC high. = 4903.8 mg (97.96%)<br>Rapa = 101.9 mg (2.04%) | SP | | |

TABLE 1-continued

| Form. # | Composition (mg), % (w/w) | Type | Median particle size | NDM, Injection volume |
|---|---|---|---|---|
| 296 | Rapa = 40.5 mg (2.03%)<br>NMP = 1958.7 mg (97.97%) | S | | |
| 297 | Rapa = 20.5 mg (2.0%)<br>DMA = 41.4 mg (4.0%)<br>PVP = 35.0 mg (3.4%)<br>H2O = 934.7 mg (90.6%) | SP | | |
| 298 | Rapa = 10.6 mg (2.0%)<br>DMA = 10.6 mg (2.0%)<br>PEG 400 = 506.1 mg (96%) | S | | |
| 299 | Rapa = 5.2 mg (2.0%)<br>1% DMA in PEG 400 = 257.4 mg (98%) | SP | | |
| 300 | Rapa = 20.0 mg (2.0%)<br>DMA = 7.8 mg (0.8%)<br>PEG 400 = 974 mg (97.2%) | S | | |
| 301 | Rapa = 20.1 mg (1.3%)<br>DMA = 19.5 mg (1.3%)<br>PEG 400 = 1449.6 mg (97.3%) | S | | |
| 302 | Rapa = 20.0 mg (2.0%)<br>PVP = 10.8 mg (1.1%)<br>PEG 400 = 994.5 mg (97.0%) | SP | | |
| 303 | Rapa = 20.4 mg (2.0%)<br>PVP = 24.5 mg (2.4%)<br>PEG 400 = 990.7 mg (95.7%) | SP | | |
| 304 | Rapa = 25.5 mg (2.4%)<br>PVP = 51.9 mg (4.8%)<br>PEG 400 = 1000.6 mg (92.8%) | SP | | |
| 305 | Rapa = 22.5 mg (2.3%)<br>BA = 27.5 mg (2.7%)<br>PEG 400 = 950.7 mg (95.0%) | S | | |
| 306 | Rapa = 30.2 mg (2.3%)<br>PVP = 240.9 mg (18.6%)<br>PEG 400 = 1021.2 mg (79.0%) | SP | | |
| 307 | Rapa = 8.7 mg (3.1%)<br>1% PVP in H2O = 273 mg (96.9%) | SP | | |
| 308 | Rapa = 12.6 mg (2.53%)<br>5% PVP in H2O = 501.6 mg (97.5%) | SP | | |
| 309 | Rapa = 20.3 mg (3.8%)<br>10% PVP in H2O = 513.9 mg (96.2%) | SP | | |
| 310 | Rapa = 100.5 mg (2.0%)<br>DMA = 67.8 mg (1.4%)<br>PEG 400 = 4838.3 mg (96.6%) | S | | Yes, 10 µL |
| 311 | Rapa = 96.8 mg (1.9%)<br>BA = 157.5 mg (3.2%)<br>PEG 400 = 4748.7 mg (94.9%) | S | | Yes, 10 µL |
| 312 | Rapa = 105.8 mg (2.1%)<br>DMA = 5.63 mg (0.1%)<br>PEG 400 = 4888.9 mg (97.8%) | S | | |
| 313 | Rapa = 20.2 mg (2.0%)<br>PVP = 99.2 mg (9.9%)<br>H2O = 882.3 mg (88.1%) | SP | | |
| 314 | Rapa = 100.3 mg (2.0%)<br>PVP = 251.4 mg (5.0%)<br>H2O = 4662.8 mg (93.0%) | SP | | |
| 315 | Rapa = 20.3 mg (2.0%)<br>DMA = 983.9 mg (98%) | S | | |
| 316 | Triamcinolone = 22.8 mg (2.0%)<br>DMA = 12.0 mg (1.1%)<br>PEG 400 = 1104.5 mg (96.9%) | S | | Yes, 10 µL |
| 317 | Triamcinolone = 1.0 mg (0.1%)<br>EtOH = 49.30 mg (4.0%)<br>PEG 400 = 1191.9 mg (96.0%) | S | | |
| 318 | Triamcinolone = 18.7 mg (0.9%)<br>PEG 400 = 959.8 mg (99.1%) | S | | |
| 319 | Triamcinolone = 25.5 mg (1.3%)<br>EtOH = 83.0 mg (4.1%)<br>PEG 400 = 1905.6 mg (94.6%) | S | | |
| 320 | Dexamethasone = 20.4 mg (1.2%)<br>EtOH = 71.7 mg (4.1%)<br>PEG 400 = 1737.6 mg (98.8%) | S | | |
| 321 | Dexamethasone = 27.5 mg (2.0%)<br>DMA = 5.6 mg (0.4%)<br>PEG 400 = 1347.3 mg (97.6%) | S | | Yes, 10 µL |
| 322 | Rapa = 9.1 mg (0.152%)<br>EtOH = 90.9 mg (1.514%)<br>F127 = 262.8 mg (4.378%) | E | | |

TABLE 1-continued

Formulations

| Form. # | Composition (mg), % (w/w) | Type | Median particle size | NDM, Injection volume |
|---|---|---|---|---|
| 323 | Water = 1489.1 mg (24.804%)<br>Sesame oil = 4151.5 mg (69.152%)<br>Rapa = 24.4 mg (0.625%)<br>Phosal 50PG = 203.1 mg (5.201%)<br>EtOH = 166.8 mg (4.272%)<br>Labrafac CC = 1502.8 mg (38.486%)<br>Sesame oil = 2007.7 mg (51.416%) | E | | |
| 324 | Form. # 174 with 2 mm beads | SP | 0.4929 μm | |
| 325 | Form. # 175 with 2 mm beads | SP | 0.4804 μm | |
| 326 | Rapa = 4 mg (4%)<br>Ethanol = 4 mg (4%)<br>PEG 400 = 92 mg (92%) | S | | |
| 327 | Rapa = 1.47%<br>Ethanol = 2.93%<br>PEG 400 = 69%<br>Saline = 26.6% | S | | |
| 328 | Rapa = 1.38%<br>Ethanol = 2.75%<br>PEG 400 = 64.62%<br>Saline = 31.25% | SP | | |
| 329 | Rapa = 0.07%<br>Cremophor (PEG 35 castor oil) = 8.35%<br>Capmul MCM (C8) (mono/diglycerides of caprylic acid) = 8.37%<br>Sterile Water = 83.21% | E | | |
| 330 | Rapa = 0.09%<br>Tyloxapol (nonionic polymer of the alkyl aryl polyether alcohol) = 8.12%<br>Capmul MCM (C8) (mono/diglycerides of caprylic acid) = 8.15%<br>Ethanol = 0.35%<br>Sterile Water = 83.29% | E | | |
| 331 | Rapa = 0.08%<br>Tyloxapol (nonionic polymer of the alkyl aryl polyether alcohol) = 6.78%<br>Capmul MCM (C8) (mono/diglycerides of caprylic acid) = 6.81%<br>Phosal ® 50PG = 3.12%<br>Sterile Water = 83.21% | E | | |
| 332 | Rapa = 0.17%<br>Cremophor (PEG 35 castor oil) = 7.18%<br>Capmul MCM (C8) (mono/diglycerides of caprylic acid) = 9.47%<br>Sterile Water = 83.18% | E | | |
| 333 | N-methyl Pyrrolidone (NMP) = 10.5%<br>Water = up to 15.8%<br>Propylene Glycol (PG) = 73.7%<br>Rapamycin = up to 5% (w/w) | S | | |
| 334 | N-methyl Pyrrolidone (NMP) = 38.9%<br>Water = up to 22.2%<br>Propylene Glycol (PG) = 38.9%<br>Rapamycin = up to 5% (w/w) | S | | |
| 335 | N-methyl Pyrrolidone (NMP) = 10.5%<br>Water = up to 15.8%<br>PEG 600 = 73.7%<br>Rapamycin = up to 5% (w/w) | S | | |
| 336 | Dimethyl Acetamine (DMA) = 10.5%<br>Water = up to 15.8%<br>Propylene Glycol (PG) = 73.7%<br>Rapamycin = up to 5% (w/w) | S | | |
| 337 | Dimethyl Sulfoxide (DMSO) = 10.5%<br>Water = up to 15.8%<br>Propylene Glycol (PG) = 73.7%<br>Rapamycin = up to 5% (w/w) | S | | |
| 338 | N-methyl Pyrrolidone (NMP) = 27.9%<br>Water = up to 28.4%<br>PEG 400 = 39%<br>Ethanol = 4.7%<br>Rapamycin = up to 5% (w/w) | S | | |
| 339 | Dasatanib = 4.84%<br>Dimethyl Acetamine (DMA) = 15%<br>PEG 400 = 80.16% | S | | |
| 340 | Rapa = 40 mg (2%)<br>Ethanol = 80 mg (4%)<br>PEG 400 = 1880 mg (94%) | S | | |

TABLE 1-continued

| Form. # | Composition (mg), % (w/w) | Type | Median particle size | NDM, Injection volume |
|---|---|---|---|---|
| 341 | Rapa = 0.3%<br>Tyloxapol = 4.8%<br>Lauroglycol = 2.8%<br>Labrafac = 1.8%<br>remainder Sterile Water | | | |
| 342 | Rapa = 0.2%<br>Tyloxapol = 2.8%<br>EtOH = 0.3%<br>Labrafac = 2.8%<br>remainder Sterile Water | | | |
| 343 | Rapa = 0.2%<br>Tyloxapol = 2.8%<br>EtOH = 0.3%<br>Labrafac = 2.8%<br>remainer Sterile Water | | | |
| 344 | Rapa = 0.2%<br>EtOH = 0.4%<br>PEG 400 = 69.4%<br>remainder Sterile Water | | | |
| 345 | Rapa = 0.2%<br>EtOH = 0.4%<br>PEG 400 = 69.2%<br>remainder Sterile Water | | | |
| 346 | Rapa = 0.6% (0.4% degradation products)<br>N-methyl pyrrolidone (NMP) = 30%<br>Propylene Glycol (PG) = 39%<br>remainder Sterile Water | S | | |
| 347 | Rapa = 2.1%<br>CMC = 1%<br>Sterile Water = 96.9% | SP | 3.5 μm | |
| 348 | Rapa = 2.1%<br>PLGA 75/25 = 21.1%<br>N-methyl pyrrolidone (NMP) = 76.8% | ISG | | |
| 349 | Rapa = 2.0%<br>N-methyl pyrrolidone (NMP) = 44.5%<br>PEG 400 = 29.0%<br>Water = 24.5% | | | |
| 350 | Rapa = 1%<br>Ethanol = 4%<br>PEG 400 = 95% | | | |
| 351 | Rapa = 10.0%<br>PVP 90 = 57.9%<br>Phosal 50 SD = 20.0%<br>PEG 400 = 10.1%<br>Gamma Tocopherol = 1.0%<br>Ascorbyl palmitate = 1.0% | SDF | | |
| 352 | Dexamethasone = 25.3%<br>HPC = 33.2%<br>Eudragit RS 30D = 32.0%<br>Xanthan Gum = 9.5% | SDF | | |

Depending on their type, the listed formulations are denoted as one or more of solutions (S), suspensions (SP), emulsions (E), in situ gels (ISG) or solid dosage forms (SDF).

TABLE 2

Aqueous Humor Rapa Concentration

| 2% Rapa-PEG-EtOH Solution | Mean [Rapa] (ng/mL) | SD (ng/mL) |
|---|---|---|
| 1.0 μL intravitreal | 0.438 (1 day after injection) | 0.141 |
| 3.0 μL intravitreal | 0.355 (1 day after injection) | 0.234 |
| 3.0 μL sub-conj | 0.338 (1 day after injection) | 0.122 |
| 5.0 μL into anterior chamber | 0.167 (14 days after injection) | 0.183 |
| 10.0 μL into anterior chamber | 0.004 (14 days after injection) | 0.006 |

TABLE 3

Topical Administration Rapamycin Levels

| time, day | Blood, ng/ml | | | Cornea, ng/g | | | | | |
|---|---|---|---|---|---|---|---|---|---|
| | Gr. I | Gr. II | Gr. III | Gr. I (n = 2) | std | Gr. II OD (n = 1) | Gr. II OS (n = 1) | Gr. III (n = 2) | std |
| 1 | 4.63 | 2.84 | | 121.72 | 2.22 | 147.26 | 4.10 | | |
| 2 | 65.72 | 4.29 | | 229.49 | 10.03 | 209.98 | 10.46 | | |
| 3 | 37.14 | 27.29 | | 173.76 | 20.17 | 184.05 | 11.94 | | |
| 8 | | 15.54 | | | | | | 168.75 | 27.93 |
| 10 | | 7.67 | | | | | | 110.10 | 42.14 |
| 12 | | 2.88 | | | | | | 97.90 | 0.71 |
| 14 | | 48.32 | | | | | | 84.20 | 31.25 |

TABLE 4

Topical Administration Rapamycin Levels

R/Ch, ng/g

| time, day | Group I (n = 2) | std | Group II OD (n = 1) | Group II OS (n = 1) | Group III (n = 2) | std |
|---|---|---|---|---|---|---|
| 1 | 20.23 | 0.0354 | 34.51 | 11.58 | | |
| 2 | 41.53 | 4.5679 | 64.86 | 25.68 | | |
| 3 | 48.92 | 36.0695 | 22.88 | 63.67 | | |
| 8 | | | | | 107.24 | 80.5748 |
| 10 | | | | | 139.98 | 150.1895 |
| 12 | | | | | 30.05 | 12.7845 |
| 14 | | | | | 117.50 | 116.9555 |

TABLE 5

Topical Administration Rapamycin Levels

Sclera, ng/g

| time, day | Group I (n = 2) | std | Group II OD (n = 1) | Group II OS (n = 1) | Group III (n = 2) | std |
|---|---|---|---|---|---|---|
| 1 | 90.80 | 40.59 | 420.60 | 34.20 | | |
| 2 | 751.35 | 471.29 | 1353.60 | 144.50 | | |
| 3 | 350.80 | 77.22 | 540.60 | 104.20 | | |
| 8 | | | | | 895.20 | 368.83 |
| 10 | | | | | 612.65 | 530.97 |
| 12 | | | | | 130.85 | 60.17 |
| 14 | | | | | 419.65 | 515.41 |

TABLE 6

Topical Administration Rapamycin Levels

Vitreous, ng/ml

| time, day | Gr. I (n = 2) | std | Gr. II OD (n = 1) | Gr. II OS (n = 1) | Gr. III (n = 2) | std |
|---|---|---|---|---|---|---|
| 1 | 1.24 | 0.1697 | 2.06 | 1.00 | | |
| 2 | 5.41 | 1.2799 | 5.01 | 2.95 | | |
| 3 | 3.03 | 0.6859 | 3.96 | 4.00 | | |
| 8 | | | | | 19.69 | 22.5072 |
| 10 | | | | | 7.90 | 7.2903 |
| 12 | | | | | 1.46 | 0.5374 |
| 14 | | | | | 5.66 | 2.6870 |

What is claimed is:

1. A method for treating wet age-related macular degeneration in a human subject by repeated administration of a first formulation and a second formulation, the method comprising:
    (a) administering to the human subject two or more doses of a volume of the first formulation by intravitreal placement, wherein the volume of the first formulation comprises an amount of and about 500 µg of ranibizumab; and
    (b) administering to the human subject two or more doses of a volume of the second formulation by intravitreal or subconjuctival placement, wherein the volume of the second formulation comprises an amount of between about 200 µg and about 2000 µg of rapamycin, or a pharmaceutically acceptable salt or ester thereof;
    wherein the administration of rapamycin or a pharmaceutically acceptable salt or ester thereof decreases the frequency at which ranibizumab is administered to treat wet age-related macular degeneration in the human subject.

2. The method of claim 1, wherein step (a) is coincident with step (b).

3. The method of claim 1, wherein step (b) is subsequent to step (a).

4. The method of claim 1, wherein step (b) is prior to step (a).

5. The method of claim 1, wherein the volume of the second formulation contains a rapamycin dose selected from the group consisting of about 220 µg, about 440 µg, about 880 µg, and about 1320 µg of rapamycin.

6. The method of claim 1, wherein the second formulation is a liquid solution that consists essentially of about 2% (w/w) rapamycin, about 4% (w/w) ethanol, and about 94% (w/w) polyethylene glycol 400 (PEG 400).

7. The method of claim 1, wherein the second formulation is a liquid solution that consists essentially of about 4% (w/w) rapamycin, about 4% (w/w) ethanol, and about 92% (w/w) polyethylene glycol 400 (PEG 400).

8. The method of claim 1, wherein the second formulation is a liquid solution that consists essentially of about 1% (w/w) rapamycin, about 4% (w/w) ethanol, and about 95% (w/w) polyethylene glycol 400 (PEG 400).

9. The method of claim 1, wherein the second formulation is a solution of rapamycin dissolved in a solvent system.

10. The method of claim 9, wherein the solvent system comprises polyethylene glycol.

11. The method of claim 10, wherein the solvent system further comprises ethanol.

* * * * *